(12) United States Patent
Reeves et al.

(10) Patent No.: US 12,428,416 B2
(45) Date of Patent: Sep. 30, 2025

(54) ERK INHIBITORS AND USES THEREOF

(71) Applicants: California Institute of Technology, Pasadena, CA (US); 1200 Pharma LLC, Culver City, CA (US); The Regents of the University of California, Oakland, CA (US)

(72) Inventors: Corey M. Reeves, San Mateo, CA (US); Brendan M. O'Boyle, Monrovia, CA (US); Justin A. Hilf, Culver City, CA (US); Dylan Conklin, Los Angeles, CA (US); Martina S. McDermott, Los Angeles, CA (US); Neil A. O'Brien, Los Angeles, CA (US); Michael J. Palazzolo, Los Angeles, CA (US); Dennis Slamon, Los Angeles, CA (US); Steven J. Wittenberger, Sherman Oaks, CA (US); Oliver C. Loson, Monrovia, CA (US); Michael D. Bartberger, Sherman Oaks, CA (US); Brian M. Stoltz, San Marino, CA (US)

(73) Assignees: California Institute of Technology, Pasadena, CA (US); 1200 Pharma LLC, Culver City, CA (US); The Regents of the University of California, Oakland, CA (US)

( * ) Notice: Subject to any disclaimer, the term of this patent is extended or adjusted under 35 U.S.C. 154(b) by 838 days.

(21) Appl. No.: 17/294,225

(22) PCT Filed: Nov. 15, 2019

(86) PCT No.: PCT/US2019/061750
§ 371 (c)(1),
(2) Date: May 14, 2021

(87) PCT Pub. No.: WO2020/102686
PCT Pub. Date: May 22, 2020

(65) Prior Publication Data
US 2022/0002294 A1    Jan. 6, 2022

Related U.S. Application Data

(60) Provisional application No. 62/908,965, filed on Oct. 1, 2019, provisional application No. 62/768,565, filed on Nov. 16, 2018.

(51) Int. Cl.
| | |
|---|---|
| C07D 471/04 | (2006.01) |
| A61K 31/506 | (2006.01) |
| A61K 31/5377 | (2006.01) |
| A61P 35/00 | (2006.01) |
| A61P 35/02 | (2006.01) |
| C07D 519/00 | (2006.01) |
| C12N 9/12 | (2006.01) |

(52) U.S. Cl.
CPC .......... *C07D 471/04* (2013.01); *A61K 31/506* (2013.01); *A61K 31/5377* (2013.01); *A61P 35/00* (2018.01); *A61P 35/02* (2018.01); *C07D 519/00* (2013.01); *C12N 9/1205* (2013.01)

(58) Field of Classification Search
None
See application file for complete search history.

(56) References Cited

U.S. PATENT DOCUMENTS

| | | | |
|---|---|---|---|
| 7,514,448 B2 * | 4/2009 | Green | A61P 17/06 546/113 |
| 8,420,820 B2 | 4/2013 | Wucherer-Plietker et al. | |
| 8,575,163 B2 | 11/2013 | Wucherer-Plietker et al. | |
| 8,802,866 B2 | 8/2014 | Emde et al. | |

FOREIGN PATENT DOCUMENTS

| | | | |
|---|---|---|---|
| CN | 101228160 A | 7/2008 | |
| CN | 107973783 A | 5/2018 | |
| EP | 2944637 A1 | 11/2015 | |
| EP | 3626718 A1 | 3/2020 | |
| WO | WO-2005103050 A2 * | 11/2005 | .......... C07D 471/04 |
| WO | WO-2007/002433 A1 | 1/2007 | |
| WO | WO-2010/000364 A1 | 1/2010 | |
| WO | WO-2010/011756 A1 | 1/2010 | |
| WO | WO-2011/035855 A1 | 3/2011 | |
| WO | WO-2011/076316 A1 | 6/2011 | |
| WO | WO-2012/094313 A1 | 7/2012 | |
| WO | WO-2013/052355 A1 | 4/2013 | |
| WO | WO-2014/060395 A1 | 4/2014 | |
| WO | WO-2014/109414 A1 | 7/2014 | |
| WO | WO-2015/051341 A1 | 4/2015 | |
| WO | WO-2016/026078 A1 | 2/2016 | |
| WO | WO-2016/118951 A2 | 7/2016 | |
| WO | WO-2017/085230 A1 | 5/2017 | |
| WO | WO-2018/210314 A1 | 11/2018 | |

OTHER PUBLICATIONS

Ali et al. (2014) Input of Isosteric and Bioisosteric Approach in Drug Design, J. Chem. Soc. Pak., 36, p. 150-169 (Year: 2014).*
International Preliminary Report on Patentability for International Application No. PCT/US2019/061750 dated May 18, 2021.
International Search Report and Written Opinion for International Application No. PCT/US2019/061750 mailed Mar. 9, 2020.

* cited by examiner

*Primary Examiner* — Juliet C Switzer
*Assistant Examiner* — Dawanna Shar-Day White
(74) *Attorney, Agent, or Firm* — Foley Hoag LLP; Janine S. Ladislaw; Lawrence P. Tardibono

(57) ABSTRACT

The present disclosure provides compounds and compositions that are inhibitors of ERK1, ERK2, or both, and methods of use thereof.

20 Claims, 14 Drawing Sheets

| Time (mins) | 10 mg/kg PO | 50 mg/kg PO | 100 mg/kg PO | 50 mg/kg IP |
|---|---|---|---|---|
| 0 | 0 | 0 | 0 | 0 |
| 30 | 89 | 1424 | 1550 | 4897 |
| 60 | 109 | 696 | 1183 | 3560 |
| 120 | 137 | 748 | 1453 | 3270 |
| 240 | 18 | 501 | 502 | 2080 |
| 480 | 0 | 245 | 58 | 750 |
| 1440 | 0 | 0 | 0 | 143 |

| | Day of Study | | | | | | | | | | | | | | |
|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 |
| Vehicle 2 5% DMSO QD | 0.00% | | 2.64% | 3.87% | 4.91% | 3.46% | 4.63% | 5.17% | 6.46% | 4.30% | 3.41% | 4.70% | -0.39% | -0.96% | -1.96% |
| 25 mg/kg QD | 0.00% | 0.99% | 2.05% | 3.14% | 4.55% | 3.74% | 4.72% | 5.31% | | | | | | | |
| 50 mg/kg QD | 0.00% | 1.07% | 0.84% | 0.52% | 0.93% | 0.17% | 1.05% | 3.42% | | | | | | | |
| 100 mg/kg QD | 0.00% | -0.23% | -0.07% | 1.10% | 2.94% | 3.12% | 3.61% | 3.69% | 4.60% | 1.78% | 1.95% | 1.03% | 0.77% | -0.64% | 0.78% |
| 200 mg/kg QD | 0.00% | -0.87% | -1.24% | -1.25% | 0.24% | 0.98% | 1.00% | 2.57% | 3.54% | 1.30% | 0.10% | 0.23% | -0.46% | 0.92% | 2.34% |
| 300 mg/kg QD | 0.00% | -0.40% | -0.25% | -2.08% | -0.12% | -1.75% | -3.55% | -3.47% | -9.41% | | | | | | |
| 400 mg/kg QD | 0.00% | 1.61% | 2.12% | 1.69% | 2.26% | 1.78% | -0.73% | 0.42% | | | | | | | |
| 5% DMSO BID | 0.00% | 0.66% | 0.19% | 3.43% | 3.18% | 2.28% | 1.73% | 1.43% | 2.15% | -1.40% | -1.03% | -1.48% | -0.39% | -0.96% | -1.96% |
| 12.5 mg/kg BID | 0.00% | 0.21% | 1.07% | 1.57% | 2.73% | 1.75% | 0.77% | 0.11% | | | | | | | |
| 25 mg/kg BID | 0.00% | 0.17% | 0.05% | 0.68% | 0.20% | -0.83% | -1.41% | -1.21% | | | | | | | |
| 50 mg/kg BID | 0.00% | 0.41% | 0.65% | 0.09% | -0.80% | -2.10% | -2.11% | -1.28% | | | | | | | |
| 100 mg/kg BID | 0.00% | -0.13% | 0.12% | 0.19% | -0.29% | -0.22% | -0.55% | -1.97% | -1.33% | -4.35% | -5.33% | -4.85% | -4.56% | -5.32% | -5.63% |
| 200 mg/kg BID | 0.00% | -0.16% | -0.29% | 0.42% | -2.57% | -4.37% | -5.23% | -4.77% | | | | | | | |

FIG. 6

| | \multicolumn{6}{c}{Day of Study} | | | | | |
|---|---|---|---|---|---|---|
| | 0 | 4 | 8 | 11 | 13 | 15 | 18 |
| Vehicle Control BID | 0.00% | 0.16% | 1.05% | -2.53% | -2.77% | -0.32% | -1.43% |
| 10mg/kg QD | 0.00% | 1.25% | 1.98% | 0.60% | 1.48% | 3.02% | 1.73% |
| 25mg/kg QD | 0.00% | 1.42% | 2.65% | -0.62% | 0.39% | 2.94% | 1.32% |
| 50mg/kg QD | 0.00% | -0.85% | -1.46% | -3.41% | -2.93% | -1.57% | -2.83% |
| 100mg/kg QD | 0.00% | 2.00% | 1.83% | -2.44% | -0.64% | 0.72% | -0.47% |
| 200mg/kg QD | 0.00% | -0.65% | -0.30% | -1.94% | -1.71% | 0.42% | -2.82% |
| 250mg/kg QD | 0.00% | -0.03% | 1.94% | 0.49% | 0.34% | 1.82% | -0.55% |
| 25mg/kg BID | 0.00% | 0.61% | 1.44% | -0.83% | -0.22% | -0.90% | -1.58% |
| 50mg/kg BID | 0.00% | -1.95% | -0.07% | -3.01% | -4.58% | -0.60% | -4.48% |

FIG. 9

| | Day of Study | | | |
|---|---|---|---|---|
| | 0 | 4 | 8 | 11 |
| Vehicle Control | 0.00% | -1.13% | 0.52% | -4.25% |
| 10 mg/kg QD | 0.00% | -0.30% | 2.45% | 0.22% |
| 25 mg/kg QD | 0.00% | -1.69% | 0.84% | -2.81% |
| 50 mg/kg QD | 0.00% | -1.14% | 1.63% | -0.46% |
| 100 mg/kg QD | 0.00% | 0.58% | 4.04% | 2.93% |
| 200 mg/kg QD | 0.00% | 0.84% | 1.80% | 0.18% |
| 250 mg/kg QD | 0.00% | 3.81% | 3.89% | 3.01% |
| 25 mg/kg BID | 0.00% | 1.46% | 2.45% | -0.30% |
| 50 mg/kg BID | 0.00% | -1.22% | 1.55% | -1.60% |

FIG. 12

| | \multicolumn{8}{c}{Day of Study} | | | | | | | |
|---|---|---|---|---|---|---|---|---|
| | 0 | 3 | 5 | 7 | 10 | 12 | 14 |
| Vehicle Control | 0.00% | 0.19% | -1.47% | -1.09% | 0.54% | -1.02% | -0.16% |
| 250 mg/kg QD | 0.00% | -1.58% | -5.06% | -4.70% | -1.06% | -2.68% | -1.10% |
| 50 mg/kg BID | 0.00% | -1.01% | -2.19% | -2.30% | -1.50% | -1.88% | -2.31% |

ERK INHIBITORS AND USES THEREOF

CROSS-REFERENCE TO RELATED APPLICATIONS

This application is a 371 (c) national stage of PCT/US2019/061750, filed Nov. 15, 2019, which claims the benefit of U.S. Provisional Application No. 62/768,565, filed Nov. 16, 2018, and U.S. Provisional Application No. 62/908,965, filed Oct. 1, 2019, each of which is incorporated by reference herein in its entirety.

BACKGROUND

Extracellular signal-regulated kinases (ERKs) are widely expressed protein kinase intracellular signaling molecules that mediate the processes involved in tumor growth, progression, and metastasis. The ERK pathway plays a central role in regulating mammalian cell growth by relaying extracellular signals from ligand-bound cell surface tyrosine kinase receptors such as ErbB family, PDGF, FGF, and VEGF receptor tyrosine kinase. Activation of the ERK pathway proceeds via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that ERK/MAPK pathway dysregulation is oncogenic. Ras genes, which are upstream of ERK1/2, are mutated in several cancers including colorectal, melanoma, breast and pancreatic tumors. High Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anticancer therapies in a broad spectrum of human tumors.

Therefore, a welcome contribution to the art would be small-molecules (i.e., compounds) that inhibit ERK activity (e.g., ERK1 activity or ERK2 activity, or both) for treating a broad spectrum of cancers, such as, for example, melanoma, pancreatic cancer, thyroid cancer, colorectal cancer, lung cancer, breast cancer, and ovarian cancer.

SUMMARY

In certain embodiments, the invention relates to a compound having
(a) the structure of Formula I:

(Formula I)

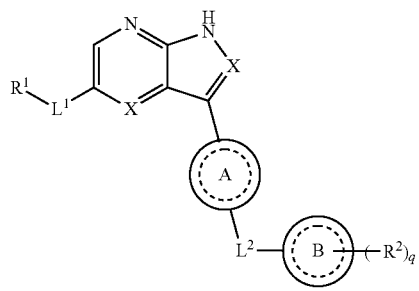

or a pharmaceutically acceptable salt thereof, wherein:

$R^1$ is hydrogen, halogen, optionally substituted $C_{1-4}$alkyl, optionally substituted $C_{2-4}$alkenyl, optionally substituted heterocyclyl, optionally substituted aryl, optionally substituted heteroaryl, CN, $OR^{1a}$, $SR^{1a}$, $NR^{1a}R^{1b}$, $N(R^{1a})C(O)R^{1a}$, or $C(O)N(R^{1a})(R^{1b})$;

$L^1$ is a bond, optionally substituted $C_{1-5}$alkyl, C(O), O, $C(O)N(R^4)(C(R^4)_2)_m$, $(C(R^4)_2)_mC(O)N(R^4)$, $N(R^4)$, $S(O)_2N(R^4)$, $N(R^4)S(O)_2$, $S(O)_2$, cycloalkyl or heterocyclyl;

is pyridinyl, pyrimidinyl, pyrazinyl, pyridazinyl, triazinyl, or

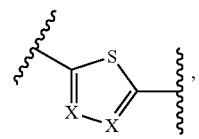

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

X in each occurrence is independently selected from CH and N;

$L^2$ is optionally substituted $C_{1-5}$alkyl, $C(O)N(R^4)(C(R^4)_2)_m$, $(C(R^4)_2)_mC(O)N(R^4)$, C(O)heterocyclyl, heterocyclyl-C(O), $N(R^4)$, $S(O)_2N(R^4)$, $N(R^4)S(O)_2$, $S(O)_2$, or heterocyclyl, wherein any of said heterocyclyl is optionally substituted with one or more optionally substituted aryl, optionally substituted $C_{1-4}$alkyl or halogen;

is aryl or heteroaryl;

$R^2$ is optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;

m is 0, 1, 2 or 3; and q is 0, 1, 2 or 3; or (b) the structure of Formula II:

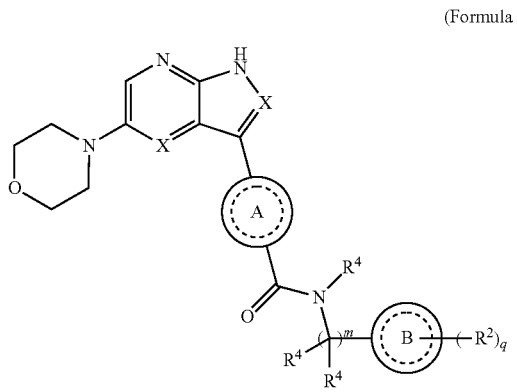
(Formula II)

or a pharmaceutically acceptable salt thereof, wherein:

is pyridinyl, pyrimidinyl, pyrazinyl, pyridazinyl, triazinyl, or

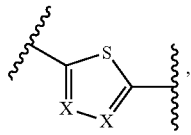

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

X in each occurrence is independently selected from CH and N;

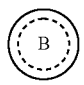

is aryl or heteroaryl;

$R^2$ is optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;

m is 0, 1, 2 or 3; and q is 0, 1, 2 or 3; or (c) the structure of Formula III:

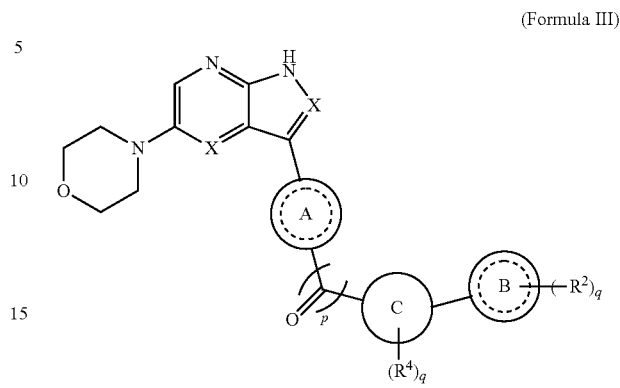
(Formula III)

or a pharmaceutically acceptable salt thereof, wherein:

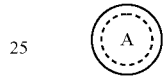

is pyridinyl, pyrimidinyl, pyrazinyl, pyridazinyl, triazinyl, or

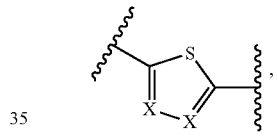

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

X in each occurrence is independently selected from CH and N;

is aryl or heteroaryl;

C is optionally substituted heterocyclyl;

$R^2$ is optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, optionally substituted aryl, optionally substituted heteroaryl, optionally substituted cycloalkyl, or optionally substituted heterocyclyl;

p is 0 or 1; and q is, in each instance, independently 0, 1, 2 or 3.

In certain embodiments, the invention relates to a compound selected from:

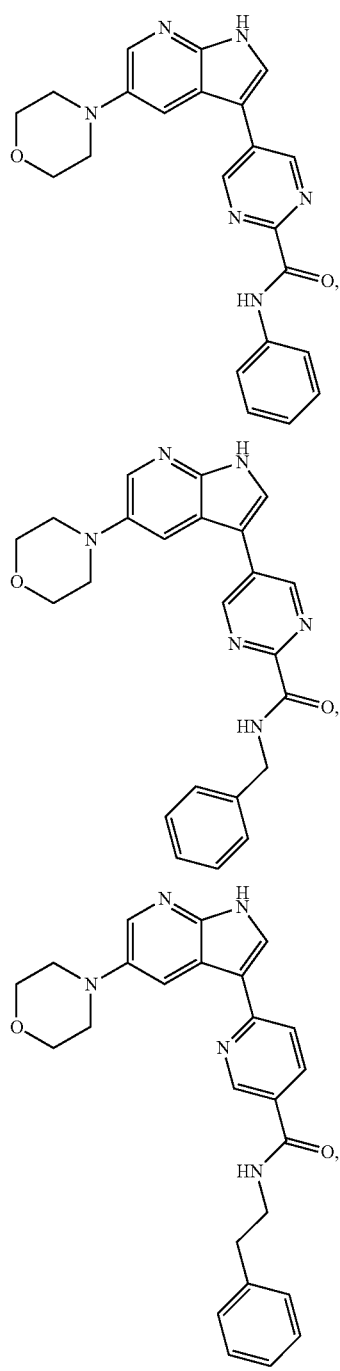

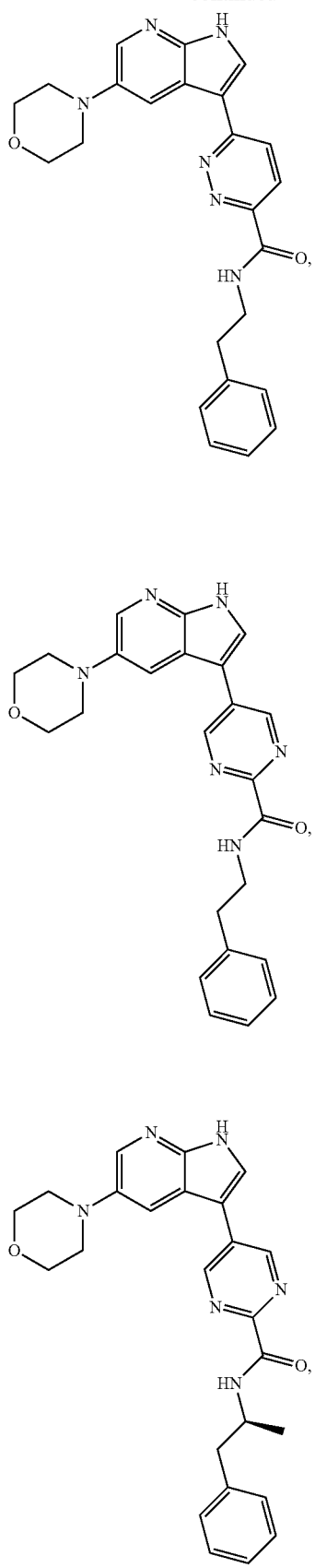

7
-continued
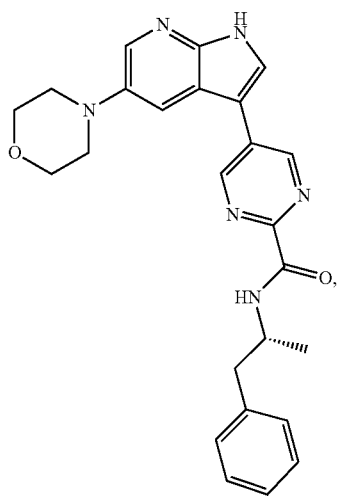
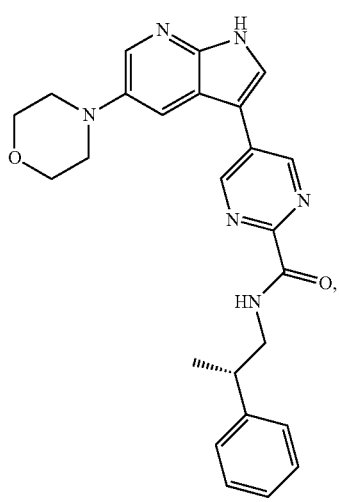
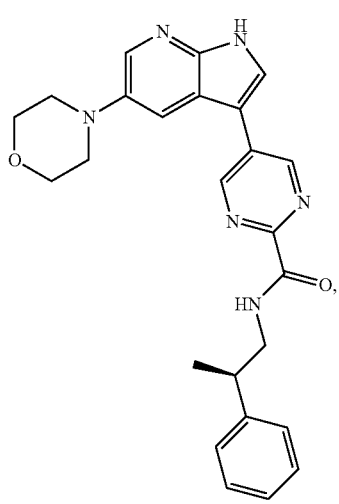
8
-continued
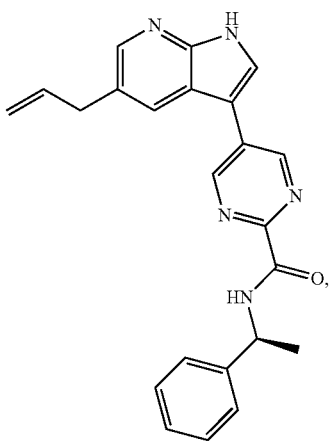
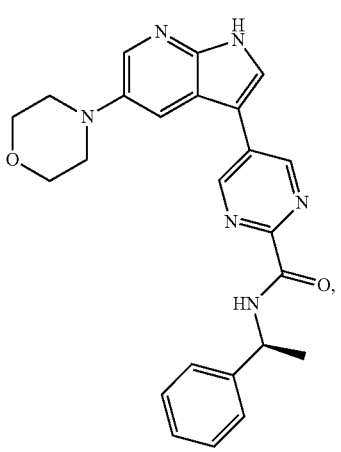

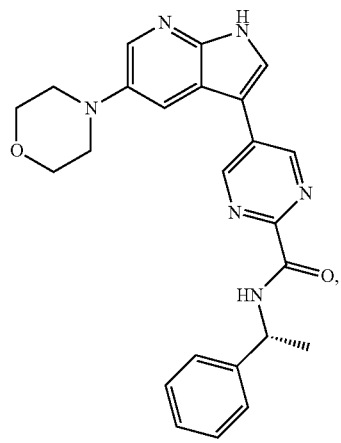
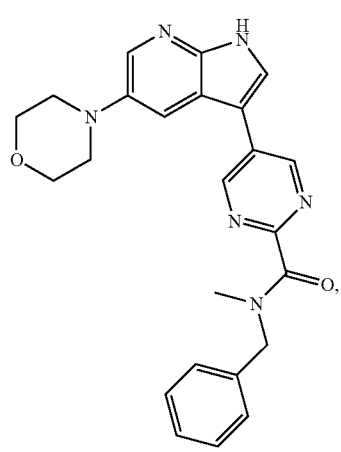
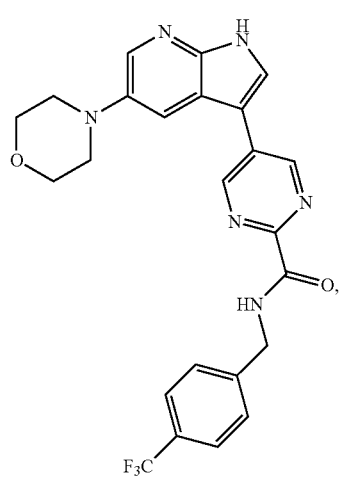
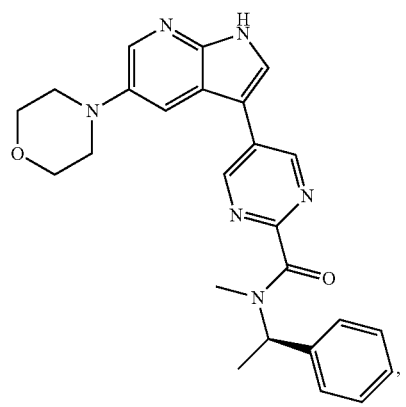
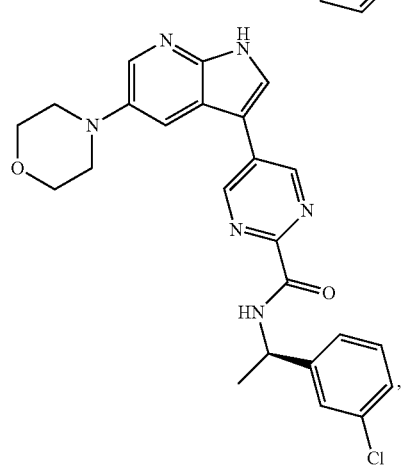
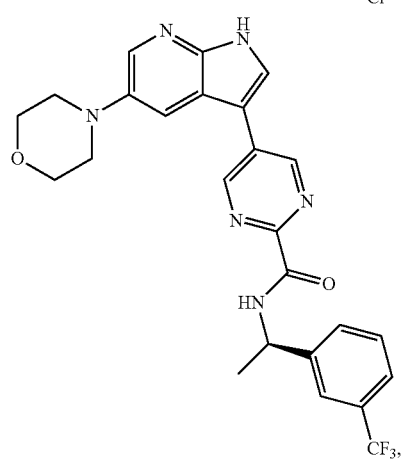
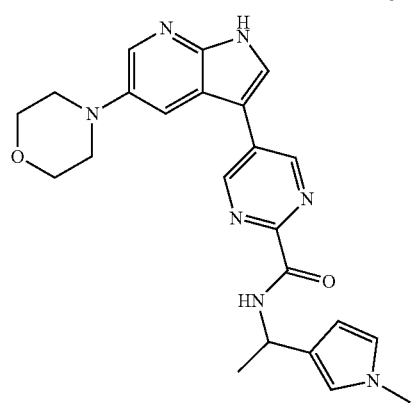

-continued
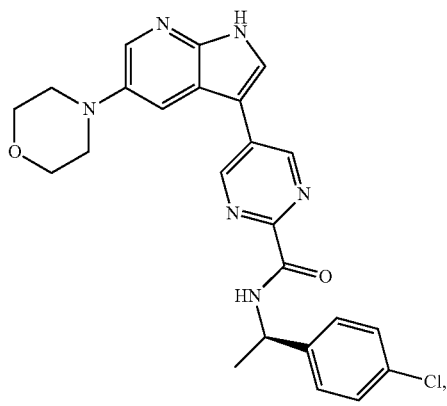
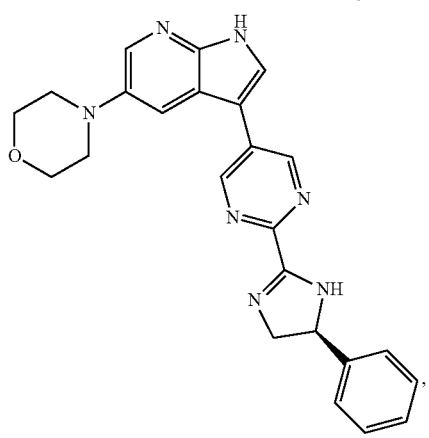
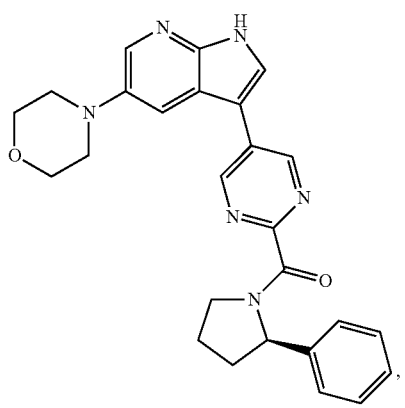
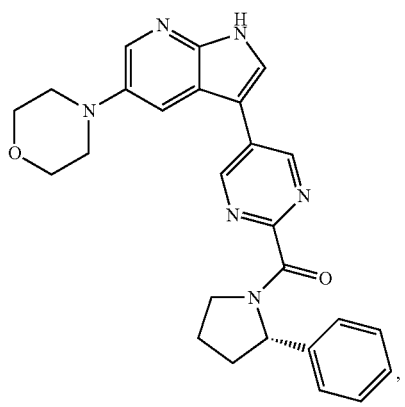
-continued
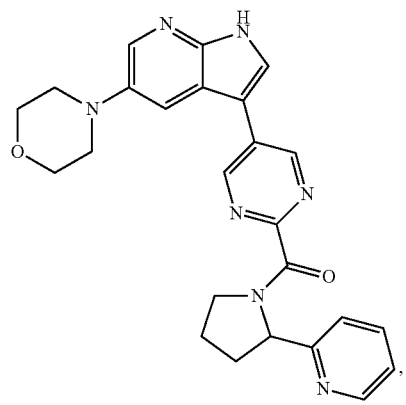
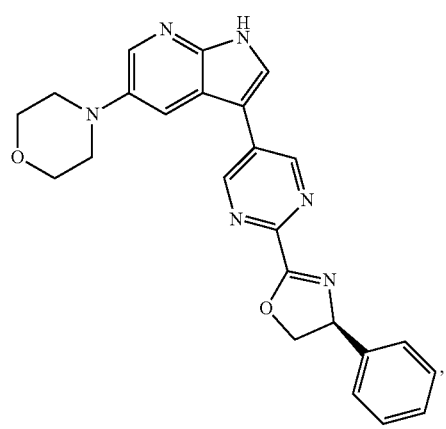
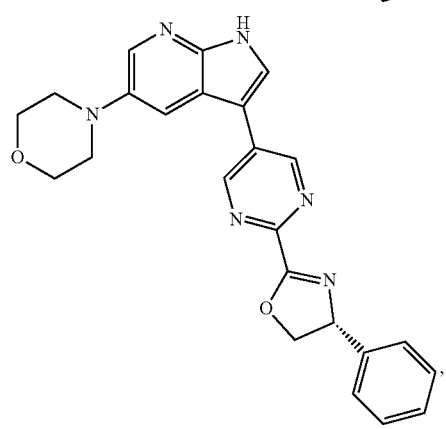
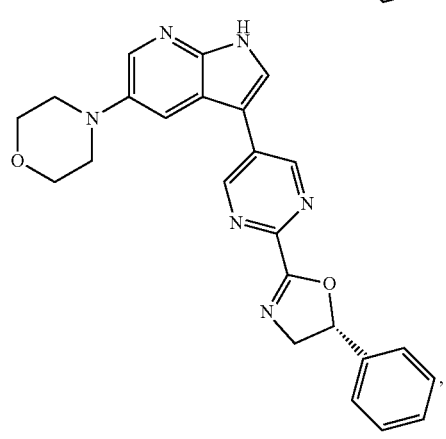

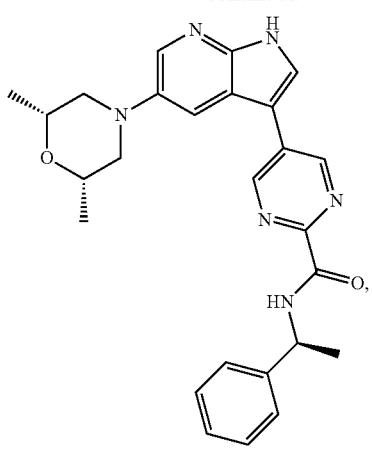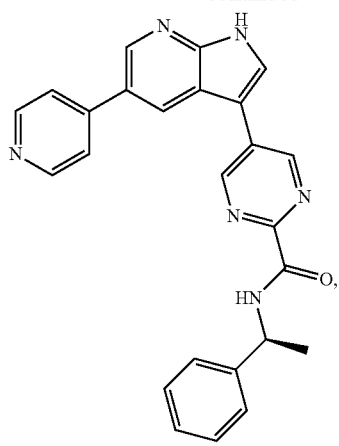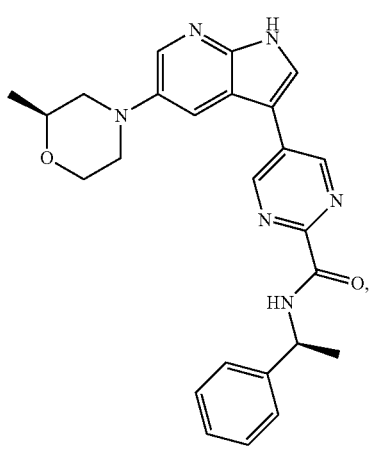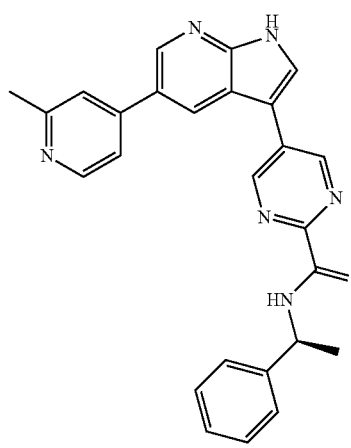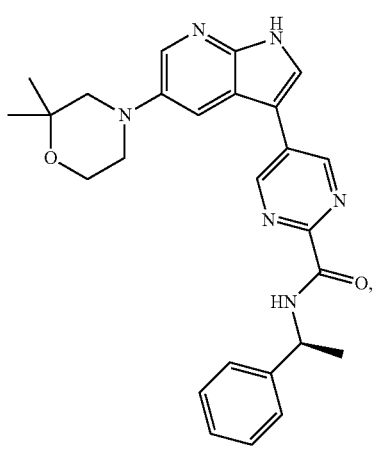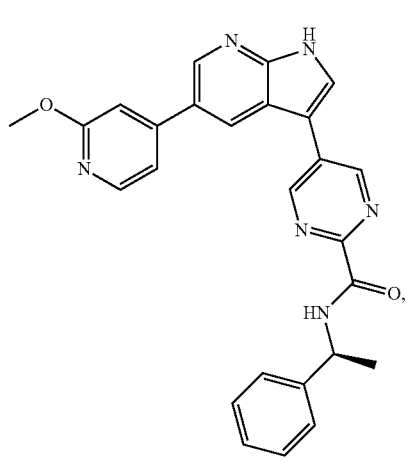

-continued
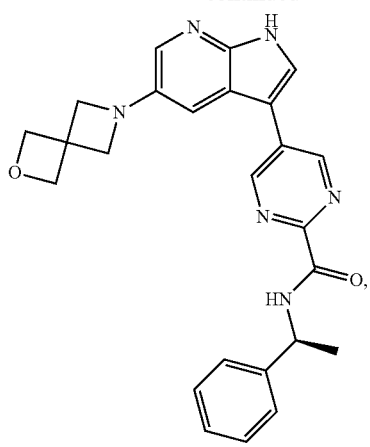
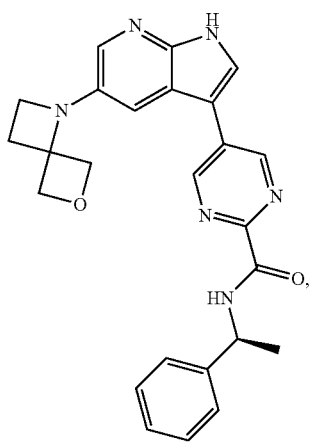
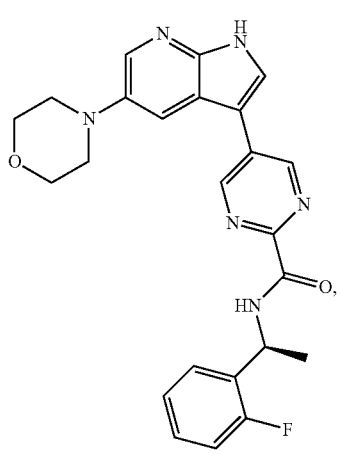
-continued
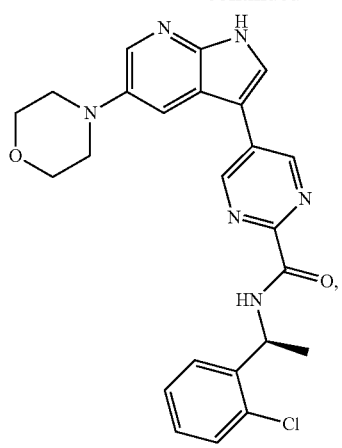
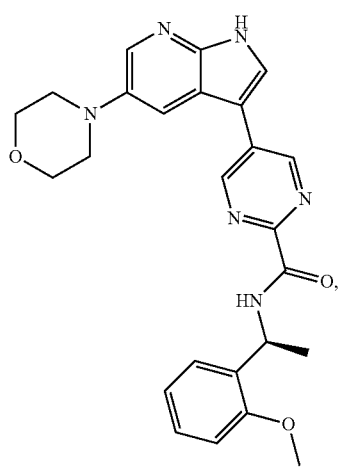
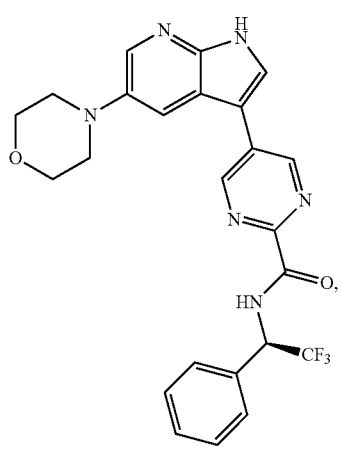

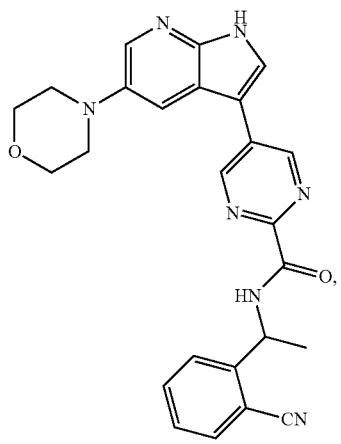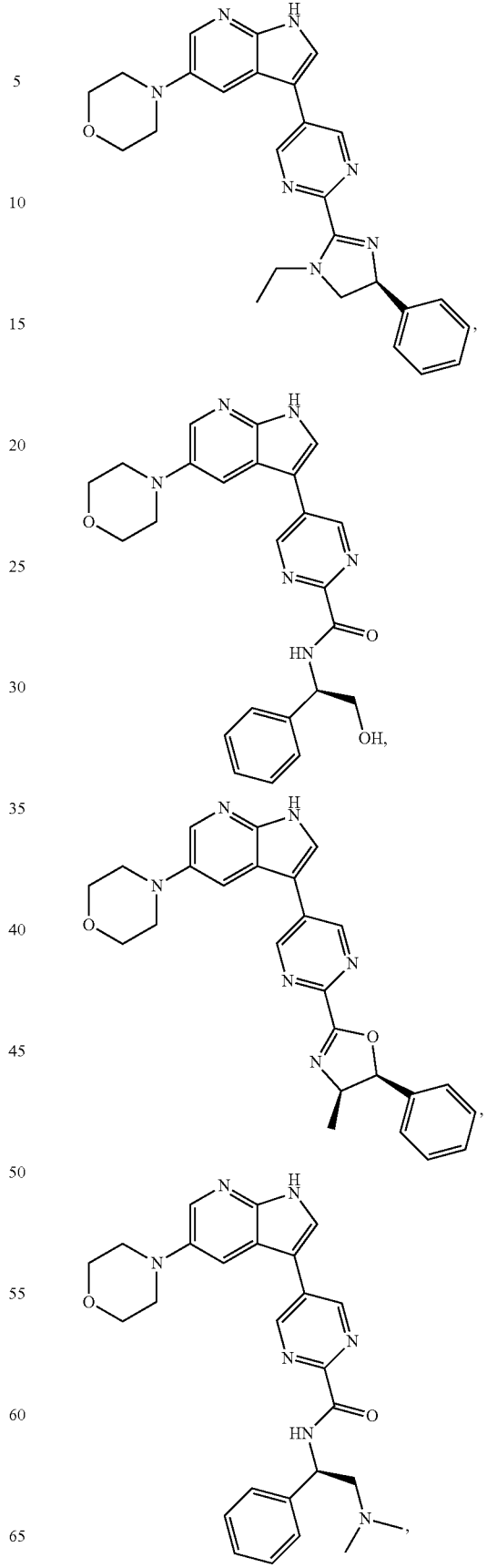

-continued
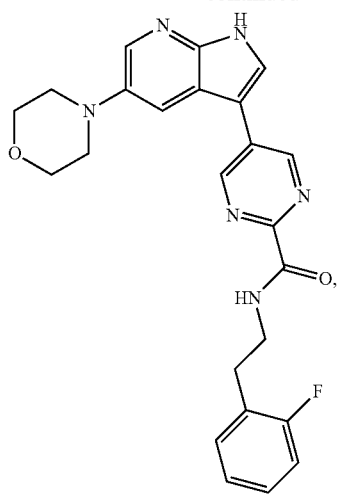
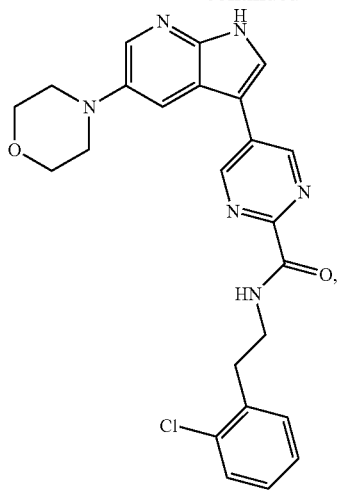
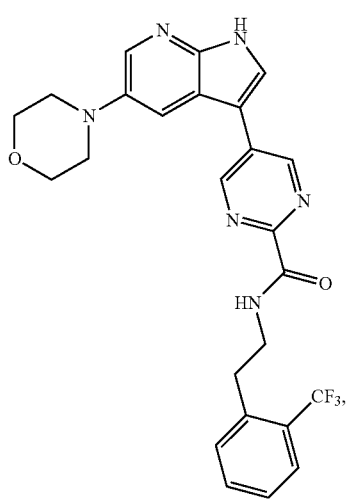
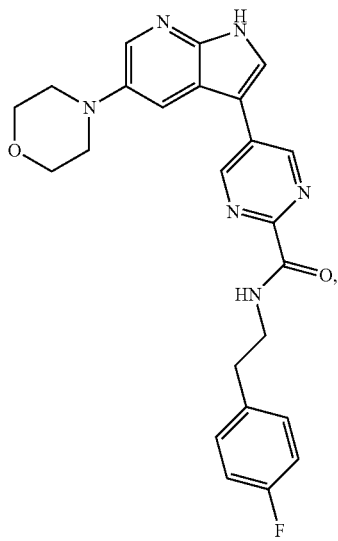
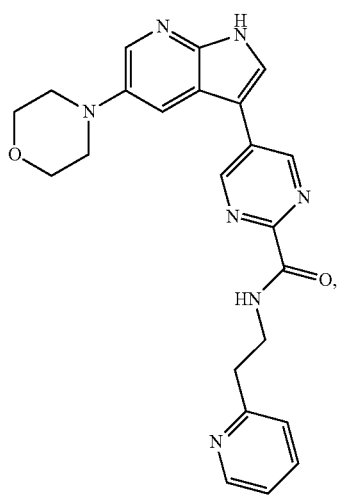
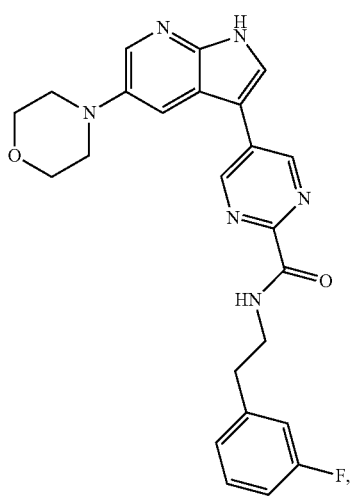

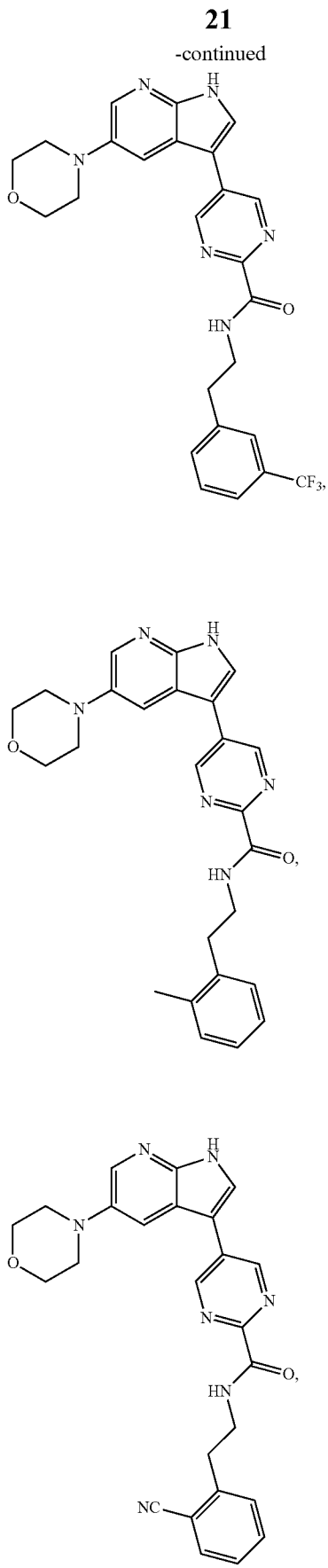

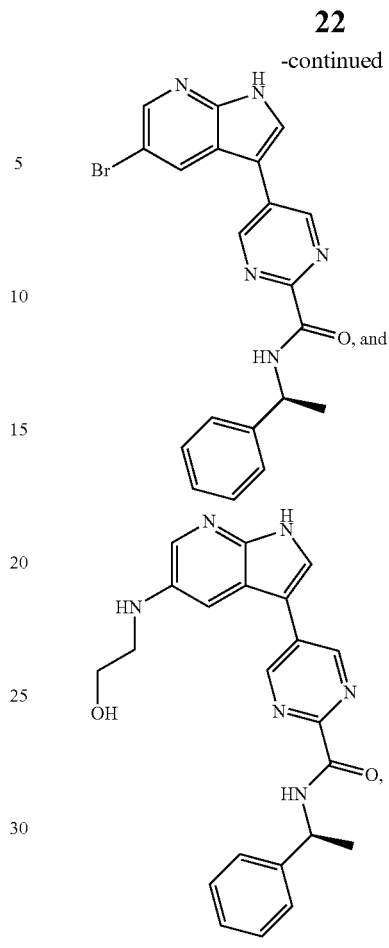

or a pharmaceutically acceptable salt thereof.

In some embodiments, the invention relates to a pharmaceutical composition comprising any compound described herein and a pharmaceutically acceptable diluent or excipient.

In certain embodiments, the invention relates to a method of treating cancer in a subject in need thereof comprising administering to the subject any compound described herein, or a pharmaceutically acceptable salt thereof.

In some embodiments, the invention relates to a method of inhibiting ERK1 or ERK2 in a cell comprising contacting said cell with any compound described herein, or a pharmaceutically acceptable salt thereof, such that ERK1 or ERK2 enzymes are inhibited in said cell.

BRIEF DESCRIPTION OF THE DRAWINGS

FIG. 2 is the tabulated blood plasma concentrations in ng/mL of compound 6 from the PK study.

FIG. 4 is the tabulation of the percentage weight changes per day of mice treated daily (QD) or twice daily (BID) with various concentrations of compound 6. Compound 6 was administered through oral gavage (PO). The maximum tolerated QD dose was 200 mg/kg and the maximum tolerated BID dose was 100 mg/kg.

FIG. 6 is the tabulation of the percentage weight changes per day of mice in the M275 melanoma cell line xenograft study.

FIG. 9 is the tabulation of the percentage weight changes per day of mice in the PSN1 pancreatic cancer cell line xenograft study.

FIG. 12 is the tabulation of the percentage weight changes per day of mice in the H2135 NSCLC cell line xenograft study.

DETAILED DESCRIPTION

Definitions

Figure 1:
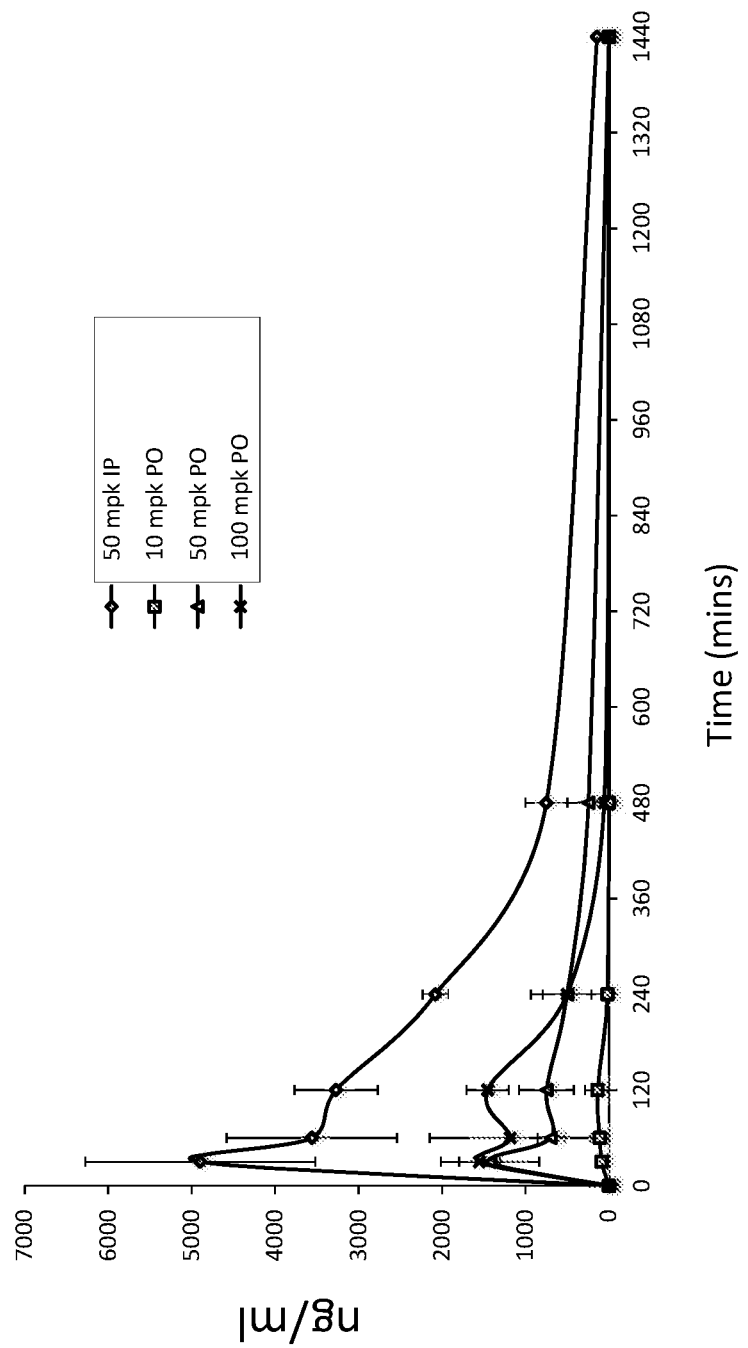
FIG. 1 are results of a mouse pharmacokinetics (PK) study with compound 6 dosed intraperitoneal (IP) at 50 mg/kg, or dosed through oral gavage (PO) at 10, 50 and 100 mg/kg.

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl," as used herein, refers to an aliphatic group containing at least one double bond and is intended to include both "unsubstituted alkenyls" and "substituted alkenyls" the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include, but are not limited to methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, an oxo, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-$C_6$ alkyl, $C_3$-$C_6$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

In addition, the term "alkyl" as used throughout the specification, examples, and claims is intended to be interchangeable, where valence requires, with the term "alkylene" (i.e., an alkyl diradical or a bivalent alkyl moiety).

The term "$C_x$-$C_y$," when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_2$-$C_y$ alkenyl" and "$C_2$-$C_y$ alkynyl" refer to substituted or unsubstituted unsaturated aliphatic groups analogous in length and possible substitution to the alkyls described above, but that contain at least one double or triple bond respectively.

The term "alkylamino," as used herein, refers to an amino group substituted with at least one alkyl group.

The term "alkylthio," as used herein, refers to a thiol group substituted with an alkyl group and may be represented by the general formula alkylS—.

The term "alkynyl," as used herein, refers to an aliphatic group containing at least one triple bond and is intended to include both "unsubstituted alkynyls" and "substituted alkynyls," the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide," as used herein, refers to a group

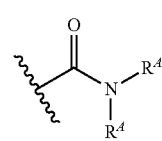

wherein each $R^A$ independently represent a hydrogen, hydrocarbyl group, aryl, heteroaryl, acyl, or alkoxy, or two $R^A$ are taken together with the N atom to which they are attached complete a heterocycle having from 3 to 8 atoms in the ring structure.

The terms "amine" and "amino" are art-recognized and refer to both unsubstituted and substituted amines and salts thereof, e.g., a moiety that can be represented by

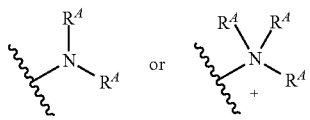

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl," as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- to 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, aniline, and the like.

The term "carbocycle" refers to a saturated or unsaturated ring in which each atom of the ring is carbon. The term carbocycle includes both aromatic carbocycles and non-aromatic carbocycles. Non-aromatic carbocycles include both cycloalkyl and cycloalkenyl rings. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—$R^A$, wherein $R^A$ represents a hydrocarbyl group.

The term "carboxy", as used herein, refers to a group represented by the formula —$CO_2H$.

A "cycloalkyl" group is a cyclic hydrocarbon which is completely saturated. "Cycloalkyl" includes monocyclic and bicyclic rings. Typically, a monocyclic cycloalkyl group has from 3- to about 10-carbon atoms, from 3- to 8-carbon atoms, or more typically from 3- to 6-carbon atoms unless otherwise defined. The second ring of a bicyclic cycloalkyl may be selected from saturated, unsaturated and aromatic rings. Cycloalkyl includes bicyclic molecules in which one, two, or three or more atoms are shared between the two rings (e.g., fused bicyclic compounds, bridged bicyclic compounds, and spirocyclic compounds).

The term "fused bicyclic compound" refers to a bicyclic molecule in which two rings share two adjacent atoms. In other words, the rings share one covalent bond, i.e., the so-called bridgehead atoms are directly connected (e.g., α-thujene and decalin). For example, in a fused cycloalkyl each of the rings shares two adjacent atoms with the other ring, and the second ring of a fused bicyclic cycloalkyl may be selected from saturated, unsaturated and aromatic rings.

A "cycloalkenyl" group is a cyclic hydrocarbon containing one or more double bonds.

The term "bridged bicyclic compound" refers to a bicyclic molecule in which the two rings share three or more atoms, separating the two bridgehead atoms by a bridge containing at least one atom. For example, norbornane, also known as bicyclo[2.2.1]heptane, can be thought of as a pair of cyclopentane rings each sharing three of their five carbon atoms.

The term "spirocyclic compound" or "spirocycle" refers to a bicyclic molecule or group in which the two rings have only one single atom, the spiro atom, in common.

The term "diazo", as used herein, refers to a group represented by the formula =N=N.

The term "disulfide" is art-recognized and refers to a group —S—S—$R^A$, wherein $R^A$ represents a hydrocarbyl group.

The term "enol ester", as used herein, refers to a group —C(O)O—C($R^A$)=C($R^A$)$_2$ wherein $R^A$ represents a hydrocarbyl group.

The term "ester", as used herein, refers to a group —C(O)O$R^A$ wherein $R^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The term "heteroalkyl", as used herein, refers to a saturated or unsaturated chain of carbon atoms and at least one heteroatom, for example, wherein no two heteroatoms are adjacent.

The terms "heteroaralkyl" and "hetaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, preferably 3- to 7-membered rings, more preferably 5- to 6-membered rings, in some instances, most preferably a 5-membered ring, in other instances, most preferably a 6-membered ring, which ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. The terms "heterocyclyl" and "heterocyclic" further include spirocycles in which one carbon is common to two adjoining rings wherein at least one of the rings is heterocyclic, e.g., the other cyclic ring can be cycloalkyl cycloalkenyl, cycloalkynyl, and/or heterocyclyl. Heterocyclyl groups include, for example, pyrrolidine, piperidine, piperazine, pyrrolidine, tetrahydropyran, tetrahydrofuran, morpholine, lactones, lactams, oxazolines, imidazolines and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer, more preferably three or fewer. A "lower alkyl", for example, refers to an alkyl group that contains ten or fewer carbon atoms, preferably six or fewer, more preferably three or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "orthoester" as used herein is art-recognized and refers to a group —C(OR$^A$)$_3$, wherein each R$^A$ independently represents hydrogen or a hydrocarbyl, such as alkyl, or any occurrence of R$^A$ taken together with another and the intervening atom(s) complete a heterocycle having from 4 to 8 atoms in the ring structure.

The term "phosphoester", as used herein, refers to a group —P(O$_2$)OH.

The term "phosphodiester", as used herein, refers to a group —P(O$_2$)OR$^A$ wherein R$^A$ represents a hydrocarbyl group.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "selenide", as used herein, is equivalent to an ether, wherein the oxygen is replaced with a selenium.

The term "selenoxide" is art-recognized and refers to the group —Se(O)—R$^A$, wherein R$^A$ represents a hydrocarbyl.

The term "siloxane" is art-recognized and refers to a group with an Si—O—Si linkage, such as the group —Si(R$^A$)$_2$—O—Si—(R$^A$)$_3$, wherein each R$^A$ independently represents hydrogen or hydrocarbyl, such as alkyl, or both R$^A$ taken together with the intervening atom(s) complete a heterocycle having from 4 to 8 atoms in the ring structure.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, an oxo, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, an oxime, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-$C_6$ alkyl, $C_3$-$C_6$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO₃H, or a pharmaceutically acceptable salt thereof.

The term "sulfonamide" is art-recognized and refers to the group represented by the general formulae

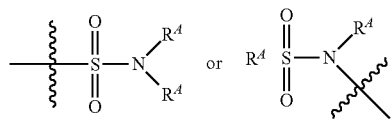

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group SO₃H, or a pharmaceutically acceptable salt thereof.

The term "sulfone" is art-recognized and refers to the group —S(O)₂—$R^A$, wherein $R^A$ represents a hydrocarbyl.

The term "thioalkyl", as used herein, refers to an alkyl group substituted with a thiol group.

The term "thioester", as used herein, refers to a group —C(O)S$R^A$ or —SC(O)$R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

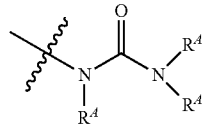

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt that is suitable for or compatible with the treatment of patients.

The term "pharmaceutically acceptable acid addition salt" as used herein means any non-toxic organic or inorganic salt of any base compounds disclosed herein. Illustrative inorganic acids that form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of the invention for laboratory use, or for subsequent conversion to a pharmaceutically acceptable acid addition salt.

The term "pharmaceutically acceptable basic addition salt" as used herein means any non-toxic organic or inorganic base addition salt of any acid compounds of the invention, or any of their intermediates. Illustrative inorganic bases that form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of the invention). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of the invention, or a pharmaceutically acceptable salt thereof. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

Exemplary Compounds

In certain embodiments, the invention relates to a compound having the structure of Formula I:

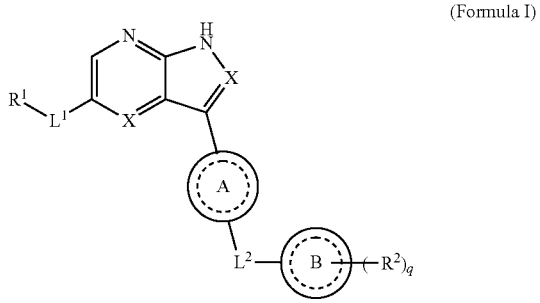

(Formula I)

or a pharmaceutically acceptable salt thereof,
wherein:

$R^1$ is hydrogen, halogen, optionally substituted $C_{1-4}$alkyl, optionally substituted $C_{2-4}$alkenyl, optionally substituted heterocyclyl, optionally substituted aryl, optionally substituted heteroaryl, CN, $OR^{1a}$, $SR^{1a}$, $NR^{1a}R^{1b}$, $N(R^{1a})C(O)R^{1a}$, or $C(O)N(R^{1a})(R^{1b})$;

$L^1$ is a bond, or is optionally substituted $C_{1-5}$alkyl, C(O), O, $C(O)N(R^4)(C(R^4)_2)_m$, $(C(R^4)_2)_mC(O)N(R^4)$, $N(R^4)$, $S(O)_2N(R^4)$, $N(R^4)S(O)_2$, $S(O)_2$, cycloalkyl, or heterocyclyl;

is pyridinyl, pyrimidinyl, pyrazinyl, pyridazinyl, triazinyl, or

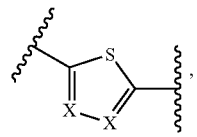

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

X in each occurrence is independently selected from CH and N;

$L^2$ is optionally substituted $C_{1-5}$alkyl, $C(O)N(R^4)(C(R^4)_2)_m$, $(C(R^4)_2)_mC(O)N(R^4)$, C(O)heterocyclyl, heterocyclyl-C(O), $N(R^4)$, $S(O)_2N(R^4)$, $N(R^4)S(O)_2$, $S(O)_2$, or heterocyclyl, wherein any of said heterocyclyl is optionally substituted with one or more optionally substituted aryl, optionally substituted $C_{1-4}$alkyl or halogen;

is aryl or heteroaryl;

$R^2$ if present, in each instance is independently optionally substituted $C_{1-6}$alkyl, alkoxy, optionally substituted cycloalkyl CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;

m is 0, 1, 2 or 3; and q is 0, 1, 2 or 3.

In some embodiments, when q is 1, 2 or 3, $R^2$ is optionally substituted $C_{1-6}$alkyl, alkoxy, optionally substituted cycloalkyl CN, $NR^{1a}R^{1b}$, $C(O)N(R^{1a})(R^{1b})$, $N(R^{1a})C(O)R^{1a}$, halogen or $CF_3$.

In some embodiments, $L^2$ is optionally substituted $C_{1-5}$alkyl, for example, substituted $C_{1-5}$alkyl, such as hydroxy-substituted $C_{1-5}$alkyl or methoxy-substituted $C_{1-5}$alkyl. In other embodiments, $L^2$ is optionally substituted heterocyclyl, for example, unsubstituted heterocyclyl, such as unsubstituted oxazolinyl or imidazolinyl, or substituted heterocyclyl, such as aryl-substituted heterocyclyl. In certain embodiments, $L^2$ is oxazolinyl.

In other embodiments, $L^2$ is $C(O)N(R^4)(C(R^4)_2)_m$. In yet other embodiments, $L^2$ is $(C(R^4)_2)_mC(O)N(R^4)$. In certain aspects, m is 1 or 2. Sometimes, when $L^2$ is $C(O)N(R^4)(C(R^4)_2)_m$ or $(C(R^4)_2)_mC(O)N(R^4)$, each instance of $R^4$ is independently hydrogen or $C_{1-4}$alkyl; and m is 0, 1, or 2.

In certain embodiments, $L^2$ is C(O)heterocyclyl. In other embodiments, $L^2$ is heterocyclyl-C(O).

In certain embodiments, L¹ is a bond, $C_{1-4}$alkyl, O, C(O), cycloalkyl, or heterocyclyl. In other embodiments, L¹ is $C_{1-4}$alkyl. In yet other embodiments, L¹ is a bond.

In certain embodiments, R¹ is

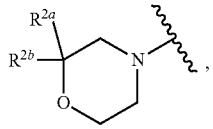

where:
$R^{2a}$ is selected from hydrogen and lower alkyl;
$R^{2b}$ is selected from hydrogen, optionally substituted $C_{1-4}$alkyl and $(CHR^{2aa})_i NR^{2bb}R^{2cc}$.
$R^{2aa}$ is selected from hydrogen and optionally substituted $C_{1-2}$alkyl;
$R^{2bb}$ is selected from hydrogen and optionally substituted $C_{1-3}$alkyl;
$R^{2cc}$ is selected from hydrogen and optionally substituted $C_{1-3}$alkyl; or
$R^{2a}$ and $R^{2b}$, together with the nitrogen atom to which they are connected, form a 4 to 6 membered optionally substituted heterocyclyl; or
$R^{2bb}$ and $R^{2cc}$, together with the nitrogen atom to which they are connected, form a 4 to 6 membered optionally substituted heterocyclyl; and
i is selected from 1, 2 or 3.

In certain embodiments, R¹ is selected from

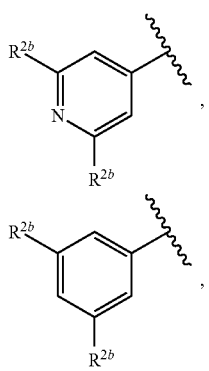
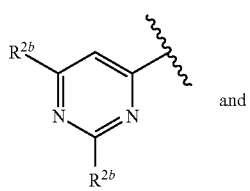

and wherein $R^{2b}$ is as defined above.

In certain embodiments, the compound of Formula I has the structure of Formula Ia':

(Formula Ia')

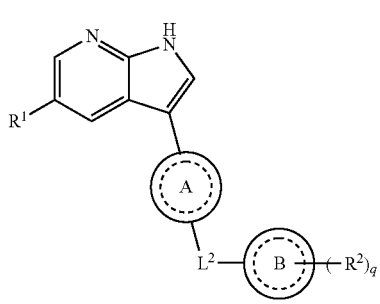

or a pharmaceutically acceptable salt thereof, wherein:
R¹ is optionally substituted heterocyclyl, optionally substituted aryl, or optionally substituted heteroaryl;

is pyridinyl, pyrimidinyl, pyrazinyl, pyridazinyl, triazinyl, or

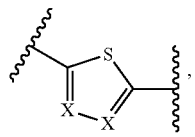

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

L² is optionally substituted $C_{1-5}$alkyl, $C(O)N(R^4)$ $(C(R^4)_2)_m$, $(C(R^4)_2)_m C(O)N(R^4)$, C(O)heterocyclyl, heterocyclyl-C(O), $N(R^4)$, $S(O)_2N(R^4)$, $N(R^4)S(O)_2$, $S(O)_2$, or heterocyclyl, wherein any of said heterocyclyl is optionally substituted with one or more optionally substituted aryl, optionally substituted $C_{1-4}$alkyl or halogen;

is aryl or heteroaryl;

R² if present, in each instance is independently optionally substituted $C_{1-6}$alkyl, alkoxy, optionally substituted cycloalkyl CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

R³ is, in each instance, independently hydrogen or optionally substituted $C_{1-4}$alkyl;

R⁴ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;

m is 0, 1, 2 or 3; and q is 0, 1, 2 or 3.

In some embodiments, R¹ is heterocyclyl, aryl or heteroaryl, wherein each is optionally substituted with one or more of optionally substituted $C_{1-4}$alkyl, halogen, alkoxy, alkoxyalkyl, hydroxy, amino or cyano.

In some embodiments, the compound of Formula I has the structure of Formula Ib':

(Formula Ib')

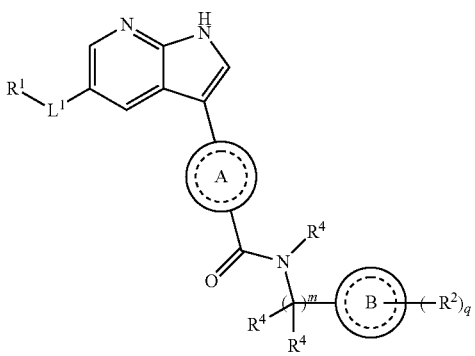

or a pharmaceutically acceptable salt thereof,
wherein:
R¹ is hydrogen, halogen, optionally substituted $C_{1-4}$alkyl, optionally substituted $C_{2-4}$alkenyl, optionally substituted heterocyclyl, optionally substituted aryl, optionally substituted heteroaryl, CN, $OR^{1a}$, $SR^{1a}$, $NR^{1a}R^{1b}$, $N(R^{1a})C(O)R^{1a}$, or $C(O)N(R^{1a})(R^{1b})$;

L¹ is a bond, or is optionally substituted $C_{1-5}$alkyl, C(O), O, $C(O)N(R^4)(C(R^4)_2)_m$, $(C(R^4)_2)_mC(O)N(R^4)$, $N(R^4)$, $S(O)_2N(R^4)$, $N(R^4)S(O)_2$, $S(O)_2$, cycloalkyl, or heterocyclyl;

is pyridinyl, pyrimidinyl, pyrazinyl, pyridazinyl, triazinyl, or

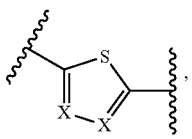

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

is aryl or heteroaryl;
R² if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

R³ is, in each instance, independently hydrogen or optionally substituted $C_{1-4}$alkyl;

R⁴ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;

m is 0, 1, 2 or 3; and
q is 0, 1, 2 or 3.

In some embodiments, the compound of Formula I has the structure of Formula Ic':

(Formula Ic')

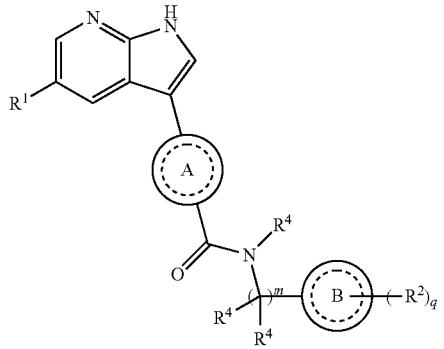

or a pharmaceutically acceptable salt thereof,
wherein:
R¹ is optionally substituted heterocyclyl, optionally substituted aryl, or optionally substituted heteroaryl;

is pyridinyl, pyrimidinyl, pyrazinyl, pyridazinyl, triazinyl, or

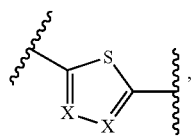

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

is aryl or heteroaryl;
R² if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl;

or R$^{1a}$ and R$^{1b}$, together with the N to which they are bonded, form an optionally substituted heterocyclyl;

R$^3$ is, in each instance, independently hydrogen or optionally substituted C$_{1-4}$alkyl;

R$^4$ is, in each instance, independently hydrogen, optionally substituted C$_{1-4}$alkyl, aminoalkyl, hydroxyalkyl, optionally substituted aryl, optionally substituted heteroaryl, optionally substituted cycloalkyl, or optionally substituted heterocyclyl;

m is 0, 1, 2 or 3; and q is 0, 1, 2 or 3.

In some embodiments, R$^1$ is heterocyclyl, aryl or heteroaryl, wherein each is optionally substituted with one or more of optionally substituted C$_{1-4}$alkyl, halogen, alkoxy, alkoxyalkyl, hydroxy, amino or cyano.

In certain embodiments, the invention relates to a compound having the structure of Formula Ia, Ib, Ic, or Id:

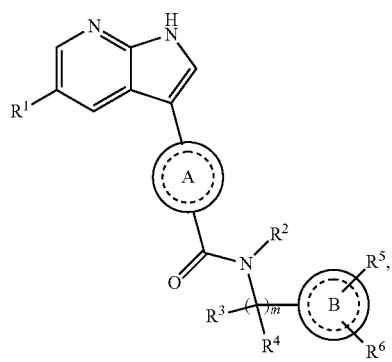

(Formula Ia)

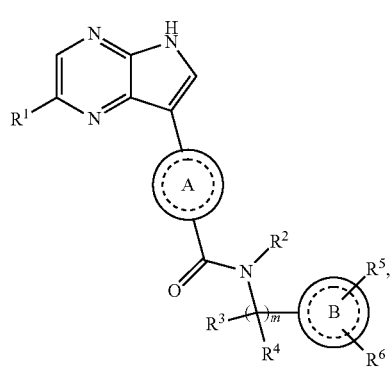

(Formula Ib)

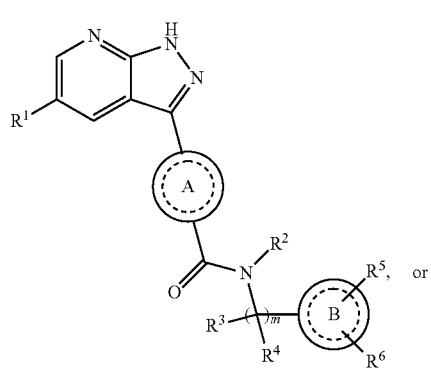

(Formula Ic)

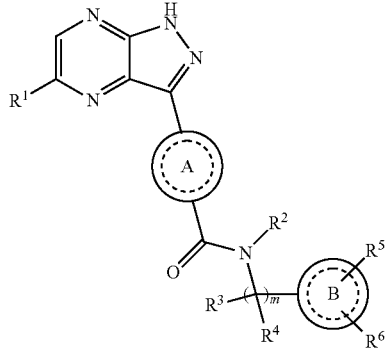

(Formula Id)

or a pharmaceutically acceptable salt thereof, wherein:

is pyridinyl, pyrimidinyl, pyrazinyl, pyridazinyl, triazinyl, thiophenyl or thiazolyl;

is phenyl, pyridinyl, pyrimidinyl, pyrazinyl, pyridazinyl, thiophenyl or thiazolyl;

m is 1 or 2;

R$^1$ is tetrahydropyranyl, morpholinyl, piperazinyl, piperidinyl, phenyl, pyridinyl, pyrimidinyl, pyrazinyl, pyridazinyl, thiophenyl, alkynyl, CN, amide, amino, acyl or acyloxy;

R$^2$ is hydrogen, C$_1$-C$_2$ alkyl, C$_3$-C$_4$ alkyl, cyclopropyl, or C$_4$-C$_6$ cycloalkyl;

R$^3$ is hydrogen, C$_1$-C$_3$ alkyl, phenyl, pyridinyl, pyrimidinyl, pyrrolidinyl, pyrrolyl, C$_3$-C$_6$ cycloalkyl, piperidinyl, morpholinyl, tetrahydropyranyl, or alkynyl;

R$^4$ is hydrogen or methyl; and

R$^5$ and R$^6$ are each independently hydrogen, halogen, C$_1$-C$_2$ alkyl or NH$_2$.

In certain embodiments, the compound of Formula I has the structure of Formula Ie:

(Formula Ie)

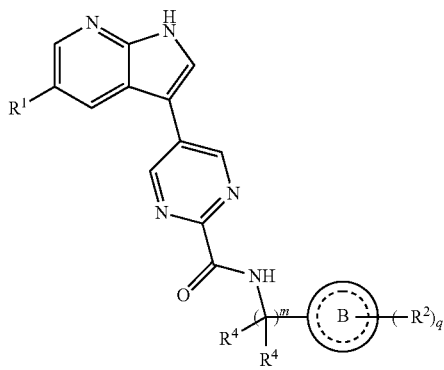

(Formula II)

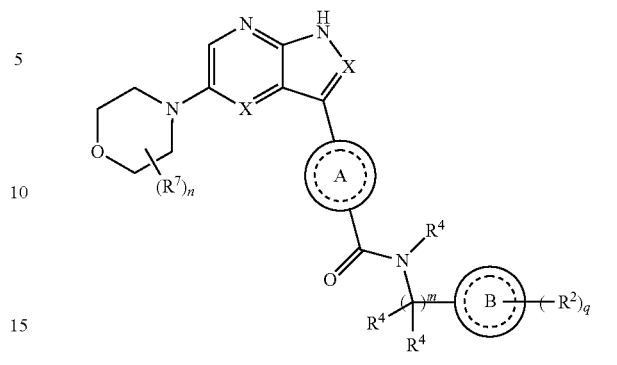

or a pharmaceutically acceptable salt thereof,
wherein:

$R^1$ is optionally substituted $C_{2-4}$alkenyl, optionally substituted heterocyclyl or optionally substituted heteroaryl;

is aryl;

$R^2$ if present, in each instance is independently optionally substituted $C_{1-6}$alkyl, alkoxy, CN, halogen or $CF_3$;

$R^4$ in each instance id independently hydrogen, optionally substituted $C_{1-4}$alkyl, or $C_{1-4}$haloalkyl, $C_{1-4}$aminoalkyl, $C_{1-4}$hydroxyalkyl or cycloalkyl;

m is 1 or 2;

q is 0, 1 or 2; and wherein the compound has an ERK1 $K_d$ of about 10 nM or lower and an ERK2 $K_d$ of about 10 nM or lower.

In further embodiments, the compound of Formula (Ie) has an average $IC_{50}$ of about 250 nM or lower for the drug-sensitive cell lines in Table 4.

In further embodiments, the compound of Formula (Ie) has an average $IC_{50}$ for the drug-sensitive cell lines in Table 4 that is at least about 4-fold more potent than the average $IC_{50}$ of the compound for the drug-resistant cell lines in Table 4.

In yet further embodiments, the compound of Formula (Ie) has a $P_{app}$ A-to-B score of about 0.07 or greater.

In yet further embodiments, the compound of Formula (Ie) has a half-life of about 25 minutes or greater.

In yet further embodiments, the compound of Formula (Ie) causes a decrease of about 70% or more in the levels of pRSK in M275 cells after about 5 hours of treatment with the compound, as compared to a vehicle control.

In some embodiments, the compound of Formula I has the structure of Formula II:

or a pharmaceutically acceptable salt thereof,
wherein:

is pyridinyl, pyrimidinyl, pyrazinyl, pyridazinyl, triazinyl, or

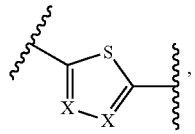

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

X in each occurrence is independently selected from CH and N;

is aryl or heteroaryl;

$R^2$ if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;

$R^7$ when present, is optionally substituted $C_{1-6}$alkyl;

m is 0, 1, 2 or 3;
n is 0, 1, 2, 3 or 4; and
q is 0, 1, 2 or 3.

In some embodiments, n is 0.

In some embodiments, when q is 1, 2 or 3, $R^2$ is optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$.

In some embodiments, $R^7$, when present, is $C_{1-6}$ alkyl optionally substituted with halogen, alkoxy, alkoxyalkyl, hydroxy, amino or cyano. In some embodiments, the compound of Formula II has the structure of Formula IIa:

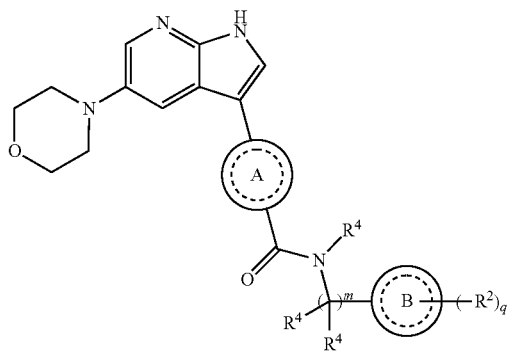

(Formula IIa)

or a pharmaceutically acceptable salt thereof, wherein:

is pyridinyl, pyrimidinyl, pyrazinyl, pyridazinyl, triazinyl, or

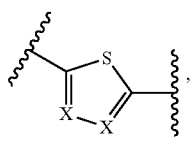

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

is aryl or heteroaryl;
$R^2$ if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;
each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl;
or $R^{1a}$ and $R^{1b}$, together with the N to which they are bonded, form an optionally substituted heterocyclyl;
$R^3$ is, in each instance, independently hydrogen or optionally substituted $C_{1-4}$alkyl;
$R^4$ is, in each instance, independently hydrogen, optionally substituted $C_{1-4}$alkyl, aminoalkyl, hydroxyalkyl, optionally substituted aryl, optionally substituted heteroaryl, optionally substituted cycloalkyl, or optionally substituted heterocyclyl;
m is 0, 1, 2 or 3; and
q is 0, 1, 2 or 3.

In certain embodiments, the invention relates to any compound described herein, wherein m is 1 or 2. In other embodiments, the invention relates to any compound described herein, wherein n is 0, 1 or 2.

In other embodiments, the invention relates to any compound described herein, wherein $R^4$ is, in each instance, independently hydrogen or $C_{1-4}$alkyl.

In some embodiments, the invention relates to a compound having the structure of Formula III:

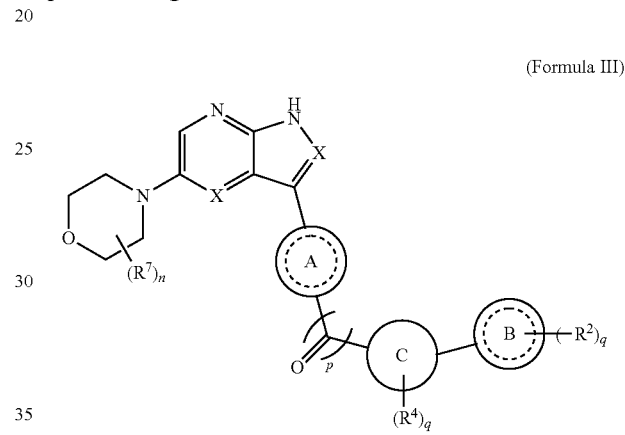

(Formula III)

or a pharmaceutically acceptable salt thereof, wherein:

is pyridinyl, pyrimidinyl, pyrazinyl, pyridazinyl, triazinyl, or

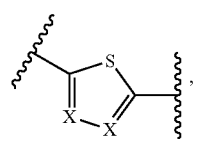

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;
X in each occurrence is independently selected from CH and N;

is aryl or heteroaryl;

is optionally substituted heterocyclyl;

$R^2$ if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, optionally substituted aryl, optionally substituted heteroaryl, optionally substituted cycloalkyl, or optionally substituted heterocyclyl;

$R^7$ when present, is optionally substituted $C_{1-6}$alkyl;

n is 0, 1, 2, 3 or 4;

p is 0 or 1; and q is, in each instance, independently 0, 1, 2 or 3.

In some embodiments, n is 0.

In some embodiments, when q is 1, 2 or 3, $R^2$ is optionally substituted $C_{1-6}$alkyl, alkoxy, optionally substituted cycloalkyl CN, $NR^{1a}R^{1b}$, $C(O)N(R^{1a})(R^{1b})$, $N(R^{1a})C(O)R^{1a}$, halogen or $CF_3$.

In some embodiments, $R^7$, when present, is $C_{1-6}$ alkyl each of which is optionally substituted with halogen, alkoxy, alkoxyalkyl, hydroxy, amino or cyano.

In some embodiments, the compound of Formula III has the structure of Formula IIIa:

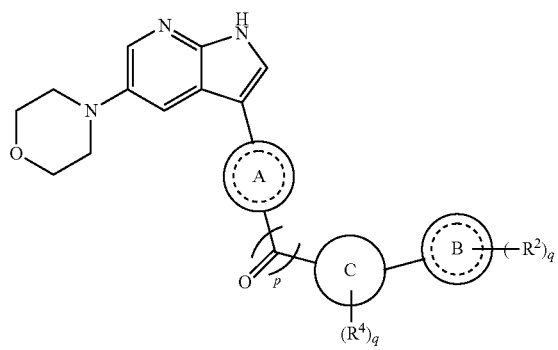

(Formula IIIa)

or a pharmaceutically acceptable salt thereof,
wherein:

is pyridinyl, pyrimidinyl, pyrazinyl, pyridazinyl, triazinyl, or

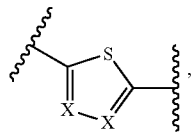

wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

is aryl or heteroaryl;

is optionally substituted heterocyclyl;

$R^2$ if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, optionally substituted aryl, optionally substituted heteroaryl, optionally substituted cycloalkyl, or optionally substituted heterocyclyl;

p is 0 or 1; and q is, in each instance, independently 0, 1, 2 or 3.

In some embodiments, the invention relates to any compound described herein, wherein

is pyridinyl, pyrimidinyl, or pyridazinyl.

In other embodiments, X is CH.

In still other embodiments,

is bicyclic aryl or bicyclic heteroaryl, or is

is aryl, such as phenyl, or

is heteroaryl, such as pyrrolyl or pyridinyl.

In certain embodiments, q is, in each instance, independently 0 or 1. Sometimes, when q is 1, $R^2$ is optionally substituted $C_{1-6}$alkyl. In other embodiments, when q is 1, $R_2$ is optionally substituted cycloalkyl, such as cyclopropyl. In other embodiments, when q is 1, $R^2$ is unsubstituted $C_{1-6}$alkyl or $R^2$ is substituted $C_{1-6}$alkyl or $R^2$ is halogen.

In certain embodiments, $R^{1a}$ is optionally substituted cycloalkyl, for example, optionally substituted cyclopropyl, preferably unsubstituted cyclopropyl.

In certain embodiments, $R^{1b}$ is optionally substituted cycloalkyl, for example, optionally substituted cyclopropyl, preferably unsubstituted cyclopropyl.

In certain embodiments, $R^4$ is optionally substituted $C_{1-4}$alkyl, for example, amino-substituted, halogen-substituted, hydroxy-substituted, or $C_{1-4}$alkyloxy-substituted $C_{1-4}$alkyl.

Additional embodiments relate to a compound of

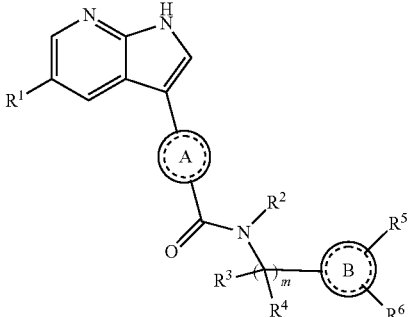

(Formula Ia)

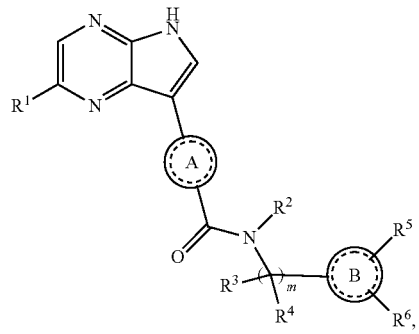

(Formula Ib)

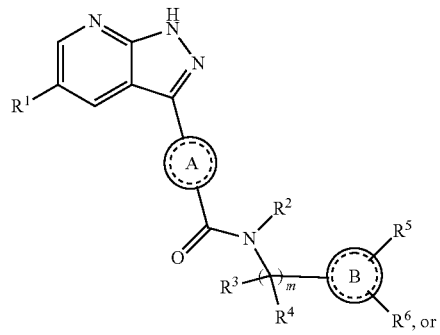

(Formula Ic)

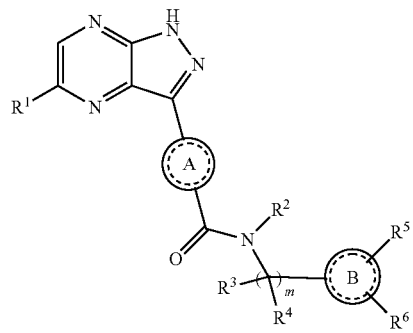

(Formula Id) wherein ring A, ring B, m, $R^1$, $R^2$, $R^3$, $R^4$, $R^5$ and $R^6$ are set forth in Table 1, in which particular example subgenera and species can be at once envisioned.

TABLE 1

| A•B•m•R1•R2•R3•R4•R5•R6 |
|---|
| Thiazolyl•Thiazolyl•2•Phenyl•H•C3-C6cycloalkyl•Methyl•H•NH2 |
| Triazinyl•Pyrazinyl•2•CN•C1-C2alkyl•C3-C6cycloalkyl•Methyl•NH2•C1-C2alkyl |
| Thiazolyl•Phenyl•1•Pyrazinyl•H•Phenyl•H•C1-C2alkyl•Halogen |
| Pyrimidinyl•Phenyl•2•Thiophenyl•C4-C6cycloalkyl•Alkynyl•Methyl•NH2•NH2 |
| Pyridazinyl•Pyrazinyl•2•Tetrahydropyranyl•Cyclopropyl•Tetrahydropyranyl•H•NH2•C1-C2alkyl |
| Thiazolyl•Pyridinyl•1•Morpholinyl•Cyclopropyl•Tetrahydropyranyl•H•Halogen•Halogen |
| Thiazolyl•Thiazolyl•1•Acyloxy•H•Pyrimidinyl•Methyl•C1-C2alkyl•H |
| Pyridazinyl•Phenyl•1•Amino•C3-C4alkyl•Morpholinyl•Methyl•H•H |
| Thiazolyl•Pyridazinyl•2•Piperazinyl•Cyclopropyl•C1-C3alkyl•H•NH2•Halogen |
| Pyridazinyl•Pyrazinyl•1•Amide•C4-C6cycloalkyl•Morpholinyl•Methyl•C1-C2alkyl•NH2 |
| Thiophenyl•Pyrimidinyl•2•Acyloxy•C1-C2alkyl•C1-C3alkyl•Methyl•C1-C2alkyl•Halogen |
| Pyrimidinyl•Pyridinyl•1•Morpholinyl•H•Phenyl•H•Halogen•Halogen |
| Triazinyl•Phenyl•2•Amide•C3-C4alkyl•Tetrahydropyranyl•H•Halogen•H |
| Thiophenyl•Pyridinyl•1•Morpholinyl•H•Pyridinyl•H•C1-C2alkyl•H |
| Pyrazinyl•Thiophenyl•2•Phenyl•C3-C4alkyl•Alkynyl•Methyl•C1-C2alkyl•H |
| Thiazolyl•Pyrazinyl•2•Amino•C3-C4alkyl•C3-C6cycloalkyl•Methyl•NH2•C1-C2alkyl |

TABLE 1-continued

A•B•m•R1•R2•R3•R4•R5•R6

Thiazolyl•Pyridazinyl•2•Acyloxy•C3-C4alkyl•C3-C6cycloalkyl•H•Halogen•H
Triazinyl•Thiazolyl•1•Piperidinyl•C3-C4alkyl•Pyrrolidinyl•Methyl•NH2•NH2
Pyrazinyl•Pyridinyl•2•Alkynyl•C3-C4alkyl•C3-C6cycloalkyl•H•H•C1-C2alkyl
Pyridinyl•Pyrimidinyl•1•Thiophenyl•C4-C6cycloalkyl•C3-C6cycloalkyl•H•H•Halogen
Pyrimidinyl•Thiophenyl•2•Alkynyl•Cyclopropyl•Pyrrolidinyl•Methyl•Halogen•H
Thiazolyl•Pyridinyl•1•Pyrimidynyl•C1-C2alkyl•Phenyl•Methyl•H•NH2
Triazinyl•Phenyl•2•Phenyl•C4-C6cycloalkyl•Pyridinyl•H•H•Halogen
Pyrimidinyl•Thiazolyl•2•Piperazinyl•C1-C2alkyl•Piperidinyl•Methyl•C1-C2alkyl•NH2
Pyridinyl•Phenyl•2•Piperidinyl•H•H•Methyl•NH2•NH2
Thiophenyl•Phenyl•1•Pyrazinyl•C4-C6cycloalkyl•Pyrrolyl•Methyl•NH2•H
Triazinyl•Pyridinyl•2•Amide•C4-C6cycloalkyl•Tetrahydropyranyl•Methyl•C1-C2alkyl•C1-C2alkyl
Pyridazinyl•Phenyl•1•Tetrahydropyranyl•Cyclopropyl•Morpholinyl•Methyl•NH2•NH2
Triazinyl•Pyridinyl•1•Thiophenyl•C3-C4alkyl•Pyrrolidinyl•Methyl•Halogen•H
Pyridinyl•Pyridinyl•2•Piperidinyl•Cyclopropyl•Pyrrolyl•H•NH2•C1-C2alkyl
Thiazolyl•Pyridinyl•1•Amino•H•Phenyl•Methyl•Halogen•NH2
Thiazolyl•Thiophenyl•1•Amino•Cyclopropyl•Pyrimidinyl•Methyl•C1-C2alkyl•NH2
Pyrimidinyl•Thiazolyl•1•Thiophenyl•Cyclopropyl•Pyrimidinyl•H•NH2•Halogen
Pyrazinyl•Pyridazinyl•1•Piperazinyl•Cyclopropyl•Tetrahydropyranyl•H•C1-C2alkyl•NH2
Pyridazinyl•Thiazolyl•1•Tetrahydropyranyl•H•Alkynyl•H•H•Halogen
Pyrazinyl•Pyrimidinyl•1•Pyrazinyl•C1-C2alkyl•Pyrrolidinyl•Methyl•C1-C2alkyl•C1-C2alkyl
Thiazolyl•Thiazolyl•2•Pyrazinyl•C1-C2alkyl•C3-C6cycloalkyl•Methyl•C1-C2alkyl•NH2
Thiazolyl•Pyridazinyl•2•Pyridazinyl•C1-C2alkyl•Pyridinyl•H•C1-C2alkyl•H
Triazinyl•Thiazolyl•2•Acyloxy•C3-C4alkyl•Phenyl•H•NH2•H
Pyrazinyl•Thiazolyl•1•CN•H•Morpholinyl•Methyl•NH2•C1-C2alkyl
Pyrimidinyl•Thiazolyl•1•Amide•H•Pyrrolyl•Methyl•NH2•Halogen
Thiophenyl•Pyrimidinyl•1•Thiophenyl•C1-C2alkyl•H•Methyl•H•Halogen
Pyrimidinyl•Thiophenyl•1•Tetrahydropyranyl•C1-C2alkyl•Morpholinyl•Methyl•C1-C2alkyl•Halogen
Triazinyl•Thiophenyl•1•Morpholinyl•Cyclopropyl•Tetrahydropyranyl•H•NH2•C1-C2alkyl
Thiazolyl•Thiophenyl•2•Alkynyl•C3-C4alkyl•Tetrahydropyranyl•H•C1-C2alkyl•Halogen
Triazinyl•Thiazolyl•1•Piperazinyl•C3-C4alkyl•Piperidinyl•H•NH2•Halogen
Thiophenyl•Phenyl•2•Alkynyl•C3-C4alkyl•Pyrrolyl•H•H•H
Pyridazinyl•Thiophenyl•2•CN•C3-C4alkyl•Pyridinyl•H•H•Halogen
Pyrazinyl•Thiazolyl•1•Pyrazinyl•C1-C2alkyl•Morpholinyl•Methyl•NH2•NH2
Pyridinyl•Pyrazinyl•1•Thiophenyl•Cyclopropyl•Phenyl•Methyl•C1-C2alkyl•C1-C2alkyl
Triazinyl•Thiazolyl•2•Amino•C3-C4alkyl•H•Methyl•H•NH2
Thiazolyl•Thiazolyl•2•Pyridinyl•C3-C4alkyl•C3-C6cycloalkyl•Methyl•H•H
Triazinyl•Pyrimidinyl•1•Pyrazinyl•H•C3-C6cycloalkyl•Methyl•NH2•H
Thiophenyl•Thiazolyl•1•Amide•C4-C6cycloalkyl•Piperidinyl•Methyl•C1-C2alkyl•H
Thiazolyl•Pyrazinyl•1•Phenyl•Cyclopropyl•C3-C6cycloalkyl•Methyl•NH2•Halogen
Pyrimidinyl•Pyridazinyl•1•Piperazinyl•C4-C6cycloalkyl•Phenyl•H•C1-C2alkyl•NH2
Thiophenyl•Thiophenyl•1•Acyloxy•C1-C2alkyl•Pyrimidinyl•Methyl•C1-C2alkyl•C1-C2alkyl
Pyrazinyl•Pyrazinyl•1•Pyrazinyl•C3-C4alkyl•Pyridinyl•H•C1-C2alkyl•NH2
Pyridazinyl•Pyrimidinyl•1•Thiophenyl•C4-C6cycloalkyl•Phenyl•Methyl•C1-C2alkyl•NH2
Pyrimidinyl•Pyridinyl•1•CN•Cyclopropyl•Pyridinyl•H•NH2•C1-C2alkyl
Thiazolyl•Pyridazinyl•2•Pyridazinyl•Cyclopropyl•Pyridinyl•Methyl•NH2•H
Pyridazinyl•Pyrazinyl•1•Phenyl•C1-C2alkyl•Pyridinyl•Methyl•NH2•H
Pyridazinyl•Thiophenyl•2•Amide•H•C3-C6cycloalkyl•Methyl•C1-C2alkyl•C1-C2alkyl
Triazinyl•Phenyl•1•Piperazinyl•C1-C2alkyl•Piperidinyl•H•C1-C2alkyl•C1-C2alkyl
Triazinyl•Phenyl•1•Alkynyl•C4-C6cycloalkyl•H•H•H•Halogen
Thiophenyl•Pyrazinyl•2•Pyrazinyl•H•Pyrrolidinyl•H•H•C1-C2alkyl
Pyridinyl•Phenyl•1•Phenyl•C1-C2alkyl•Alkynyl•Methyl•Halogen•Halogen
Pyridinyl•Phenyl•2•Tetrahydropyranyl•H•Pyrimidinyl•Methyl•C1-C2alkyl•H
Pyrimidinyl•Pyrimidinyl•2•Pyrimidynyl•C3-C4alkyl•Phenyl•H•H•Halogen
Thiazolyl•Pyridazinyl•2•Phenyl•C1-C2alkyl•H•Methyl•H•Halogen
Thiazolyl•Pyrimidinyl•2•Tetrahydropyranyl•C1-C2alkyl•Pyrrolyl•H•Halogen•NH2
Thiazolyl•Thiophenyl•1•Alkynyl•C4-C6cycloalkyl•Morpholinyl•Methyl•C1-C2alkyl•H
Pyridinyl•Thiophenyl•1•Phenyl•C1-C2alkyl•Pyrrolidinyl•H•C1-C2alkyl•Halogen
Thiazolyl•Phenyl•1•Tetrahydropyranyl•C3-C4alkyl•Tetrahydropyranyl•H•NH2•H
Pyrimidinyl•Thiazolyl•1•Acyloxy•C1-C2alkyl•Pyrrolyl•H•H•H
Triazinyl•Pyridazinyl•1•Pyrimidynyl•C3-C4alkyl•Morpholinyl•Methyl•H•C1-C2alkyl
Pyridazinyl•Pyrazinyl•2•Phenyl•C3-C4alkyl•Morpholinyl•Methyl•Halogen•Halogen
Pyrimidinyl•Phenyl•1•Amide•C4-C6cycloalkyl•H•Methyl•Halogen•C1-C2alkyl
Pyrazinyl•Thiophenyl•1•Morpholinyl•Cyclopropyl•Phenyl•H•NH2•Halogen
Pyrazinyl•Pyridinyl•1•Tetrahydropyranyl•H•Pyrrolyl•Methyl•NH2•NH2
Thiazolyl•Pyridazinyl•1•Pyrimidynyl•Cyclopropyl•Phenyl•H•NH2•NH2
Pyridazinyl•Pyrazinyl•2•Alkynyl•C1-C2alkyl•Morpholinyl•Methyl•NH2•C1-C2alkyl
Thiazolyl•Thiazolyl•1•Thiophenyl•Cyclopropyl•Pyrrolyl•Methyl•Halogen•Halogen
Thiazolyl•Thiazolyl•1•Alkynyl•C3-C4alkyl•Alkynyl•Methyl•H•C1-C2alkyl
Pyrazinyl•Phenyl•2•Pyridazinyl•C3-C4alkyl•Alkynyl•Methyl•NH2•H
Pyrimidinyl•Pyridinyl•2•Pyridazinyl•C1-C2alkyl•Piperidinyl•H•H•H
Triazinyl•Pyrimidinyl•1•Acyl•Cyclopropyl•Pyrrolidinyl•H•H•H
Pyridazinyl•Pyrimidinyl•1•Thiophenyl•H•Tetrahydropyranyl•H•Halogen•H
Pyridinyl•Phenyl•1•Phenyl•C4-C6cycloalkyl•C3-C6cycloalkyl•Methyl•H•H
Pyrimidinyl•Thiophenyl•1•Morpholinyl•C3-C4alkyl•Pyrrolyl•Methyl•H•C1-C2alkyl
Thiophenyl•Pyrimidinyl•2•Piperazinyl•H•C1-C3alkyl•Methyl•C1-C2alkyl•NH2
Triazinyl•Pyridinyl•2•Acyl•H•Pyridinyl•H•H•C1-C2alkyl
Pyrazinyl•Pyrazinyl•2•Alkynyl•H•H•H•C1-C2alkyl•H
Thiazolyl•Thiophenyl•2•Amino•C4-C6cycloalkyl•Pyrimidinyl•H•C1-C2alkyl•C1-C2alkyl TABLE 1-continued A•B•m•R1•R2•R3•R4•R5•R6

Thiophenyl•Pyrimidinyl•2•Acyl•H•Alkynyl•Methyl•Halogen•H
Thiazolyl•Pyrazinyl•1•Amide•C4-C6cycloalkyl•Pyridinyl•Methyl•Halogen•H
Pyridinyl•Pyridazinyl•2•Morpholinyl•C3-C4alkyl•Pyrrolidinyl•Methyl•Halogen•Halogen
Pyridazinyl•Pyrazinyl•2•Pyridinyl•H•Alkynyl•Methyl•H•Halogen
Thiazolyl•Pyrazinyl•1•Phenyl•C4-C6cycloalkyl•Pyrimidinyl•H•H•NH2
Thiophenyl•Pyridazinyl•2•Phenyl•H•Phenyl•H•H•NH2
Triazinyl•Phenyl•2•Tetrahydropyranyl•Cyclopropyl•Phenyl•Methyl•C1-C2alkyl•C1-C2alkyl
Thiazolyl•Phenyl•1•Acyloxy•C1-C2alkyl•Piperidinyl•H•NH2•H
Thiazolyl•Thiazolyl•2•Acyloxy•H•Pyridinyl•H•H•NH2
Pyridinyl•Pyridinyl•2•Amino•H•C3-C6cycloalkyl•Methyl•Halogen•C1-C2alkyl
Thiazolyl•Pyridazinyl•2•Amino•C4-C6cycloalkyl•Pyridinyl•Methyl•NH2•NH2
Pyridinyl•Pyridazinyl•2•Tetrahydropyranyl•Cyclopropyl•C1-C3alkyl•H•Halogen•C1-C2alkyl
Pyrimidinyl•Pyridinyl•1•CN•H•Morpholinyl•H•H•H
Thiazolyl•Pyridazinyl•2•Phenyl•C1-C2alkyl•Tetrahydropyranyl•Methyl•C1-C2alkyl•C1-C2alkyl
Thiazolyl•Pyrimidinyl•1•Alkynyl•C3-C4alkyl•Tetrahydropyranyl•H•Halogen•Halogen
Triazinyl•Pyridinyl•1•CN•C1-C2alkyl•Pyrimidinyl•Methyl•H•H
Pyrimidinyl•Phenyl•2•Alkynyl•H•C3-C6cycloalkyl•H•Halogen•Halogen
Thiophenyl•Thiophenyl•1•Thiophenyl•H•Phenyl•H•H•C1-C2alkyl
Thiazolyl•Phenyl•1•Tetrahydropyranyl•H•Alkynyl•H•NH2•Halogen
Pyrazinyl•Thiophenyl•2•Thiophenyl•C3-C4alkyl•Tetrahydropyranyl•Methyl•NH2•NH2
Pyrazinyl•Pyridinyl•1•CN•Cyclopropyl•Pyridinyl•Methyl•C1-C2alkyl•NH2
Pyrimidinyl•Pyridazinyl•2•Pyrazinyl•H•C3-C6cycloalkyl•Methyl•H•Halogen
Pyrazinyl•Thiophenyl•2•Pyrazinyl•Cyclopropyl•Alkynyl•Methyl•NH2•C1-C2alkyl
Pyrazinyl•Pyrazinyl•2•CN•H•H•Methyl•H•H
Pyrimidinyl•Thiazolyl•2•Pyrazinyl•C3-C4alkyl•Phenyl•Methyl•C1-C2alkyl•NH2
Pyrazinyl•Phenyl•1•Piperazinyl•H•C1-C3alkyl•H•H•C1-C2alkyl
Thiazolyl•Pyridazinyl•1•Amino•C4-C6cycloalkyl•Pyrimidinyl•H•NH2•Halogen
Pyrimidinyl•Pyridinyl•2•Acyl•C4-C6cycloalkyl•C3-C6cycloalkyl•H•Halogen•NH2
Triazinyl•Pyrimidinyl•1•Thiophenyl•H•Morpholinyl•Methyl•H•C1-C2alkyl
Thiazolyl•Thiophenyl•2•Piperazinyl•C3-C4alkyl•C3-C6cycloalkyl•H•H•C1-C2alkyl
Thiazolyl•Pyrimidinyl•2•Amino•C4-C6cycloalkyl•H•Methyl•C1-C2alkyl•NH2
Pyridazinyl•Pyrimidinyl•1•Pyrimidynyl•Cyclopropyl•Piperidinyl•Methyl•C1-C2alkyl•Halogen
Thiophenyl•Pyridazinyl•1•Piperazinyl•C3-C4alkyl•Piperidinyl•Methyl•Halogen•Halogen
Thiophenyl•Thiophenyl•1•Acyloxy•H•Pyrrolidinyl•H•H•H
Thiazolyl•Thiophenyl•1•Tetrahydropyranyl•C1-C2alkyl•Morpholinyl•H•NH2•C1-C2alkyl
Pyridinyl•Phenyl•2•Piperidinyl•C1-C2alkyl•Pyrrolidinyl•Methyl•H•Halogen
Thiophenyl•Pyridazinyl•1•Acyloxy•C4-C6cycloalkyl•C3-C6cycloalkyl•Methyl•Halogen•C1-C2alkyl
Thiophenyl•Pyrimidinyl•1•Amino•C4-C6cycloalkyl•H•H•H•H
Triazinyl•Phenyl•2•Amide•H•Alkynyl•H•C1-C2alkyl•H
Thiazolyl•Thiophenyl•1•Acyloxy•C3-C4alkyl•Morpholinyl•Methyl•H•NH2
Triazinyl•Thiophenyl•2•Amide•C4-C6cycloalkyl•Morpholinyl•Methyl•NH2•H
Pyridinyl•Phenyl•1•Pyrazinyl•C1-C2alkyl•Tetrahydropyranyl•Methyl•Halogen•Halogen
Thiazolyl•Pyridinyl•2•Pyrazinyl•C4-C6cycloalkyl•H•H•C1-C2alkyl•Halogen
Pyridinyl•Pyrazinyl•1•Pyrazinyl•C4-C6cycloalkyl•C3-C6cycloalkyl•Methyl•H•NH2
Thiophenyl•Pyrazinyl•2•CN•H•Pyrrolidinyl•H•Halogen•H
Thiazolyl•Pyridinyl•2•Pyrazinyl•C3-C4alkyl•Pyrimidinyl•Methyl•C1-C2alkyl•H
Thiazolyl•Thiophenyl•1•Pyridinyl•H•Pyridinyl•Methyl•H•NH2
Pyrazinyl•Pyrazinyl•1•Acyl•H•Piperidinyl•Methyl•Halogen•H
Thiophenyl•Thiophenyl•2•Pyrimidynyl•C3-C4alkyl•Tetrahydropyranyl•Methyl•H•NH2
Pyrazinyl•Pyridinyl•2•Alkynyl•Cyclopropyl•Tetrahydropyranyl•H•C1-C2alkyl•NH2
Thiophenyl•Thiazolyl•2•Phenyl•H•Pyrrolidinyl•H•NH2•C1-C2alkyl
Triazinyl•Thiazolyl•1•Acyl•C1-C2alkyl•Pyridinyl•H•Halogen•H
Thiazolyl•Pyrimidinyl•1•Thiophenyl•Cyclopropyl•Morpholinyl•Methyl•Halogen•H
Pyrazinyl•Pyrimidinyl•1•Acyl•C3-C4alkyl•Tetrahydropyranyl•H•Halogen•Halogen
Pyrimidinyl•Pyridinyl•1•Thiophenyl•Cyclopropyl•Pyrimidinyl•H•H•Halogen
Pyridinyl•Pyrazinyl•1•Morpholinyl•C3-C4alkyl•Morpholinyl•H•H•H
Pyrimidinyl•Phenyl•2•Acyloxy•C1-C2alkyl•Pyrrolidinyl•Methyl•Halogen•C1-C2alkyl
Thiophenyl•Pyrazinyl•1•Amide•H•H•Methyl•C1-C2alkyl•H
Pyrazinyl•Pyrimidinyl•1•Pyrimidynyl•C3-C4alkyl•Pyrrolidinyl•Methyl•H•Halogen
Pyrimidinyl•Pyrimidinyl•1•Acyl•C4-C6cycloalkyl•Pyridinyl•Methyl•C1-C2alkyl•Halogen
Pyridazinyl•Thiophenyl•1•Amino•C3-C4alkyl•Tetrahydropyranyl•Methyl•NH2•C1-C2alkyl
Pyrimidinyl•Pyridazinyl•1•Piperidinyl•C1-C2alkyl•Pyrimidinyl•Methyl•H•Halogen
Triazinyl•Pyridazinyl•1•Amino•H•C3-C6cycloalkyl•H•H•C1-C2alkyl
Triazinyl•Thiazolyl•1•Pyrimidynyl•Cyclopropyl•Pyridinyl•Methyl•NH2•NH2
Pyrimidinyl•Thiazolyl•2•Acyloxy•C3-C4alkyl•Piperidinyl•H•NH2•Halogen
Thiazolyl•Thiophenyl•2•Pyridazinyl•C1-C2alkyl•Pyrrolidinyl•H•H•H
Pyrimidinyl•Thiophenyl•1•Phenyl•C1-C2alkyl•Alkynyl•Methyl•C1-C2alkyl•C1-C2alkyl
Pyrimidinyl•Pyrazinyl•2•Piperazinyl•Cyclopropyl•H•Methyl•NH2•H
Pyridinyl•Pyrazinyl•2•Phenyl•H•Phenyl•Methyl•C1-C2alkyl•Halogen
Pyrazinyl•Phenyl•1•Thiophenyl•C3-C4alkyl•Phenyl•H•H•Halogen
Pyridazinyl•Phenyl•2•Piperazinyl•C1-C2alkyl•C3-C6cycloalkyl•H•H•Halogen
Triazinyl•Pyrazinyl•2•Acyloxy•C1-C2alkyl•Alkynyl•H•Halogen•Halogen
Thiazolyl•Thiophenyl•2•Piperidinyl•C4-C6cycloalkyl•C3-C6cycloalkyl•H•NH2•Halogen
Pyrazinyl•Pyrimidinyl•1•Tetrahydropyranyl•C1-C2alkyl•Pyrrolyl•Methyl•H•C1-C2alkyl
Pyrimidinyl•Pyridinyl•2•Acyl•Cyclopropyl•Morpholinyl•Methyl•NH2•H
Pyridazinyl•Pyridazinyl•1•CN•Cyclopropyl•Morpholinyl•H•NH2•H
Thiophenyl•Thiazolyl•1•Amide•C1-C2alkyl•Morpholinyl•Methyl•NH2•Halogen
Pyrazinyl•Pyrimidinyl•2•Tetrahydropyranyl•C3-C4alkyl•C1-C3alkyl•Methyl•H•NH2

TABLE 1-continued

A•B•m•R1•R2•R3•R4•R5•R6

Pyridinyl•Pyridazinyl•2•Pyrimidynyl•Cyclopropyl•Phenyl•Methyl•H•C1-C2alkyl
Pyridinyl•Thiazolyl•1•Pyrazinyl•C3-C4alkyl•Pyrrolyl•Methyl•Halogen•H
Pyridazinyl•Pyridazinyl•1•Pyrimidynyl•Cyclopropyl•Tetrahydropyranyl•H•Halogen•H
Pyridazinyl•Pyrimidinyl•1•Alkynyl•C1-C2alkyl•Morpholinyl•H•C1-C2alkyl•NH2
Triazinyl•Pyrazinyl•2•Phenyl•H•Pyrrolyl•H•NH2•C1-C2alkyl
Pyrazinyl•Phenyl•1•Piperazinyl•C4-C6cycloalkyl•Phenyl•H•Halogen•NH2
Triazinyl•Thiophenyl•2•Thiophenyl•Cyclopropyl•Pyridinyl•Methyl•C1-C2alkyl•NH2
Thiazolyl•Pyrimidinyl•2•Amide•C3-C4alkyl•C1-C3alkyl•H•H•C1-C2alkyl
Pyrimidinyl•Thiazolyl•1•Pyrimidynyl•C4-C6cycloalkyl•Alkynyl•H•NH2•Halogen
Thiazolyl•Pyridinyl•2•Pyrimidynyl•C4-C6cycloalkyl•Pyridinyl•Methyl•Halogen•H
Pyrimidinyl•Thiophenyl•2•Alkynyl•Cyclopropyl•Piperidinyl•Methyl•H•H
Pyrimidinyl•Thiazolyl•2•Tetrahydropyranyl•C1-C2alkyl•Pyridinyl•H•Halogen•NH2
Pyridinyl•Phenyl•1•Phenyl•C4-C6cycloalkyl•C1-C3alkyl•Methyl•Halogen•H
Pyrimidinyl•Thiazolyl•2•Piperazinyl•C4-C6cycloalkyl•Phenyl•H•NH2•C1-C2alkyl
Thiazolyl•Phenyl•2•Tetrahydropyranyl•C3-C4alkyl•Piperidinyl•H•H•Halogen
Thiazolyl•Thiophenyl•1•Tetrahydropyranyl•H•Tetrahydropyranyl•H•NH2•NH2
Triazinyl•Thiazolyl•1•CN•C4-C6cycloalkyl•C3-C6cycloalkyl•Methyl•H•NH2
Thiophenyl•Pyrazinyl•1•Acyl•Cyclopropyl•C3-C6cycloalkyl•Methyl•H•C1-C2alkyl
Pyrimidinyl•Pyridinyl•2•Piperidinyl•C3-C4alkyl•Pyrimidinyl•Methyl•NH2•NH2
Triazinyl•Pyrimidinyl•2•Amino•H•Alkynyl•H•NH2•Halogen
Thiophenyl•Pyridazinyl•2•Piperidinyl•H•H•Methyl•Halogen•Halogen
Thiophenyl•Pyrazinyl•2•Pyrazinyl•H•Pyridinyl•H•C1-C2alkyl•H
Pyridinyl•Phenyl•1•Pyridazinyl•H•Alkynyl•H•C1-C2alkyl•C1-C2alkyl
Thiazolyl•Pyrimidinyl•2•Pyrazinyl•C4-C6cycloalkyl•Tetrahydropyranyl•Methyl•C1-C2alkyl•C1-C2alkyl
Thiazolyl•Thiophenyl•1•Pyridazinyl•Cyclopropyl•Pyrrolidinyl•H•C1-C2alkyl•H
Pyrimidinyl•Phenyl•2•Tetrahydropyranyl•C1-C2alkyl•Pyrrolyl•H•NH2•Halogen
Thiazolyl•Pyrimidinyl•2•Acyl•C1-C2alkyl•C1-C3alkyl•H•H•NH2
Pyridinyl•Pyridazinyl•2•Pyridinyl•C3-C4alkyl•Morpholinyl•Methyl•H•Halogen
Thiazolyl•Pyridinyl•1•Acyloxy•H•Pyrrolyl•H•H•Halogen
Thiazolyl•Pyrimidinyl•1•Amino•C1-C2alkyl•Pyrrolidinyl•Methyl•Halogen•C1-C2alkyl
Triazinyl•Pyridinyl•2•Amino•C4-C6cycloalkyl•H•Methyl•NH2•C1-C2alkyl
Pyridinyl•Thiazolyl•2•Acyloxy•C1-C2alkyl•H•Methyl•C1-C2alkyl•Halogen
Triazinyl•Pyridazinyl•1•Thiophenyl•Cyclopropyl•Pyrrolidinyl•H•NH2•C1-C2alkyl
Pyrazinyl•Thiophenyl•1•Thiophenyl•H•Piperidinyl•Methyl•Halogen•Halogen
Triazinyl•Thiazolyl•1•Piperidinyl•Cyclopropyl•Phenyl•Methyl•Halogen•H
Pyridinyl•Pyrazinyl•2•Amino•C4-C6cycloalkyl•Pyrrolidinyl•Methyl•H•Halogen
Pyridinyl•Pyrimidinyl•2•Acyl•H•Alkynyl•H•NH2•Halogen
Thiazolyl•Pyridinyl•2•Acyloxy•C1-C2alkyl•Alkynyl•H•H•NH2
Pyridazinyl•Pyrimidinyl•2•Pyridinyl•H•Piperidinyl•Methyl•NH2•C1-C2alkyl
Triazinyl•Phenyl•1•CN•C3-C4alkyl•Morpholinyl•H•NH2•NH2
Thiazolyl•Pyrimidinyl•1•Pyridazinyl•C3-C4alkyl•Pyrrolyl•Methyl•C1-C2alkyl•Halogen
Triazinyl•Thiazolyl•1•Amide•C1-C2alkyl•Pyrimidinyl•Methyl•Halogen•C1-C2alkyl
Pyridinyl•Thiophenyl•2•Piperidinyl•Cyclopropyl•H•H•NH2•Halogen
Pyrimidinyl•Pyridinyl•1•Acyl•Cyclopropyl•Pyrrolyl•H•Halogen•Halogen
Pyridinyl•Thiophenyl•1•Amide•C3-C4alkyl•Piperidinyl•H•Halogen•NH2
Pyridinyl•Pyrazinyl•2•Morpholinyl•C4-C6cycloalkyl•Alkynyl•Methyl•NH2•H
Pyrimidinyl•Pyridinyl•2•Acyloxy•C3-C4alkyl•Alkynyl•Methyl•NH2•H
Pyridazinyl•Pyridinyl•2•Acyl•C4-C6cycloalkyl•Tetrahydropyranyl•H•NH2•H
Pyridinyl•Pyrimidinyl•2•Piperidinyl•C1-C2alkyl•Pyrimidinyl•Methyl•C1-C2alkyl•NH2
Thiophenyl•Thiophenyl•1•Tetrahydropyranyl•C1-C2alkyl•Phenyl•H•H•C1-C2alkyl
Triazinyl•Pyrazinyl•2•Acyl•C4-C6cycloalkyl•Phenyl•Methyl•NH2•H
Pyrimidinyl•Pyridazinyl•1•Alkynyl•C3-C4alkyl•Alkynyl•Methyl•H•C1-C2alkyl
Pyridazinyl•Pyridinyl•2•Amide•H•Pyrimidinyl•Methyl•NH2•Halogen
Thiazolyl•Pyrazinyl•2•Pyridinyl•C3-C4alkyl•Pyrimidinyl•Methyl•NH2•C1-C2alkyl
Pyrazinyl•Thiazolyl•1•Piperazinyl•Cyclopropyl•H•H•C1-C2alkyl•Halogen
Thiophenyl•Pyridazinyl•2•Amino•Cyclopropyl•Pyrrolyl•Methyl•Halogen•NH2
Pyridinyl•Thiophenyl•1•Alkynyl•C1-C2alkyl•Piperidinyl•Methyl•NH2•Halogen
Thiazolyl•Pyridazinyl•1•Amino•C4-C6cycloalkyl•Pyridinyl•H•Halogen•NH2
Thiazolyl•Pyrazinyl•2•Pyrimidynyl•C1-C2alkyl•Pyrrolidinyl•H•Halogen•C1-C2alkyl
Pyrimidinyl•Phenyl•1•Pyridazinyl•C4-C6cycloalkyl•Pyrrolyl•Methyl•H•Halogen
Thiazolyl•Pyrimidinyl•1•Acyloxy•Cyclopropyl•Tetrahydropyranyl•Methyl•H•C1-C2alkyl
Pyrazinyl•Pyridazinyl•2•Thiophenyl•H•H•Methyl•C1-C2alkyl•NH2
Pyrazinyl•Pyridinyl•1•CN•C3-C4alkyl•C1-C3alkyl•H•Halogen•H
Pyridinyl•Pyrimidinyl•1•Pyrimidynyl•Cyclopropyl•Morpholinyl•H•C1-C2alkyl•C1-C2alkyl
Pyrimidinyl•Thiophenyl•2•Piperazinyl•H•C1-C3alkyl•H•C1-C2alkyl•H
Thiophenyl•Phenyl•1•CN•H•Piperidinyl•Methyl•Halogen•NH2
Thiophenyl•Thiazolyl•2•Pyrazinyl•C4-C6cycloalkyl•Piperidinyl•Methyl•H•Halogen
Thiazolyl•Thiazolyl•1•Piperazinyl•C3-C4alkyl•Pyrrolidinyl•H•C1-C2alkyl•NH2
Thiazolyl•Pyrazinyl•1•Acyloxy•H•Pyrrolinyl•Methyl•Halogen•C1-C2alkyl
Pyrazinyl•Pyrimidinyl•1•Pyridazinyl•Cyclopropyl•Pyrrolidinyl•Methyl•Halogen•Halogen
Thiophenyl•Thiophenyl•1•Piperidinyl•C4-C6cycloalkyl•C3-C6cycloalkyl•H•NH2•Halogen
Thiazolyl•Pyridinyl•2•Piperazinyl•Cyclopropyl•Alkynyl•H•H•H
Pyrimidinyl•Thiazolyl•1•Pyridinyl•H•Pyrrolyl•H•NH2•Halogen
Pyrimidinyl•Thiophenyl•1•Amide•C4-C6cycloalkyl•Phenyl•H•C1-C2alkyl•NH2
Thiazolyl•Thiazolyl•1•CN•Cyclopropyl•Pyrrolyl•Methyl•H•C1-C2alkyl
Pyrazinyl•Pyrimidinyl•2•Piperazinyl•C1-C2alkyl•Pyrrolyl•H•NH2•NH2
Triazinyl•Pyridinyl•2•Amino•H•H•H•H•H
Thiophenyl•Pyridazinyl•2•Acyl•C1-C2alkyl•Morpholinyl•H•C1-C2alkyl•H TABLE 1-continued A•B•m•R1•R2•R3•R4•R5•R6

Thiazolyl•Pyridazinyl•1•Tetrahydropyranyl•Cyclopropyl•H•H•NH2•Halogen
Thiazolyl•Pyrazinyl•2•Amino•Cyclopropyl•Piperidinyl•Methyl•Halogen•NH2
Thiophenyl•Thiazolyl•2•Amino•Cyclopropyl•Piperidinyl•Methyl•NH2•NH2
Thiophenyl•Pyridinyl•1•Amide•H•Tetrahydropyranyl•Methyl•NH2•NH2
Triazinyl•Pyridazinyl•1•Pyridinyl•C3-C4alkyl•Piperidinyl•Methyl•NH2•Halogen
Thiazolyl•Pyridazinyl•1•Acyl•C1-C2alkyl•C3-C6cycloalkyl•H•NH2•Halogen
Pyrazinyl•Pyrimidinyl•1•Acyloxy•C4-C6cycloalkyl•H•Methyl•NH2•NH2
Thiazolyl•Thiazolyl•2•Alkynyl•C4-C6cycloalkyl•Pyrrolidinyl•Methyl•Halogen•C1-C2alkyl
Triazinyl•Thiophenyl•1•Pyridinyl•C3-C4alkyl•C3-C6cycloalkyl•H•H•Halogen
Thiazolyl•Pyridazinyl•1•Tetrahydropyranyl•C1-C2alkyl•Alkynyl•H•C1-C2alkyl•H
Thiazolyl•Pyrimidinyl•1•Piperazinyl•H•Pyrrolyl•H•H•H
Pyridazinyl•Pyridinyl•2•Acyl•C1-C2alkyl•Tetrahydropyranyl•H•NH2•NH2
Thiazolyl•Phenyl•2•Pyrimidynyl•H•Alkynyl•Methyl•Halogen•NH2
Thiazolyl•Pyridazinyl•1•Pyrazinyl•H•Pyrimidinyl•H•H•NH2
Triazinyl•Pyridazinyl•1•Pyridinyl•C4-C6cycloalkyl•Piperidinyl•H•H•C1-C2alkyl
Thiazolyl•Thiazolyl•2•Tetrahydropyranyl•C1-C2alkyl•Pyrimidinyl•H•H•NH2
Thiazolyl•Pyrazinyl•1•Tetrahydropyranyl•C4-C6cycloalkyl•Pyridinyl•Methyl•Halogen•C1-C2alkyl
Thiazolyl•Thiophenyl•2•Pyridinyl•C3-C4alkyl•Phenyl•Methyl•C1-C2alkyl•NH2
Pyridazinyl•Thiophenyl•1•Pyrazinyl•Cyclopropyl•Tetrahydropyranyl•Methyl•NH2•C1-C2alkyl
Thiazolyl•Thiazolyl•2•Piperidinyl•H•Pyrimidinyl•Methyl•C1-C2alkyl•Halogen
Thiazolyl•Thiazolyl•1•Pyridinyl•C4-C6cycloalkyl•Tetrahydropyranyl•Methyl•C1-C2alkyl•Halogen
Thiophenyl•Pyridazinyl•1•Alkynyl•H•Morpholinyl•Methyl•C1-C2alkyl•NH2
Thiophenyl•Pyrimidinyl•2•Piperidinyl•Cyclopropyl•Pyrrolidinyl•H•C1-C2alkyl•H
Thiophenyl•Pyridinyl•1•Acyl•C4-C6cycloalkyl•Pyrimidinyl•Methyl•H•Halogen
Triazinyl•Thiazolyl•2•Pyrimidynyl•C1-C2alkyl•H•H•C1-C2alkyl•NH2
Triazinyl•Pyrimidinyl•2•Pyrimidynyl•C4-C6cycloalkyl•Pyridinyl•H•C1-C2alkyl•NH2
Thiazolyl•Pyrazinyl•1•Piperidinyl•H•Pyridinyl•H•C1-C2alkyl•Halogen
Pyridazinyl•Phenyl•1•Acyl•C4-C6cycloalkyl•Alkynyl•Methyl•NH2•H
Pyrimidinyl•Phenyl•2•Acyloxy•C3-C4alkyl•Pyridinyl•H•H•NH2
Triazinyl•Thiazolyl•2•Piperazinyl•H•Pyrrolyl•Methyl•Halogen•C1-C2alkyl
Thiophenyl•Pyridazinyl•2•Acyl•C1-C2alkyl•Pyridinyl•H•H•C1-C2alkyl
Triazinyl•Phenyl•1•Piperidinyl•H•Phenyl•H•Halogen•H
Pyridinyl•Pyrimidinyl•1•Pyridazinyl•C3-C4alkyl•Tetrahydropyranyl•Methyl•C1-C2alkyl•NH2
Thiophenyl•Phenyl•1•Morpholinyl•H•Pyrrolidinyl•H•C1-C2alkyl•NH2
Pyrimidinyl•Pyrimidinyl•1•Amino•Cyclopropyl•Pyrrolyl•Methyl•H•H
Pyrazinyl•Thiazolyl•2•Alkynyl•C1-C2alkyl•Pyrimidinyl•H•Halogen•H
Pyridinyl•Phenyl•2•Tetrahydropyranyl•H•C1-C3alkyl•Methyl•Halogen•NH2
Pyrimidinyl•Pyrazinyl•1•Thiophenyl•C4-C6cycloalkyl•Pyrrolyl•H•C1-C2alkyl•C1-C2alkyl
Thiazolyl•Thiazolyl•2•Acyloxy•H•Morpholinyl•H•H•H
Thiazolyl•Pyrimidinyl•1•Morpholinyl•C3-C4alkyl•Alkynyl•H•NH2•Halogen
Thiazolyl•Phenyl•2•Tetrahydropyranyl•Cyclopropyl•Tetrahydropyranyl•Methyl•H•H
Pyrimidinyl•Thiophenyl•1•Amide•C4-C6cycloalkyl•Tetrahydropyranyl•H•H•Halogen
Triazinyl•Phenyl•2•Pyrimidynyl•H•Pyrrolyl•Methyl•H•NH2
Thiazolyl•Pyridinyl•1•Amino•C1-C2alkyl•Piperidinyl•Methyl•NH2•Halogen
Pyrazinyl•Thiazolyl•2•Thiophenyl•C1-C2alkyl•Tetrahydropyranyl•H•NH2•NH2
Thiazolyl•Phenyl•1•Phenyl•C4-C6cycloalkyl•Piperidinyl•H•Halogen•C1-C2alkyl
Pyridinyl•Thiazolyl•1•Thiophenyl•C4-C6cycloalkyl•Morpholinyl•H•H•C1-C2alkyl
Pyrazinyl•Pyrimidinyl•2•Pyrazinyl•Cyclopropyl•H•H•NH2•H
Thiazolyl•Phenyl•1•Acyloxy•C3-C4alkyl•H•Methyl•C1-C2alkyl•H
Thiophenyl•Phenyl•1•Alkynyl•Cyclopropyl•Tetrahydropyranyl•H•H•NH2
Pyridazinyl•Pyrimidinyl•1•Tetrahydropyranyl•C1-C2alkyl•Pyrimidinyl•H•Halogen•H
Thiophenyl•Thiazolyl•2•Thiophenyl•C3-C4alkyl•Alkynyl•Methyl•H•Halogen
Thiazolyl•Phenyl•2•Thiophenyl•C4-C6cycloalkyl•Pyrrolyl•H•H•H
Pyridazinyl•Thiazolyl•2•Phenyl•C3-C4alkyl•Pyridinyl•Methyl•C1-C2alkyl•NH2
Pyridinyl•Thiophenyl•2•Pyrazinyl•H•Pyrrolyl•Methyl•H•H
Pyrimidinyl•Pyrimidinyl•1•CN•Cyclopropyl•H•C1-C2alkyl•H•NH2
Pyridinyl•Pyrazinyl•1•Amide•C1-C2alkyl•Pyridinyl•Methyl•Halogen•Halogen
Pyridazinyl•Pyridinyl•2•Pyrazinyl•C3-C4alkyl•Pyridinyl•H•H•NH2
Thiophenyl•Phenyl•1•Pyrazinyl•C1-C2alkyl•Pyrrolidinyl•Methyl•NH2•C1-C2alkyl
Thiazolyl•Thiazolyl•2•Phenyl•H•Phenyl•Methyl•Halogen•Halogen
Thiazolyl•Pyridinyl•1•Piperidinyl•C3-C4alkyl•Pyridinyl•Methyl•H•H
Thiazolyl•Pyridinyl•1•Alkynyl•C4-C6cycloalkyl•Pyrrolyl•Methyl•Halogen•H
Thiazolyl•Pyrazinyl•2•Amino•Cyclopropyl•C1-C3alkyl•H•NH2•H
Pyrazinyl•Pyridazinyl•1•Pyridazinyl•C1-C2alkyl•Pyrrolidinyl•Methyl•H•H
Pyrazinyl•Phenyl•2•Morpholinyl•C1-C2alkyl•Pyridinyl•Methyl•C1-C2alkyl•Halogen
Pyridazinyl•Phenyl•2•Piperazinyl•H•Morpholinyl•Methyl•C1-C2alkyl•Halogen
Pyridazinyl•Phenyl•2•Pyrimidynyl•C4-C6cycloalkyl•Pyrimidinyl•H•NH2•C1-C2alkyl
Pyridazinyl•Phenyl•1•Alkynyl•C4-C6cycloalkyl•H•Methyl•H•H
Thiophenyl•Pyridazinyl•2•Thiophenyl•H•Morpholinyl•Methyl•NH2•H
Pyrazinyl•Pyridazinyl•2•CN•C3-C4alkyl•H•Methyl•H•C1-C2alkyl
Pyrazinyl•Pyrazinyl•1•Piperazinyl•C4-C6cycloalkyl•Phenyl•H•Halogen•H
Pyridinyl•Pyridazinyl•1•Amide•C4-C6cycloalkyl•C1-C3alkyl•H•NH2•Halogen
Pyrimidinyl•Phenyl•1•Morpholinyl•Cyclopropyl•Piperidinyl•Methyl•C1-C2alkyl•NH2
Pyrazinyl•Phenyl•2•Alkynyl•H•Piperidinyl•Methyl•C1-C2alkyl•H
Pyridinyl•Phenyl•2•Pyrazinyl•C3-C4alkyl•Piperidinyl•Methyl•NH2•H
Thiazolyl•Pyrazinyl•1•Piperidinyl•C3-C4alkyl•Pyridinyl•H•NH2•C1-C2alkyl
Pyrazinyl•Thiophenyl•2•Tetrahydropyranyl•C1-C2alkyl•Phenyl•Methyl•Halogen•Halogen
Pyrazinyl•Pyridinyl•1•Alkynyl•C1-C2alkyl•Pyrrolidinyl•H•Halogen•Halogen TABLE 1-continued A•B•m•R1•R2•R3•R4•R5•R6

Triazinyl•Phenyl•1•Piperazinyl•C3-C4alkyl•Tetrahydropyranyl•Methyl•H•C1-C2alkyl
Thiazolyl•Phenyl•1•Pyrazinyl•H•Pyrrolidinyl•H•H•H
Pyrimidinyl•Thiazolyl•1•Morpholinyl•C3-C4alkyl•H•Methyl•NH2•NH2
Triazinyl•Phenyl•1•Thiophenyl•H•Pyrrolyl•H•C1-C2alkyl•H
Triazinyl•Thiazolyl•1•Phenyl•C4-C6cycloalkyl•Tetrahydropyranyl•H•Halogen•C1-C2alkyl
Triazinyl•Thiophenyl•2•Amide•H•C1-C3alkyl•Methyl•Halogen•C1-C2alkyl
Pyridinyl•Pyrimidinyl•2•Acyloxy•C4-C6cycloalkyl•Phenyl•Methyl•H•H
Triazinyl•Phenyl•1•Tetrahydropyranyl•H•C3-C6cycloalkyl•Methyl•C1-C2alkyl•Halogen
Triazinyl•Thiazolyl•1•CN•C1-C2alkyl•Tetrahydropyranyl•H•Halogen•H
Pyrazinyl•Pyridazinyl•1•Thiophenyl•C3-C4alkyl•H•H•H•H
Pyrimidinyl•Phenyl•2•Pyridinyl•C1-C2alkyl•Pyrrolidinyl•Methyl•Halogen•Halogen
Pyridazinyl•Pyrimidinyl•2•Thiophenyl•C3-C4alkyl•C3-C6cycloalkyl•Methyl•Halogen•H
Thiazolyl•Pyridazinyl•2•Pyrazinyl•C4-C6cycloalkyl•Morpholinyl•H•Halogen•NH2
Pyridazinyl•Thiophenyl•2•Amino•Cyclopropyl•Pyrrolidinyl•H•Halogen•Halogen
Thiazolyl•Pyridazinyl•2•Pyridazinyl•C3-C4alkyl•Phenyl•H•NH2•H
Pyrazinyl•Thiazolyl•2•Morpholinyl•H•Pyrimidinyl•H•H•Halogen
Pyridazinyl•Pyridinyl•2•CN•C1-C2alkyl•Piperidinyl•Methyl•Halogen•NH2
Thiazolyl•Pyridinyl•2•Thiophenyl•C1-C2alkyl•Pyrrolidinyl•H•H•C1-C2alkyl
Triazinyl•Pyridinyl•2•Piperazinyl•H•C3-C6cycloalkyl•Methyl•H•Halogen
Pyrazinyl•Pyridazinyl•1•Pyridinyl•C1-C2alkyl•H•H•H•NH2
Thiazolyl•Phenyl•1•Amino•C3-C4alkyl•H•H•H•NH2
Pyridinyl•Pyrimidinyl•1•Alkynyl•Cyclopropyl•H•H•Halogen•C1-C2alkyl
Pyridazinyl•Pyridazinyl•2•Tetrahydropyranyl•C4-C6cycloalkyl•Pyrrolyl•H•H•H
Thiazolyl•Pyrimidinyl•1•Acyloxy•C4-C6cycloalkyl•Morpholinyl•Methyl•Halogen•H
Thiazolyl•Pyrazinyl•2•Pyrazinyl•C4-C6cycloalkyl•Pyridinyl•H•C1-C2alkyl•Halogen
Pyridinyl•Thiophenyl•2•Alkynyl•C1-C2alkyl•H•H•C1-C2alkyl•NH2
Pyridinyl•Phenyl•1•Acyl•C3-C4alkyl•Pyrrolyl•Methyl•H•NH2
Thiazolyl•Pyridinyl•1•Amide•C1-C2alkyl•C3-C6cycloalkyl•H•C1-C2alkyl•H
Pyrazinyl•Phenyl•2•Pyridinyl•C4-C6cycloalkyl•Pyrimidinyl•Methyl•C1-C2alkyl•NH2
Pyridazinyl•Pyridazinyl•1•Thiophenyl•C1-C2alkyl•Alkynyl•Methyl•H•NH2
Pyrimidinyl•Phenyl•1•Acyloxyl•C1-C3alkyl•H•H•NH2
Pyrimidinyl•Thiazolyl•1•Alkynyl•C4-C6cycloalkyl•Morpholinyl•Methyl•H•C1-C2alkyl
Pyridazinyl•Thiophenyl•1•Pyrimidynyl•C4-C6cycloalkyl•Pyrimidinyl•Methyl•Halogen•H
Thiazolyl•Pyrazinyl•1•Tetrahydropyranyl•C1-C2alkyl•Phenyl•H•Halogen•H
Thiazolyl•Pyridinyl•1•CN•C4-C6cycloalkyl•C3-C6cycloalkyl•H•H•H
Pyrazinyl•Phenyl•1•Piperidinyl•Cyclopropyl•C1-C3alkyl•H•C1-C2alkyl•C1-C2alkyl
Triazinyl•Thiazolyl•1•Phenyl•C4-C6cycloalkyl•Morpholinyl•H•H•NH2
Triazinyl•Pyridinyl•1•Phenyl•H•Pyridinyl•Methyl•Halogen•H
Pyridazinyl•Pyridinyl•1•Amide•C4-C6cycloalkyl•Piperidinyl•Methyl•Halogen•Halogen
Pyrazinyl•Pyrimidinyl•2•Tetrahydropyranyl•C3-C4alkyl•Tetrahydropyranyl•H•H•C1-C2alkyl
Thiazolyl•Pyrimidinyl•1•Tetrahydropyranyl•Cyclopropyl•Alkynyl•H•H•H
Pyridazinyl•Thiophenyl•1•Piperazinyl•H•Pyrrolidinyl•Methyl•C1-C2alkyl•NH2
Pyridazinyl•Pyrimidinyl•1•Amino•H•Alkynyl•H•Halogen•H
Pyridinyl•Phenyl•1•Thiophenyl•C1-C2alkyl•Morpholinyl•H•H•C1-C2alkyl
Thiazolyl•Pyridazinyl•2•Pyrimidynyl•C4-C6cycloalkyl•Phenyl•Methyl•C1-C2alkyl•C1-C2alkyl
Pyridinyl•Pyrazinyl•1•Piperidinyl•H•Piperidinyl•Methyl•Halogen•NH2
Thiazolyl•Pyridazinyl•1•CN•Cyclopropyl•Pyrimidinyl•Methyl•H•C1-C2alkyl
Pyrimidinyl•Pyridinyl•1•Morpholinyl•Cyclopropyl•Pyrrolidinyl•Methyl•C1-C2alkyl•C1-C2alkyl
Pyridazinyl•Thiophenyl•2•Amino•H•Pyridinyl•H•H•NH2
Triazinyl•Phenyl•2•Tetrahydropyranyl•C4-C6cycloalkyl•Piperidinyl•H•Halogen•C1-C2alkyl
Pyrimidinyl•Thiophenyl•1•Phenyl•C4-C6cycloalkyl•C3-C6cycloalkyl•Methyl•H•C1-C2alkyl
Thiophenyl•Thiazolyl•1•Piperidinyl•C3-C4alkyl•C3-C6cycloalkyl•Methyl•NH2•C1-C2alkyl
Thiazolyl•Thiazolyl•2•Alkynyl•Cyclopropyl•Pyrimidinyl•Methyl•H•C1-C2alkyl
Pyrimidinyl•Phenyl•2•Pyrimidynyl•H•Pyrimidinyl•Methyl•NH2•C1-C2alkyl
Triazinyl•Pyridazinyl•2•Pyrimidynyl•H•Tetrahydropyranyl•H•H•Halogen
Pyrazinyl•Pyrazinyl•2•Morpholinyl•C4-C6cycloalkyl•Morpholinyl•H•H•NH2
Thiophenyl•Pyridinyl•1•Acyl•C4-C6cycloalkyl•Alkynyl•Methyl•C1-C2alkyl•Halogen
Thiazolyl•Pyridinyl•1•Piperazinyl•H•Phenyl•Methyl•H•C1-C2alkyl
Pyridinyl•Thiophenyl•2•Tetrahydropyranyl•H•C1-C3alkyl•H•H•H
Triazinyl•Pyridinyl•2•Acyl•H•Morpholinyl•Methyl•H•Halogen
Thiophenyl•Thiophenyl•1•Amino•C1-C2alkyl•Morpholinyl•Methyl•H•Halogen
Pyridazinyl•Pyridazinyl•2•Piperazinyl•H•C3-C6cycloalkyl•H•Halogen•C1-C2alkyl
Pyrazinyl•Pyrazinyl•2•Morpholinyl•C4-C6cycloalkyl•Tetrahydropyranyl•Methyl•C1-C2alkyl•H
Pyrimidinyl•Pyridinyl•1•Acyl•C1-C2alkyl•Pyrrolidinyl•Methyl•Halogen•NH2
Pyrazinyl•Phenyl•2•CN•C4-C6cycloalkyl•Piperidinyl•Methyl•Halogen•Halogen
Pyridinyl•Pyridinyl•1•Acyl•C4-C6cycloalkyl•Pyrimidinyl•Methyl•C1-C2alkyl•C1-C2alkyl
Thiazolyl•Pyridinyl•2•Pyridinyl•C4-C6cycloalkyl•Alkynyl•Methyl•H•Halogen
Pyrazinyl•Phenyl•1•Pyrimidynyl•C4-C6cycloalkyl•Pyrrolyl•H•NH2•H
Thiazolyl•Pyridazinyl•1•Phenyl•Cyclopropyl•Morpholinyl•H•C1-C2alkyl•NH2
Thiazolyl•Pyrimidinyl•2•Amino•C4-C6cycloalkyl•H•H•NH2•NH2
Thiazolyl•Pyrimidinyl•2•Amino•C3-C4alkyl•Phenyl•H•H•C1-C2alkyl
Thiazolyl•Pyrazinyl•2•Phenyl•C1-C2alkyl•C1-C3alkyl•H•H•H
Pyridazinyl•Pyridazinyl•1•Tetrahydropyranyl•C3-C4alkyl•Pyridinyl•H•Halogen•Halogen
Pyrazinyl•Pyridazinyl•2•Morpholinyl•H•H•H•NH2•NH2
Thiazolyl•Pyridazinyl•2•Acyl•C3-C4alkyl•Phenyl•H•Halogen•H
Pyridinyl•Thiazolyl•2•Thiophenyl•Cyclopropyl•Pyrimidinyl•H•NH2•C1-C2alkyl
Thiophenyl•Pyridazinyl•2•Pyridinyl•H•Morpholinyl•H•Halogen•NH2
Thiophenyl•Pyridazinyl•1•Amino•C4-C6cycloalkyl•Pyrimidinyl•Methyl•H•C1-C2alkyl TABLE 1-continued

| A•B•m•R1•R2•R3•R4•R5•R6 |
|---|

Pyridinyl•Pyridinyl•1•Pyridinyl•C1-C2alkyl•C1-C3alkyl•Methyl•H•C1-C2alkyl
Triazinyl•Thiophenyl•1•Phenyl•H•Pyridinyl•Methyl•C1-C2alkyl•Halogen
Pyridazinyl•Phenyl•1•Acyl•C1-C2alkyl•Piperidinyl•H•Halogen•H
Triazinyl•Phenyl•2•Pyridinyl•Cyclopropyl•C1-C3alkyl•H•Halogen•C1-C2alkyl
Pyrimidinyl•Thiazolyl•2•Phenyl•C3-C4alkyl•Pyrimidinyl•Methyl•Halogen•Halogen
Thiazolyl•Thiazolyl•1•Piperazinyl•C1-C2alkyl•Pyrrolidinyl•H•Halogen•H
Pyridinyl•Pyridinyl•1•CN•C4-C6cycloalkyl•Pyridinyl•Methyl•C1-C2alkyl•C1-C2alkyl
Pyridazinyl•Thiophenyl•2•Pyridinyl•Cyclopropyl•Pyrrolyl•H•H•C1-C2alkyl
Thiophenyl•Pyridinyl•1•Morpholinyl•H•C1-C3alkyl•H•C1-C2alkyl•NH2
Pyridazinyl•Pyridazinyl•2•Tetrahydropyranyl•C4-C6cycloalkyl•Alkynyl•Methyl•NH2•H
Pyrimidinyl•Pyridazinyl•2•Phenyl•C3-C4alkyl•Alkynyl•Methyl•C1-C2alkyl•H
Pyrazinyl•Pyrimidinyl•1•Amino•Cyclopropyl•Pyrrolyl•Methyl•C1-C2alkyl•Halogen
Thiazolyl•Pyridinyl•2•Acyloxy•H•C1-C3alkyl•H•NH2•Halogen
Thiazolyl•Pyridazinyl•2•Acyl•C3-C4alkyl•Pyrrolyl•H•H•H
Pyrimidinyl•Thiophenyl•1•Amide•Cyclopropyl•C3-C6cycloalkyl•H•H•NH2
Triazinyl•Thiazolyl•2•Acyloxy•C3-C4alkyl•C1-C3alkyl•H•H•C1-C2alkyl
Triazinyl•Pyrimidinyl•2•Piperidinyl•C1-C2alkyl•Morpholinyl•H•NH2•NH2
Pyridinyl•Pyridazinyl•1•Amide•Cyclopropyl•Pyrrolyl•Methyl•C1-C2alkyl•H
Pyrazinyl•Pyridazinyl•1•Phenyl•C4-C6cycloalkyl•C3-C6cycloalkyl•H•NH2•NH2
Pyridinyl•Pyridazinyl•2•Pyridinyl•C4-C6cycloalkyl•Alkynyl•H•Halogen•H
Triazinyl•Pyridinyl•1•Acyloxy•C3-C4alkyl•C1-C3alkyl•H•NH2•Halogen
Pyrazinyl•Phenyl•2•Alkynyl•Cyclopropyl•H•H•NH2•C1-C2alkyl
Pyridinyl•Pyrazinyl•1•Alkynyl•C1-C2alkyl•H•H•H•Halogen
Thiophenyl•Thiophenyl•1•Pyrimidynyl•Cyclopropyl•Pyridinyl•H•NH2•NH2
Thiazolyl•Thiazolyl•1•Acyl•Cyclopropyl•H•H•NH2•Halogen
Pyrazinyl•Thiophenyl•2•Amino•H•Pyrrolyl•H•NH2•C1-C2alkyl
Thiophenyl•Pyridinyl•1•Tetrahydropyranyl•C4-C6cycloalkyl•Phenyl•H•NH2•C1-C2alkyl
Pyrazinyl•Pyridinyl•2•Pyrazinyl•C4-C6cycloalkyl•Pyrrolyl•Methyl•C1-C2alkyl•NH2
Pyrimidinyl•Pyrimidinyl•1•Tetrahydropyranyl•C4-C6cycloalkyl•Pyrimidinyl•Methyl•NH2•H
Pyridinyl•Pyrimidinyl•1•Pyrimidynyl•C1-C2alkyl•Phenyl•H•Halogen•Halogen
Thiophenyl•Pyridazinyl•1•Acyl•C3-C4alkyl•Pyrimidinyl•H•H•C1-C2alkyl
Triazinyl•Phenyl•2•Piperidinyl•Cyclopropyl•Pyrrolidinyl•H•C1-C2alkyl•NH2
Triazinyl•Pyrimidinyl•2•Pyridinyl•C4-C6cycloalkyl•Pyrrolidinyl•Methyl•H•H
Triazinyl•Pyridinyl•2•Pyrazinyl•C1-C2alkyl•Phenyl•Methyl•C1-C2alkyl•Halogen
Pyridazinyl•Thiophenyl•1•Pyridinyl•Cyclopropyl•C3-C6cycloalkyl•H•Halogen•H
Pyrazinyl•Thiophenyl•2•Thiophenyl•Cyclopropyl•Piperidinyl•Methyl•H•NH2
Pyridinyl•Pyridinyl•1•CN•C3-C4alkyl•Pyrrolyl•Methyl•Halogen•NH2
Triazinyl•Pyridazinyl•1•Amide•C4-C6cycloalkyl•Tetrahydropyranyl•H•H•Halogen
Pyridinyl•Pyridinyl•2•Amide•C3-C4alkyl•H•H•NH2•Halogen
Pyridinyl•Thiazolyl•2•Acyl•Cyclopropyl•Pyrrolidinyl•H•C1-C2alkyl•H
Pyridinyl•Pyridinyl•1•Morpholinyl•C3-C4alkyl•Pyrrolyl•Methyl•Halogen•C1-C2alkyl
Pyrazinyl•Pyrimidinyl•1•Pyridazinyl•H•Piperidinyl•H•C1-C2alkyl•Halogen
Thiazolyl•Thiophenyl•2•Piperazinyl•C1-C2alkyl•Pyrrolidinyl•Methyl•Halogen•C1-C2alkyl
Thiophenyl•Pyrazinyl•2•Acyloxy•C3-C4alkyl•Pyridinyl•Methyl•NH2•H
Triazinyl•Pyrimidinyl•1•Pyrimidynyl•H•Pyrrolidinyl•H•C1-C2alkyl•H
Pyrimidinyl•Pyridazinyl•1•Phenyl•C4-C6cycloalkyl•Tetrahydropyranyl•Methyl•NH2•NH2
Pyridazinyl•Pyridazinyl•2•Pyridazinyl•C1-C2alkyl•H•H•NH2•C1-C2alkyl
Triazinyl•Phenyl•1•Pyridinyl•C3-C4alkyl•Tetrahydropyranyl•Methyl•NH2•Halogen
Pyrimidinyl•Pyrazinyl•2•Amino•H•Alkynyl•H•Halogen•NH2
Pyrazinyl•Thiazolyl•1•CN•Cyclopropyl•Piperidinyl•Methyl•C1-C2alkyl•Halogen
Pyridinyl•Phenyl•2•Phenyl•C1-C2alkyl•Phenyl•Methyl•C1-C2alkyl•NH2
Thiophenyl•Pyrimidinyl•1•Alkynyl•C4-C6cycloalkyl•Tetrahydropyranyl•Methyl•H•H
Thiazolyl•Pyridinyl•1•Piperazinyl•C1-C2alkyl•Morpholinyl•Methyl•Halogen•H
Pyridinyl•Phenyl•2•Tetrahydropyranyl•H•Pyridinyl•H•H•H
Thiazolyl•Pyrazinyl•1•Amide•C4-C6cycloalkyl•Tetrahydropyranyl•Methyl•NH2•C1-C2alkyl
Thiazolyl•Thiazolyl•1•Tetrahydropyranyl•C3-C4alkyl•C3-C6cycloalkyl•Methyl•C1-C2alkyl•Halogen
Pyridinyl•Pyrimidinyl•1•Thiophenyl•C4-C6cycloalkyl•Pyrimidinyl•Methyl•H•Halogen
Pyridinyl•Pyrazinyl•1•Piperidinyl•C4-C6cycloalkyl•H•Methyl•C1-C2alkyl•Halogen
Thiophenyl•Pyrazinyl•1•Pyridazinyl•H•Pyridinyl•H•Halogen•Halogen
Pyridazinyl•Thiophenyl•2•Acyl•C1-C2alkyl•Pyrrolidinyl•H•Halogen•NH2
Pyridazinyl•Thiazolyl•1•Morpholinyl•C3-C4alkyl•Tetrahydropyranyl•H•C1-C2alkyl•NH2
Thiophenyl•Thiophenyl•2•Acyl•C1-C2alkyl•C3-C6cycloalkyl•H•Halogen•C1-C2alkyl
Pyrimidinyl•Pyrimidinyl•1•Amide•Cyclopropyl•Pyridinyl•Methyl•H•NH2
Pyridinyl•Thiophenyl•1•Morpholinyl•Cyclopropyl•Pyrrolyl•H•C1-C2alkyl•H
Thiophenyl•Pyrimidinyl•1•Amide•C4-C6cycloalkyl•Pyrrolyl•H•H•NH2
Thiazolyl•Pyrazinyl•2•Pyrazinyl•C1-C2alkyl•Piperidinyl•H•NH2•C1-C2alkyl TABLE 1-continued

| A•B•m•R1•R2•R3•R4•R5•R6 |
|---|
| Pyrazinyl•Thiophenyl•2•Piperazinyl•C4-C6cycloalkyl•Alkynyl•H•C1-C2alkyl•H |
| Pyrazinyl•Thiophenyl•1•Piperazinyl•C4-C6cycloalkyl•Piperidinyl•Methyl•H•H |
| Triazinyl•Pyridinyl•1•Alkynyl•Cyclopropyl•Tetrahydropyranyl•H•H•H |
| Thiophenyl•Phenyl•2•Acyloxy•C1-C2alkyl•Pyrimidinyl•H•Halogen•Halogen |
| Thiazolyl•Pyrazinyl•1•Pyridinyl•C3-C4alkyl•C1-C3alkyl•Methyl•NH2•H |
| Pyridinyl•Pyrazinyl•2•Amino•C4-C6cycloalkyl•Tetrahydropyranyl•H•Halogen•NH2 |
| Pyridazinyl•Thiazolyl•2•Pyridinyl•Cyclopropyl•Pyridinyl•Methyl•H•H |
| Pyrimidinyl•Pyrazinyl•1•Amino•C1-C2alkyl•Piperidinyl•H•C1-C2alkyl•Halogen |
| Pyrimidinyl•Pyrimidinyl•1•Amino•C3-C4alkyl•Pyrrolidinyl•H•NH2•NH2 |
| Thiazolyl•Pyridinyl•1•Pyridazinyl•C3-C4alkyl•Pyrrolidinyl•H•H•Halogen |
| Pyridazinyl•Pyridinyl•2•Acyloxy•Cyclopropyl•Pyrrolidinyl•H•H•NH2 |
| Thiophenyl•Pyridazinyl•2•Morpholinyl•C4-C6cycloalkyl•Phenyl•H•NH2•C1-C2alkyl |
| Pyrazinyl•Thiazolyl•1•CN•C1-C2alkyl•Alkynyl•Methyl•NH2•H |
| Pyridazinyl•Phenyl•2•Piperidinyl•Cyclopropyl•Pyridinyl•H•NH2•C1-C2alkyl |
| Pyrazinyl•Thiophenyl•2•Amide•C3-C4alkyl•Phenyl•Methyl•C1-C2alkyl•H |
| Pyrazinyl•Phenyl•1•Morpholinyl•C3-C4alkyl•H•H•NH2•H |
| Thiazolyl•Thiophenyl•1•Phenyl•H•Phenyl•H•NH2•NH2 |
| Pyridazinyl•Thiazolyl•2•Thiophenyl•C4-C6cycloalkyl•Pyridinyl•Methyl•Halogen•Halogen |
| Thiazolyl•Pyrimidinyl•1•CN•C3-C4alkyl•Pyrimidinyl•H•H•H |
| Thiazolyl•Thiophenyl•2•Piperidinyl•C3-C4alkyl•Pyrrolyl•H•NH2•C1-C2alkyl |
| Pyridinyl•Pyrimidinyl•1•Alkynyl•C4-C6cycloalkyl•Pyrrolyl•H•NH2•H |
| Thiazolyl•Pyridinyl•2•Amide•C4-C6cycloalkyl•Pyrrolyl•Methyl•NH2•NH2 |
| Thiophenyl•Pyrimidinyl•1•Amide•C1-C2alkyl•H•Methyl•C1-C2alkyl•H |
| Pyrimidinyl•Thiazolyl•2•Acyloxy•Cyclopropyl•Pyrrolyl•Methyl•NH2•H |
| Triazinyl•Pyrimidinyl•2•Piperidinyl•H•C1-C3alkyl•H•C1-C2alkyl•H |
| Thiazolyl•Phenyl•1•CN•C3-C4alkyl•C3-C6cycloalkyl•Methyl•Halogen•C1-C2alkyl |
| Pyridinyl•Pyridazinyl•2•Tetrahydropyranyl•C3-C4alkyl•Pyrimidinyl•H•H•Halogen |
| Thiazolyl•Pyrazinyl•2•CN•C1-C2alkyl•Pyridinyl•H•C1-C2alkyl•H |
| Pyridinyl•Pyrimidinyl•2•Phenyl•H•Morpholinyl•H•C1-C2alkyl•Halogen |
| Thiazolyl•Thiazolyl•2•Tetrahydropyranyl•Cyclopropyl•Pyridinyl•H•NH2•Halogen |
| Pyrazinyl•Thiophenyl•2•Pyridazinyl•C4-C6cycloalkyl•Piperidinyl•H•Halogen•H |
| Pyridazinyl•Pyrimidinyl•2•Pyridazinyl•C3-C4alkyl•Phenyl•H•Halogen•NH2 |
| Pyrimidinyl•Thiazolyl•2•Alkynyl•C4-C6cycloalkyl•Morpholinyl•Methyl•H•C1-C2alkyl |
| Triazinyl•Phenyl•1•Tetrahydropyranyl•C1-C2alkyl•Phenyl•Methyl•C1-C2alkyl•C1-C2alkyl |
| Pyrazinyl•Pyrazinyl•2•Piperazinyl•C4-C6cycloalkyl•Piperidinyl•Methyl•C1-C2alkyl•C1-C2alkyl |
| Pyridazinyl•Pyridinyl•2•Amide•Cyclopropyl•Phenyl•Methyl•H•NH2 |
| Thiazolyl•Thiazolyl•2•Morpholinyl•C1-C2alkyl•Pyridinyl•H•C1-C2alkyl•Halogen |
| Pyrazinyl•Thiazolyl•1•Pyridinyl•H•Pyrimidinyl•Methyl•C1-C2alkyl•H |
| Thiazolyl•Thiazolyl•2•Pyridinyl•Cyclopropyl•Pyrimidinyl•Methyl•H•C1-C2alkyl |
| Pyridinyl•Phenyl•1•Piperidinyl•C1-C2alkyl•C3-C6cycloalkyl•H•C1-C2alkyl•Halogen |
| Pyridazinyl•Pyrimidinyl•2•Tetrahydropyranyl•C3-C4alkyl•Pyridinyl•Methyl•NH2•Halogen |
| Pyridazinyl•Pyrazinyl•1•Pyrimidynyl•Cyclopropyl•Pyridinyl•H•NH2•NH2 |
| Pyrazinyl•Pyridinyl•2•Pyrimidynyl•Cyclopropyl•Phenyl•H•H•H |
| Triazinyl•Thiophenyl•2•Pyrimidynyl•C1-C2alkyl•C3-C6cycloalkyl•H•C1-C2alkyl•C1-C2alkyl |

In some aspects, the invention relates to a compound of Formula I (more particularly, of Formula Ia) having a structure selected from:

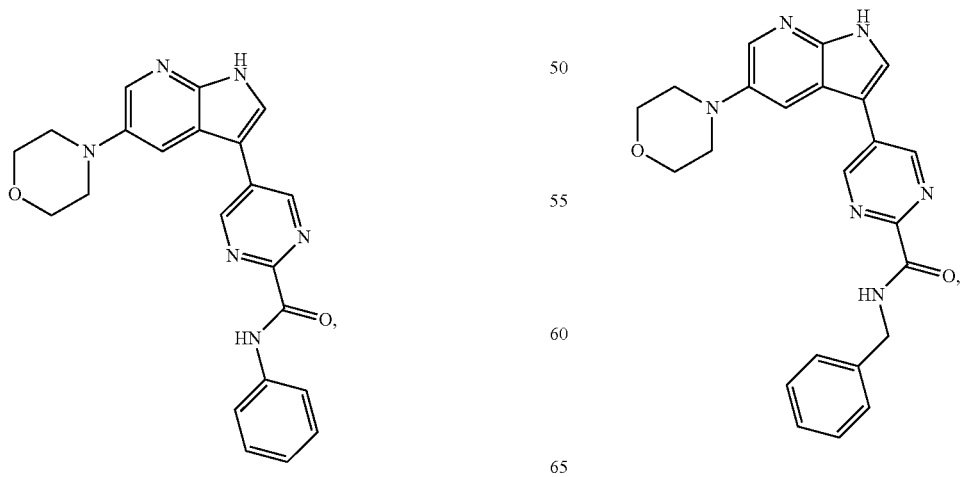

-continued
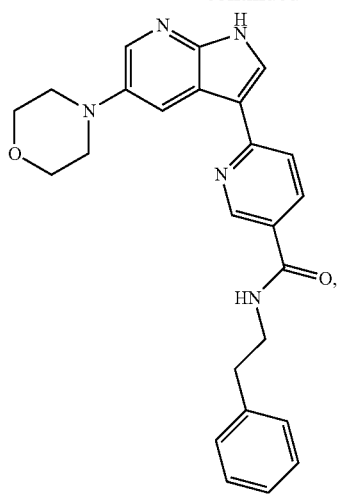
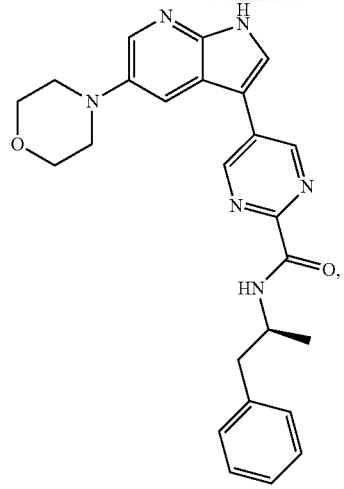
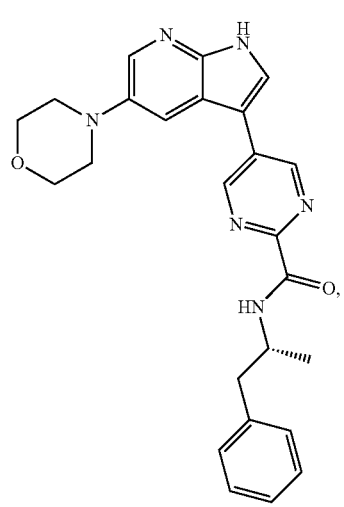
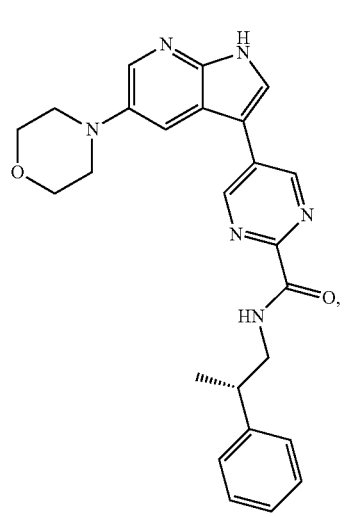

65
-continued
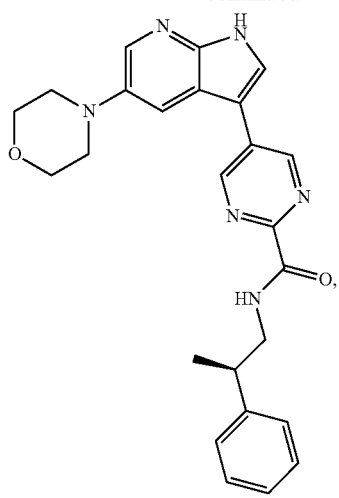
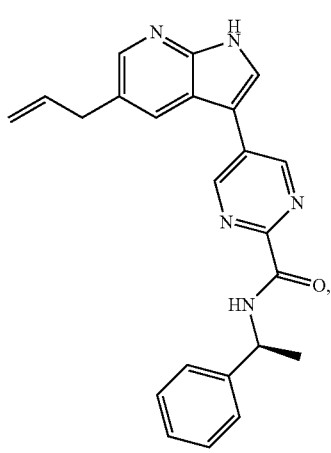
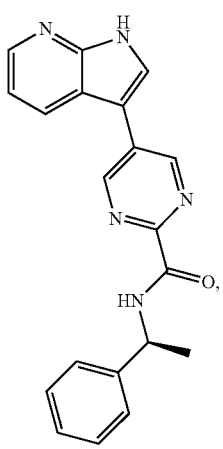
66
-continued
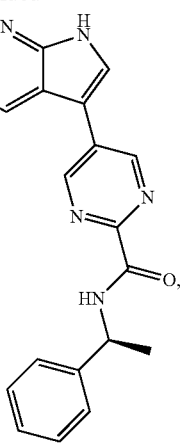
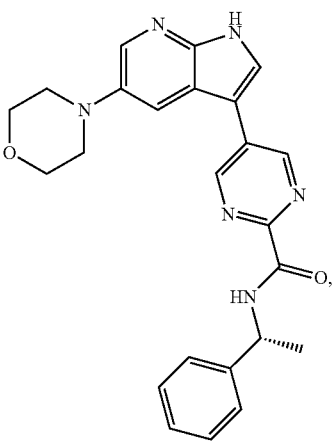
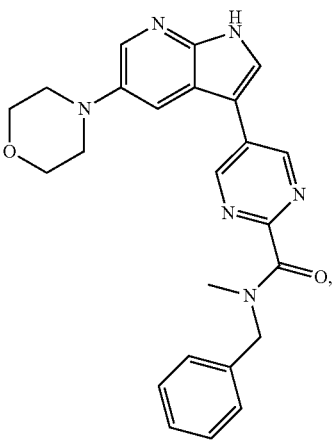

-continued
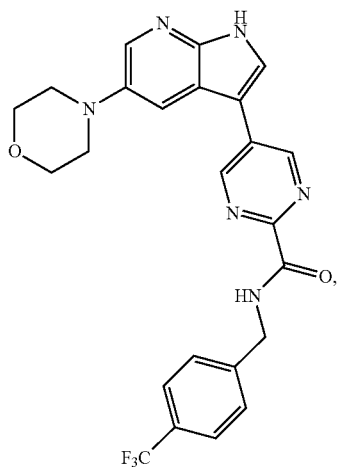
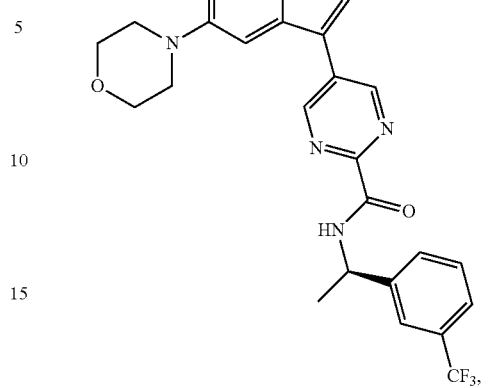
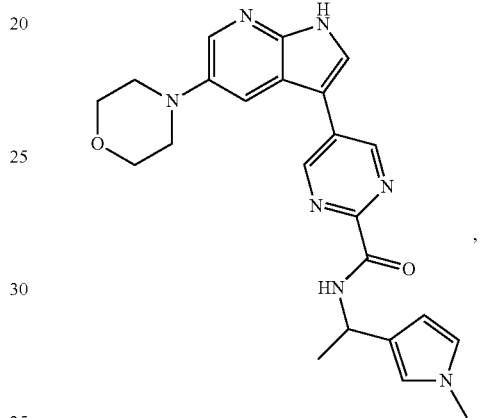
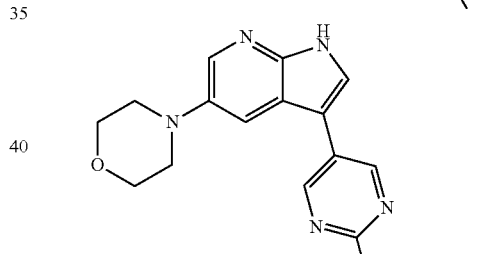
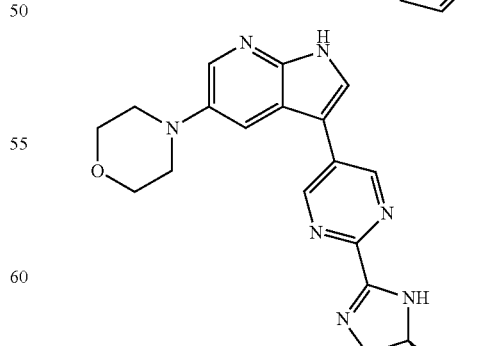

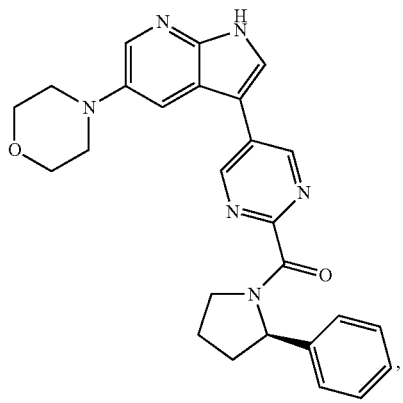
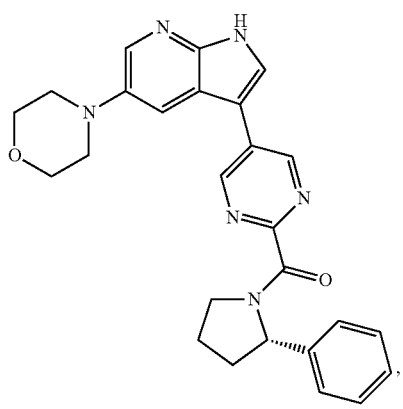
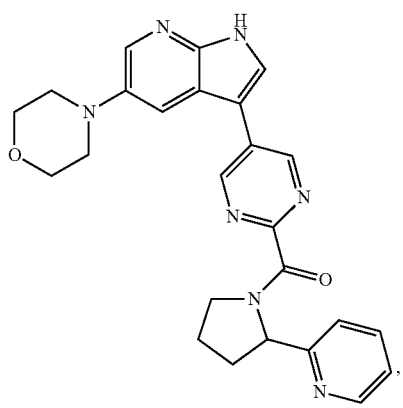
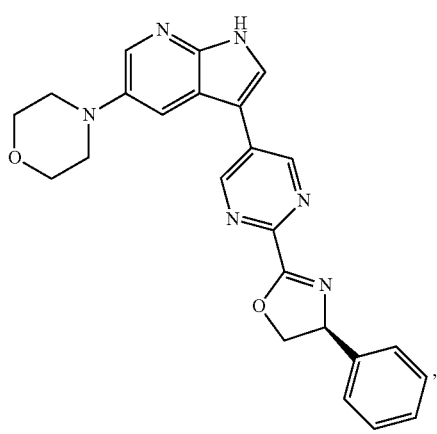
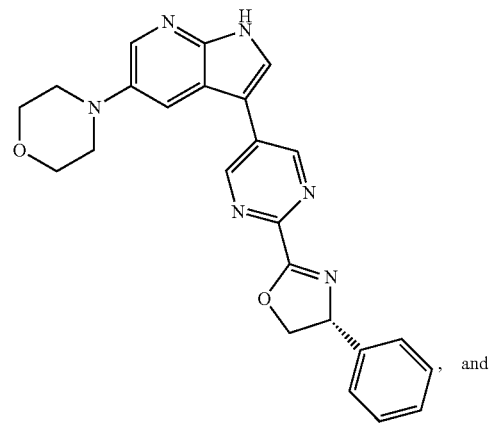
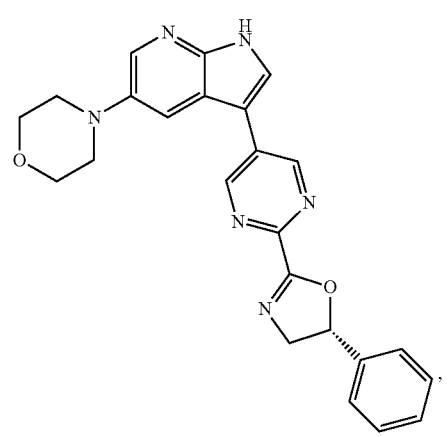
and or a pharmaceutically acceptable salt thereof.
In certain embodiments, the invention relates to a compound selected from:
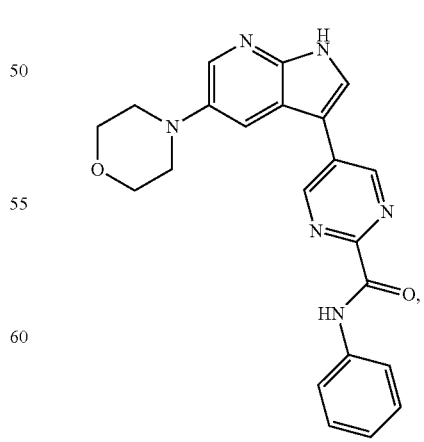

71
-continued
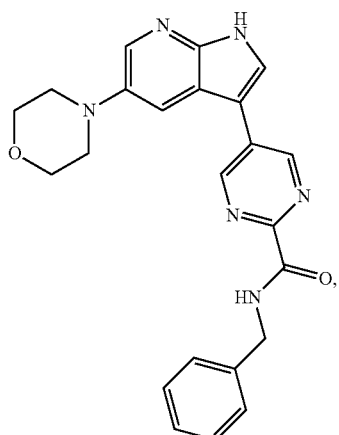
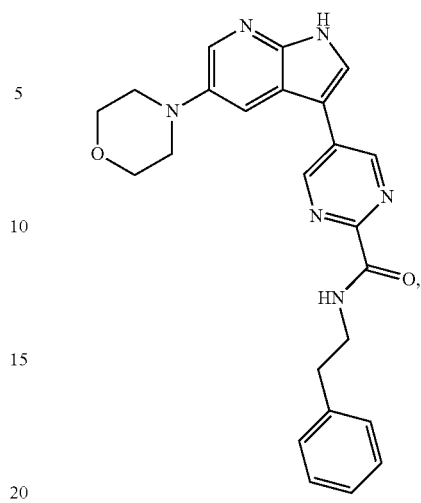
72
-continued
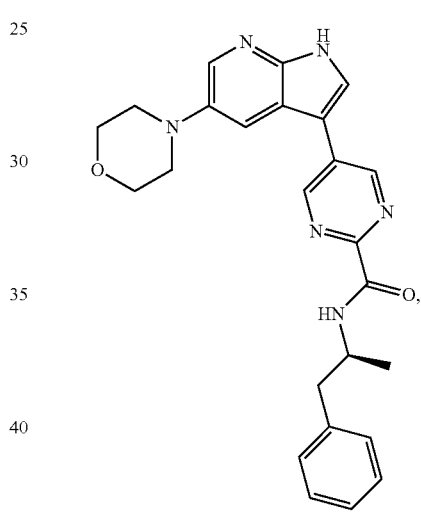
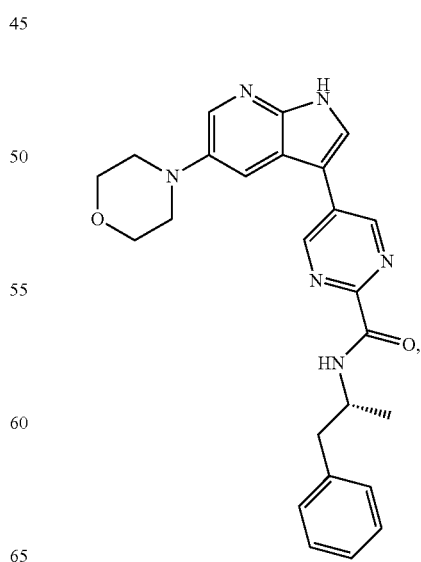

73
-continued
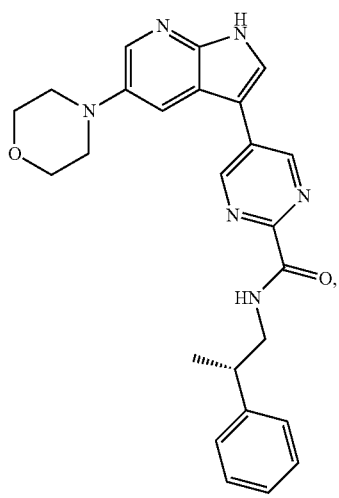
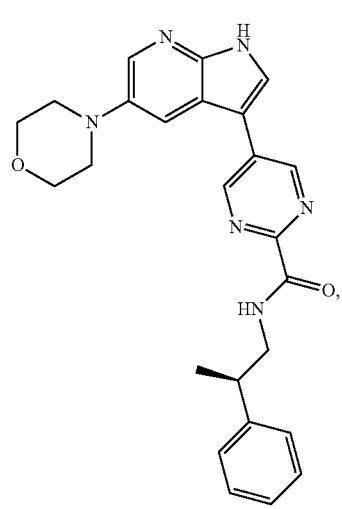 [SMILES: C[C@@H](CNC(=O)c1ncc(-c2c[nH]c3ncc(N4CCOCC4)cc23)cn1)c1ccccc1]
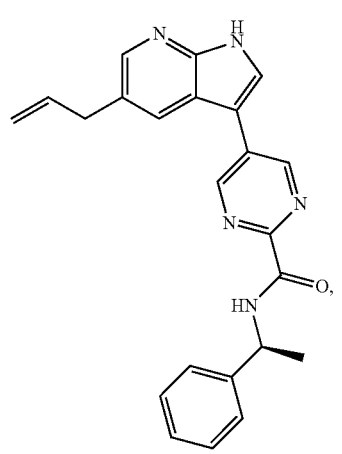
74
-continued
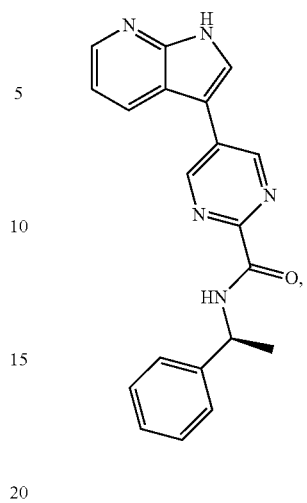
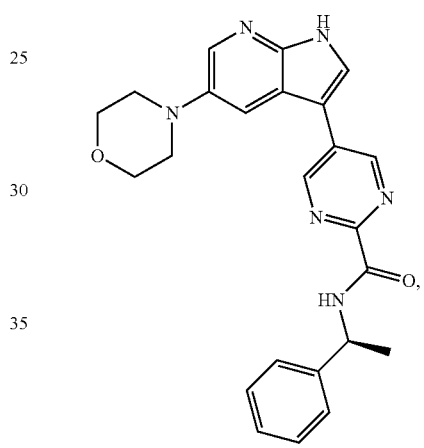
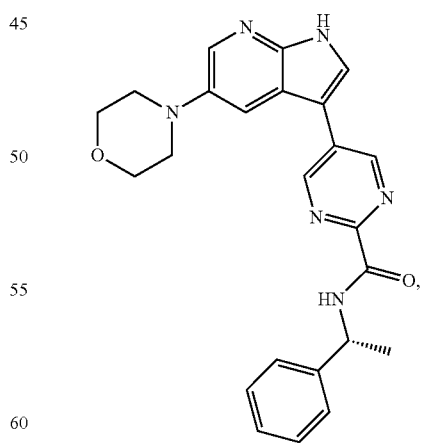

75
-continued
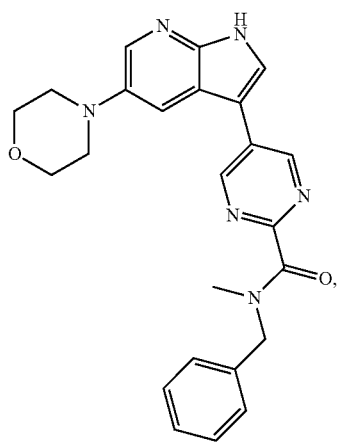
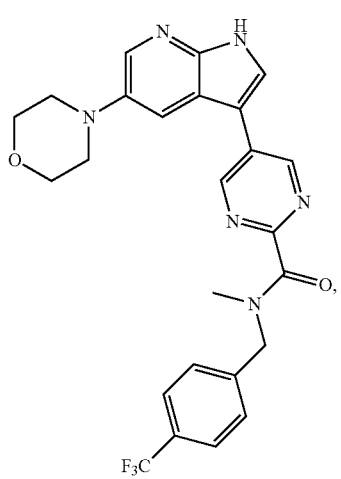
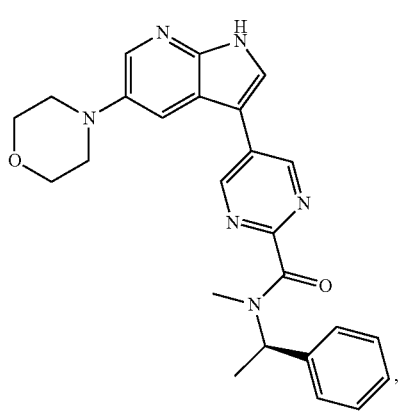
76
-continued
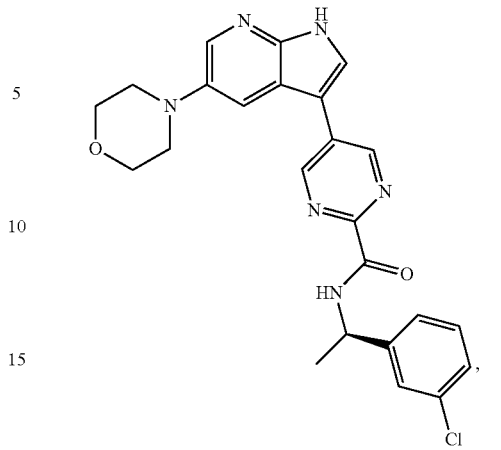
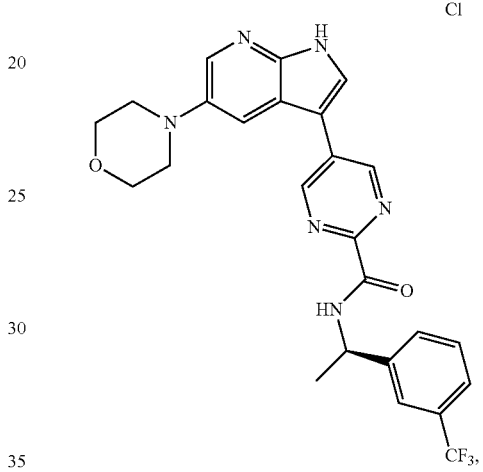
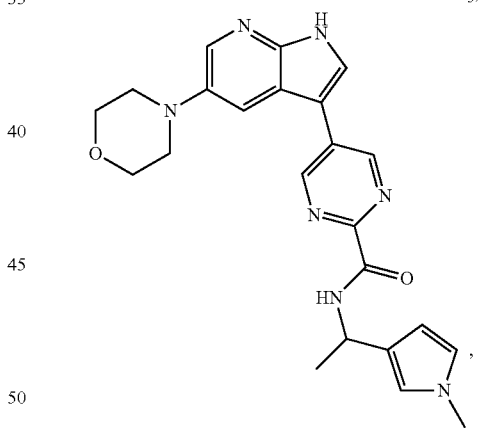
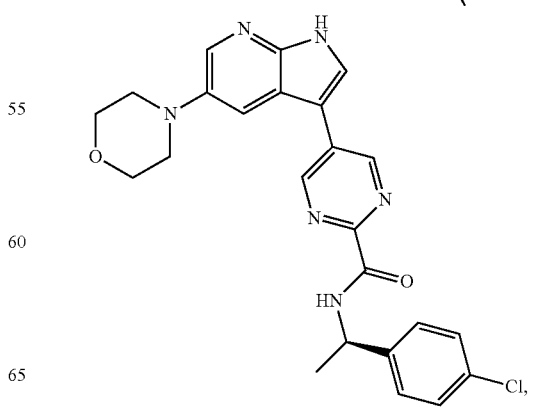

77
-continued
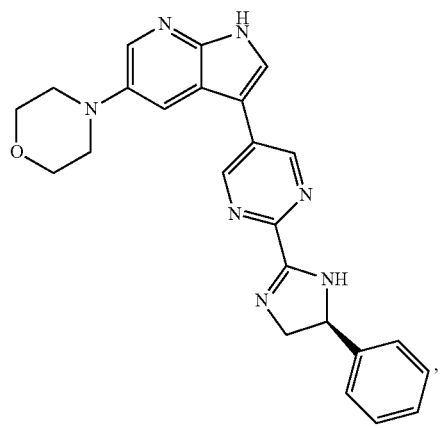
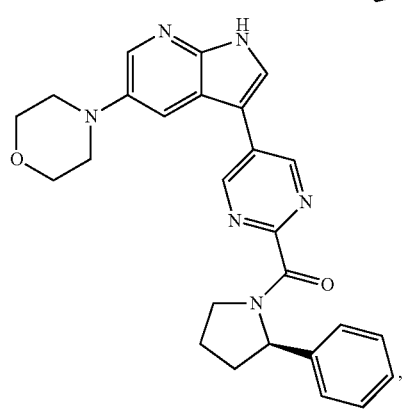
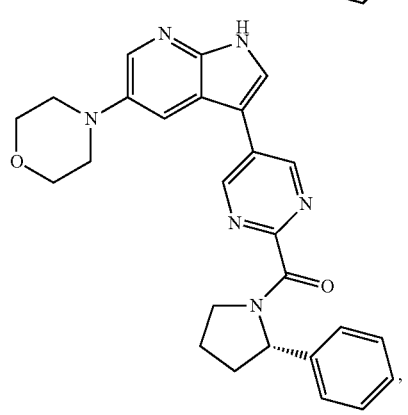
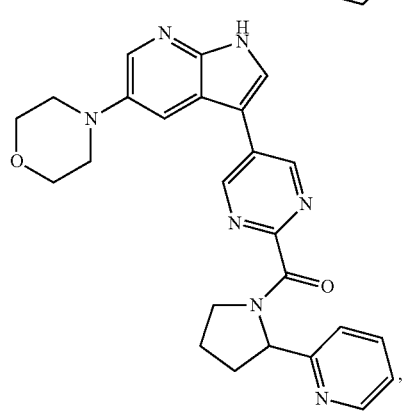
78
-continued
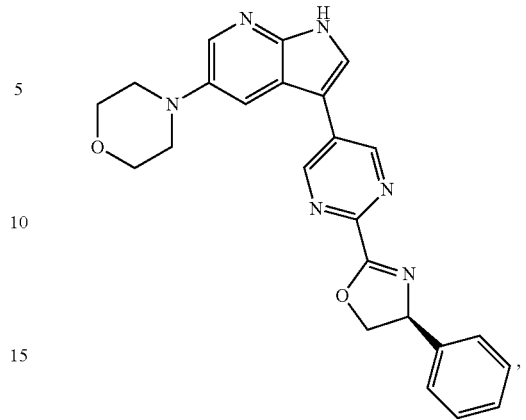
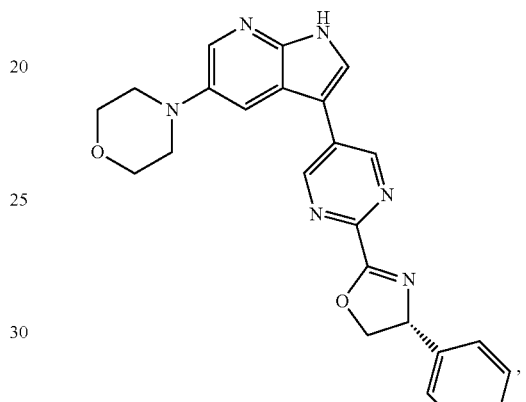
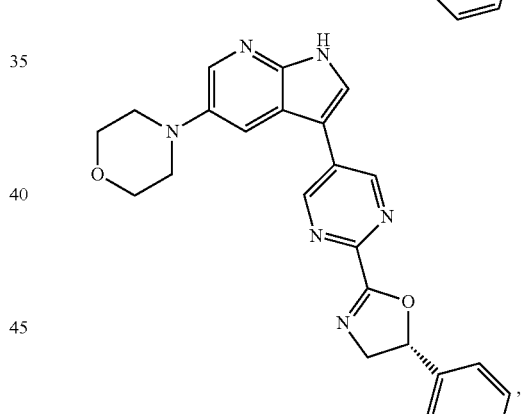
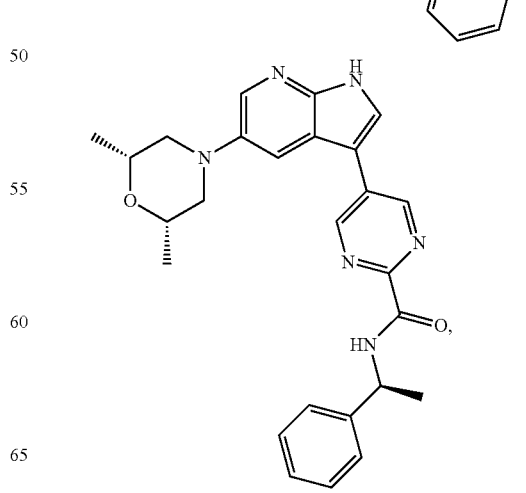

79
-continued
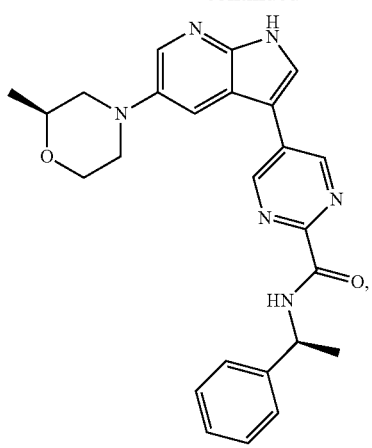
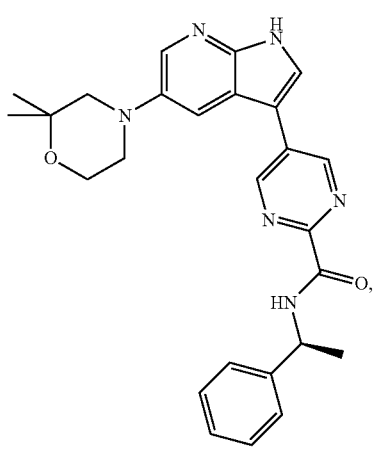
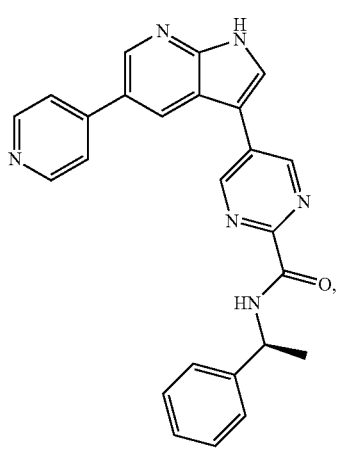
80
-continued
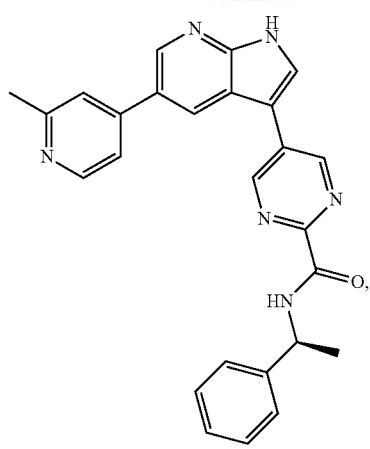
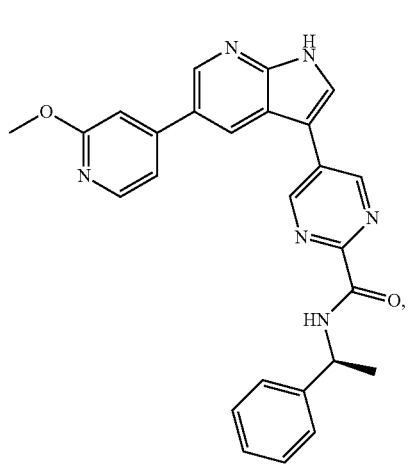
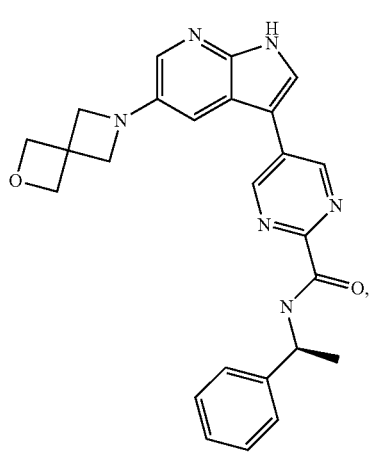

81
-continued
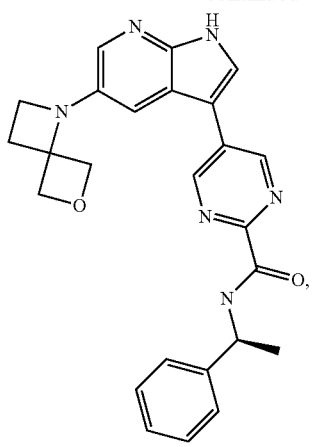
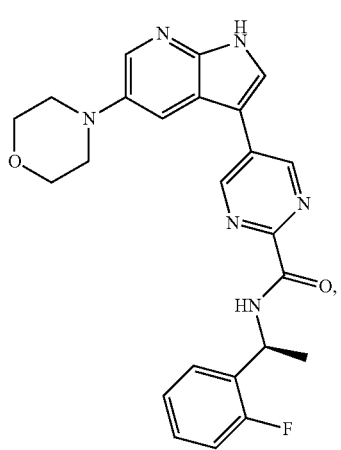
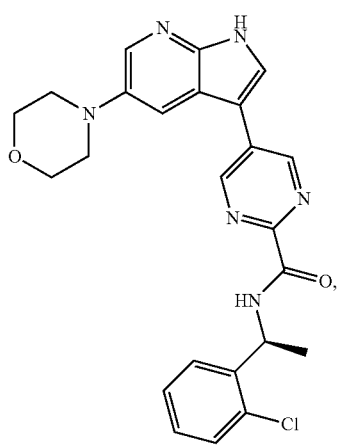
82
-continued
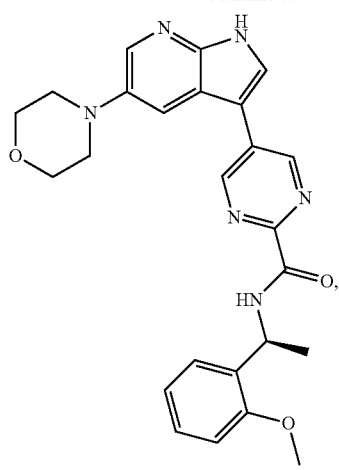
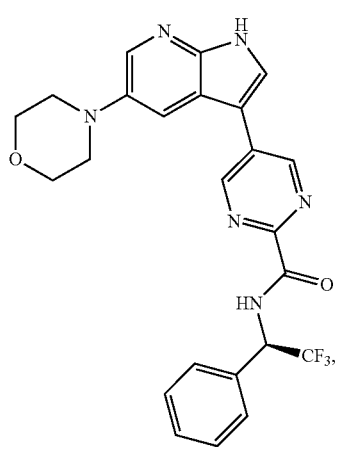
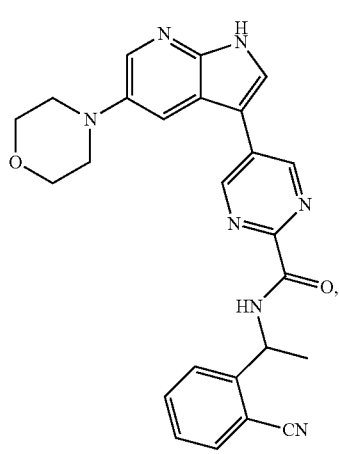

83
-continued
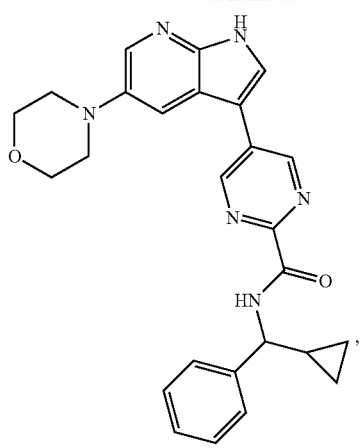
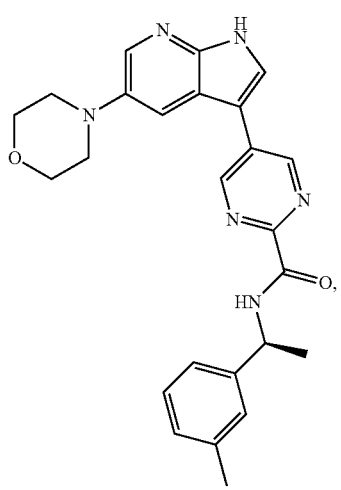
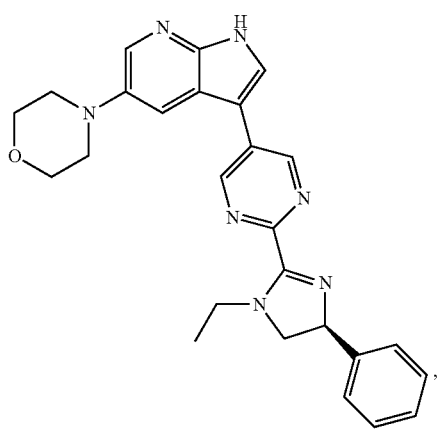
84
-continued
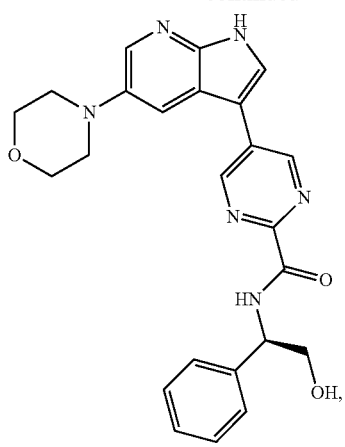
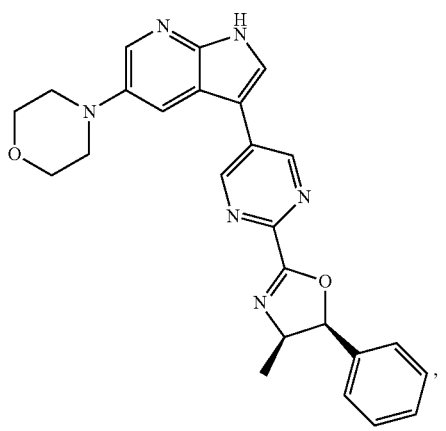
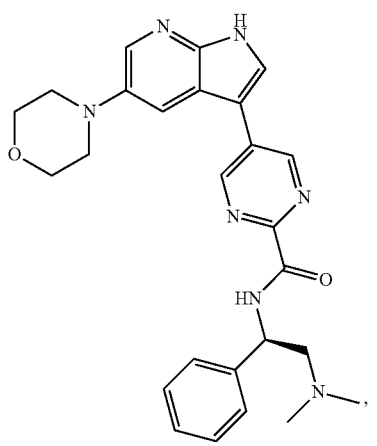

85
-continued
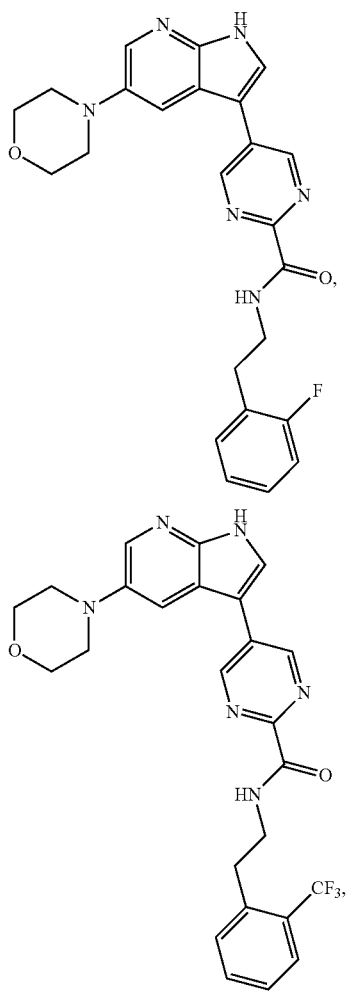
86
-continued
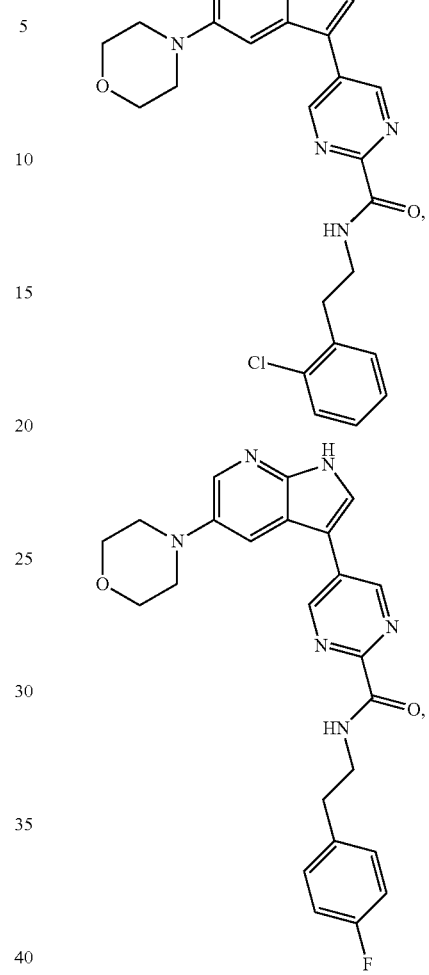
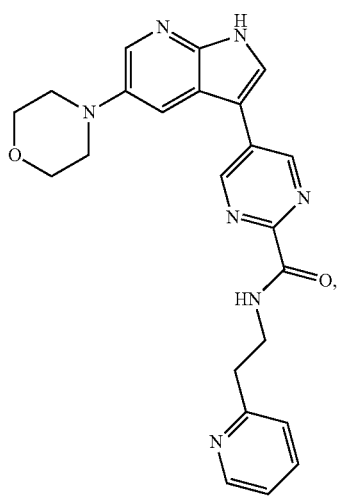
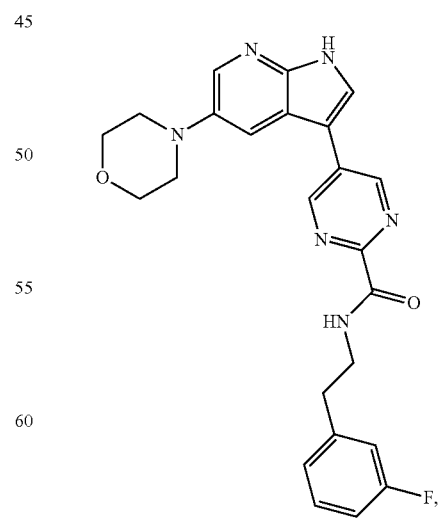

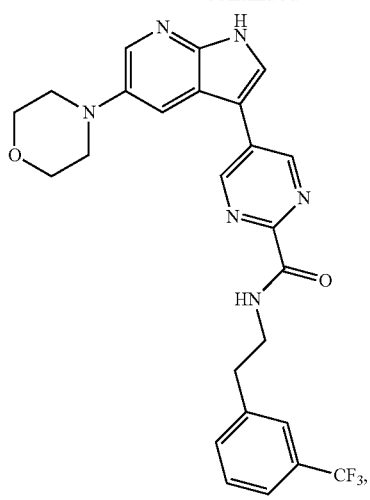
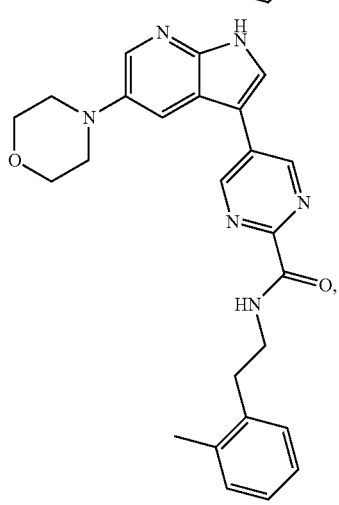
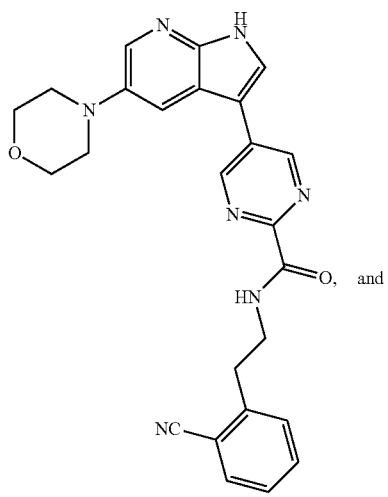 and
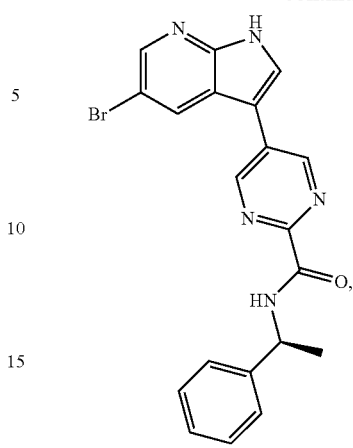
or a pharmaceutically acceptable salt thereof.
In certain embodiments, the invention relates to a compound selected from:
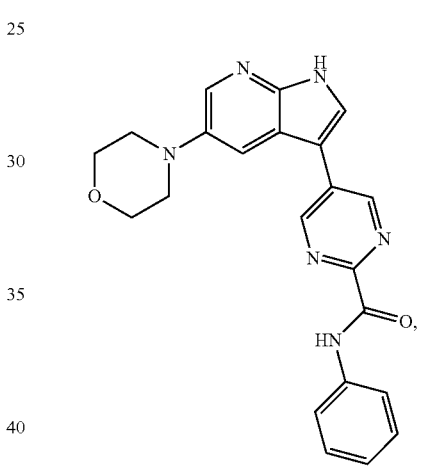
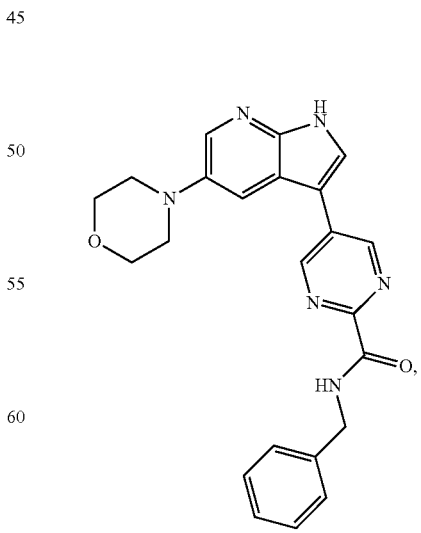

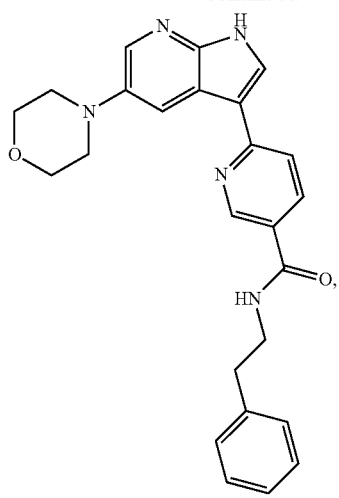
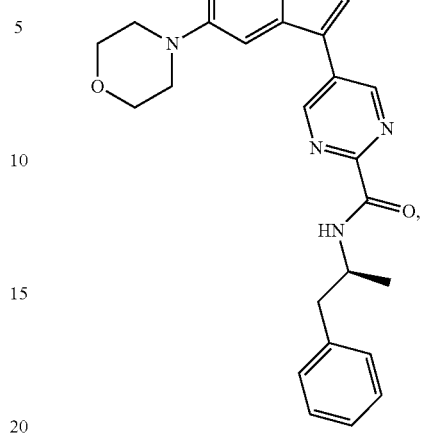
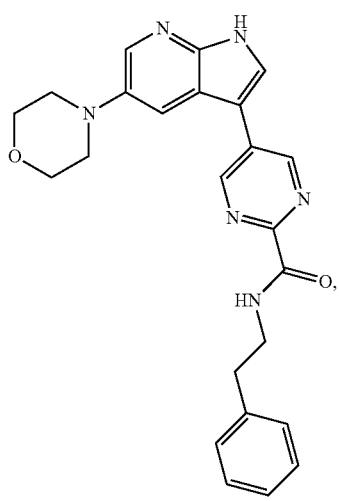
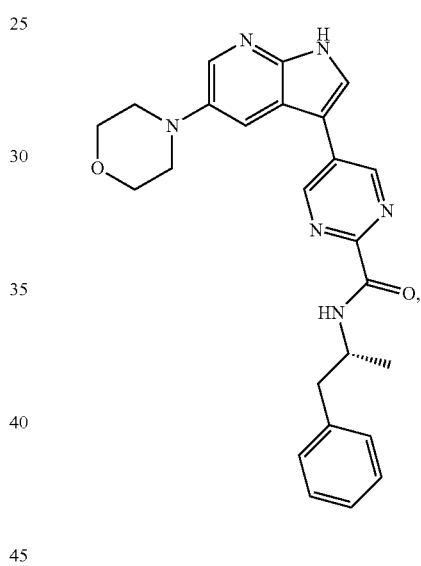
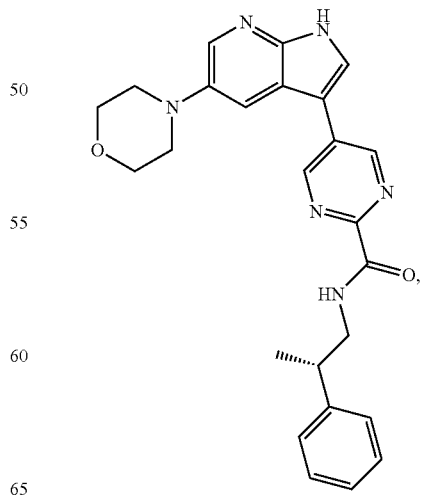

91
-continued
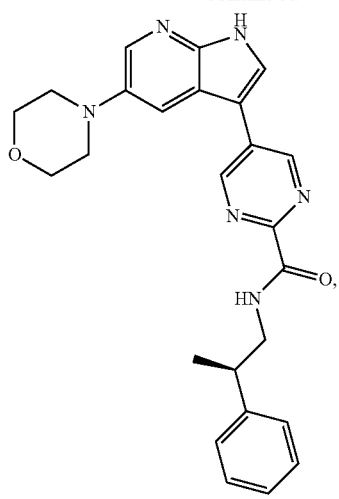
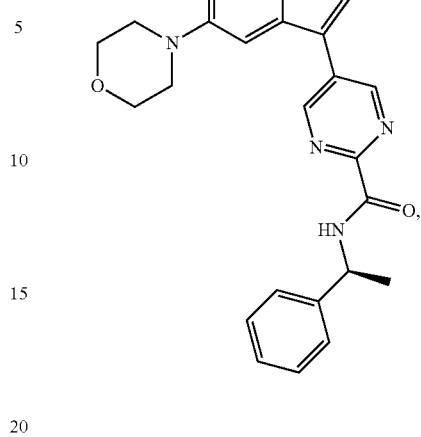
92
-continued
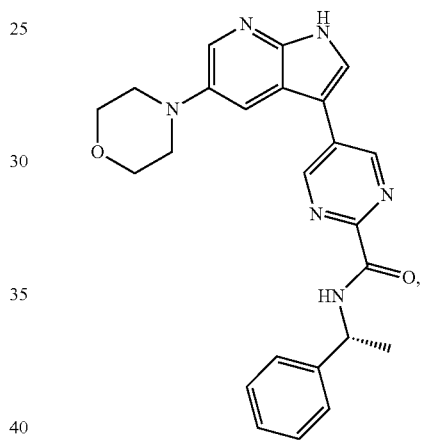
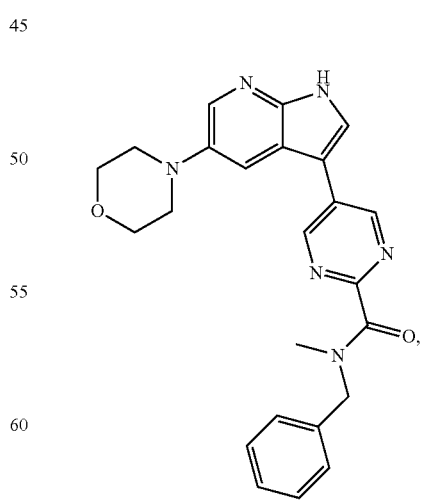

93
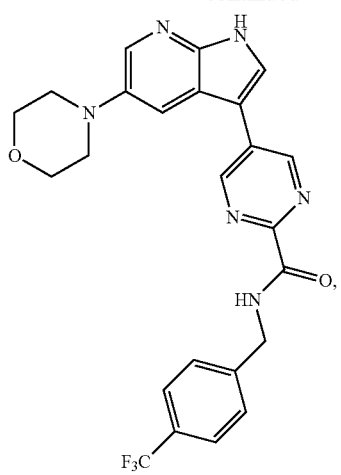
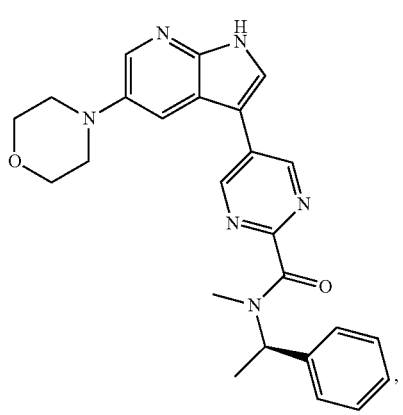
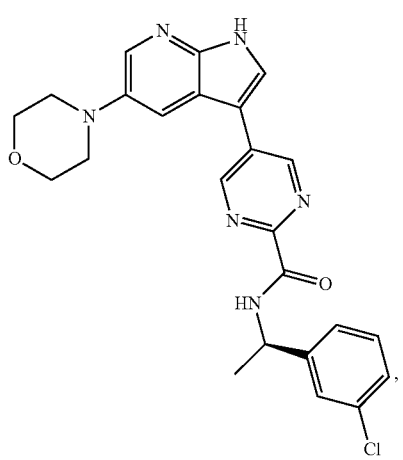
94
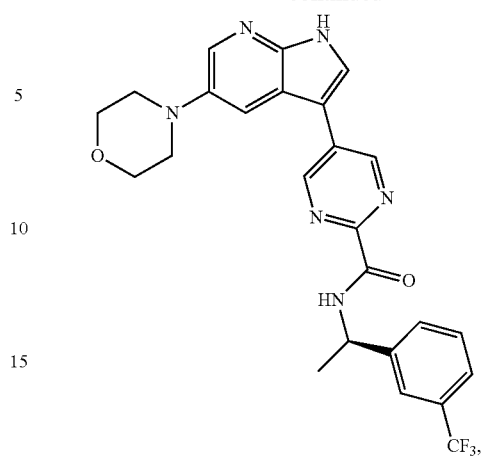
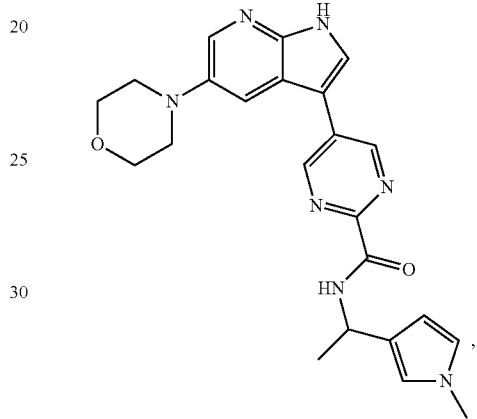
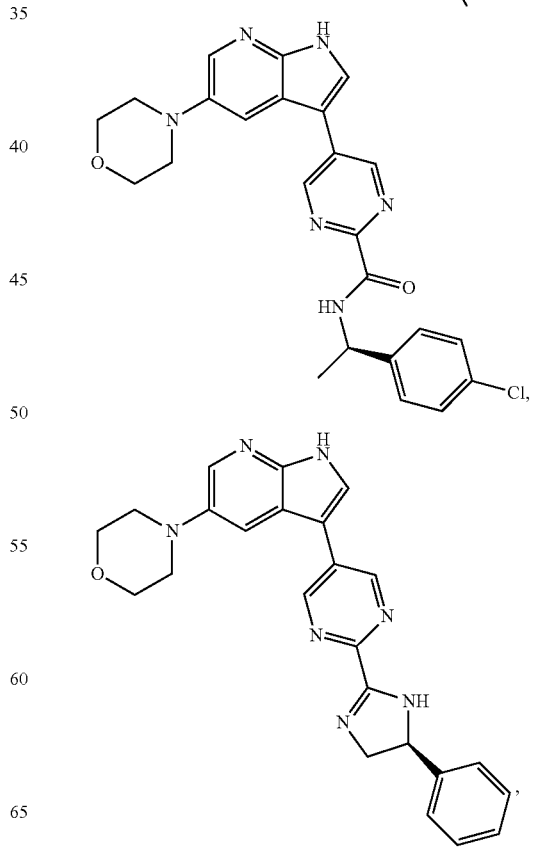
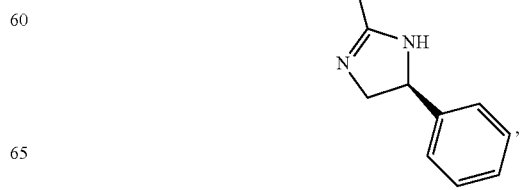

95
-continued
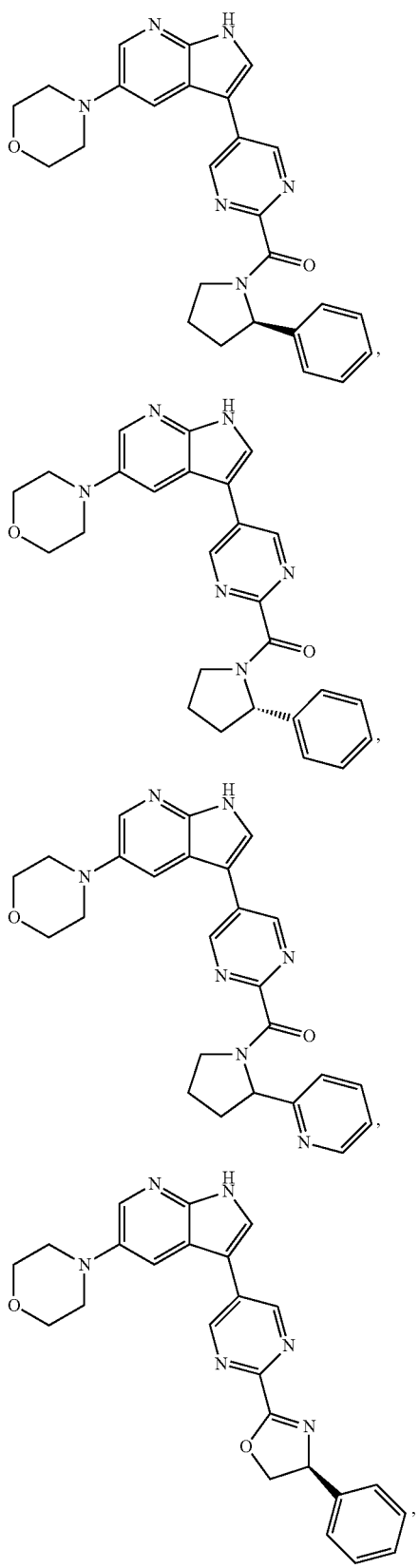
96
-continued
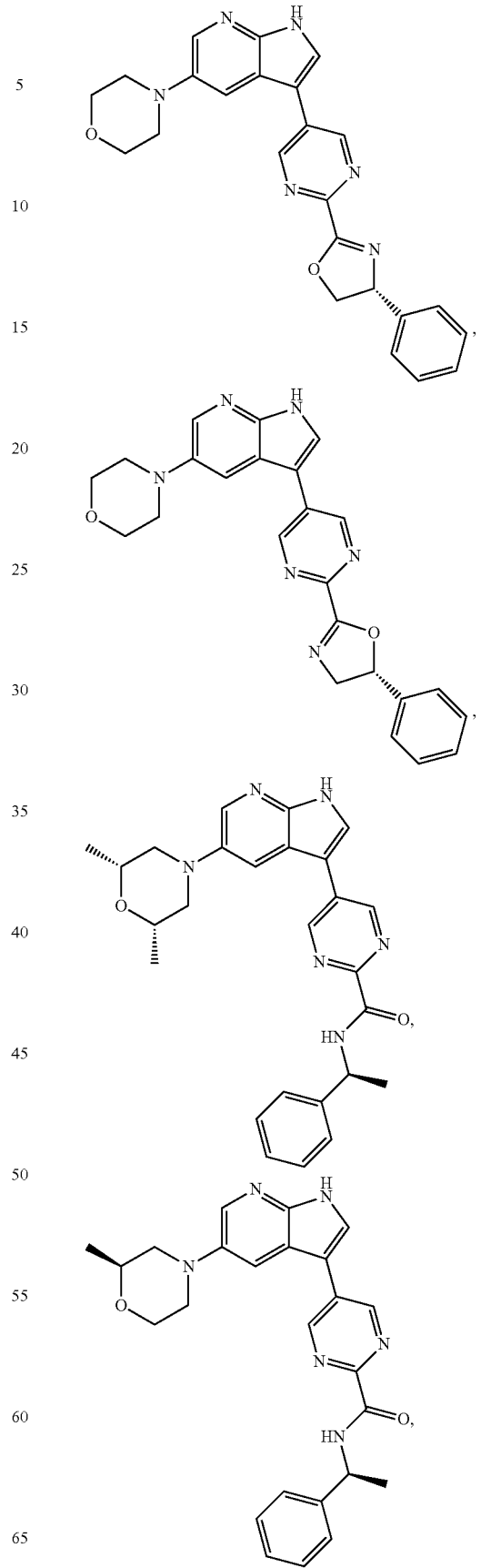

97
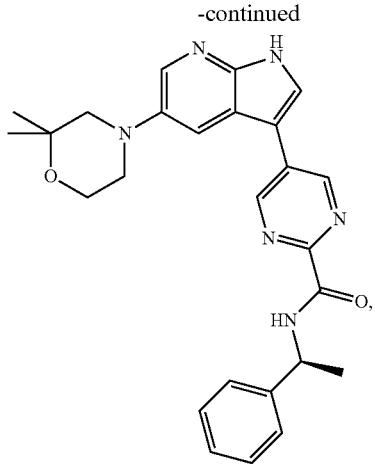
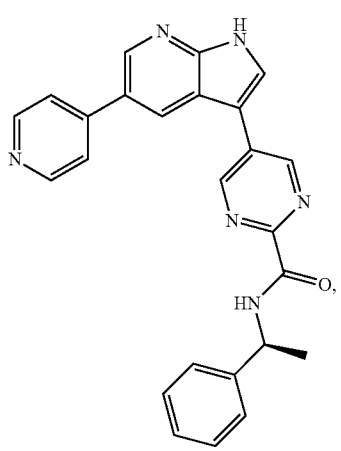
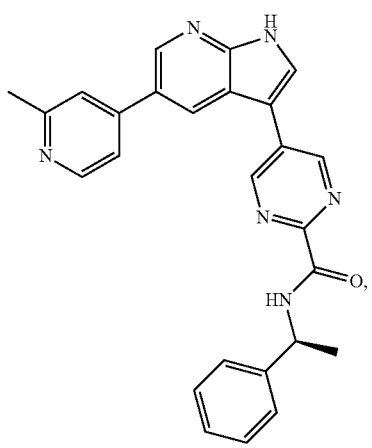
98
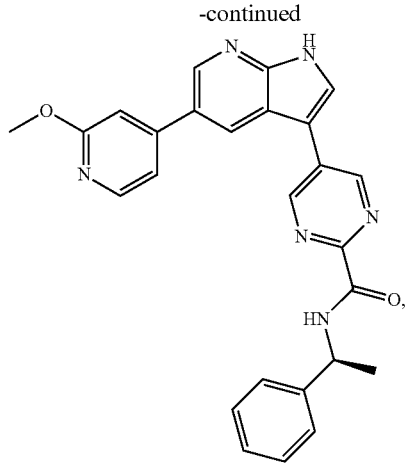
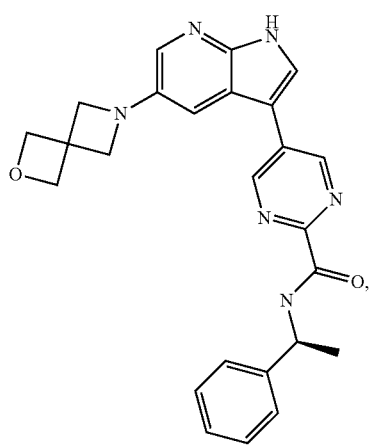
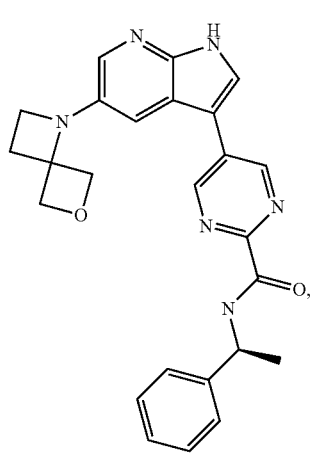

99
-continued
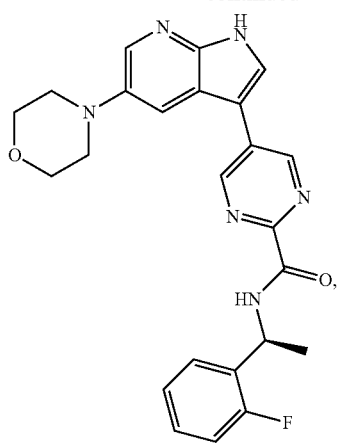
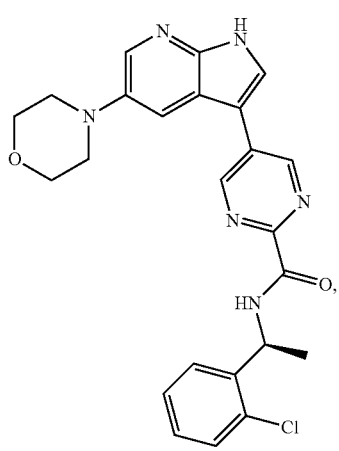
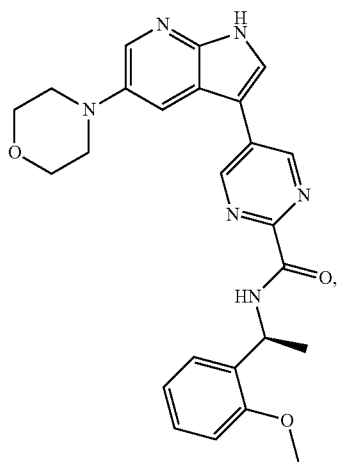
100
-continued
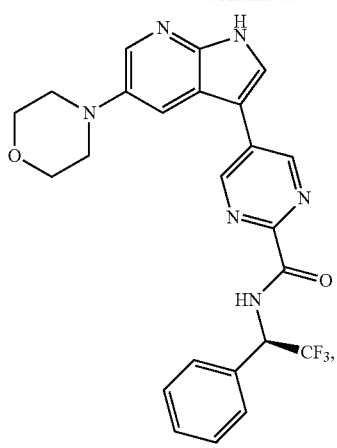
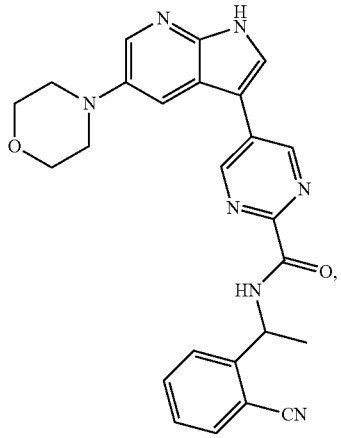
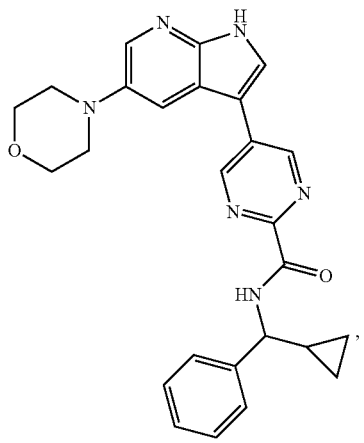

101
-continued
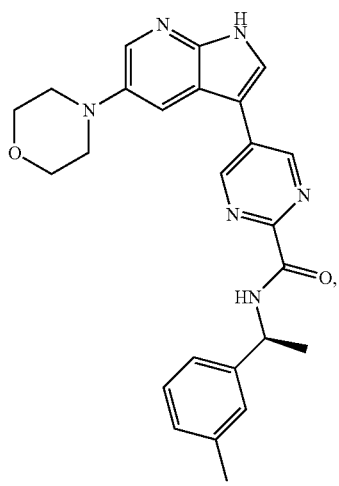
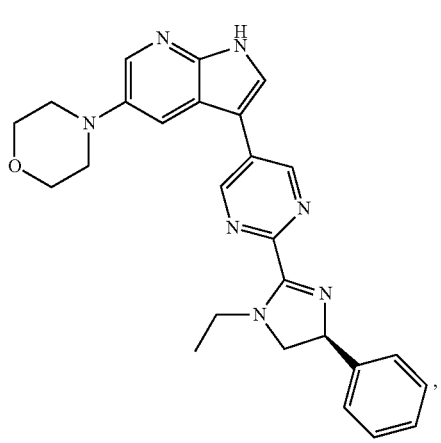
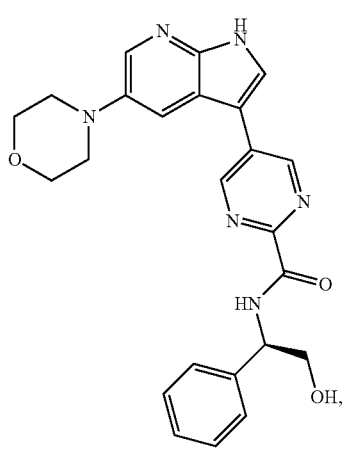
102
-continued
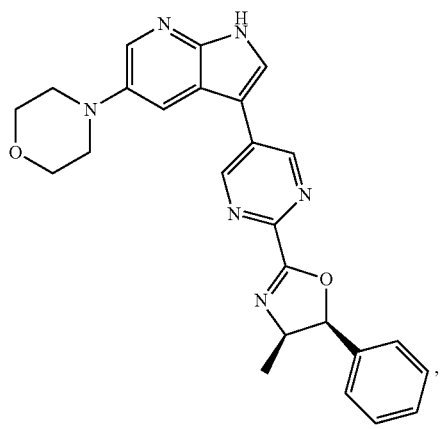
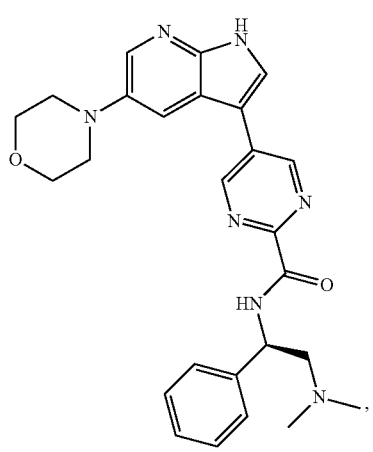
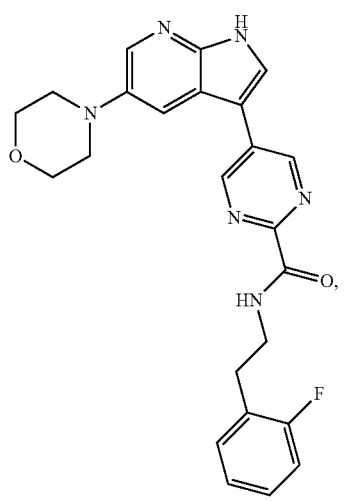

103
-continued
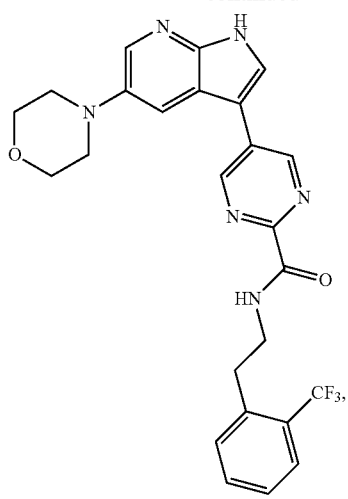
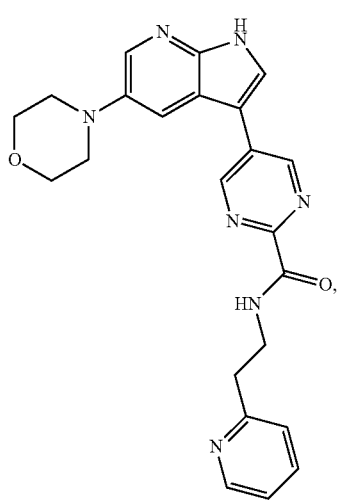
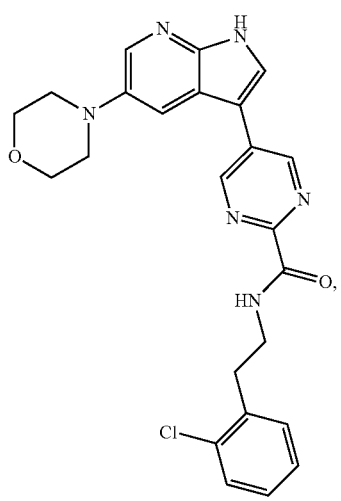
104
-continued
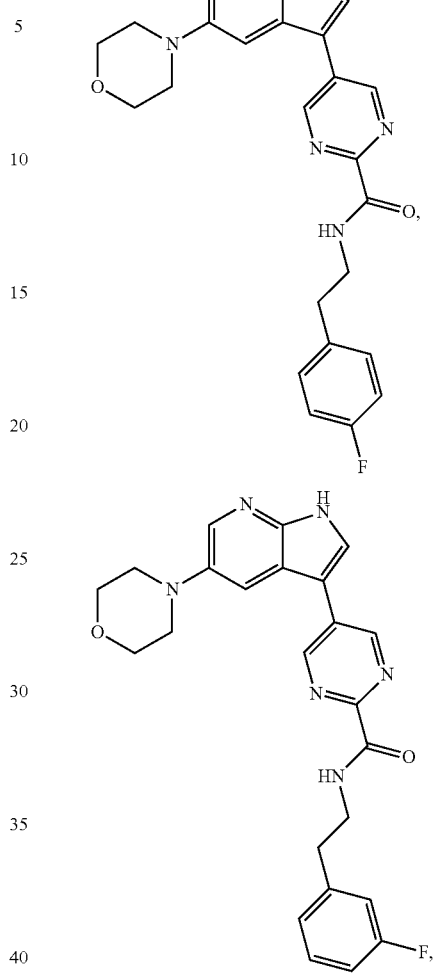
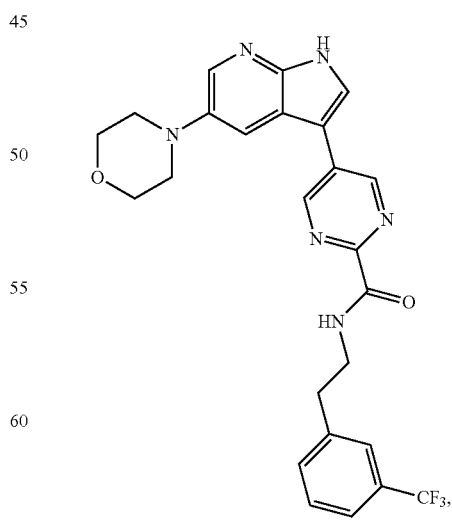

105
-continued
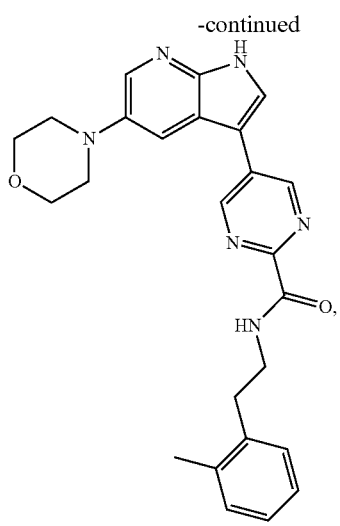
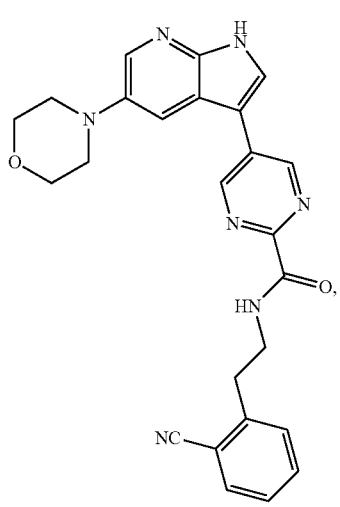
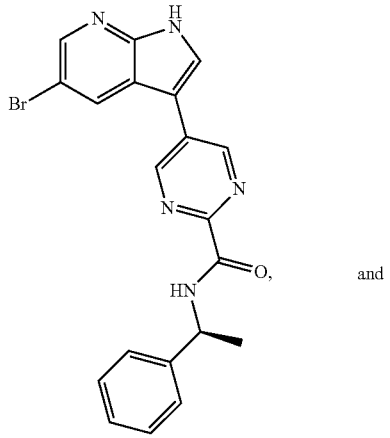
and
106
-continued
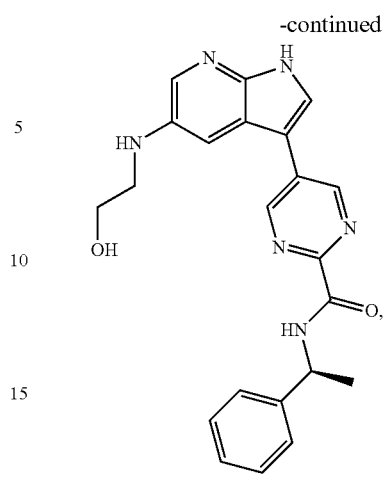
or a pharmaceutically acceptable salt thereof.
In particular aspects, the invention relates to a compound selected from:
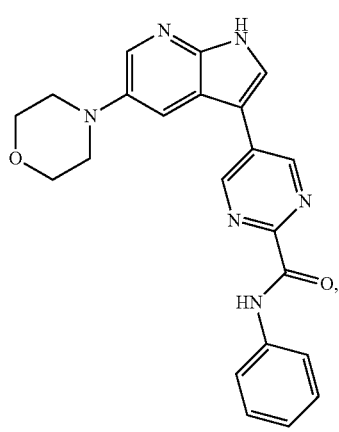
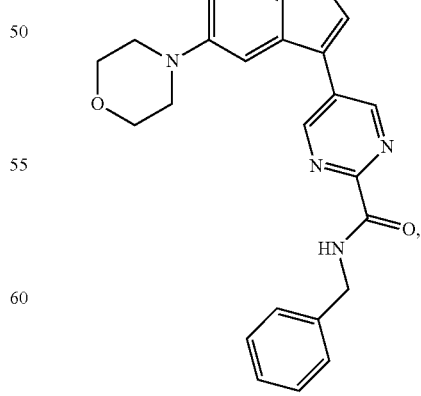

107
-continued
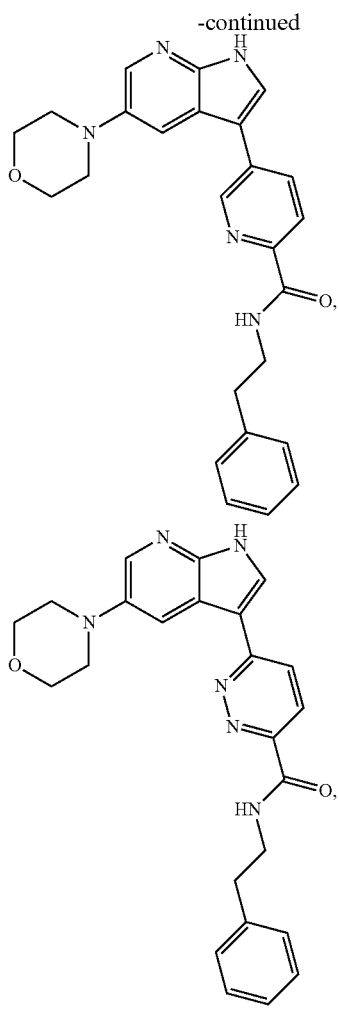
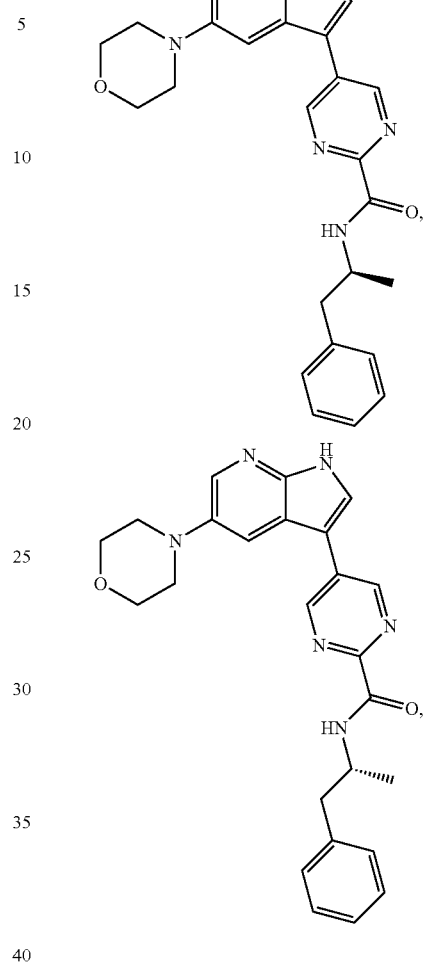
or a pharmaceutically acceptable salt thereof.
In further aspects, the invention relates to a compound selected from:
108
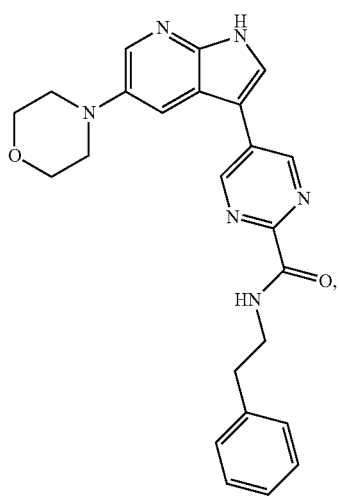
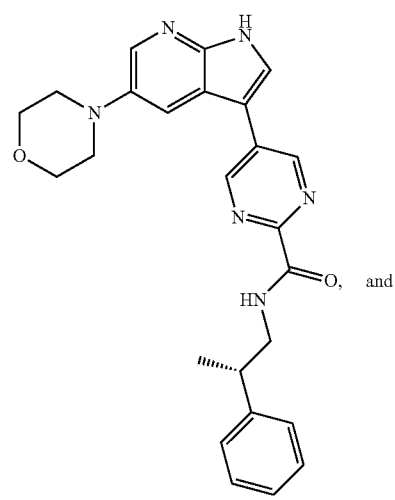

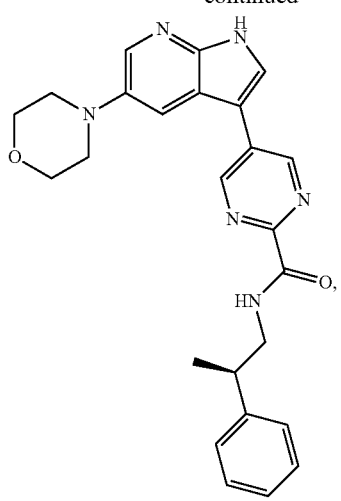
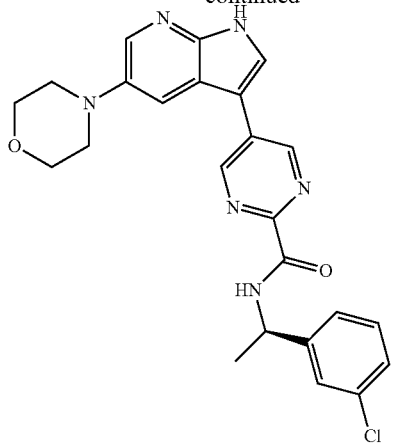
or a pharmaceutically acceptable salt thereof.
In yet other aspects, the invention relates to a compound selected from:
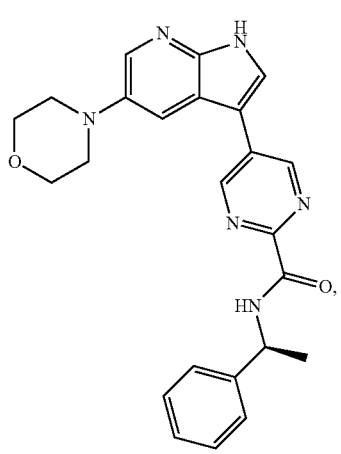
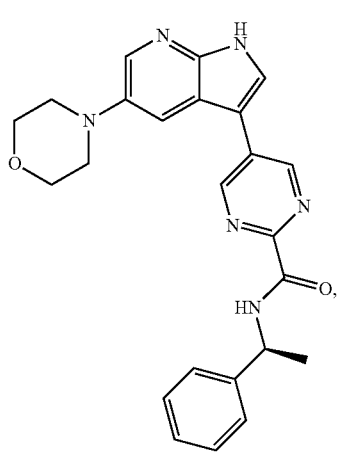
or a pharmaceutically acceptable salt thereof.
In still other aspects, the invention relates to a compound selected from:

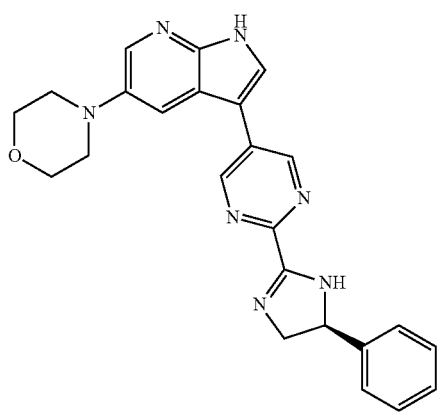
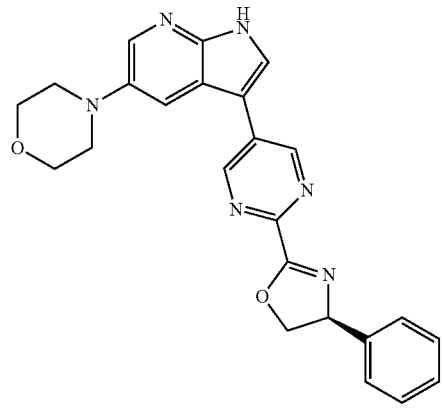
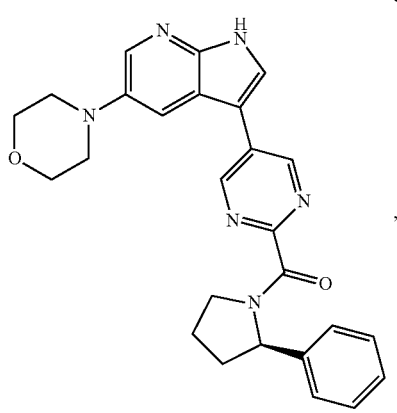
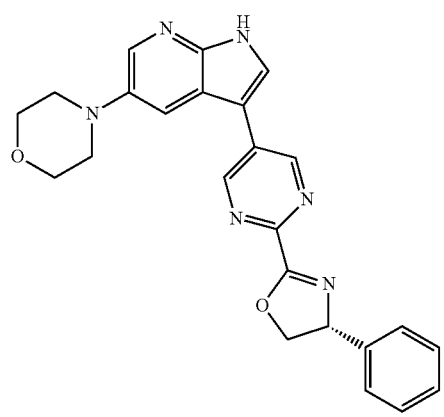
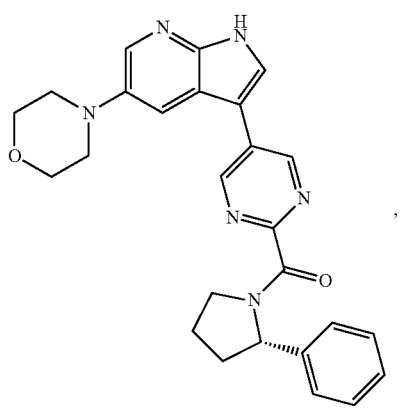
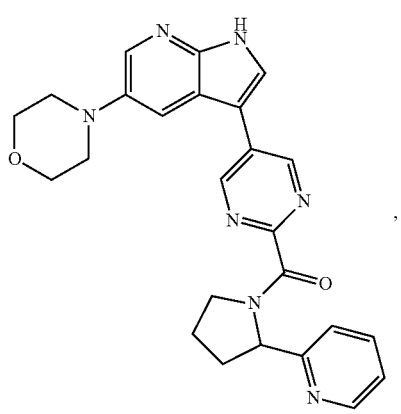
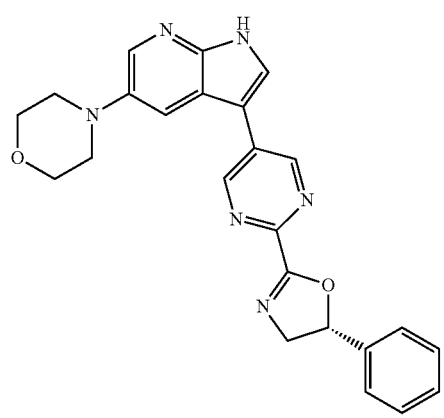
or a pharmaceutically acceptable salt thereof.
In yet other aspects, the invention relates to a compound selected from:

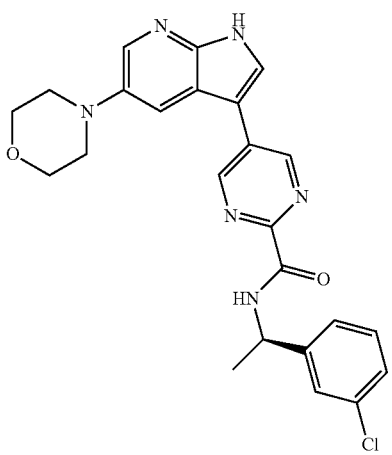

,

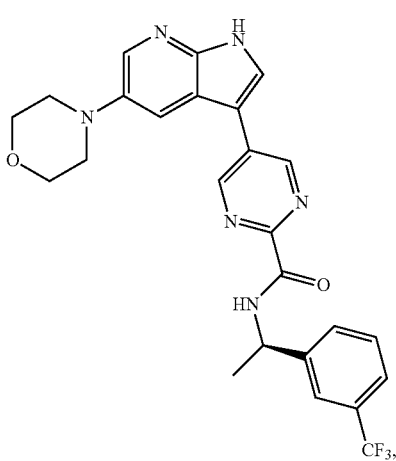

,

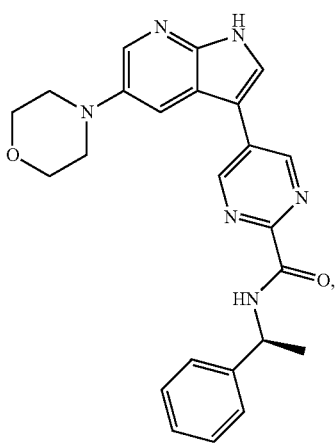

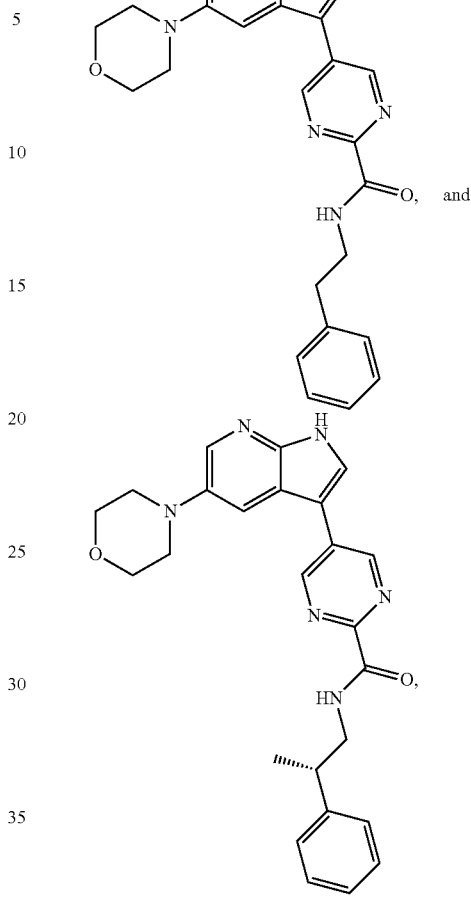

or a pharmaceutically acceptable salt thereof.

In certain embodiments, the invention relates to a pharmaceutical composition comprising any of the compounds described herein and a pharmaceutically acceptable diluent or excipient.

Exemplary Methods of Treatment

The compounds described herein are inhibitors of ERK and therefore may be useful for treating diseases wherein the underlying pathology is (at least in part) mediated by ERK. Such diseases include cancer and other diseases in which there is a disorder of cell proliferation, apoptosis, or differentiation.

In certain embodiments, the invention relates to a method of treating cancer in a subject in need thereof comprising administering to the subject any of the compounds described herein, or a pharmaceutically acceptable salt thereof. For example, the cancer may be selected from carcinoma (e.g., a carcinoma of the endometrium, bladder, breast, colon (e.g., colorectal carcinomas such as colon adenocarcinoma and colon adenoma)), sarcoma (e.g., a sarcoma such as Kaposi's, osteosarcoma, tumor of mesenchymal origin, for example fibrosarcoma or habdomyosarcoma), kidney, epidermis, liver, lung (e.g., adenocarcinoma, small cell lung cancer and non-small cell lung carcinomas), oesophagus, gall bladder, ovary, pancreas (e.g., exocrine pancreatic carcinoma), stomach, cervix, thyroid, nose, head and neck, prostate, and skin (e.g., squamous cell carcinoma), human breast cancers (e.g., primary breast tumors, node-negative breast cancer, invasive duct adenocarcinomas of the breast, non-endometrioid breast cancers), familial melanoma, and melanoma. Other examples of cancers that may be treated with a compound of the present invention include hematopoietic tumors of lymphoid lineage (e.g. leukemia, acute lymphocytic leukemia, mantle cell lymphoma, chronic lymphocytic leukaemia, B-cell lymphoma (such as diffuse large B cell lymphoma), T-cell lymphoma, multiple myeloma, Hodgkin's lymphoma, non-Hodgkin's lymphoma, hairy cell lymphoma, and Burkett's lymphoma; hematopoietic tumors of myeloid lineage, for example acute and chronic myelogenous leukemias, myelodysplastic syndrome, and promyelocytic leukemia. Other cancers include a tumor of the central or peripheral nervous system, for example astrocytoma, neuroblastoma, glioma or schwannoma; seminoma; teratocarcinoma; xeroderma pigmentosum; retinoblastoma; keratoctanthoma; and thyroid follicular cancer.

In particular embodiments, the treated cancer is selected from melanoma, pancreatic cancer, thryroid cancer, colorectal cancer, lung cancer, breast cancer, ovarian cancer, non-small cell lung cancer, liver cancer, head and neck cancer, bladder cancer, and acute myelogenous leukemia.

In some aspects, the subject is a mammal, for example, a human.

Further disclosed herein are methods of inhibiting ERK1 or ERK2, or both, in a cell comprising contacting said cell with any of the compounds described herein, or a pharmaceutically acceptable salt thereof, such that ERK1 or ERK2 or both enzymes are inhibited in said cell. For example, the cell is a cancer cell. In preferred embodiments, proliferation of the cell is inhibited or cell death is induced.

Further disclosed herein is a method of treating a disease treatable by inhibition of ERK in a patient, comprising administering to the patient in recognized need of such treatment, an effective amount any of the compounds described herein and/or a pharmaceutically acceptable salt thereof. Diseases treatable by inhibition of ERK include, for example, cancers and inflammatory diseases, and skin diseases. Further exemplary diseases include colon cancer, gastric cancer, leukemia, lymphoma, melanoma, pancreatic cancer, bladder cancer, liver cancer, head and neck cancer, rheumatoid arthritis, psoriasis, and eczema.

The methods of treatment of the invention comprise administering a compound of the invention, or a pharmaceutically acceptable salt thereof, to a subject in need thereof. Individual embodiments of the invention include methods of treating any one of the above mentioned disorders or diseases by administering an effective amount of a compound of the invention, or a pharmaceutically acceptable salt thereof, to a subject in need thereof.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-9}$ molar and $10^{-3}$ molar concentrations. A therapeutically effective amount in vivo may range depending on the route of administration, between about 0.1-500 mg/kg, between about 1-100 mg/kg, or between about 100-300 mg/kg.

Certain embodiments of the present invention include a method of modulating ERK activity in a subject comprising administering to the subject a compound of the invention, or a pharmaceutically acceptable salt thereof. Additional embodiments of the present invention provide a method for the treatment of a disorder or a disease mediated by ERK in a subject in need thereof, comprising administering to the subject the compound of formula (I), (II), or (III), or a pharmaceutically acceptable salt thereof. Other embodiments of the present invention provide a method of treating a disorder or a disease mediated by ERK, in a subject in need of treatment thereof comprising administering a compound of the invention, or a pharmaceutically acceptable salt thereof, wherein the disorder or the disease is selected from carcinomas with genetic aberrations that activate the ERK activity. These include, but are not limited to, cancers.

The present invention also provides the use of a compound of the invention, or a pharmaceutically acceptable salt thereof, for the treatment of a disorder or disease mediated by ERK1 or ERK2.

In some embodiments, a compound of the invention, or a pharmaceutically acceptable salt thereof, is used for the treatment of a disorder or a disease mediated by ERK.

Yet other embodiments of the present invention provide a compound according to Formula (I), (II), or (III), or a pharmaceutically acceptable salt thereof, for use as a medicament.

Still other embodiments of the present invention encompass the use of a compound of Formula (I), (II), or (III), or a pharmaceutically acceptable salt thereof, in the manufacture of a medicament for the treatment of a disorder or disease mediated by ERK.

Exemplary Combinations

The compounds of the present invention may be conjointly administered either simultaneously with, or before or after, one or more other therapeutic agents. The compounds of the present invention may be administered separately, by the same or different route of administration, or together in the same pharmaceutical composition as the other agents.

In some embodiments, the invention provides a product comprising a compound of the invention, or a pharmaceutically acceptable salt thereof, and at least one other therapeutic agent as a combined preparation for simultaneous, separate or sequential use in therapy. In some such embodiments, the therapy is the treatment of a disease or condition mediated by ERK inhibition. Products provided as a combined preparation include a composition comprising the compound of the present invention and the other therapeutic agent(s) together in the same pharmaceutical composition, or the compound of the present invention and the other therapeutic agent(s) in separate form, e.g., in the form of a kit. In certain embodiments, the invention provides a pharmaceutical composition comprising a compound of the invention, or a pharmaceutically acceptable salt thereof, and another therapeutic agent(s). Optionally, the pharmaceutical composition may comprise a pharmaceutically acceptable excipient, as described above.

In some embodiments, the invention provides a kit comprising two or more separate pharmaceutical compositions, at least one of which contains a compound of the invention, or a pharmaceutically acceptable salt thereof. In some such embodiments, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration. In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g., in the case of a kit comprising the compound of the invention and the other therapeutic agent); (ii) by the physician themselves (or under the guidance of the physician) shortly before administration; (iii) in the patient themselves, e.g., during sequential administration of the compound of the invention and the other therapeutic agent. Accordingly, the invention provides the use of a compound of the invention, or a pharmaceutically acceptable salt thereof, for treating a disease or condition mediated by inhibition of ERK, wherein the medicament is prepared for administration with another therapeutic agent. The invention also provides the use of another therapeutic agent for treating a disease or condition mediated by inhibition of ERK, wherein the medicament is administered with a compound of the present invention. The invention also provides a compound of the invention, or a pharmaceutically acceptable salt thereof, for use in a method of treating a disease or condition mediated by ERK inhibition, wherein the compound of the invention, or a pharmaceutically acceptable salt thereof, is prepared for administration with another therapeutic agent. The invention also provides another therapeutic agent for use in a method of treating a disease or condition mediated by ERK inhibition, wherein the other therapeutic agent is prepared for administration with a compound of the invention, or a pharmaceutically acceptable salt thereof. The invention also provides a compound of the invention, or a pharmaceutically acceptable salt thereof, for use in a method of treating a disease or condition mediated by ERK inhibition, wherein the compound of the invention, or a pharmaceutically acceptable salt thereof, is administered with another therapeutic agent. The invention also provides another therapeutic agent for use in a method of treating a disease or condition mediated by ERK inhibition, wherein the other therapeutic agent is administered with a compound of the invention, or a pharmaceutically acceptable salt thereof. The invention also provides the use of a compound of the invention, or a pharmaceutically acceptable salt thereof, for treating a disease or condition mediated by ERK, wherein the patient has previously (e.g. within 24 hours) been treated with another therapeutic agent. The invention also provides the use of another therapeutic agent for treating a disease or condition mediated by ERK, wherein the patient has previously (e.g., within 24 hours) been treated with a compound of the invention, or a pharmaceutically acceptable salt thereof.

In some embodiments, the other therapeutic agent is selected from an anti-inflammatory, anti-proliferative, chemotherapeutic agent, radiotherapeutic agent, immunosuppressant, anti-cancer, cytotoxic agent or kinase inhibitor other than a compound of the present invention, or salt thereof. Further examples of agents that may be administered in combination with the compounds of the invention include, but are not limited to, a PTK inhibitor, cyclosporin A, CTLA4-lg, antibodies selected from anti-iCAM-3, anti-TL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal anti-inflammatory drugs, steroids, gold compounds, antiproliferative agents, FK506, mycophenolate mofetil, cytotoxic drugs, TNF-a inhibitors, anti-TNF antibodies or soluble TNF receptor, rapamycin, mTOR inhibitors, leflunimide, cyclooxygenase-2 inhibitors, paclitaxel, cisplatin, carboplatin, doxorubicin, carminomycin, daunorubicin, aminopterin, methotrexate, methopterin, mitomycin C, ecteinascidin 743, porfiromycin, 5-fluorouracii, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, B-Raf inhibitor, MEK inhibitor, PI3K inhibitor, HSP90 inhibitor, CDK1 inhibitor, CDK2 inhibitor, CDK4 inhibitor, CDK5 inhibitor, CDK6 inhibitor, CDK7 inhibitor, CDK8 inhibitor, CDK9 inhibitor, EGFR inhibitor, FGFR inhibitor, PDGFR inhibitor, Her2 neu inhibitor, FLT3 inhibitor, Antagonists of androgen, glucocorticoid and prosterone receptors, S O inhibitor, WNT inhibitor, Bel inhibitor, IAP inhibitor, cl inhibitor, MD 2 inhibitor, p52 inhibitor, proteosome inhibitors (Velcade), or derivatives thereof.

In some embodiments, a compound of the present invention may also be used in combination with other agents, e.g., an additional protein kinase inhibitor that is or is not a compound of the invention, for treatment of a protein kinase-associated disorder in a subject. By the term "combination" is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

The compounds of the invention may be administered, simultaneously or sequentially, with an anti-inflammatory, anti-proliferative, chemotherapeutic agent, immunosuppressant, anti-cancer, cytotoxic agent or kinase inhibitor other than a compound of the Formula I or pharmaceutically acceptable salt thereof. Further examples of agents that may be administered in combination with the compounds of the invention include, but are not limited to, a CDK inhibitor, a PTK inhibitor, cyclosporin A, CTLA4-lg, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal anti-inflammatory drugs, steroids, gold compounds, antiproliferative agents, FK506, mycophenolate mofetil, cytotoxic drugs, TNF-ct inhibitors, anti-TNF antibodies or soluble TNF receptor, rapamycin, leflunimide, cyclooxygenase-2 inhibitors, paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

A compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention may comprise an additional agent as described herein. Each component may be present in individual compositions, combination compositions, or in a single composition.

Pharmaceutical Compositions and Administration Thereof

The compositions and methods disclosed herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a disclosed compound and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an ointment or cream.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary, or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups, and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697, and 2005/004074; and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1% to about 99.5% (more preferably, about 0.5% to about 90.0%) of active ingredient in combination with a pharmaceutically acceptable carrier.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXEMPLIFICATION

Synthetic Protocols

TABLE 2

| Compound No | Structure |
|---|---|
| 6 | 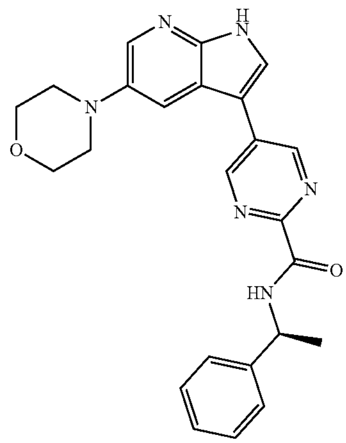 [SMILES: C[C@H](NC(=O)c1ncc(-c2c[nH]c3ncc(N4CCOCC4)cc23)cn1)c1ccccc1] |
| 7 | 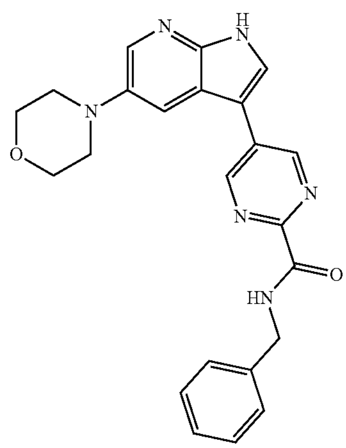 [SMILES: O=C(NCc1ccccc1)c1ncc(-c2c[nH]c3ncc(N4CCOCC4)cc23)cn1] |
| 8 | 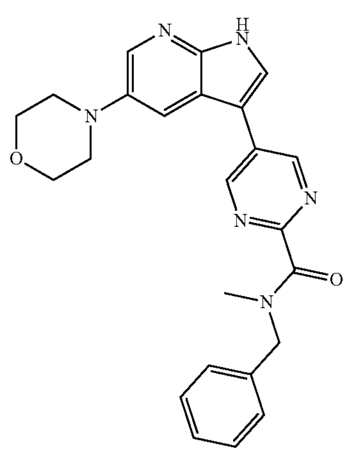 [SMILES: CN(Cc1ccccc1)C(=O)c1ncc(-c2c[nH]c3ncc(N4CCOCC4)cc23)cn1] |

TABLE 2-continued

| Compound No | Structure |
|---|---|
| 9 | 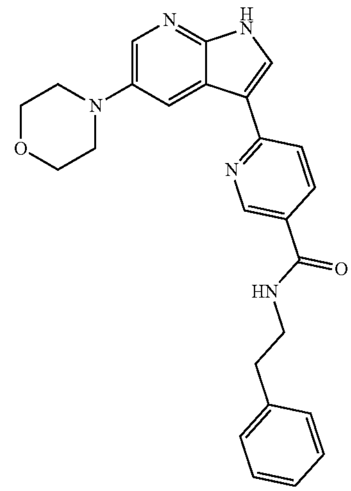 [SMILES: O=C(NCCc1ccccc1)c1ccc(-c2c[nH]c3ncc(N4CCOCC4)cc23)nc1] |
| 10 | 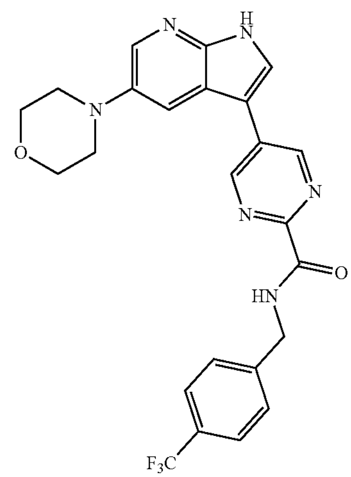 [SMILES: O=C(NCc1ccc(C(F)(F)F)cc1)c1ncc(-c2c[nH]c3ncc(N4CCOCC4)cc23)cn1] |
| 11 | 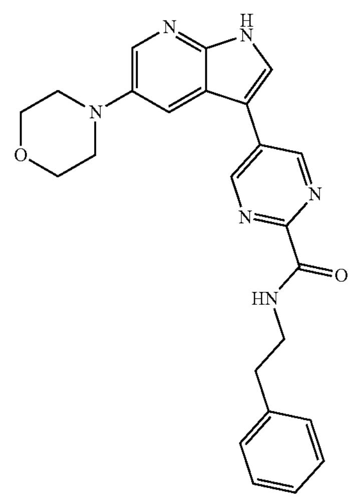 [SMILES: O=C(NCCc1ccccc1)c1ncc(-c2c[nH]c3ncc(N4CCOCC4)cc23)cn1] |

TABLE 2-continued

| Compound No | Structure |
|---|---|
| 13 | (structure) |
| 15 | (structure) |
| 17 | (structure) |
| 18 | (structure) |
| 19 | (structure) |
| 20 | (structure) |

TABLE 2-continued
| Compound No | Structure |
|---|---|
| 21 | 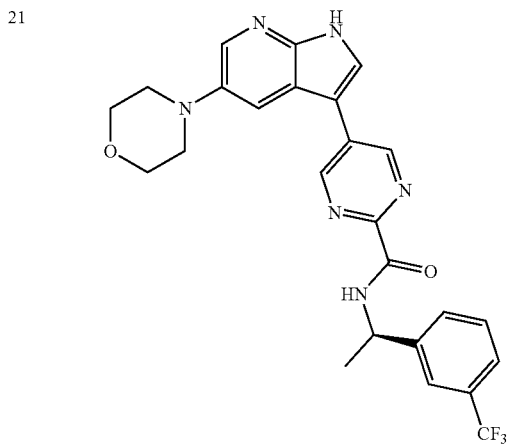 |
| 22 | 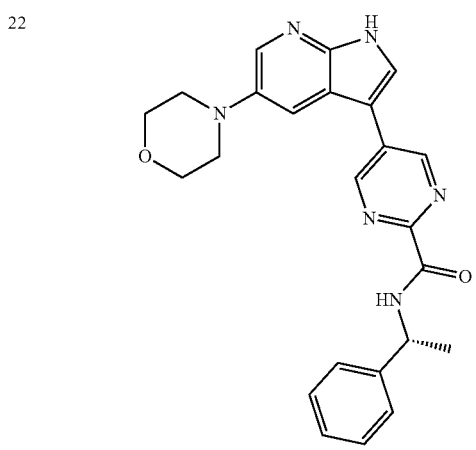 |
| 23 | 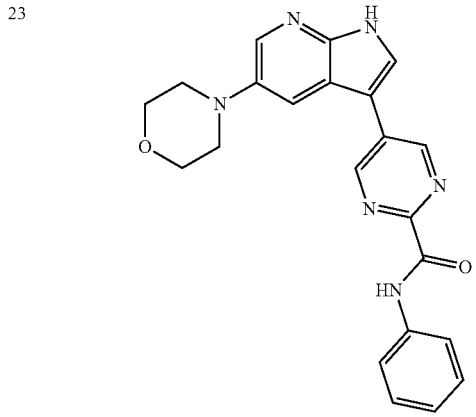 |
| 24 | 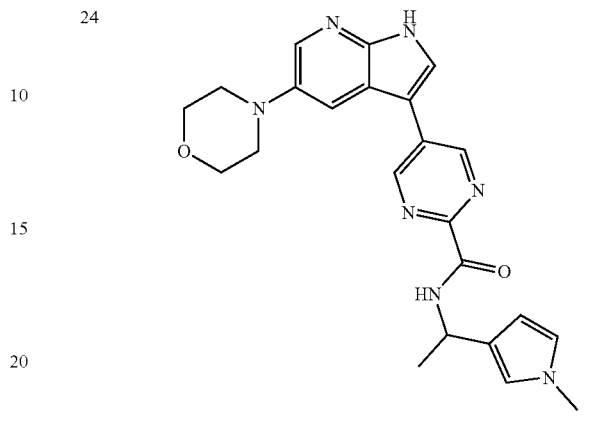 |
| 25 | 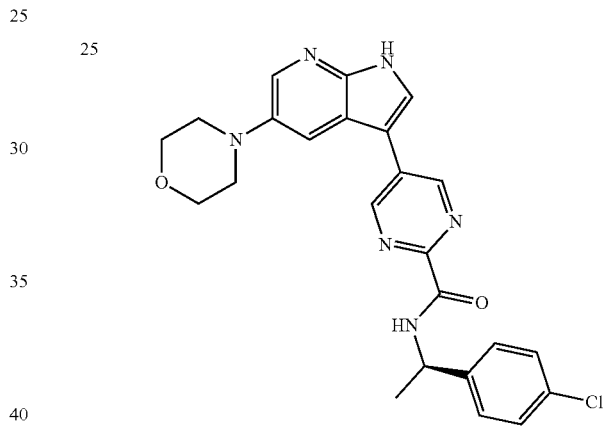 |
| 26 | 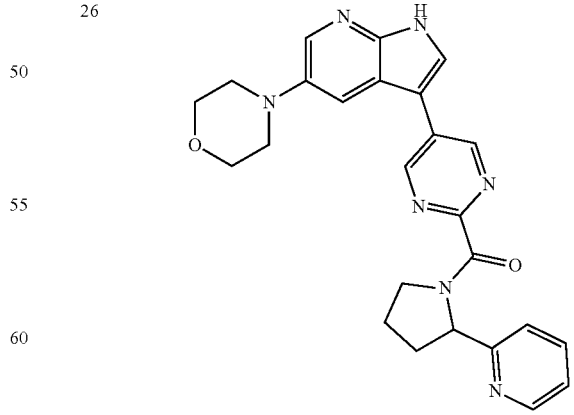 |

TABLE 2-continued
| Compound No | Structure |
|---|---|
| 27 | 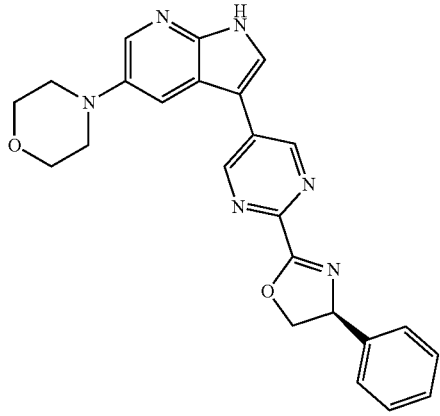 [SMILES: c1ccc([C@H]2COC(c3ncc(-c4c[nH]c5ncc(N6CCOCC6)cc45)cn3)=N2)cc1] |
| 28 | 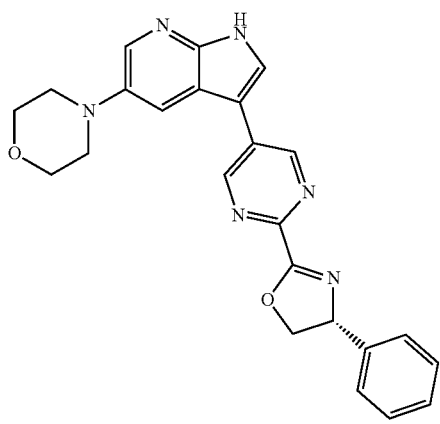 [SMILES: c1ccc([C@@H]2COC(c3ncc(-c4c[nH]c5ncc(N6CCOCC6)cc45)cn3)=N2)cc1] |
| 29 | 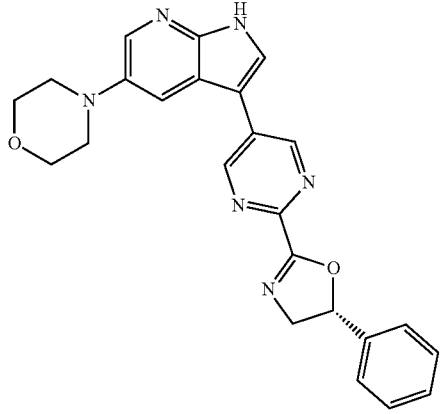 [SMILES: c1ccc([C@@H]2CN=C(c3ncc(-c4c[nH]c5ncc(N6CCOCC6)cc45)cn3)O2)cc1] |
| 30 | 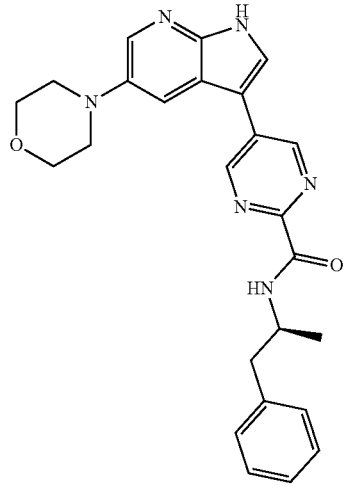 [SMILES: C[C@@H](Cc1ccccc1)NC(=O)c1ncc(-c2c[nH]c3ncc(N4CCOCC4)cc23)cn1] |
| 31 | 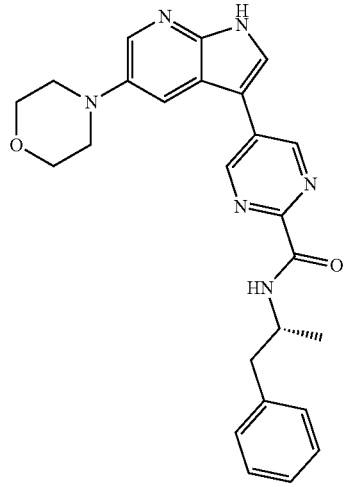 [SMILES: C[C@H](Cc1ccccc1)NC(=O)c1ncc(-c2c[nH]c3ncc(N4CCOCC4)cc23)cn1] |
| 32 | 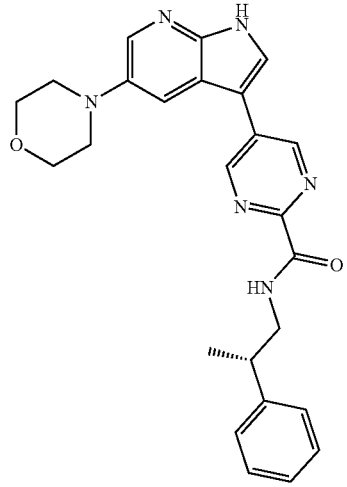 [SMILES: C[C@H](CNC(=O)c1ncc(-c2c[nH]c3ncc(N4CCOCC4)cc23)cn1)c1ccccc1] |

TABLE 2-continued

| Compound No | Structure |
|---|---|
| 33 | (structure) |
| 34 | (structure) |
| 35 | (structure) |
| 36 | (structure) |
| 37 | (structure) |
| 38 | (structure) |

TABLE 2-continued

| Compound No | Structure |
|---|---|
| 39 | 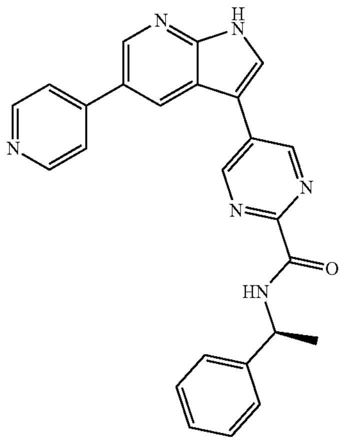 [SMILES: C[C@H](NC(=O)c1ncc(-c2c[nH]c3ncc(-c4ccncc4)cc23)cn1)c1ccccc1] |
| 40 | 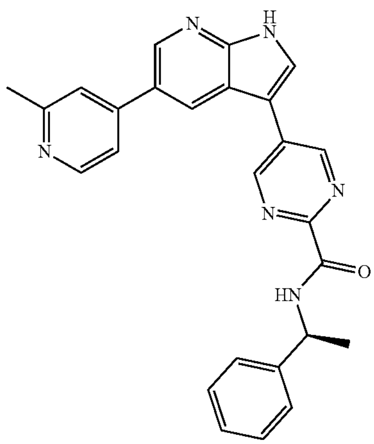 [SMILES: Cc1cc(-c2cnc3[nH]cc(-c4cnc(C(=O)N[C@@H](C)c5ccccc5)nc4)c3c2)ccn1] |
| 41 | 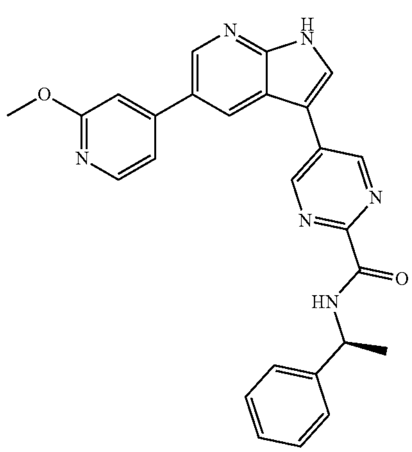 [SMILES: COc1cc(-c2cnc3[nH]cc(-c4cnc(C(=O)N[C@@H](C)c5ccccc5)nc4)c3c2)ccn1] |
| 42 | 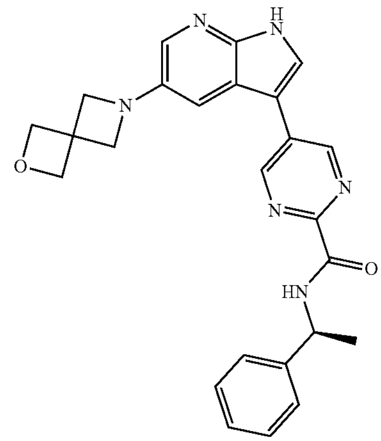 [SMILES: C[C@H](NC(=O)c1ncc(-c2c[nH]c3ncc(N4CC5(COC5)C4)cc23)cn1)c1ccccc1] |
| 43 | 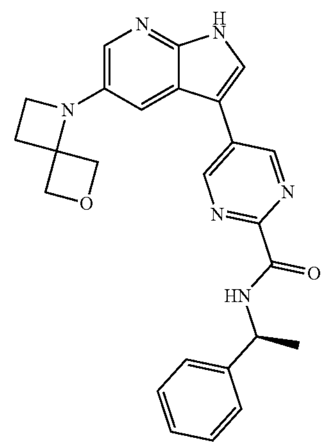 [SMILES: C[C@H](NC(=O)c1ncc(-c2c[nH]c3ncc(N4CCC45COC5)cc23)cn1)c1ccccc1] |
| 44 | 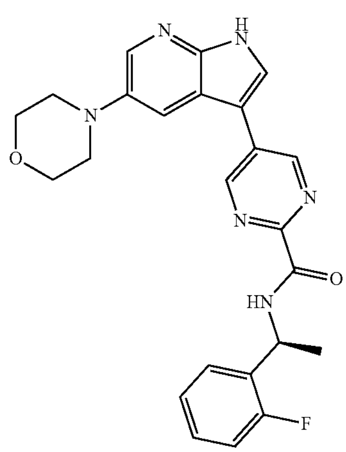 [SMILES: C[C@H](NC(=O)c1ncc(-c2c[nH]c3ncc(N4CCOCC4)cc23)cn1)c1ccccc1F] |

TABLE 2-continued

| Compound No | Structure |
|---|---|
| 45 | (7-azaindole-morpholine-pyrimidine-C(O)NH-CH(CH3)-(2-Cl-phenyl)) |
| 46 | (7-azaindole-morpholine-pyrimidine-C(O)NH-CH(CH3)-(2-OMe-phenyl)) |
| 47 | (7-azaindole-morpholine-pyrimidine-C(O)NH-CH(CF3)-phenyl) |
| 48 | (7-azaindole-morpholine-pyrimidine-C(O)NH-CH(CH3)-(2-CN-phenyl)) |
| 49 | (7-azaindole-morpholine-pyrimidine-C(O)NH-CH(cyclopropyl)-phenyl) |
| 50 | (7-azaindole-morpholine-pyrimidine-C(O)NH-CH(CH3)-(3-Me-phenyl)) |

TABLE 2-continued
| Compound No | Structure |
|---|---|
| 51 | 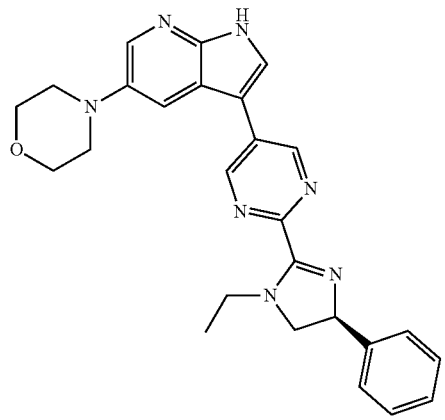 [SMILES: CCN1C[C@H](c2ccccc2)N=C1c1ncc(-c2c[nH]c3ncc(N4CCOCC4)cc23)cn1] |
| 52 | 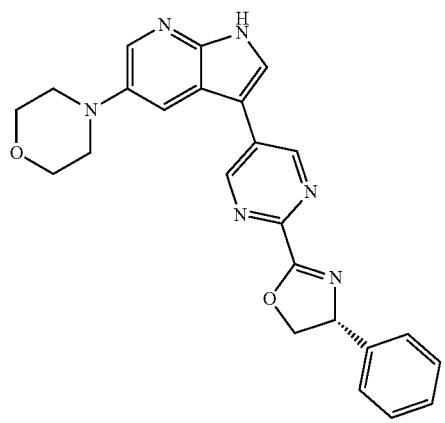 [SMILES: c1ccc([C@@H]2COC(c3ncc(-c4c[nH]c5ncc(N6CCOCC6)cc45)cn3)=N2)cc1] |
| 53 | 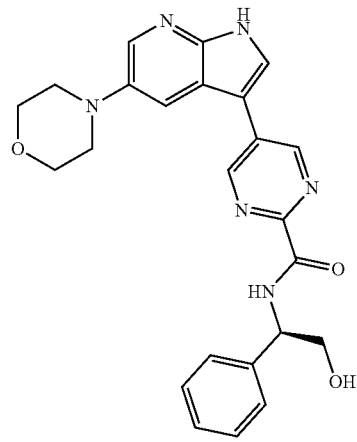 [SMILES: O=C(N[C@@H](CO)c1ccccc1)c1ncc(-c2c[nH]c3ncc(N4CCOCC4)cc23)cn1] |
| 54 | 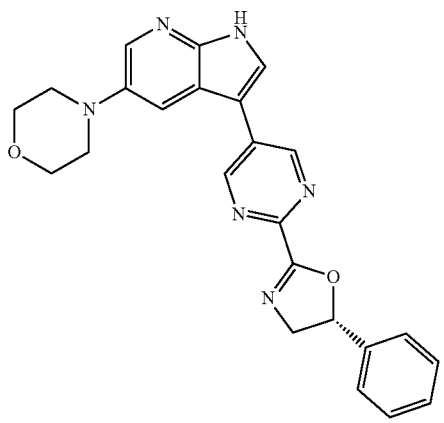 [SMILES: c1ccc([C@@H]2CN=C(c3ncc(-c4c[nH]c5ncc(N6CCOCC6)cc45)cn3)O2)cc1] |
| 55 | 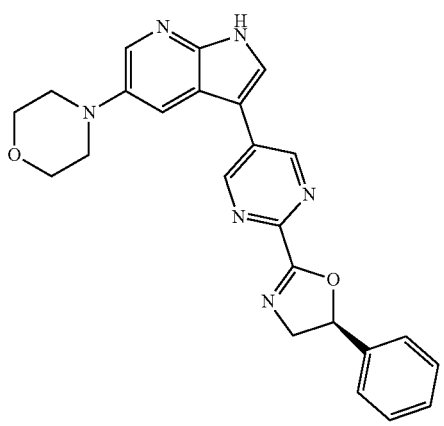 [SMILES: c1ccc([C@H]2CN=C(c3ncc(-c4c[nH]c5ncc(N6CCOCC6)cc45)cn3)O2)cc1] |
| 56 | 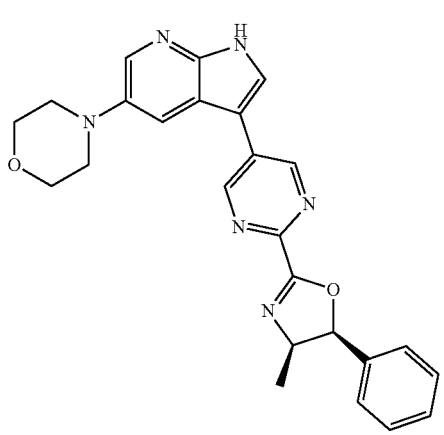 [SMILES: C[C@H]1N=C(c2ncc(-c3c[nH]c4ncc(N5CCOCC5)cc34)cn2)O[C@H]1c1ccccc1] |

TABLE 2-continued
| Compound No | Structure |
|---|---|
| 57 | 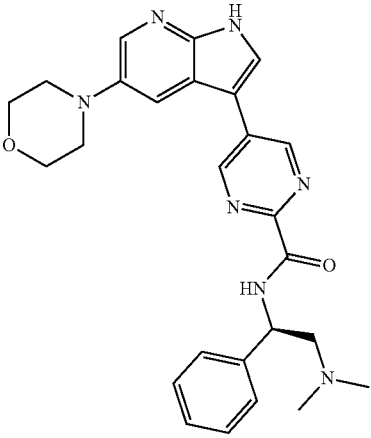 [SMILES: CN(C)C[C@H](NC(=O)c1ncc(-c2c[nH]c3ncc(N4CCOCC4)cc23)cn1)c1ccccc1] |
| 58 | 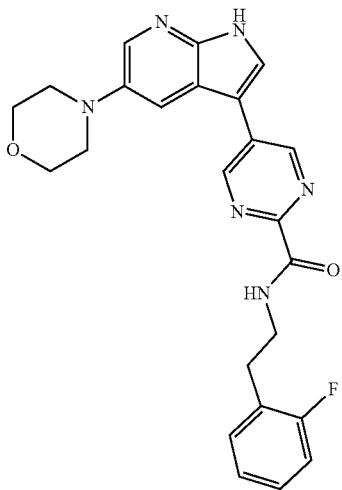 [SMILES: O=C(NCCc1ccccc1F)c1ncc(-c2c[nH]c3ncc(N4CCOCC4)cc23)cn1] |
| 59 | 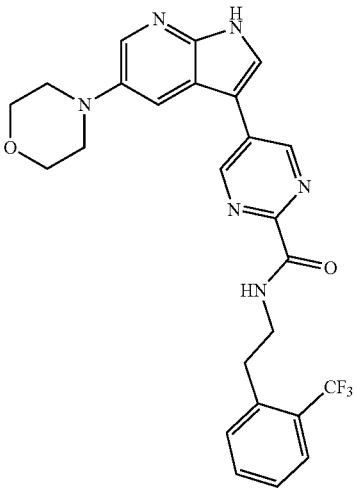 [SMILES: O=C(NCCc1ccccc1C(F)(F)F)c1ncc(-c2c[nH]c3ncc(N4CCOCC4)cc23)cn1] |
| 60 | 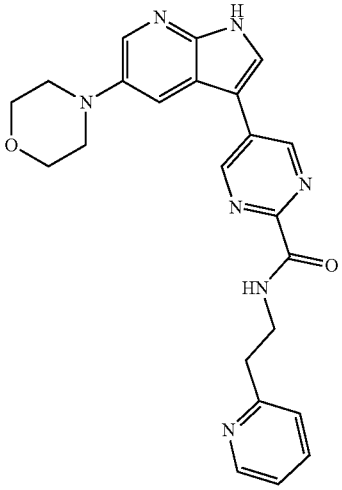 [SMILES: O=C(NCCc1ccccn1)c1ncc(-c2c[nH]c3ncc(N4CCOCC4)cc23)cn1] |
| 61 | 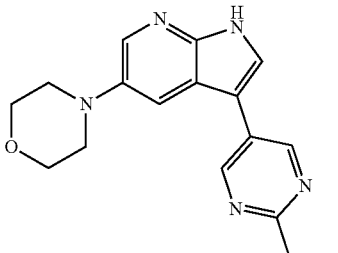 |
| 62 | 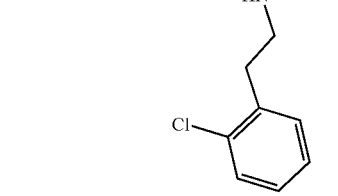 |

TABLE 2-continued
| Compound No | Structure |
|---|---|
| 63 | 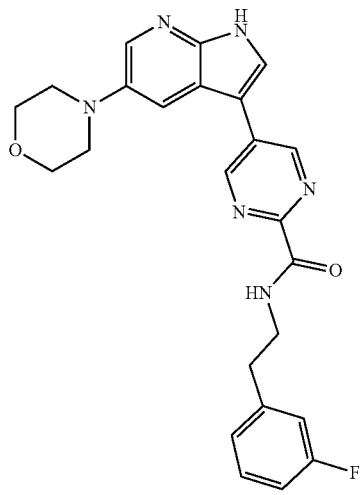 [SMILES: O=C(NCCc1cccc(F)c1)c1ncc(-c2c[nH]c3ncc(N4CCOCC4)cc23)cn1] |
| 64 | 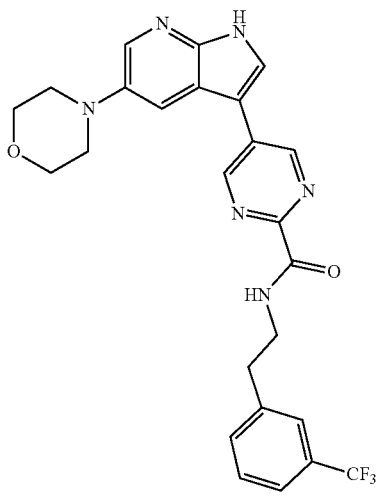 [SMILES: O=C(NCCc1cccc(C(F)(F)F)c1)c1ncc(-c2c[nH]c3ncc(N4CCOCC4)cc23)cn1] |
| 65 | 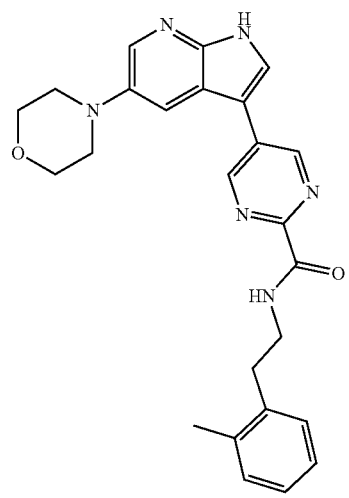 [SMILES: Cc1ccccc1CCNC(=O)c1ncc(-c2c[nH]c3ncc(N4CCOCC4)cc23)cn1] |
| 66 | 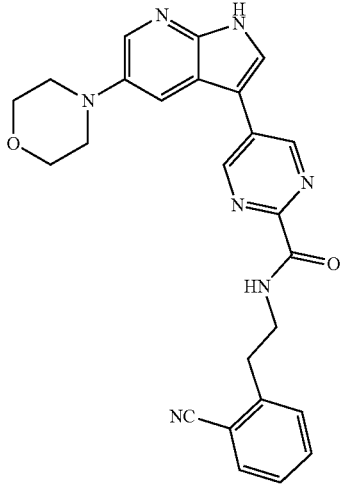 [SMILES: N#Cc1ccccc1CCNC(=O)c1ncc(-c2c[nH]c3ncc(N4CCOCC4)cc23)cn1] |
| 67 | 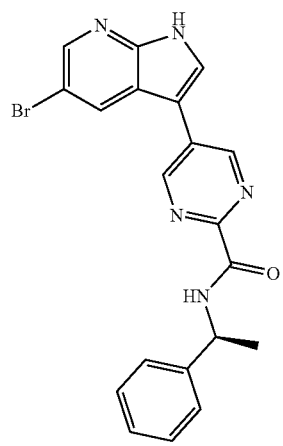 [SMILES: C[C@H](NC(=O)c1ncc(-c2c[nH]c3ncc(Br)cc23)cn1)c1ccccc1] |
| 68 | 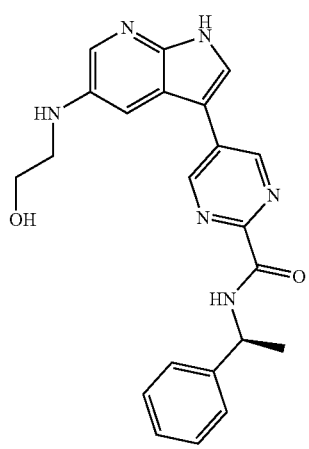 [SMILES: C[C@H](NC(=O)c1ncc(-c2c[nH]c3ncc(NCCO)cc23)cn1)c1ccccc1] |

Example 1: Synthesis of Compounds 6 Through 10, 13, 15, 17 Through 29, 44 Through 47, and 51 Through 57

General Route for Example 1

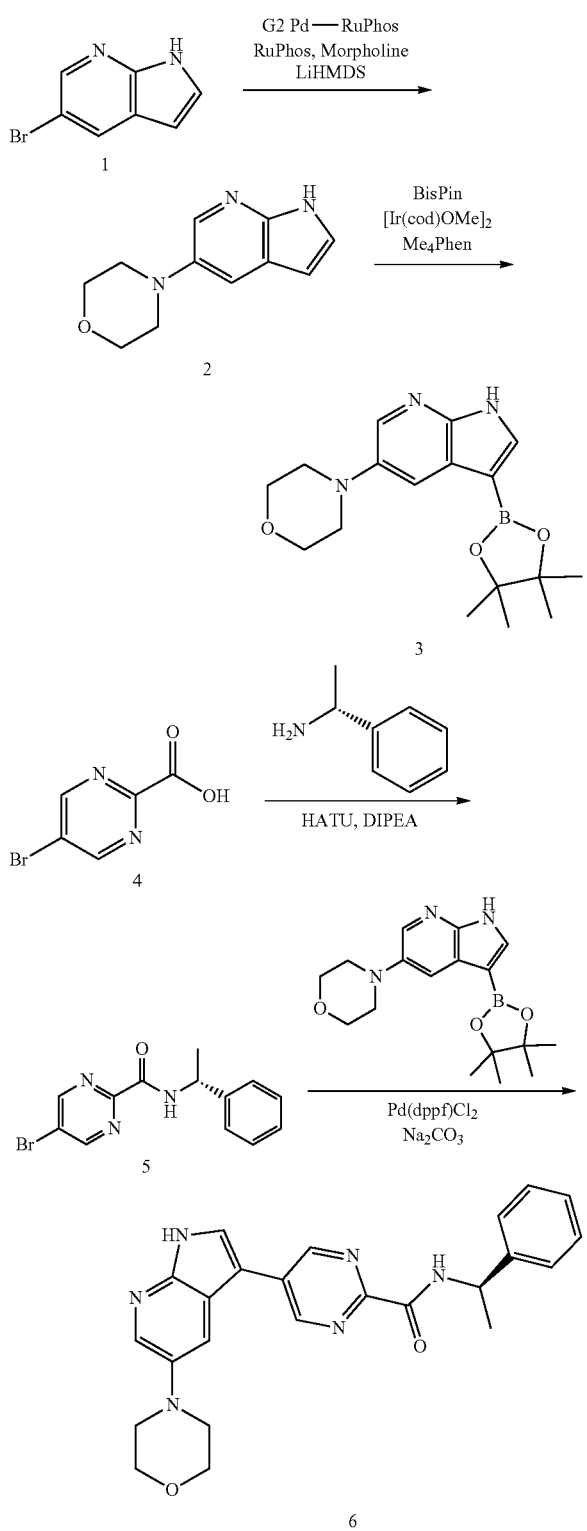

Preparation of Compound 2

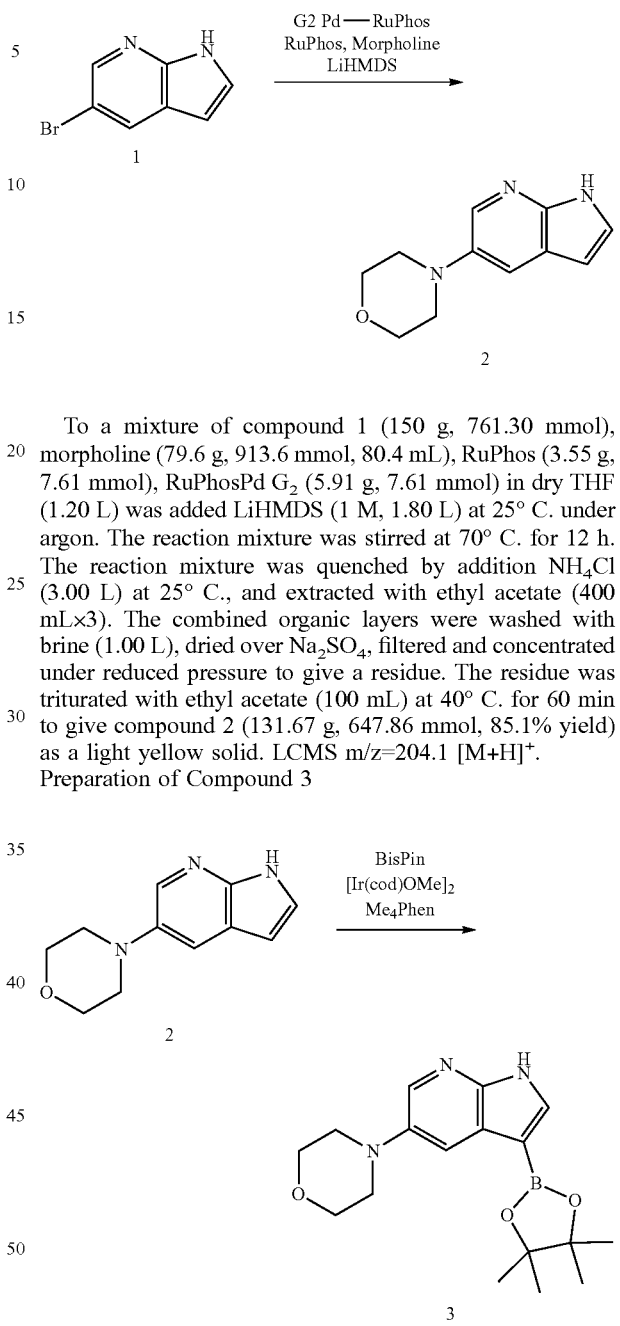

To a mixture of compound 1 (150 g, 761.30 mmol), morpholine (79.6 g, 913.6 mmol, 80.4 mL), RuPhos (3.55 g, 7.61 mmol), RuPhosPd $G_2$ (5.91 g, 7.61 mmol) in dry THF (1.20 L) was added LiHMDS (1 M, 1.80 L) at 25° C. under argon. The reaction mixture was stirred at 70° C. for 12 h. The reaction mixture was quenched by addition $NH_4Cl$ (3.00 L) at 25° C., and extracted with ethyl acetate (400 mL×3). The combined organic layers were washed with brine (1.00 L), dried over $Na_2SO_4$, filtered and concentrated under reduced pressure to give a residue. The residue was triturated with ethyl acetate (100 mL) at 40° C. for 60 min to give compound 2 (131.67 g, 647.86 mmol, 85.1% yield) as a light yellow solid. LCMS m/z=204.1 $[M+H]^+$.

Preparation of Compound 3

Under an inert nitrogen atmosphere, a solution of $[Ir(cod)OMe]_2$ (2.97 g, 4.48 mmol) and $Me_4Phen$ (2.12 g, 8.95 mmol) in dry THF (600 mL) was treated with BisPin (170.6 g, 671.6 mmol) in dry THF (200 mL). The reaction mixture was stirred at 80° C. for 30 min. Then to the reaction mixture was added a solution of compound 2 (91.0 g, 447.75 mmol) in dry THF (300 mL). The reaction mixture was stirred at 80° C. for 12 h. The reaction mixture was concentrated under reduced pressure to give brown oil. The brown oil was dissolved in 6.00 L of MTBE and filtered through 100 g of silica gel. The plug was washed with 400 mL of MTBE (×3) and the filtrate was concentrated under reduced pressure to give a brown oil. The brown oil was triturated with methanol (80.0 mL) at 40° C. for 60 min to give compound 3 (79.3 g, 236.88 mmol, 52.91% yield) as a white solid. ¹H NMR: (400 MHz, DMSO) δ 11.7-11.9 (m, 1H), 8.08 (d, 1H, J=2.7 Hz), 7.70 (d, 1H, J=2.6 Hz), 7.6-7.6 (m, 1H), 3.8-3.8 (m, 4H), 3.0-3.1 (m, 4H), 1.2-1.3 (m, 12H) ppm. LCMS m/z=415.2 [M+H]⁺.

General Procedure A and Preparation of Compound 5

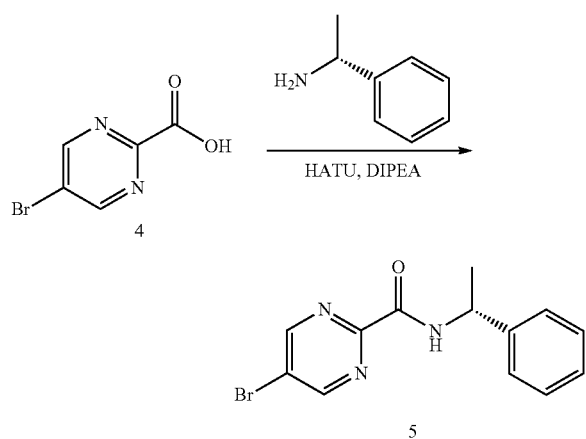

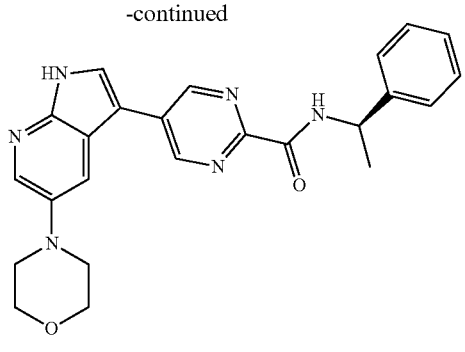

6

To a solution of 5-bromopyrimidine-2-carboxylic acid (compound 4, 15.0 g, 73.89 mmol, 1.00 eq) in DCM (50.0 mL) was added oxalyl chloride (12.2 g, 96.1 mmol, 8.41 mL, 1.30 eq) and DMF (54.0 mg, 738.9 μmol, 56.8 μL, 0.01 eq) at 0° C., and the mixture was stirred at 20° C. for 2 hours. The mixture was then concentrated under vacuum to give the residue that was added to a mixture of (R)-1-phenylethan-1-amine (9.85 g, 81.3 mmol, 10.5 mL, 1.10 eq) and TEA (16.5 g, 162.6 mmol, 22.6 mL, 2.20 eq) in DCM (100.0 mL). The mixture was stirred at 20° C. for 3 hours. The resulting mixture was concentrated under vacuum, and water added (100.0 mL) to the residue which was then extracted with ethyl acetate (100.0 mL, 3 times). The combined organic layers were dried over Na₂SO₄, filtered and concentrated under reduced pressure to give crude compound 5 (14.0 g) as a white solid that was used directly in subsequent steps without purification. ¹H NMR: (400 MHz, CDCl₃) δ 8.91 (s, 2H), 8.12 (br d, J=7.2 Hz, 1H), 7.47-7.33 (m, 4H), 7.33-7.27 (m, 1H), 5.48-5.35 (m, 1H), 1.65 (d, J=7.2 Hz, 3H) ppm. LCMS m/z=308.0 [M+H]⁺.

General Procedure B and Preparation of Compound 6

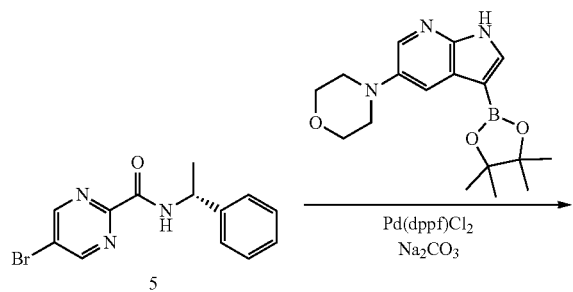

(R)-5-bromo-N-(1-phenylethyl)pyrimidine-2-carboxamide (compound 5) (0.08 g, 0.26 mmol), 4-(3-(4,4,5,5-tetramethyl-1,3-dioxolan-2-yl)-1H-pyrrolo[2,3-b]pyridin-5-yl)morpholine (compound 3) (0.103 g, 0.31 mmol), and Pd(dppf)Cl₂ (0.02 g, 0.03 mmol) were combined in a vial which was then evacuated and backfilled with nitrogen. Dioxane (2 mL) and 2M aqueous Na₂CO₃ (0.4 mL) were added and the resulting suspension was heated to 100° C. for 12 h. The mixture was cooled to ambient temperature, diluted with DCM (5 mL), 0.2 g of Quadrapure-TU® was added and stirring continued for 2 h. The mixture was then filtered, concentrated onto silica and purified via silica gel chromatography eluting with a gradient of 0-20% MeOH in DCM. (R)-5-(5-morpholino-1H-pyrrolo[2,3-b]pyridin-3-yl)-N-(1-phenylethyl)pyrimidine-2-carboxamide (compound 6) was isolated as a yellow solid (0.021 g, 0.15 mmol, 19% yield). ¹H NMR: (300 MHz, Methanol-d₄) δ 9.24 (s, 2H), 8.17 (d, J=2.6 Hz, 1H), 7.99 (s, 1H), 7.91 (d, J=2.6 Hz, 1H), 7.50-7.40 (m, 2H), 7.40-7.31 (m, 2H), 7.28-7.19 (m, 1H), 5.30 (q, J=7.0 Hz, 1H), 3.94-3.81 (m, 5H), 3.24-3.16 (m, 4H), 1.63 (d, J=7.0 Hz, 3H) ppm. LCMS m/z=429.2 [M+H]⁺.

Preparation of Compound 7

Compound 7 was prepared via general procedure B from compound 3 and the corresponding aryl bromide, which was prepared via general procedure A. N-benzyl-5-(5-morpholino-1H-pyrrolo[2,3-b]pyridin-3-yl)pyrimidine-2-carboxamide (compound 7), was isolated as a yellow solid. ¹H NMR: (300 MHz, Methanol-d₄) δ 9.26 (s, 2H), 8.18 (d, J=2.7 Hz, 1H), 8.00 (s, 1H), 7.92 (d, J=2.5 Hz, 1H), 7.62-7.43 (m, 3H), 7.42-7.25 (m, 2H), 4.67 (s, 2H), 3.94-3.80 (m, 4H), 3.23-3.13 (m, 4H) ppm. LCMS m/z=415.2 [M+H]⁺.

Preparation of Compound 8

Compound 8 was prepared via general procedure B from compound 3 and the corresponding aryl bromide, which was prepared via general procedure A. N-benzyl-N-methyl-5-(5-morpholino-1H-pyrrolo[2,3-b]pyridin-3-yl)pyrimidine-2-carboxamide (Compound 8) was isolated as a yellow solid. ¹H NMR: (300 MHz, Chloroform-d) δ 11.44 (d, J=12.1 Hz, 1H), 9.08 (d, J=10.5 Hz, 2H), 8.27 (dd, J=3.7, 2.5 Hz, 1H), 7.74-7.63 (m, 2H), 7.48-7.22 (m, 4H), 4.83 (s, 1H), 4.57 (s, 1H), 3.92 (ddd, J=6.4, 2.9, 1.3 Hz, 4H), 3.18 (ddt, J=4.7, 3.1, 1.5 Hz, 4H), 3.06 (s, 1H), 2.96 (s, 1H) ppm. LCMS m/z=429.2 [M+H]⁺.

Preparation of Compound 9

Compound 9 was prepared via general procedure B from compound 3 and the corresponding aryl bromide, which was prepared via general procedure A. 6-(5-morpholino-1H-pyrrolo[2,3-b]pyridin-3-yl)-N-phenethylnicotinamide (compound 9) was isolated as a yellow solid. ¹H NMR: (300

MHz, Methanol-d4) δ 8.96 (d, J=2.2 Hz, 1H), 8.41 (d, J=2.7 Hz, 1H), 8.18-7.96 (m, 3H), 7.84 (d, J=8.2 Hz, 1H), 7.64-7.38 (m, 4H), 7.20 (td, J=5.8, 2.4 Hz, 1H), 4.69 (d, J=2.0 Hz, 1H), 4.29 (q, J=1.9 Hz, 1H), 3.90 (dd, J=5.8, 3.6 Hz, 5H), 3.63 (dd, J=8.2, 6.6 Hz, 2H), 3.23-3.14 (m, 5H), 2.94 (t, J=7.3 Hz, 2H) ppm. LCMS m/z=428.2 [M+H]+.

Preparation of Compound 10

Compound 10 was prepared via general procedure B from compound 3 and the corresponding aryl bromide, which was prepared via general procedure A. 5-(5-morpholino-1H-pyrrolo[2,3-b]pyridin-3-yl)-N-(4-(trifluoromethyl)benzyl) pyrimidine-2-carboxamide (compound 10) was isolated as a yellow solid. ¹H NMR: (300 MHz, Methanol-d₄) δ 9.27 (s, 2H), 8.18 (d, J=2.5 Hz, 1H), 8.01 (s, 1H), 7.97 (s, 2H), 7.92 (d, J=2.6 Hz, 1H), 7.60 (s, 1H), 7.55-7.42 (m, 2H), 4.71-4.67 (m, 1H), 4.32-4.24 (m, 4H), 3.88 (s, 1H), 3.23-3.17 (m, 4H) ppm. LCMS m/z=483.2 [M+H]+.

Preparation of Compound 11

Compound 11 was prepared via general procedure B from compound 3 and the corresponding aryl bromide, which was prepared via general procedure A. 5-(5-morpholino-1H-pyrrolo[2,3-b]pyridin-3-yl)-N-phenethylpyrimidine-2-carboxamide (compound 11), was isolated as a yellow solid. ¹H NMR: (500 MHz, DMSO-d₆) δ 12.13 (broad s, 1H), 9.30 (s, 2H), 8.87 (t, J=6.0 Hz, 1H), 8.22 (d, J=2.9 Hz, 1H), 8.20 (d, J=2.5 Hz, 1H), 7.92-7.78 (m, 1H), 7.34-7.25 (m, 4H), 7.23-7.19 (m, 1H), 3.83-3.74 (m, 4H), 3.57 (ddd, J=8.3, 7.3, 6.1 Hz, 2H), 3.22-3.14 (m, 4H), 2.89 (t, J=7.4 Hz, 2H) ppm. LCMS m/z=429.2 [M+H]+.

Preparation of Compound 12

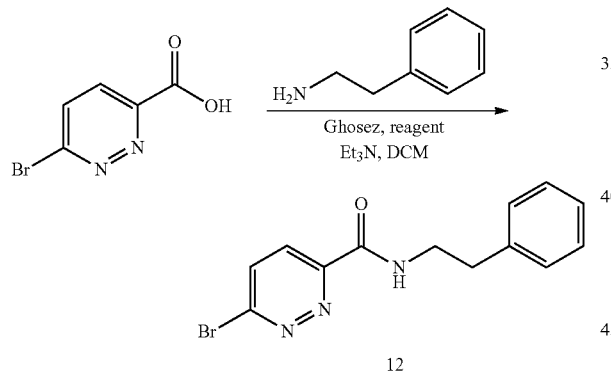

6-Bromopyridazine-3-carboxylic acid (0.15 g, 0.74 mmol) was taken up in 4 mL of DCM, and the suspension was cooled to 0° C. Ghosez reagent (0.11 mL, 0.81 mmol) was added dropwise and stirring was continued for 15 min, before slowly warming to ambient temperature. The mixture was then adsorbed directly onto silica gel and subsequently purified via silica gel chromatography eluting with a 0-100% gradient of ethyl acetate in hexanes. 6-bromo-N-phenethylpyridazine-3-carboxamide (compound 12) (0.14 g, 0.468 mmol) was isolated as yellow oil and used directly. LCMS m/z=306.0 [M+H]+.

Preparation of Compound 13

Compound 13 was prepared via general procedure B using compound 3 and compound 12. 6-(5-morpholino-1H-pyrrolo[2,3-b]pyridin-3-yl)-N-phenethylpyridazine-3-carboxamide (compound 13) was obtained as a yellow solid. ¹H NMR: (300 MHz, DMSO-d₆) δ 9.33 (t, J=6.0 Hz, 1H), 8.45 (d, J=3.0 Hz, 1H), 8.35 (d, J=2.8 Hz, 1H), 8.31 (d, J=9.0 Hz, 1H), 8.21 (d, J=2.7 Hz, 1H), 8.07 (d, J=9.0 Hz, 1H), 7.32-7.22 (m, 4H), 7.19 (td, J=6.2, 2.6 Hz, 1H), 3.80 (dd, J=5.9, 3.4 Hz, 4H), 3.58 (q, J=7.0 Hz, 2H), 3.11 (dd, J=6.0, 3.6 Hz, 4H), 2.90 (t, J=7.4 Hz, 2H) ppm. LCMS m/z=429.2 [M+H]+.

General Procedure C and Preparation of Compound 14

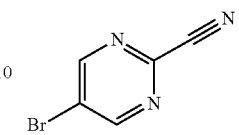
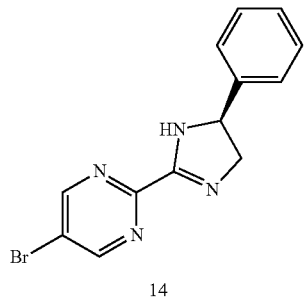

5-bromopyrimidine-2-carbonitrile (2.2 g, 12 mmol) was dissolved in 25 mL MeOH, and NaOMe added in a single portion (0.064 g, 1.2 mmol). The mixture was stirred for 48 h and then concentrated to give a crude residue, which was then diluted with 30 mL DCM. To this solution was added (S)-1-phenylethane-1,2-diamine (1 g, 7.35 mmol) and mixture was then heated to 50° C. for 8 h. The solution was then concentrated onto silica gel and purified via silica gel chromatography using a 20-80% gradient of ethyl acetate in hexanes to give compound 14 as a brown solid (2.1 g, 6.47 mmol, 88% yield). LCMS m/z=304.1 [M+H]+.

Preparation of Compound 14a

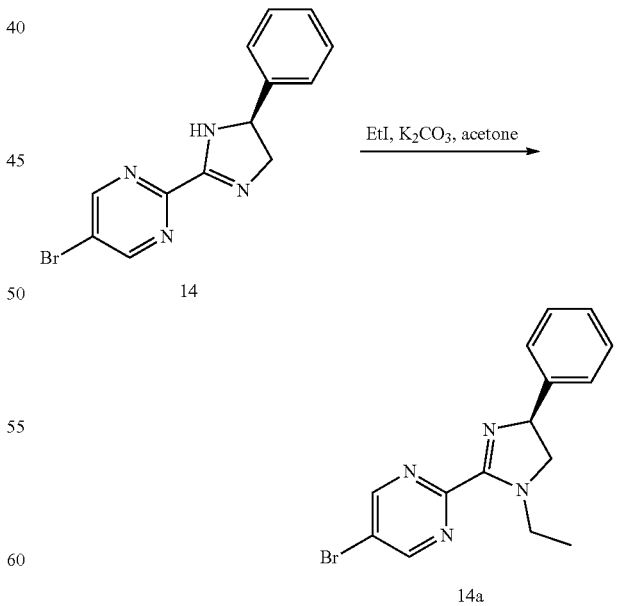

Compound 14 (2.1 g, 6.47 mmol) was taken up in 30 mL of acetone. K₂CO₃ (2.67 g, 19.5 mmol) was added in a single portion, followed by EtI (2 g, 12.9 mmol) drop wise and the mixture was heated to 40° C. for 12 hours. The mixture was cooled, diluted with brine, and extracted with ethyl acetate to give crude compound 14a, which was used directly in subsequent syntheses. LCMS m/z=331.2 [M+H]+.
Preparation of Compound 15

Compound 15 was prepared via general procedure B using compound 3 and the compound 13. (S)-4-(3-(2-(5-phenyl-4,5-dihydro-1H-imidazol-2-yl)pyrimidin-5-yl)-1H-pyrrolo[2,3-b]pyridin-5-yl)morpholine (compound 15) was obtained as a yellow-orange solid. $^1$H NMR: (300 MHz, Methanol-d$_4$) δ 9.25 (s, 2H), 8.17 (d, J=2.5 Hz, 1H), 7.99 (s, 1H), 7.88 (d, J=2.5 Hz, 1H), 7.47 (d, J=7.1 Hz, 2H), 7.44-7.27 (m, 3H), 4.33 (t, J=6.7 Hz, 1H), 3.94-3.86 (m, 4H), 3.86-3.66 (m, 2H), 3.27-3.15 (m, 2H), 2.65 (s, 1H), 1.28 (s, 1H) ppm. LCMS m/z=425.2 [M+H]+.
Preparation of Compound 16

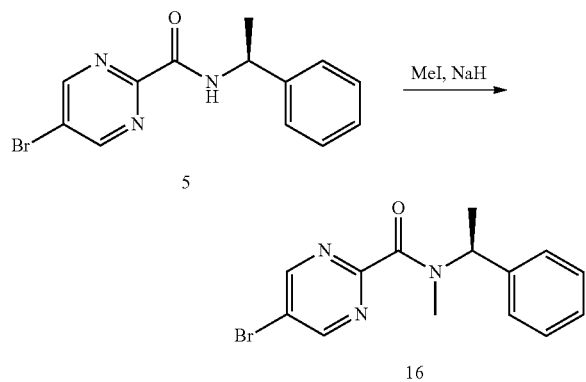

Compound 5 (0.23 g, 0.75 mmol) was taken up in 2 mL DMF and MeI (0.073 mL, 1.17 mmol) added. This mixture was cooled to 0° C. and NaH (0.04 g, 60% dispersion in mineral oil, 0.9 mmol) was then added portion-wise over 5 min. The mixture was then allowed to slowly warm to ambient temperature and stirred for 12 h. The mixture was then diluted with ethyl acetate, washed with brine (×4), dried over MgSO$_4$ and concentrated onto silica. This crude residue was then purified using silica gel chromatography eluting with 20-80% ethyl acetate in hexanes. (S)-5-bromo-N-methyl-N-(1-phenylethyl)pyrimidine-2-carboxamide (compound 16) was isolated as a yellow oil (0.15 g, 0.047 mmol, 63% yield) and used immediately.
Preparation of Compound 17

Compound 17 was prepared via general procedure B with compound 3 and compound 16. (S)-4-(3-(2-(5-phenyl-4,5-dihydro-1H-imidazol-2-yl)pyrimidin-5-yl)-1H-pyrrolo[2,3-b]pyridin-5-yl)morpholine (compound 17) was obtained as a yellow-orange solid. $^1$H NMR: (300 MHz, Methanol-d$_4$) δ 9.21 (s, 1H), 9.18 (s, 1H), 8.14 (t, J=2.9 Hz, 1H), 7.92 (s, 1H), 7.89-7.84 (m, 1H), 7.48-7.40 (m, 3H), 7.39-7.27 (m, 3H), 3.91-3.82 (m, 5H), 3.17 (td, J=4.6, 1.5 Hz, 4H), 2.72 (d, J=35.9 Hz, 3H), 1.66 (dd, J=7.0, 2.7 Hz, 3H) ppm. LCMS m/z=443.2 [M+H]+.
Preparation of Compound 18

Compound 18 was prepared via general procedure B using compound 3 and the corresponding aryl bromide, which was prepared via general procedure A. (R)-(5-(5-morpholino-1H-pyrrolo[2,3-b]pyridin-3-yl)pyrimidin-2-yl)(2-phenylpyrrolidin-1-yl)methanone (compound 18) was obtained as a yellow solid. $^1$H NMR: (300 MHz, Methanol-d4) δ 9.24 (s, 1H), 8.87 (s, 1H), 8.20-8.12 (m, 1H), 7.98 (s, 1H), 7.81 (s, 1H), 7.73 (d, J=2.6 Hz, 1H), 7.39-7.32 (m, 1H), 7.13-6.96 (m, 3H), 5.48-5.31 (m, 1H), 4.04-3.94 (m, 1H), 3.92-3.85 (m, 4H), 3.23-3.15 (m, 4H), 2.49 (dt, J=12.3, 6.6 Hz, 1H), 2.01 (s, 5H) ppm. LCMS m/z=454.2 [M+H]+.
Preparation of Compound 19

Compound 19 was prepared via general procedure B using compound 3 and the corresponding aryl bromide, which was prepared via general procedure A. (S)-(5-(5-morpholino-1H-pyrrolo[2,3-b]pyridin-3-yl)pyrimidin-2-yl)(2-phenylpyrrolidin-1-yl)methanone (compound 19) was obtained as a yellow solid. $^1$H NMR: (300 MHz, Methanol-d$_4$) δ 9.24 (s, 1H), 8.86 (s, 1H), 8.15 (s, 1H), 7.94 (s, 1H), 7.92-7.83 (m, 1H), 7.78 (s, 1H), 7.69 (d, J=2.5 Hz, 1H), 7.33 (d, J=4.5 Hz, 1H), 7.14-6.92 (m, 2H), 5.40 (d, J=6.6 Hz, 1H), 4.74-4.22 (m, OH), 4.12-3.91 (m, 2H), 3.87 (dq, J=4.9, 2.2 Hz, 4H), 3.21-3.02 (m, 4H), 2.45 (td, J=13.2, 8.1 Hz, 1H), 2.17-1.78 (m, 2H) ppm. LCMS m/z=454.2 [M+H]+.
Preparation of Compound 20

Compound 20 was prepared via general procedure B using compound 3 and the corresponding aryl bromide, which was prepared via general procedure A. (R)—N-(1-(3-chlorophenyl)ethyl)-5-(5-morpholino-1H-pyrrolo[2,3-b]pyridin-3-yl)pyrimidine-2-carboxamide (compound 20) was obtained as a yellow solid. $^1$H NMR: (300 MHz, Methanol-d4) δ 9.19 (d, J=19.1 Hz, 2H), 8.15 (d, J=2.5 Hz, 1H), 7.97 (s, 1H), 7.87 (d, J=2.5 Hz, 1H), 7.62-7.45 (m, 2H), 7.40-7.20 (m, 2H), 5.28 (q, J=7.0 Hz, 1H), 3.94-3.79 (m, 5H), 3.18 (dd, J=5.9, 3.5 Hz, 4H), 1.61 (t, J=7.0 Hz, 3H) ppm. LCMS m/z=462.2 [M+H]+.
Preparation of Compound 21

Compound 21 was prepared via general procedure B using compound 3 and the corresponding aryl bromide, which was prepared via general procedure A. (R)-5-(5-morpholino-1H-pyrrolo[2,3-b]pyridin-3-yl)-N-(1-(3-(trifluoromethyl)phenyl)ethyl)pyrimidine-2-carboxamide (compound 21) was obtained as a yellow solid. $^1$H NMR: (300 MHz, Methanol-d$_4$) δ 9.24 (s, 2H), 8.16 (d, J=2.5 Hz, 1H), 7.98 (s, 1H), 7.89 (d, J=2.5 Hz, 1H), 7.75-7.68 (m, 1H), 7.59-7.51 (m, 3H), 5.37 (q, J=7.0 Hz, 1H), 3.91-3.79 (m, 5H), 3.21-3.15 (m, 4H), 1.66 (d, J=7.0 Hz, 3H) ppm. LCMS m/z=496.2 [M+H]+.
Preparation of Compound 22

Compound 22 was prepared via general procedure B using compound 3 and the corresponding aryl bromide, which was prepared via general procedure A. (S)-5-(5-morpholino-1H-pyrrolo[2,3-b]pyridin-3-yl)-N-(1-phenylethyl)pyrimidine-2-carboxamide (compound 22) was obtained as a yellow solid. $^1$H NMR: (300 MHz, Chloroform-d) δ 10.22 (s, 1H), 9.12 (s, 2H), 8.27 (d, J=5.9 Hz, 2H), 7.67 (s, 1H), 7.49-7.28 (m, 5H), 5.50-5.40 (m, 1H), 3.92 (t, J=4.7 Hz, 4H), 3.18 (t, J=4.6 Hz, 4H), 1.67 (d, J=6.9 Hz, 3H) ppm. LCMS m/z=429.2 [M+H]+.
Preparation of Compound 23

Compound 23 was prepared via general procedure B using compound 3 and the corresponding aryl bromide, which was prepared via general procedure A. 5-(5-morpholino-1H-pyrrolo[2,3-b]pyridin-3-yl)-N-phenylpyrimidine-2-carboxamide (compound 23) was obtained as a yellow solid. $^1$H NMR: (300 MHz, Methanol-d$_4$) δ 9.33 (s, 2H), 8.05 (s, 1H), 7.96 (s, 1H), 7.85 (d, J=8.8 Hz, 1H), 7.69-7.47 (m, 5H), 3.91 (d, J=9.5 Hz, 4H), 3.21-3.19 (m, 4H) ppm. LCMS m/z=401.1 [M+H]+.
Preparation of Compound 24

Compound 24 was prepared via general procedure B using compound 3 and the corresponding aryl bromide, which was prepared via general procedure A. N-(1-(1-methyl-1H-pyrrol-3-yl)ethyl)-5-(5-morpholino-1H-pyrrolo[2,3-b]pyridin-3-yl)pyrimidine-2-carboxamide (compound 24) was obtained as a yellow solid. $^1$H NMR: (300 MHz, Methanol-d$_4$) δ 9.23 (s, 2H), 8.17 (d, J=2.5 Hz, 1H), 7.98 (s, 1H), 7.90 (d, J=2.5 Hz, 1H), 7.62-7.45 (m, 1H), 6.67 (d, J=2.1 Hz, 1H), 6.59 (t, J=2.5 Hz, 1H), 6.09 (dd, J=2.7, 1.8 Hz, 1H), 5.21 (q, J=6.8 Hz, 1H), 3.94-3.84 (m, 4H), 3.62 (s, 3H), 3.29-3.15 (m, 4H), 1.57 (d, J=6.8 Hz, 3H), 1.41-1.30 (m, 2H) ppm. LCMS m/z=432.3 [M+H]$^+$.

Preparation of Compound 25

Compound 25 was prepared via general procedure B using compound 3 and the corresponding aryl bromide, which was prepared via general procedure A. (R)—N-(1-(4-chlorophenyl)ethyl)-5-(5-morpholino-1H-pyrrolo[2,3-b]pyridin-3-yl)pyrimidine-2-carboxamide (compound 25) was obtained as a yellow solid. $^1$H NMR: (300 MHz, Methanol-d$_4$) δ 9.24 (s, 2H), 8.18 (d, J=2.5 Hz, 1H), 8.00 (s, 1H), 7.90 (d, J=2.6 Hz, 1H), 7.51-7.39 (m, 2H), 7.39-7.29 (m, 2H), 5.29 (q, J=7.0 Hz, 1H), 3.94-3.85 (m, 4H), 3.27-3.15 (m, 4H), 1.62 (d, J=7.0 Hz, 3H) ppm. LCMS m/z=463.2 [M+H]$^+$.

Preparation of Compound 26

Compound 26 was prepared via general procedure B using compound 3 and the corresponding aryl bromide, which was prepared via general procedure A. (5-(5-morpholino-1H-pyrrolo[2,3-b]pyridin-3-yl)pyrimidin-2-yl)(2-(pyridin-2-yl)pyrrolidin-1-yl)methanone (compound 26) was obtained as a yellow solid. $^1$H NMR: (300 MHz, Methanol-d$_4$) δ 8.94 (s, 2H), 8.44 (s, 1H), 8.16 (s, 1H), 7.98 (s, 1H), 7.92 (d, J=2.5 Hz, 1H), 7.61 (d, J=8.2 Hz, 1H), 7.46 (s, 1H), 7.26 (s, 1H), 5.38 (d, J=8.0 Hz, 1H), 3.94-3.83 (m, 4H), 3.72 (p, J=6.6 Hz, 2H), 3.21 (ddd, J=7.0, 5.9, 3.6 Hz, 4H), 2.55 (dt, J=13.3, 7.1 Hz, 2H), 2.09 (dt, J=13.3, 6.7 Hz, 2H), 1.39-1.35 (m, 3H) ppm. LCMS m/z=456.2 [M+H]$^+$.

Preparation of Compound 27

Compound 27 was prepared via general procedure B using compound 3 and the corresponding aryl bromide, which was prepared via general procedure C. ((S)-4-(3-(2-(4-phenyl-4,5-dihydrooxazol-2-yl)pyrimidin-5-yl)-1H-pyrrolo[2,3-b]pyridin-5-yl)morpholine (compound 27) was obtained as a white solid. $^1$H NMR: (300 MHz, Methanol-d$_4$) δ 9.25 (s, 2H), 8.17 (d, J=2.5 Hz, 1H), 8.02 (s, 1H), 7.91 (d, J=2.5 Hz, 1H), 7.61-7.55 (m, 1H), 7.53-7.46 (m, 1H), 7.41-7.37 (m, 3H), 5.55 (dd, J=10.3, 8.4 Hz, 1H), 5.03 (dd, J=10.3, 8.6 Hz, 1H), 4.43 (t, J=8.5 Hz, 1H), 3.92-3.85 (m, 4H), 3.24-3.18 (m, 4H) ppm. LCMS m/z=427.2 [M+H]$^+$.

Preparation of Compound 28

Compound 28 was prepared via general procedure B using compound 3 and the corresponding aryl bromide, which was prepared via general procedure C. (R)-4-(3-(2-(4-phenyl-4,5-dihydrooxazol-2-yl)pyrimidin-5-yl)-1H-pyrrolo[2,3-b]pyridin-5-yl)morpholine (compound 28) was obtained as a white solid. $^1$H NMR: (300 MHz, Methanol-d$_4$) δ 9.24 (s, 2H), 8.16 (d, J=2.5 Hz, 1H), 8.01 (s, 1H), 7.90 (d, J=2.5 Hz, 1H), 7.60-7.45 (m, 2H), 7.38 (d, J=2.9 Hz, 3H), 5.54 (dd, J=10.3, 8.4 Hz, 1H), 5.03 (dd, J=10.4, 8.7 Hz, 1H), 4.43 (t, J=8.5 Hz, 1H), 3.94-3.84 (m, 5H), 3.25-3.13 (m, 4H) ppm. LCMS m/z=427.2 [M+H]$^+$.

Preparation of Compound 29

Compound 29 was prepared via general procedure B using compound 3 and the corresponding aryl bromide, which was prepared via general procedure C. (R)-4-(3-(2-(5-phenyl-4,5-dihydrooxazol-2-yl)pyrimidin-5-yl)-1H-pyrrolo[2,3-b]pyridin-5-yl)morpholine (compound 29) was obtained as a white solid. $^1$H NMR: (300 MHz, Methanol-d$_4$) δ 9.25 (s, 2H), 8.18 (d, J=2.5 Hz, 1H), 8.03 (s, 1H), 7.92 (d, J=2.5 Hz, 1H), 7.62-7.31 (m, 5H), 5.94 (dd, J=10.3, 8.0 Hz, 1H), 4.67-4.53 (m, 1H), 4.06 (dd, J=15.4, 8.0 Hz, 1H), 3.92-3.82 (m, 4H), 3.25-3.16 (m, 4H) ppm. LCMS m/z=427.2 [M+H]$^+$.

Preparation of Compound 44

Compound 44, (S)—N-(1-(2-fluorophenyl)ethyl)-5-(5-morpholino-1H-pyrrolo[2,3-b]pyridin-3-yl)pyrimidine-2-carboxamide, was prepared following general procedures A and B using (R)-1-(2-fluorophenyl)ethan-1-amine as a starting material, and isolated as a yellow powder. $^1$H NMR: (400 MHz, CDCl$_3$) δ 10.40 (br s, 1H), 9.15 (s, 2H), 8.53 (br d, J=8.8 Hz, 1H), 8.28 (d, J=2.4 Hz, 1H), 7.71 (dd, J=2.4, 11.7 Hz, 2H), 7.42 (dt, J=1.6, 7.6 Hz, 1H), 7.34-7.27 (m, 1H), 7.18-7.06 (m, 2H), 5.64-5.54 (m, 1H), 3.96-3.92 (m, 4H), 3.22-3.18 (m, 4H), 1.69 (s, 3H) ppm. LCMS m/z=447.3 [M+H]$^+$.

Preparation of Compound 45

Compound 45, (S)—N-(1-(2-chlorophenyl)ethyl)-5-(5-morpholino-1H-pyrrolo[2,3-b]pyridin-3-yl)pyrimidine-2-carboxamide, was prepared following general procedures A and B using (R)-1-(2-chlorophenyl)ethan-1-amine as a starting material, and isolated as a yellow solid. $^1$H NMR: (400 MHz, CDCl$_3$) δ 9.62 (br s, 1H), 9.13 (s, 2H), 8.47 (br d, J=8.0 Hz, 1H), 8.27 (d, J=2.4 Hz, 1H), 7.69 (dd, J=2.4, 4.5 Hz, 2H), 7.48 (dd, J=1.6, 7.6 Hz, 1H), 7.41 (dd, J=1.6, 7.7 Hz, 1H), 7.29 (d, J=1.6 Hz, 1H), 7.26-7.21 (m, 1H), 5.75-5.65 (m, 1H), 3.98-3.90 (m, 4H), 3.23-3.17 (m, 4H), 1.69 (d, J=7.2 Hz, 3H) ppm. LCMS m/z=463.3 [M+H]$^+$.

Preparation of Compound 46

Compound 46, (S)—N-(1-(2-methoxyphenyl)ethyl)-5-(5-morpholino-1H-pyrrolo[2,3-b]pyridin-3-yl)pyrimidine-2-carboxamide, was prepared following general procedures A and B using (R)-1-(2-methoxyphenyl)ethan-1-amine as a starting material, and isolated as a yellow solid. $^1$H NMR: (400 MHz, CDCl$_3$) δ 10.63 (br s, 1H), 9.07 (s, 2H), 8.91-8.73 (m, 1H), 8.21 (d, J=2.4 Hz, 1H), 7.65 (dd, J=2.4, 11.1 Hz, 2H), 7.27 (dd, J=1.6, 7.3 Hz, 1H), 7.23-7.19 (m, 1H), 6.92-6.84 (m, 2H), 5.58-5.47 (m, 1H), 3.88 (s, 3H), 3.88-3.83 (m, 4H), 3.12 (dd, J=4.0, 5.6 Hz, 4H), 1.55 (d, J=7.2 Hz, 3H) ppm. LCMS m/z=459.3 [M+H]$^+$.

Preparation of Compound 47

Compound 47, (S)-5-(5-morpholino-1H-pyrrolo[2,3-b]pyridin-3-yl)-N-(2,2,2-trifluoro-1-phenylethyl)pyrimidine-2-carboxamide, was prepared following general procedures A and B using (S)-2,2,2-trifluoro-1-phenylethan-1-amine as a starting material, and isolated as a yellow solid. LCMS m/z=483.3 [M+H]$^+$.

Preparation of Compound 51

Compound 51, (S)-4-(3-(2-(1-ethyl-4-phenyl-4,5-dihydro-1H-imidazol-2-yl)pyrimidin-5-yl)-1H-pyrrolo[2,3-b]pyridin-5-yl)morpholine, was prepared following general procedure B using compound 14a, and was isolated as a brown oil. $^1$H NMR: (300 MHz, Methanol-d$_4$) δ 9.25 (s, 2H), 8.18 (d, J=2.6 Hz, 1H), 7.99-7.85 (m, 4H), 7.75 (s, 1H), 7.65-7.44 (m, 6H), 7.40 (t, J=7.6 Hz, 2H), 7.28 (d, J=7.4 Hz, 1H), 4.82 (s, 1H), 4.78-4.65 (m, 4H), 4.29 (q, J=2.0 Hz, 2H), 3.95-3.86 (m, 5H), 3.27-3.18 (m, 5H), 1.54 (t, J=7.1 Hz, 3H), 1.28 (s, 1H) ppm. LCMS m/z=454.2 [M+H]$^+$.

Preparation of Compound 52

Compound 52, (R)-4-(3-(2-(4-phenyl-4,5-dihydrooxazol-2-yl)pyrimidin-5-yl)-1H-pyrrolo[2,3-b]pyridin-5-yl)morpholine, was prepared following general procedure C employing the corresponding amino alcohol, then via general procedure B using compound 3, and was isolated as an orange solid. $^1$H NMR: (300 MHz, Methanol-d$_4$) δ 9.24 (s, 2H), 8.16 (d, J=2.5 Hz, 1H), 8.01 (s, 1H), 7.90 (d, J=2.5 Hz, 1H), 7.66-7.54 (m, 1H), 7.52 (dddd, J=13.9, 7.1, 3.0, 1.4 Hz, 2H), 7.45-7.35 (m, 1H), 7.38 (s, 3H), 7.39-7.26 (m, 1H), 5.54 (dd, J=10.3, 8.4 Hz, 1H), 5.03 (dd, J=10.4, 8.7 Hz, 1H), 4.69 (q, J=1.9 Hz, 1H), 4.43 (t, J=8.5 Hz, 1H), 4.29 (q, J=2.0 Hz, 1H), 3.93-3.82 (m, 5H), 3.27-3.08 (m, 5H) ppm. LCMS m/z=427.2 [M+H]⁺.

Preparation of Compound 53

Compound 53, (S)—N-(2-hydroxy-1-phenylethyl)-5-(5-morpholino-1H-pyrrolo[2,3-b]pyridin-3-yl)pyrimidine-2-carboxamide, was prepared following general procedure C employing the corresponding amino alcohol, then via general procedure B using compound 3, and was isolated as a brown oil. ¹H NMR: (300 MHz, Methanol-d₄) δ 9.25 (s, 2H), 8.17 (d, J=2.5 Hz, 1H), 8.00 (s, 1H), 7.90 (d, J=2.5 Hz, 1H), 7.50-7.41 (m, 2H), 7.41-7.30 (m, 2H), 7.35-7.21 (m, 1H), 5.24 (t, J=5.8 Hz, 1H), 3.99-3.84 (m, 6H), 3.28-3.15 (m, 4H), 1.99 (d, J=12.5 Hz, 1H), 1.31-1.16 (m, 1H) ppm. LCMS m/z=445.2 [M+H]⁺.

Preparation of Compound 54

Compound 54, (R)-4-(3-(2-(5-phenyl-4,5-dihydrooxazol-2-yl)pyrimidin-5-yl)-1H-pyrrolo[2,3-b]pyridin-5-yl)morpholine, was prepared following general procedure C employing the corresponding amino alcohol, then via general procedure B using compound 3, and was isolated as a brown oil. ¹H NMR: (300 MHz, Methanol-d₄) δ 9.25 (s, 2H), 8.18 (d, J=2.5 Hz, 1H), 8.03 (s, 1H), 7.92 (d, J=2.5 Hz, 1H), 7.63-7.48 (m, 1H), 7.48-7.36 (m, 4H), 7.42-7.31 (m, 1H), 5.94 (dd, J=10.3, 8.0 Hz, 1H), 4.82 (s, 1H), 4.69-4.54 (m, 2H), 4.06 (dd, J=15.4, 8.0 Hz, 1H), 3.94-3.83 (m, 6H), 3.22 (s, 1H), 3.24-3.09 (m, 5H), 1.28 (s, 1H) ppm. LCMS m/z=427.2 [M+H]⁺.

Preparation of Compound 55

Compound 55, (S)-4-(3-(2-(5-phenyl-4,5-dihydrooxazol-2-yl)pyrimidin-5-yl)-1H-pyrrolo[2,3-b]pyridin-5-yl)morpholine, was prepared following general procedure C employing the corresponding amino alcohol, then via general procedure B using compound 3, and was isolated as a brown oil. ¹H NMR (300 MHz, Methanol-d₄) δ 9.25 (s, 2H), 8.18 (d, J=2.5 Hz, 1H), 8.03 (s, 1H), 7.92 (d, J=2.5 Hz, 1H), 7.63-7.48 (m, 1H), 7.48-7.36 (m, 4H), 7.42-7.31 (m, 1H), 5.94 (dd, J=10.3, 8.0 Hz, 1H), 4.82 (s, 1H), 4.69-4.54 (m, 2H), 4.06 (dd, J=15.4, 8.0 Hz, 1H), 3.94-3.83 (m, 6H), 3.22 (s, 1H), 3.24-3.09 (m, 5H), 1.28 (s, 1H). LCMS m/z=427.2 [M+H]⁺.

Preparation of Compound 56

Compound 56, 4-(3-(2-((4R,5S)-4-methyl-5-phenyl-4,5-dihydrooxazol-2-yl)pyrimidin-5-yl)-1H-pyrrolo[2,3-b]pyridin-5-yl)morpholine, was prepared following general procedure C employing the corresponding amino alcohol, then via general procedure B using compound 3, and was isolated as a brown oil. ¹H NMR: (300 MHz, Methanol-d₄) δ 9.24 (s, 2H), 8.16 (d, J=2.5 Hz, 1H), 8.01 (s, 1H), 7.90 (d, J=2.5 Hz, 1H), 7.58-7.36 (m, 1H), 7.42-7.28 (m, 4H), 6.03 (d, J=10.0 Hz, 1H), 4.86-4.65 (m, 1H), 3.93-3.84 (m, 4H), 3.65 (s, 2H), 3.27-3.15 (m, 4H), 0.90 (d, J=7.1 Hz, 3H) ppm. LCMS m/z=441.2 [M+H]⁺.

Preparation of Compound 57

Compound 57, (S)—N-(2-(dimethylamino)-1-phenylethyl)-5-(5-morpholino-1H-pyrrolo[2,3-b]pyridin-3-yl)pyrimidine-2-carboxamide, was prepared via general procedure B from compound 3 and the corresponding aryl bromide, which was prepared via general procedure A, and was isolated as a yellow oil. ¹H NMR: (500 MHz, Methanol-d₄) δ 9.40 (s, 2H), 8.21 (d, J=2.6 Hz, 1H), 7.70 (d, J=2.6 Hz, 1H), 7.54-7.48 (m, 2H), 7.45-7.36 (m, 2H), 7.36-7.29 (m, 1H), 7.18 (s, 1H), 5.42 (dd, J=10.4, 4.5 Hz, 1H), 4.15 (q, J=7.1 Hz, 1H), 3.97-3.92 (m, 4H), 3.24-3.18 (m, 4H), 3.12 (dd, J=12.9, 10.4 Hz, 1H), 2.67 (dd, J=12.9, 4.6 Hz, 1H), 2.43 (s, 6H), 2.07 (s, 1H), 1.33-1.24 (m, 1H) ppm. LCMS m/z=472.2 [M+H]⁺.

Example 2: Synthesis of Compounds 30 Through 35, 58 Through 67

General Procedure D and Preparation of Compounds 30 and 31

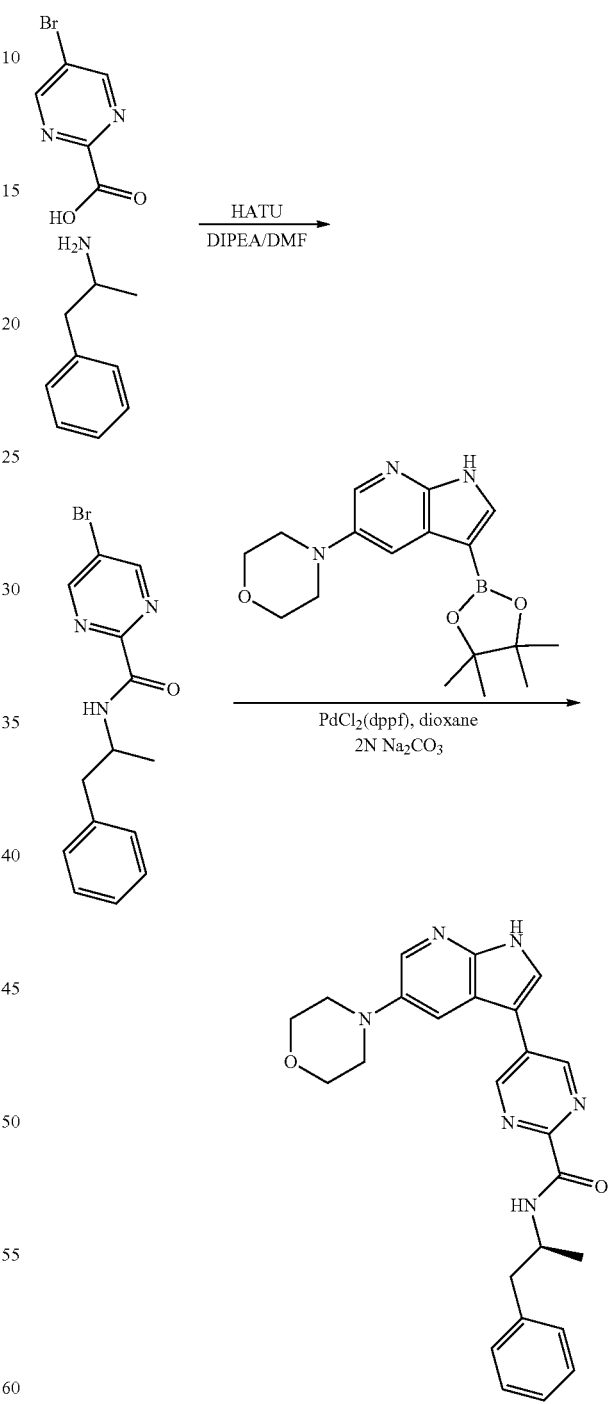

30

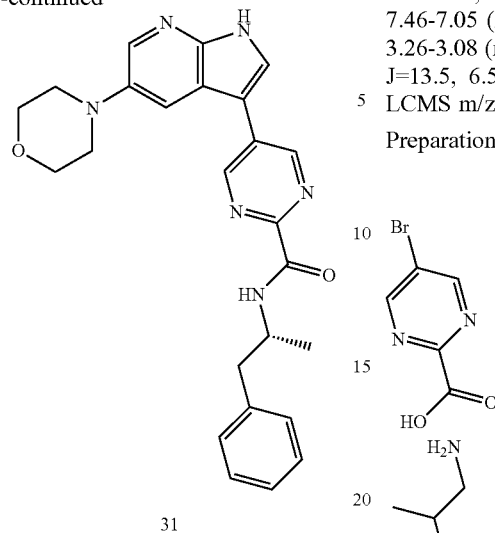

31

A vial was charged with 5-bromo-1,3-pyrimidine-2-carboxylic acid (250 mg, 1.23 mmol), followed by dimethylformamide (5 mL) and diisopropylethylamine (2 mL, 6.2 mmol). 1-[Bis(dimethylamino)methylene]-1H-1,2,3-triazolo[4,5-b]pyridinium 3-oxid hexafluorophosphate (575 mg, 1.5 mmol) was added as a solution in dimethylformamide (1 mL) via syringe. After five minutes 1-phenylpropan-2-amine (216 mg, 1.60 mmol) was injected and the reaction was stirred for one hour at ambient temperature. The mixture was diluted with 9 mL water and 1 mL saturated sodium bicarbonate. The product precipitated and was filtered off. The filtrate was washed with two portions of water (3 mL) and dried on a lyophilizer to yield 5-bromo-N-(1-phenylpropan-2-yl)pyrimidine-2-carboxamide (144.4 mg), 4-(3-(4,4,5,5-tetramethyl-1,3,2-dioxaborolan-2-yl)-1H-pyrrolo[2,3-b]pyridin-5-yl)morpholine as a white solid (144.4 mg, 37%).

A reaction vial was charged with 5-bromo-N-(1-phenylpropan-2-yl)pyrimidine-2-carboxamide (144.4 mg), 4-(3-(4,4,5,5-tetramethyl-1,3,2-dioxaborolan-2-yl)-1H-pyrrolo[2,3-b]pyridin-5-yl)morpholine (100 mg, 0.27 mmol) and [1,1'-bis(diphenylphosphino)ferrocene]dichloropalladium(II) (14.6 mg, 0.02 mmol). Under an atmosphere of nitrogen, dioxane (1.5 mL) and 2N aqueous sodium carbonate (0.4 mL, 0.8 mmol) were injected. The reaction was sealed and heated for 90 min at 100° C. After cooling the reaction was diluted with dichloromethane (5 mL) and stirred with QuadraPure® TU (150 mg). After one hour the mixture was filtered and the filtrate was concentrated and purified by reverse phase HPLC (20 mm–C18, 10-60% water+0.25% acetic acid/acetonitrile).

The active fractions were pooled and concentrated to dryness. The resulting solid was dissolved in methanol and further purified to separate enantiomers by chiral HPLC (IA column, 20×250 mm, methanol, 310 nM, 20 mL/min). (S)-5-(5-morpholino-1H-pyrrolo[2,3-b]pyridin-3-yl)-N-(1-phenylpropan-2-yl)pyrimidine-2-carboxamide (compound 30) and (R)-5-(5-morpholino-1H-pyrrolo[2,3-b]pyridin-3-yl)-N-(1-phenylpropan-2-yl)pyrimidine-2-carboxamide (compound 31) were each isolated as fine white powders with identical NMR and LC/MS data. They were analyzed via SFC with 55% IPA/carbon dioxide on an AD-H column at 2.5 mL/min with detection at 310 nM (greater than 9:1 enantiomeric ratio was found for each). $^1$H NMR: (400 MHz, DMSO-$d_6$) δ 12.14 (s, 1H), 9.30 (s, 2H), 8.65 (d, J=8.7 Hz, 1H), 8.36-8.04 (m, 2H), 7.86 (d, J=2.6 Hz, 1H), 7.46-7.05 (m, 5H), 4.46-4.14 (m, 1H), 3.92-3.64 (m, 4H), 3.26-3.08 (m, 4H), 2.98 (dd, J=13.5, 7.5 Hz, 1H), 2.80 (dd, J=13.5, 6.5 Hz, 1H), 1.28-1.11 (d, J=6.6 Hz, 3H) ppm. LCMS m/z=443.2 [M+H]$^+$.

Preparation of Compounds 32 and 33

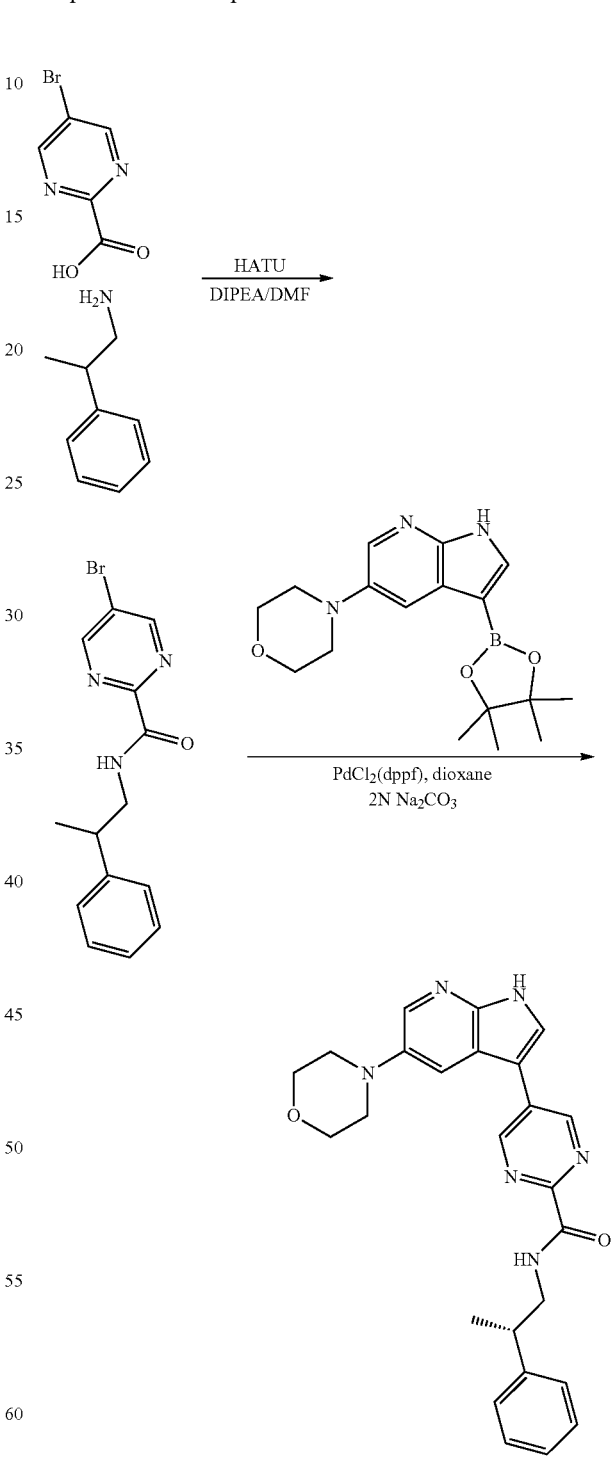

32

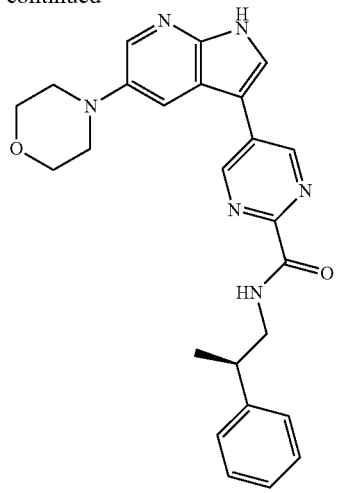

33

A vial was charged with 5-bromo-1,3-pyrimidine-2-carboxylic acid (250.0 mg, 1.23 mmol), followed by dimethylformamide (4 mL) and diisopropylethylamine (0.65 mL, 3.7 mmol). 1-[Bis(dimethylamino)methylene]-1H-1,2,3-triazolo[4,5-b]pyridinium 3-oxid hexafluorophosphate (561 mg, 1.48 mmol) was added as a solution in dimethylformamide (1 mL) via syringe. After 5 min 2-phenylpropan-1-amine (216 mg, 1.60 mmol) was injected and the reaction was stirred for one hour at ambient temperature. The mixture was then diluted with water (9 mL) and saturated sodium bicarbonate (1 mL). The product precipitated and was filtered off. The filtrate was washed with two portions of water (3 mL) and dried. A white solid was obtained after overnight drying (100 mg, 27% yield).

A reaction vial was charged with 5-bromo-N-(1-phenylpropan-2-yl)pyrimidine-2-carboxamide (100.2 mg), 4-(3-(4,4,5,5-tetramethyl-1,3,2-dioxaborolan-2-yl)-1H-pyrrolo[2,3-b]pyridin-5-yl)morpholine (114 mg, 0.344 mmol) and [1,1'-bis(diphenylphosphino)ferrocene]dichloropalladium(II) (11 mg, 0.03 mmol). Under an atmosphere of nitrogen, dioxane (3 mL) and 2N aqueous sodium carbonate (0.5 mL, 1 mmole) were injected. The reaction was sealed and heated for 90 min at 100° C. After cooling the reaction was diluted with dichloromethane (10 mL) and stirred with QuadraPure® TU (200 mg). After one hour the mixture was filtered and the filtrate was concentrated and purified by reversed phase HPLC (20 mm–C18, 10-60% water+0.25% acetic acid/acetonitrile).

The resulting solid was dissolved in methanol and further purified to separate enantiomers by chiral HPLC (IC column, 20×250 mm, methanol, 310 nM, 30 mL/min). (S)-5-(5-morpholino-1H-pyrrolo[2,3-b]pyridin-3-yl)-N-(1-phenylpropan-2-yl)pyrimidine-2-carboxamide (compound 32) and (R)-5-(5-morpholino-1H-pyrrolo[2,3-b]pyridin-3-yl)-N-(1-phenylpropan-2-yl)pyrimidine-2-carboxamide (compound 33) were each isolated as fine white powders with identical NMR and LC/MS data. They were analyzed via SFC with methanol on an analytical IC column at 1.5 mL/min with detection at 310 nM (greater than 9:1 enantiomeric ratio was found for each). $^1$H NMR: (400 MHz, DMSO-$d_6$) δ 12.13 (s, 1H), 9.30 (s, 2H), 8.73 (t, J=6.1 Hz, 1H), 8.21 (dd, J=4.2, 2.5 Hz, 2H), 7.86 (d, J=2.5 Hz, 1H), 7.45-7.09 (m, 5H), 3.79 (dd, J=5.9, 3.5 Hz, 4H), 3.51 (dd, J=7.4, 6.1 Hz, 2H), 3.29-3.04 (m, 5H), 1.24 (d, J=7.0 Hz, 3H) ppm. LCMS m/z=443.2 [M+H]$^+$.

Preparation of Compound 58

Compound 58, N-(2-fluorophenethyl)-5-(5-morpholino-1H-pyrrolo[2,3-b]pyridin-3-yl)pyrimidine-2-carboxamide, was prepared via general procedure D using 2-(2-fluorophenyl)ethan-1-amine. $^1$H NMR: (400 MHz, DMSO-$d_6$) δ 12.13 (d, J=2.9 Hz, 1H), 9.30 (s, 2H), 8.94 (t, J=6.0 Hz, 1H), 8.21 (dd, J=8.9, 2.8 Hz, 2H), 7.86 (d, J=2.6 Hz, 1H), 7.42-7.20 (m, 2H), 7.21-7.06 (m, 2H), 3.79 (dd, J=5.9, 3.6 Hz, 4H), 3.70-3.50 (m, 2H), 3.24-3.09 (m, 4H), 2.93 (t, J=7.3 Hz, 2H) ppm. LCMS m/z=447.2 [M+H]$^+$.

Preparation of Compound 59

Compound 59, 5-(5-morpholino-1H-pyrrolo[2,3-b]pyridin-3-yl)-N-(2-(trifluoromethyl)phenethyl)pyrimidine-2-carboxamide, was prepared via general procedure D using 2-(2-(trifluoromethyl)phenyl)ethan-1-amine. $^1$H NMR: (400 MHz, DMSO-$d_6$) δ 12.13 (d, J=2.8 Hz, 1H), 9.31 (s, 2H), 9.04 (t, J=6.0 Hz, 1H), 8.21 (dd, J=10.6, 2.7 Hz, 2H), 7.86 (d, J=2.6 Hz, 1H), 7.78-7.36 (m, 4H), 3.79 (dd, J=5.9, 3.6 Hz, 4H), 3.69-3.48 (m, 2H), 3.27-3.14 (m, 4H), 3.07 (t, J=7.4 Hz, 2H) ppm. LCMS m/z=497.2 [M+H]$^+$.

Preparation of Compound 60

Compound 60, 5-(5-morpholino-1H-pyrrolo[2,3-b]pyridin-3-yl)-N-(2-(pyridin-2-yl)ethyl)pyrimidine-2-carboxamide, was prepared via general procedure D using 2-(pyridine-2-yl)ethan-1-amine. $^1$H NMR: (400 MHz, DMSO-$d_6$) δ 9.31 (s, 2H), 8.95 (t, J=5.9 Hz, 1H), 8.53 (ddd, J=4.8, 1.9, 0.9 Hz, 1H), 8.21 (dd, J=8.4, 2.8 Hz, 2H), 7.86 (d, J=2.6 Hz, 1H), 7.72 (td, J=7.6, 1.9 Hz, 1H), 7.41-7.07 (m, 2H), 3.87-3.74 (m, 4H), 3.71 (q, J=6.9 Hz, 2H), 3.25-3.13 (m, 3H), 3.05 (t, J=7.2 Hz, 2H) ppm. LCMS m/z=430.2 [M+H]$^+$.

Preparation of Compound 61

Compound 61, N-(2-chlorophenethyl)-5-(5-morpholino-1H-pyrrolo[2,3-b]pyridin-3-yl)pyrimidine-2-carboxamide, was prepared via general procedure D using 2-(2-chlorophenyl)ethan-1-amine. $^1$H NMR: (400 MHz, DMSO-$d_6$) δ 9.30 (s, 2H), 8.96 (t, J=6.0 Hz, 1H), 8.21 (dd, J=9.5, 2.7 Hz, 2H), 7.86 (d, J=2.5 Hz, 1H), 7.49-7.33 (m, 2H), 7.33-7.14 (m, 2H), 3.86-3.71 (m, 4H), 3.71-3.49 (m, 2H), 3.24-3.11 (m, 4H), 3.02 (t, J=7.2 Hz, 2H) ppm. LCMS m/z=463.2 [M+H]$^+$.

Preparation of Compound 62

Compound 62, N-(4-fluorophenethyl)-5-(5-morpholino-1H-pyrrolo[2,3-b]pyridin-3-yl)pyrimidine-2-carboxamide, was prepared via general procedure D using 2-(4-fluorophenyl)ethan-1-amine. $^1$H NMR: (400 MHz, DMSO-$d_6$) δ 12.06 (d, J=2.9 Hz, 1H), 9.23 (s, 2H), 8.81 (s, OH), 8.14 (dd, J=8.1, 2.7 Hz, 2H), 7.79 (d, J=2.6 Hz, 1H), 7.32-7.14 (m, 2H), 7.15-6.97 (m, 2H), 3.85-3.58 (m, 4H), 3.49 (ddd, J=7.9, 5.6, 4.3 Hz, 2H), 3.11 (td, J=5.0, 2.6 Hz, 4H), 2.81 (t, J=7.3 Hz, 2H) ppm. LCMS m/z=447.2 [M+H]$^+$.

Preparation of Compound 63

Compound 63, N-(3-fluorophenethyl)-5-(5-morpholino-1H-pyrrolo[2,3-b]pyridin-3-yl)pyrimidine-2-carboxamide, was prepared via general procedure D using 2-(3-fluorophenyl)ethan-1-amine. $^1$H NMR: (400 MHz, DMSO-$d_6$) δ 12.06 (d, J=2.8 Hz, 1H), 9.24 (s, 2H), 8.83 (t, J=6.0 Hz, 1H), 8.14 (dd, J=8.4, 2.7 Hz, 2H), 7.79 (d, J=2.6 Hz, 1H), 7.27 (td, J=8.1, 6.4 Hz, 1H), 7.15-6.88 (m, 3H), 3.84-3.64 (m, 4H), 3.64-3.41 (m, 2H), 3.11 (td, J=5.0, 2.6 Hz, 5H), 2.85 (t, J=7.2 Hz, 2H) ppm. LCMS m/z=447.2 [M+H]$^+$.

Preparation of Compound 64

Compound 64, 5-(5-morpholino-1H-pyrrolo[2,3-b]pyridin-3-yl)-N-(3-(trifluoromethyl)phenethyl)pyrimidine-2-carboxamide, was prepared via general procedure D using 2-(3-(trifluoromethyl)phenyl)ethan-1-amine. $^1$H NMR: (400

MHz, DMSO-d$_6$) δ 12.14 (d, J=2.8 Hz, 1H), 9.31 (s, 2H), 8.94 (t, J=6.0 Hz, 1H), 8.22 (dd, J=8.1, 2.7 Hz, 2H), 7.85 (d, J=2.6 Hz, 1H), 7.69-7.46 (m, 5H), 3.91-3.69 (m, 5H), 3.69-3.48 (m, 2H), 3.18 (td, J=4.9, 2.4 Hz, 4H), 3.01 (t, J=7.2 Hz, 2H) ppm. LCMS m/z=497.2 [M+H]$^+$.

Preparation of Compound 65

Compound 65, N-(2-methylphenethyl)-5-(5-morpholino-1H-pyrrolo[2,3-b]pyridin-3-yl)pyrimidine-2-carboxamide, was prepared via general procedure D using 2-(2-methylphenyl)ethan-1-amine. $^1$H NMR: (400 MHz, DMSO-d$_6$) δ 12.14 (d, J=2.9 Hz, 1H), 9.32 (s, 2H), 8.98 (t, J=6.1 Hz, 1H), 8.22 (dd, J=10.6, 2.7 Hz, 2H), 7.87 (d, J=2.6 Hz, 1H), 7.32-6.97 (m, 4H), 3.91-3.68 (m, 4H), 3.63-3.41 (m, 2H), 3.27-3.11 (m, 4H), 2.88 (dd, J=8.8, 6.5 Hz, 2H) ppm. LCMS m/z=443.2 [M+H]$^+$.

Preparation of Compound 66

Compound 66, N-(2-cyanophenethyl)-5-(5-morpholino-1H-pyrrolo[2,3-b]pyridin-3-yl)pyrimidine-2-carboxamide, was prepared via general procedure D using 2-(2-aminoethyl)benzonitrile. $^1$H NMR: (400 MHz, DMSO-d$_6$) δ 12.06 (d, J=2.9 Hz, 1H), 9.23 (s, 2H), 8.93 (t, J=6.0 Hz, 1H), 8.14 (dd, J=9.0, 2.7 Hz, 2H), 7.87-7.66 (m, 2H), 7.66-7.27 (m, 4H), 3.83-3.67 (m, 4H), 3.59 (q, J=6.8 Hz, 2H), 3.17-3.09 (m, 4H), 3.05 (t, J=6.9 Hz, 2H) ppm. LCMS m/z=454.2 [M+H]$^+$.

Preparation of Compounds 34 and 35

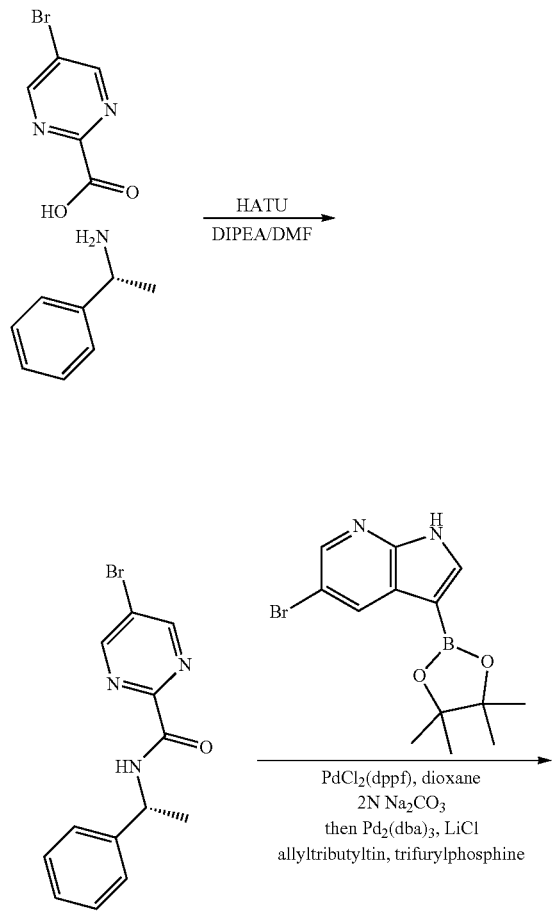

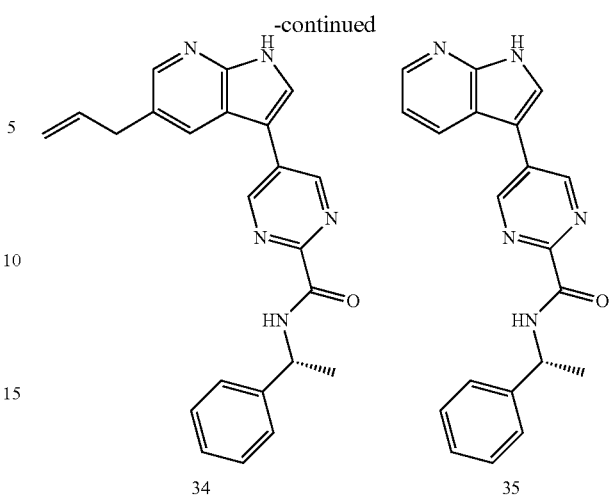

A reaction vial was charged with (R)-5-bromo-N-(1-phenylethyl)pyrimidine-2-carboxamide (100 mg, 0.327 mmol, prepared as above), 5-bromo-3-(4,4,5,5-tetramethyl-1,3,2-dioxaborolan-2-yl)-1H-pyrrolo[2,3-b]pyridine (158 mg, 0.489 mmol) and [1,1'-bis(diphenylphosphino)ferrocene]dichloropalladium(II) (22.9 mg, 0.03 mmol). A mixture of dioxane and dimethylformamide (10 mL:1 mL) was injected followed by 2N sodium carbonate in water (1 mL, 2 mmol). The reaction was heated to 100° C. for a period of two hours, allowed to cool and tris(dibenzylideneacetone)dipalladium(0) (29.9 mg, 0.03 mmol), lithium chloride (147 mg, 3.27 mmol) trifurylphosphine (15.3 mg, 0.066 mmol) and allyl-tributylstannane (0.33 mL, 0.983 mmol) were added. The reaction was sealed and heated to 140° C. in the microwave for a period of 90 min. The reaction was poured into water and ethyl acetate. The organic phase was dried over sodium sulfate, filtered through celite and concentrated. The material obtained was further purified by reversed phase HPLC (20 mm–C18, 10-100% water+0.25% acetic acid/acetonitrile).

The active fractions were pooled, frozen and concentrated under reduced pressure to yield (R)—N-(1-phenylethyl)-5-(1H-pyrrolo[2,3-b]pyridin-3-yl)pyrimidine-2-carboxamide (compound 34) and (R)-5-(5-allyl-1H-pyrrolo[2,3-b]pyridin-3-yl)-N-(1-phenylethyl)pyrimidine-2-carboxamide (compound 35) as white powders.

Compound 34:

$^1$H NMR: (500 MHz, DMSO-d$_6$) δ 12.38 (s, 1H), 9.34 (s, 2H), 9.13 (d, J=8.5 Hz, 1H), 8.45 (dd, J=8.0, 1.5 Hz, 1H), 8.39-8.28 (m, 2H), 7.53-7.40 (m, 2H), 7.35 (dd, J=8.3, 6.9 Hz, 2H), 7.29-7.20 (m, 2H), 5.31-5.08 (m, 1H), 1.55 (d, J=7.0 Hz, 3H). LCMS m/z=344.1 [M+H]$^+$.

Compound 35:

$^1$H NMR: (500 MHz, DMSO-d$_6$) δ 12.30 (s, 1H), 9.33 (s, 2H), 9.12 (d, J=8.4 Hz, 1H), 8.30 (s, 1H), 8.26 (d, J=2.0 Hz, 1H), 8.20 (d, J=2.0 Hz, 1H), 7.53-7.41 (m, 2H), 7.41-7.30 (m, 2H), 7.30-7.19 (m, 1H), 6.07 (ddt, J=16.8, 10.0, 6.7 Hz, 1H), 5.24-5.16 (m, 1H), 5.16-5.11 (m, 1H), 5.08 (ddt, J=10.0, 2.3, 1.2 Hz, 1H), 3.58-3.49 (m, 2H), 1.55 (d, J=7.0 Hz, 3H) ppm. LCMS m/z=384.2 [M+H]$^+$.

Preparation of Compound 67

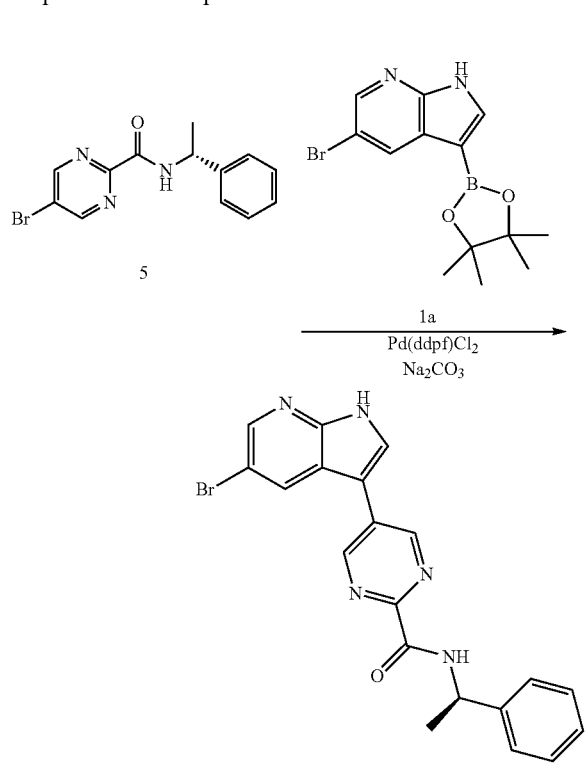

A reaction vial was charged with compound 5 (100 mg, 0.327 mmol, prepared as above), compound 1a (158 mg, 0.489 mmol, prepared as above) and [1,1'-bis(diphenylphosphino)ferrocene]-dichloropalladium(II) (22.9 mg, 0.03 mmol). A mixture of dioxane and dimethylformamide (10 mL:1 mL) was injected followed by 2N sodium carbonate in water (1 mL, 2 mmol). Once complete, the reaction was poured into water and ethyl acetate. The organic phase was dried over sodium sulfate, filtered through celite and concentrated. The material obtained was further purified by reversed phase HPLC (20 mm–C18, 10-100% water+0.25% acetic acid/acetonitrile).

The active fractions were pooled, frozen and concentrated under reduced pressure to yield compound 67, (R)-5-(5-bromo-1H-pyrrolo[2,3-b]pyridin-3-yl)-N-(1-phenylethyl) pyrimidine-2-carboxamide, as a white powder. $^1$H NMR: (400 MHz, DMSO-$d_6$) δ 12.53 (s, 1H), 9.27 (s, 2H), 9.05 (d, J=8.4 Hz, 1H), 8.60 (d, J=2.1 Hz, 1H), 8.33 (dd, J=14.3, 2.4 Hz, 2H), 7.39 (dd, J=7.6, 1.6 Hz, 2H), 7.28 (t, J=7.6 Hz, 2H), 7.23-7.11 (m, 1H), 5.12 (p, J=7.2 Hz, 1H), 1.47 (d, J=7.0 Hz, 3H) ppm. LCMS m/z=422.1 [M+H]$^+$.

Example 3: Synthesis of Compounds 36 Through 43

General Procedure E and Preparation of Compound 2a

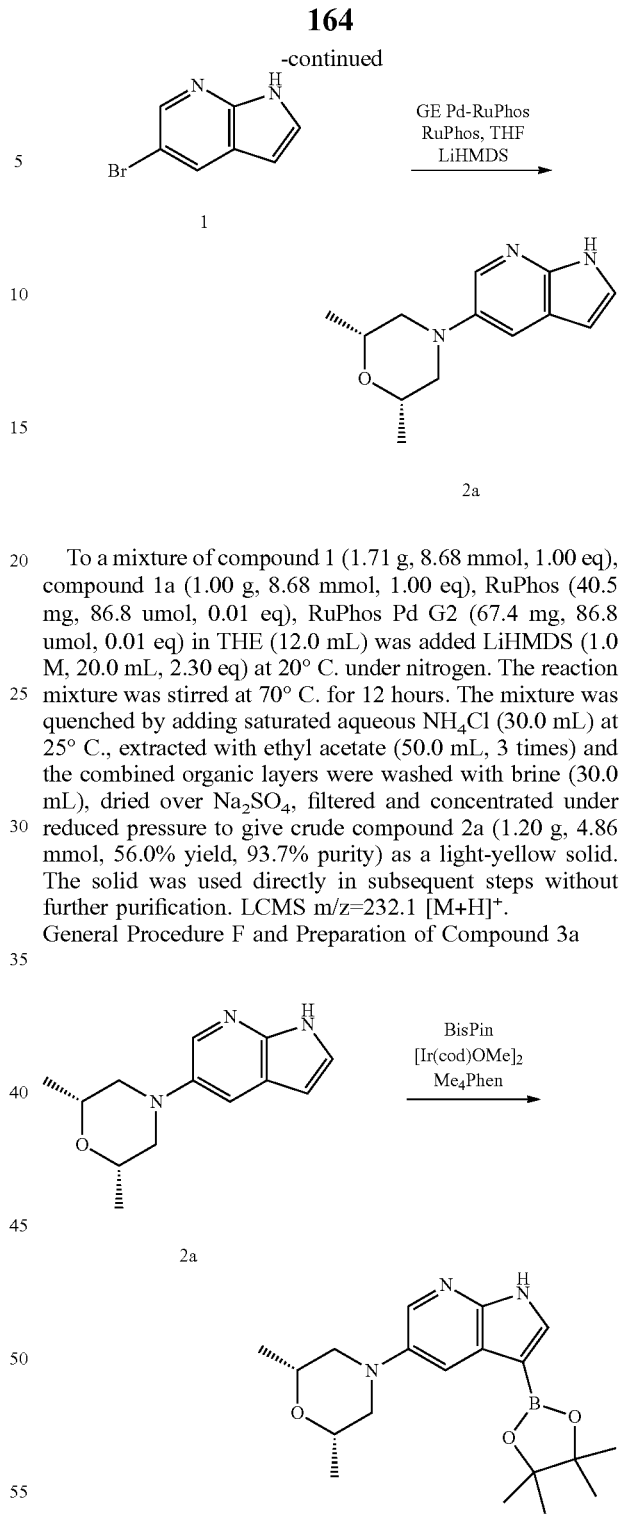

To a mixture of compound 1 (1.71 g, 8.68 mmol, 1.00 eq), compound 1a (1.00 g, 8.68 mmol, 1.00 eq), RuPhos (40.5 mg, 86.8 umol, 0.01 eq), RuPhos Pd G2 (67.4 mg, 86.8 umol, 0.01 eq) in THF (12.0 mL) was added LiHMDS (1.0 M, 20.0 mL, 2.30 eq) at 20° C. under nitrogen. The reaction mixture was stirred at 70° C. for 12 hours. The mixture was quenched by adding saturated aqueous NH$_4$Cl (30.0 mL) at 25° C., extracted with ethyl acetate (50.0 mL, 3 times) and the combined organic layers were washed with brine (30.0 mL), dried over Na$_2$SO$_4$, filtered and concentrated under reduced pressure to give crude compound 2a (1.20 g, 4.86 mmol, 56.0% yield, 93.7% purity) as a light-yellow solid. The solid was used directly in subsequent steps without further purification. LCMS m/z=232.1 [M+H]$^+$.

General Procedure F and Preparation of Compound 3a

A mixture of (1,5-cyclooctadiene)(methoxy)iridium(i) dimer (71.6 mg, 108.1 μmol, 0.05 eq) and 3,4,7,8-tetramethyl-1,10-phenanthroline (25.5 mg, 108.1 μmol, 0.05 eq), bispin (1.65 g, 6.49 mmol, 3.00 eq) in THF (8.00 mL) was stirred at 80° C. for 30 minutes under nitrogen. Then to the mixture was added a solution of compound 2a (500.0 mg, 2.16 mmol, 1.00 eq) in THF (10.0 mL). The mixture was stirred at 80° C. for 2 hours. The mixture was concentrated under vacuum to give crude product (compound 3a), which was purified by silica gel column chromatography (DCM/ethyl acetate=1/0~0/1; ethyl acetate, LCMS m/z=358.6 [M+H]⁺).

General Procedure G and Preparation of Compound 36

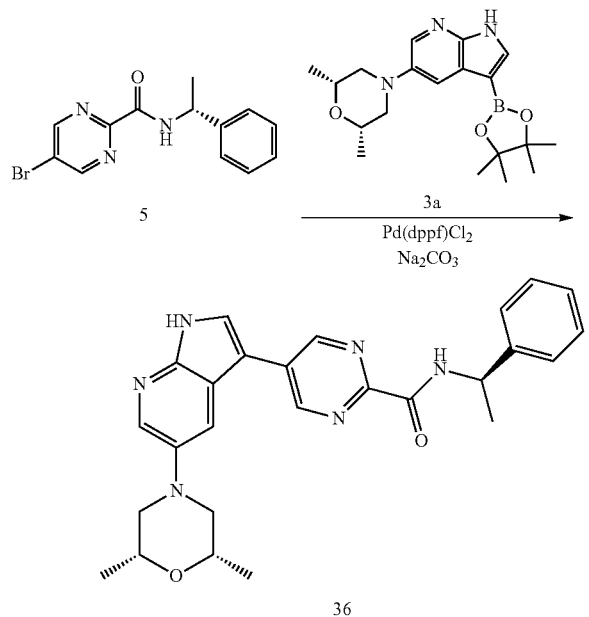

To a mixture of compound 5 (500.0 mg, 1.40 mmol, 1.00 eq), compound 3a (428.5 mg, 1.40 mmol, 1.00 eq) and Pd(dppf)Cl$_2$ (102.4 mg, 139.9 μmol, 0.10 eq) in dioxane (10.0 mL) was added a solution of Na$_2$CO$_3$ (445.0 mg, 4.20 mmol, 3.00 eq) in H$_2$O (2.50 mL). The formed mixture was degassed and purged with nitrogen gas 3 times, and the mixture was stirred at 100° C. for 1 hour under nitrogen atmosphere. The mixture was then cooled to ambient temperature, diluted with water and extracted with ethyl acetate. The combined organic layers were washed with brine (50.0 mL), dried over Na$_2$SO$_4$, filtered and concentrated under reduced pressure to give a residue. The residue was purified by prep-HPLC (column: Waters Xbridge C18 150 mm*50 mm*10 μm; mobile phase: [water(10 mM NH$_4$HCO$_3$)-ACN]; B %: 28%-58%, 11.5 minutes) and lyophilized to give 5-(5-((2R,6S)-2,6-dimethylmorpholino)-1H-pyrrolo[2,3-b]pyridin-3-yl)-N—((R)-1-phenylethyl)pyrimidine-2-carboxamide (compound 36, 120.8 mg, 259.6 μmol, 18.6% yield, 98.1% purity) as a yellow solid. $^1$H NMR: (400 MHz, CDCl$_3$) δ 9.68 (br s, 1H), 9.13 (s, 2H), 8.38-8.05 (m, 2H), 7.66 (dd, J=2.4, 12.3 Hz, 2H), 7.50-7.43 (m, 2H), 7.42-7.34 (m, 2H), 7.33-7.28 (m, 1H), 5.63-5.27 (m, 1H), 4.06-3.81 (m, 2H), 3.40 (br d, J=10.4 Hz, 2H), 2.51 (t, J=10.8 Hz, 2H), 1.68 (d, J=6.8 Hz, 3H), 1.30 (d, J=6.4 Hz, 6H) ppm. LCMS m/z=457.1 [M+H]⁺.

Preparation of Compound 37

5-(5-((S)-2-methylmorpholino)-1H-pyrrolo[2,3-b]pyridin-3-yl)-N—((R)-1-phenylethyl)pyrimidine-2-carboxamide (compound 37) was prepared using the general procedures D-F and the corresponding morpholine starting material, and isolated as a yellow solid. $^1$H NMR: (400 MHz, CDCl$_3$) δ 9.57 (br s, 1H), 9.12 (s, 2H), 8.92 (s, 1H), 8.32-8.23 (m, 2H), 7.67 (dd, J=2.8, 9.8 Hz, 2H), 7.49-7.44 (m, 2H), 7.42-7.37 (m, 2H), 7.33-7.30 (m, 1H), 5.51-5.43 (m, 1H), 4.09-4.03 (m, 1H), 3.94-3.82 (m, 2H), 3.44-3.35 (m, 2H), 2.97-2.88 (m, 1H), 2.59 (dd, J=10.0, 11.5 Hz, 1H), 1.68 (d, J=7.2 Hz, 3H), 1.29 (d, J=6.4 Hz, 3H) ppm. LCMS m/z=443.1 [M+H]⁺.

Preparation of Compound 38

(R)-5-(5-(2,2-dimethylmorpholino)-1H-pyrrolo[2,3-b]pyridin-3-yl)-N-(1-phenylethyl)pyrimidine-2-carboxamide (compound 38) was prepared using the general procedures D-F and the corresponding morpholine starting material, and isolated as a yellow solid. $^1$H NMR: (400 MHz, CDCl$_3$) δ 10.19-10.01 (m, 1H), 9.13 (s, 2H), 8.39-8.17 (m, 2H), 7.78-7.59 (m, 2H), 7.49-7.43 (m, 2H), 7.42-7.35 (m, 2H), 7.34-7.28 (m, 1H), 5.53-5.40 (m, 1H), 3.96 (dd, J=4.0, 5.6 Hz, 2H), 3.17-3.09 (m, 2H), 2.95 (s, 2H), 1.68 (d, J=6.8 Hz, 3H), 1.40 (s, 6H) ppm. LCMS m/z=457.4 [M+H]⁺.

General Procedure H for Preparation of Compound 2b

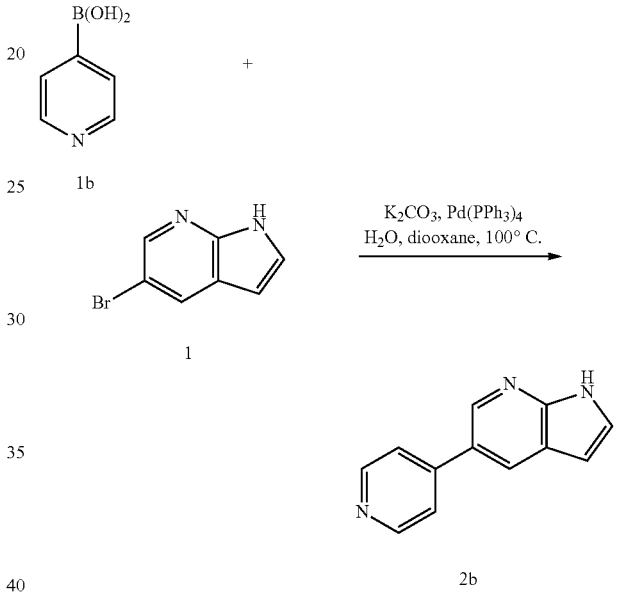

To a mixture of compound 1 (4.50 g, 22.8 mmol, 1.00 eq), compound 1b (3.37 g, 27.4 mmol, 1.20 eq) and Pd(PPh$_3$)$_4$ (2.64 g, 2.28 mmol, 0.10 eq) in dioxane (30.0 mL) was added a solution of K$_2$CO$_3$ (9.47 g, 68.5 mmol, 3.00 eq) in H$_2$O (6.00 mL). The mixture was stirred at 100° C. for 15 hours under nitrogen atmosphere. The reaction mixture was filtered and concentrated under reduced pressure to give a residue which was triturated with petroleum ether:ethyl acetate (2:1, 100.0 mL) at 20° C. for 30 minutes to give compound 2b (4.00 g, 20.5 mmol, 89.7% yield) as a yellow solid. $^1$H NMR: (400 MHz, DMSO-d$_6$) δ 11.84 (br s, 1H), 8.66 (d, J=2.0 Hz, 1H), 8.65-8.59 (m, 2H), 8.39 (d, J=2.0 Hz, 1H), 7.82-7.76 (m, 2H), 7.55 (br d, J=3.2 Hz, 1H), 6.54 (d, J=3.2 Hz, 1H) ppm. LCMS m/z=196.1 (M+1)⁺.

Preparation of Compound 39

Compound 39, (S)—N-(1-phenylethyl)-5-(5-(pyridin-4-yl)-1H-pyrrolo[2,3-b]pyridin-3-yl)pyrimidine-2-carboxamide, was prepared from compound 2b following general procedures E and F, and isolated as a light yellow solid. $^1$H NMR: (400 MHz, DMSO-d$_6$) δ 12.71 (br d, J=1.2 Hz, 1H), 9.46 (s, 2H), 9.10 (d, J=8.8 Hz, 1H), 8.97 (br d, J=6.0 Hz, 2H), 8.87 (br d, J=6.0 Hz, 2H), 8.45-8.39 (m, 3H), 7.46 (d, J=7.2 Hz, 2H), 7.35 (t, J=7.2 Hz, 2H), 7.28-7.23 (m, 1H), 5.24-5.16 (m, 1H), 1.55 (d, J=6.8 Hz, 3H) ppm. LCMS m/z=421.3 [M+H]⁺.

Preparation of Compound 40

Compound 40, (R)-5-(5-(2-methylpyridin-4-yl)-1H-pyrrolo[2,3-b]pyridin-3-yl)-N-(1-phenylethyl)pyrimidine-2-carboxamide, was prepared via general procedures G, E and F using the corresponding pyridine starting material, and isolated as light yellow solid. $^1$H NMR: (400 MHz, DMSO-$d_6$) δ 12.73 (d, J=2.4 Hz, 1H), 9.46 (s, 2H), 9.10 (d, J=8.4 Hz, 1H), 8.97 (s, 2H), 8.77 (d, J=6.0 Hz, 1H), 8.45 (d, J=2.8 Hz, 1H), 8.39 (br s, 1H), 8.33-8.25 (m, 1H), 7.46 (d, J=7.2 Hz, 2H), 7.39-7.30 (m, 2H), 7.29-7.19 (m, 1H), 5.27-5.13 (m, 1H), 2.73 (s, 3H), 1.55 (d, J=7.2 Hz, 3H) ppm. LCMS m/z=435.0 [M+H]$^+$.

Preparation of Compound 41

Compound 41, (R)-5-(5-(2-methoxypyridin-4-yl)-1H-pyrrolo[2,3-b]pyridin-3-yl)-N-(1-phenylethyl)pyrimidine-2-carboxamide, was prepared via general procedures G, E and F using the corresponding pyridine starting material, and isolated as light yellow solid. $^1$H NMR: (400 MHz, CDCl$_3$) 6.98 (br s, 1H), 9.19 (s, 2H), 8.71 (d, J=2.0 Hz, 1H), 8.39 (d, J=2.0 Hz, 1H), 8.32-8.25 (m, 2H), 7.82 (d, J=1.6 Hz, 1H), 7.50-7.44 (m, 2H), 7.42-7.37 (m, 2H), 7.33-7.29 (m, 1H), 7.16 (dd, J=1.6, 5.4 Hz, 1H), 7.01 (d, J=0.8 Hz, 1H), 5.54-5.43 (m, 1H), 4.02 (s, 3H), 1.69 (d, J=6.8 Hz, 3H) ppm. LCMS m/z=451.0 [M+H]$^+$.

Preparation of Compound 42

Compound 42, (R)-5-(5-(2-oxa-6-azaspiro[3.3]heptan-6-yl)-1H-pyrrolo[2,3-b]pyridin-3-yl)-N-(1-phenylethyl)pyrimidine-2-carboxamide, was prepared following general procedures D, E and F using 2-oxa-6-azaspiro[3.3]heptane as a starting material, and isolated as a light yellow solid. $^1$H NMR: (400 MHz, DMSO-$d_6$) δ 12.05 (br s, 1H), 9.28 (s, 2H), 9.06 (d, J=8.4 Hz, 1H), 8.19 (d, J=1.6 Hz, 1H), 7.71 (d, J=2.4 Hz, 1H), 7.45 (d, J=7.6 Hz, 2H), 7.40-7.30 (m, 3H), 7.28-7.21 (m, 1H), 5.24-5.14 (m, 1H), 4.74 (s, 4H), 4.06 (s, 4H), 1.54 (d, J=7.2 Hz, 3H) ppm. LCMS m/z=441.0 [M+H]$^+$.

Preparation of Compound 43

Compound 43, (R)-5-(5-(6-oxa-1-azaspiro[3.3]heptan-6-yl)-1H-pyrrolo[2,3-b]pyridin-3-yl)-N-(1-phenylethyl)pyrimidine-2-carboxamide, was prepared following general procedures D, E and F using 6-oxa-1-azaspiro[3.3]heptane as a starting material, and isolated as a light yellow solid. $^1$H NMR: (400 MHz, CDCl$_3$) δ 13.02-12.81 (m, 1H), 9.11 (s, 2H), 8.27 (br d, J=8.8 Hz, 1H), 7.91 (dd, J=2.0, 18.3 Hz, 2H), 7.78 (d, J=2.0 Hz, 1H), 7.49-7.43 (m, 2H), 7.41-7.36 (m, 2H), 7.33-7.28 (m, 1H), 5.50-5.41 (m, 1H), 5.13 (d, J=8.8 Hz, 2H), 4.95-4.84 (m, 2H), 3.83-3.79 (m, 2H), 2.64 (t, J=6.8 Hz, 2H), 1.67 (d, J=6.8 Hz, 3H) ppm. LCMS m/z=441.1 [M+H]$^+$.

Example 4: Synthesis of Compounds 48 Through 50

General Procedure I and Preparation of Compound 4b

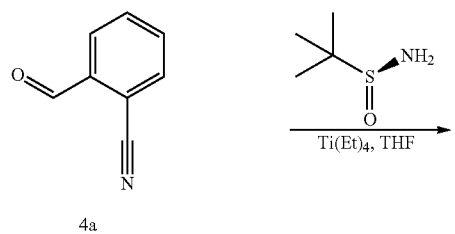

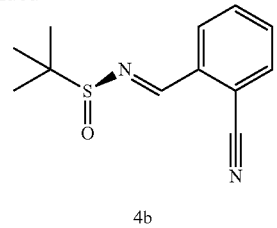

4b

To a mixture of (S)-2-methylpropane-2-sulfinamide (23.1 g, 190.6 mmol, 1.00 eq) and compound 4a (25.0 g, 190.6 mmol, 9.52 mL, 1.00 eq) in THF (130.0 mL) was added Ti(OEt)$_4$ (87.0 g, 381.3 mmol, 79.1 mL, 2.00 eq), and the mixture was stirred at 60° C. for 1 hour. The mixture was diluted with ethyl acetate (300.0 mL) and water (100.0 mL). Then the mixture was filtered. The filtrate was washed with brine (50.0 mL, 3 times), dried over Na$_2$SO$_4$ and concentrated to give crude product, which was purified by flash silica gel column chromatography (petroleum ether/ethyl acetate=1/0~3/1; petroleum ether/ethyl acetate=3/1) to give compound 4b (38.2 g, 158.1 mmol, 82.9% yield, 97.0% purity) as a yellow solid. LCMS m/z=235.6 [M+H]$^+$.

General Procedure J and Preparation of Compound 4c

A mixture of compound 4b (20.0 g, 85.4 mmol, 1.00 eq) in DCM (100.0 mL) was cooled to −45° C. Methyl Grignard reagent (3 M in ether, 71.1 mL, 2.50 eq) was slowly added over 1 hour. The mixture was stirred at −45° C. for 4 hours. The mixture was diluted with saturated aqueous NH$_4$Cl (300.0 mL), and the solution was extracted with DCM (300.0 mL, 2 times). The combined organic phase was dried over Na$_2$SO$_4$, filtered and concentrated under vacuum to give crude compound 4c (22.0 g) as a brown oil, which was used in subsequent reactions without purification. LCMS m/z=251.7 [M+H]$^+$.

General Procedure K and Preparation of Compound 4d

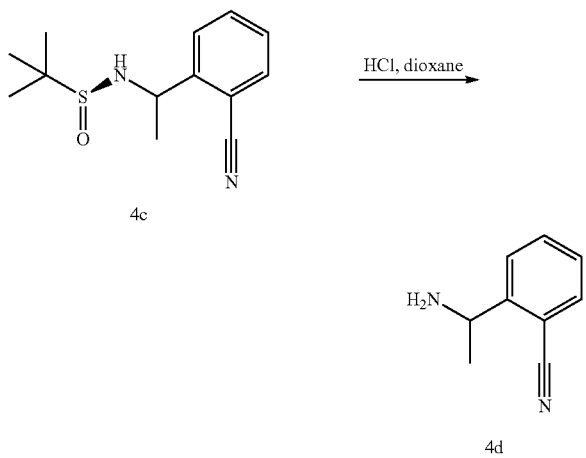

To a solution of compound 4c (5.00 g, 20.0 mmol, 1.00 eq) in dioxane (30.0 mL) was added HCl/dioxane (4 M, 30.0 mL, 6.01 eq) at 0° C. The mixture was stirred at 0° C. for 3 hours. The mixture was concentrated under vacuum to give crude product, which was purified by reversed phase column chromatography (5%~30% acetonitrile in water and 0.1% TFA) and concentrated under vacuum to give compound 4d (2.60 g, 8.06 mmol, 40.4% yield, 80.7% purity) as a yellow solid. LCMS m/z=146.9 [M+H]$^+$.

Preparation of Compound 48

Compound 48, (S)—N-(1-(2-cyanophenyl)ethyl)-5-(5-morpholino-1H-pyrrolo[2,3-b]pyridin-3-yl)pyrimidine-2-carboxamide, was prepared following general procedures A and B using compound 4d as a starting material, and was isolated as a yellow solid. $^1$H NMR: (400 MHz, DMSO-d$_6$) δ 12.19 (br d, J=2.0 Hz, 1H), 9.52-9.40 (m, 1H), 9.34 (s, 2H), 8.29-8.15 (m, 2H), 7.90 (d, J=2.0 Hz, 1H), 7.87-7.78 (m, 1H), 7.78-7.65 (m, 2H), 7.46 (dt, J=1.6, 7.4 Hz, 1H), 5.39 (quin, J=7.2 Hz, 1H), 3.80 (br d, J=4.8 Hz, 4H), 3.26-3.15 (m, 4H), 1.66-1.49 (m, 3H) ppm. LCMS m/z=454.0 [M+H]$^+$.

Preparation of Compound 49

Compound 49, N-(cyclopropyl(phenyl)methyl)-5-(5-morpholino-1H-pyrrolo[2,3-b]pyridin-3-yl)pyrimidine-2-carboxamide, was prepared following general procedures A and B, and was isolated as a yellow solid. The starting material used was prepared following general procedures H-J. $^1$H NMR: (400 MHz, CDCl$_3$) δ 9.49 (br s, 1H), 9.13 (s, 2H), 8.44 (br d, J=8.8 Hz, 1H), 8.27 (d, J=2.8 Hz, 1H), 7.68 (dd, J=2.8, 4.0 Hz, 2H), 7.52 (d, J=7.2 Hz, 2H), 7.41-7.28 (m, 3H), 4.82 (t, J=8.8 Hz, 1H), 3.98-3.90 (m, 4H), 3.23-3.16 (m, 4H), 1.42-1.25 (m, 1H), 0.74-0.62 (m, 3H), 0.55-0.44 (m, 1H) ppm. LCMS m/z=455.1 [M+H]$^+$.

Preparation of Compound 50

Compound 50, (R)-5-(5-morpholino-1H-pyrrolo[2,3-b]pyridin-3-yl)-N-(1-(m-tolyl)ethyl)pyrimidine-2-carboxamide, was prepared following general procedures A and B, and was isolated as a yellow solid. The starting material used was prepared following general procedures H-J. $^1$H NMR: (300 MHz, Methanol-d$_4$) δ 9.24 (s, 2H), 8.16 (d, J=2.5 Hz, 1H), 7.99 (s, 1H), 7.89 (d, J=2.5 Hz, 1H), 7.50-7.40 (m, 2H), 7.40-7.30 (m, 2H), 7.35-7.21 (m, 1H), 5.24 (t, J=5.8 Hz, 1H), 3.99-3.84 (m, 6H), 3.27-3.10 (m, 4H), 1.98 (d, J=13.6 Hz, 1H), 1.23 (t, J=7.1 Hz, 1H) ppm. LCMS m/z=443.2 [M+H]$^+$.

Example 5: Synthesis of Compound 68

General Procedure L and Preparation of Compound 5b

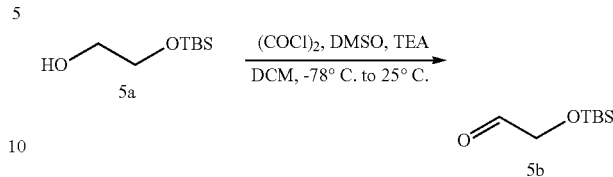

To a solution of (COCl)$_2$ (7.92 g, 62.4 mmol, 5.46 mL, 1.10 eq) in DCM (90 mL) was added DMSO (10.7 g, 136 mmol, 10.6 mL, 2.40 eq) at −78° C. under nitrogen atmosphere. After being stirred for 30 minutes, compound 5a (10.0 g, 56.7 mmol, 1.00 eq) in DCM (45 mL) was added to the solution. After being stirred for 30 minutes, TEA (28.7 g, 284 mmol, 39.5 mL, 5.00 eq) was added to the solution at −78° C. After being stirred for 30 minutes, the mixture was stirred at 25° C. for 1 hour. TLC (petroleum ether:ethyl acetate=3:1) indicated compound 5a (R$_f$=0.30) was consumed, and one major new spot with lower polarity (R$_f$=0.40) was detected. The reaction mixture was acidified with 2 N aqueous HCl solution to pH=4 at 0° C., and then extracted with DCM (20 mL). The combined organic layers were washed with saturated NaCl (20 mL), dried over Na$_2$SO$_4$, filtered and concentrated under reduced pressure to give a residue. The residue was purified by column chromatography (SiO$_2$, petroleum ether:ethyl acetate=3:1 to 1:1, TLC:petroleum ether:ethyl acetate=3:1, R$_f$=0.40). Compound 5b (9.00 g, 51.6 mmol, 91.0% yield) was obtained as a yellow oil. $^1$H NMR: (400 MHz, DMSO) δ ppm 9.54 (s, 1H) 4.35 (s, 2H) 0.90 (m, 1H) 0.88 (s, 9H) 0.06 (s, 6H).

General Procedure M and Preparation of Compound 5c

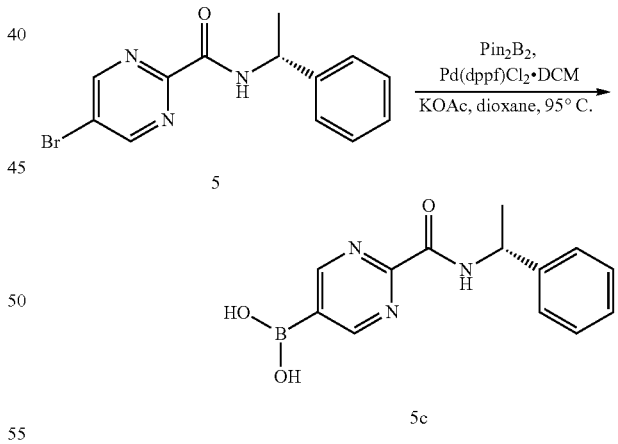

A mixture of compound 5 (4.00 g, 13.1 mmol, 1.00 eq), Pin$_2$B$_2$ (6.64 g, 26.1 mmol, 2.00 eq), Pd(dppf)Cl$_2$•DCM (10.7 g, 13.1 mmol, 1.00 eq), KOAc (2.56 g, 26.1 mmol, 2.00 eq) in dioxane (40 mL) was degassed and purged with nitrogen gas 3 times, and then the mixture was stirred at 95° C. for 2 hours under nitrogen atmosphere. LCMS showed compound 2 was consumed. Several new peaks were shown on LCMS and 83.9% of desired compound (R$_f$=0.795) was detected. The reaction mixture was concentrated under reduced pressure to give a residue. The residue was purified by reverse column chromatography (FA condition). Compound 5c (1.40 g, 5.16 mmol, 39.5% yield) was obtained as a white solid. LCMS m/z=R$_f$=272.1 [M+H]$^+$.

General Procedure N and Preparation of Compound 5e

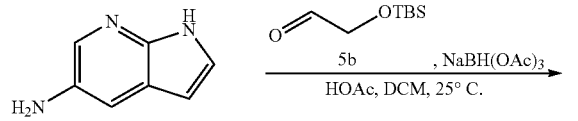

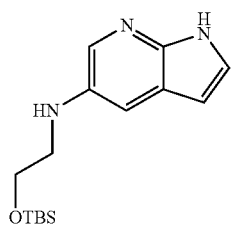

A mixture of compound 5d (8.00 g, 60.1 mmol, 1.00 eq), compound 5b (8.38 g, 48.1 mmol, 9.16 mL, 0.8 eq), HOAc (36.1 mg, 601 μmol, 34.4 μL, 0.01 eq) and in DCM (50 mL) was stirred at 25° C. for 1 hour, then NaBH(OAc)$_3$ (25.5 g, 120 mmol, 2.00 eq) was add to the mixture. The mixture was stirred at 25° C. for 1 hour. TLC (petroleum ether:ethyl acetat=3:1) indicated compound 5d (R$_f$=0.50) was consumed, and one major new spot with larger polarity (R$_f$=0.30) was detected. LCMS showed compound 5d was consumed, several new peaks emerged, and 79.7% of total peak area was the desired compound (R$_f$=0.822). The reaction mixture was diluted with saturated NaHCO$_3$ (200 mL) and extracted with DCM (200 mL). The combined organic layers were washed with saturated NaCl (100 mL), dried over Na$_2$SO$_4$, filtered and concentrated under reduced pressure to give a residue. The residue was purified by column chromatography (SiO$_2$, petroleum ether:ethyl acetate=100:1 to 10:1, TLC (petroleum ether:ethyl acetate=3:1, R$_f$=0.3) Compound 5e (1.50 g, 5.15 mmol, 8.57% yield) was obtained as a white solid. $^1$H NMR: (400 MHz, DMSO) δ ppm 11.10 (s, 1H) 7.76 (d, J=2.58 Hz, 1H) 7.25 (t, J=2.92 Hz, 1H) 7.09 (d, J=2.46 Hz, 1H) 6.19 (d J=3.30, 1.96 Hz, 1H) 5.06 (t, J=6.12 Hz, 1H) 3.75 (t, J=6.04 Hz, 2H) 3.16 (q, J=5.98 Hz, 2H) 0.86-0.90 (m, 9H) 0.02-0.06 (m, 6H). LCMS m/z=292.1 [M+H]$^+$.

General Procedure O and Preparation of Compound 5f

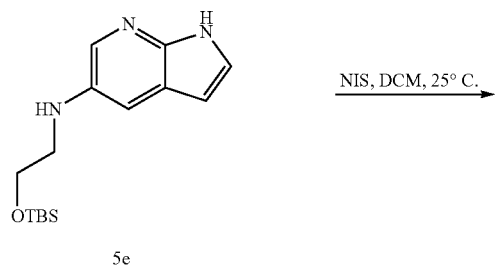

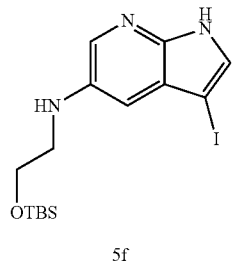

To a solution of compound 5e (1.00 g, 3.43 mmol, 1.00 eq) in DCM (20 mL) was added NIS (849 mg, 3.77 mmol, 1.10 eq) at 0° C. The mixture was stirred a 0° C. for 30 minutes. TLC (petroleum ether:ethyl acetate=3:1) indicated compound 5e (R$_f$=0.40) was consumed, and one major new spot with lower polarity (R$_f$=0.45) was detected. The reaction mixture was concentrated under reduced pressure to give a residue. The residue was purified by column chromatography (SiO$_2$, petroleum ether:ethyl acetate=2:1, TLC: petroleum ether:ethyl acetate=3:1, R$_f$=0.45). Compound 5f (333 mg, 798 μmol, 23.3% yield) was obtained as a white solid.

General Procedure P and Preparation of Compound 5g

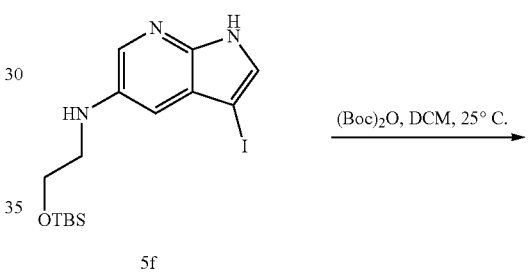

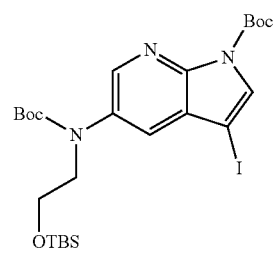

A mixture of compound 5f (333 mg, 798 μmol, 1.00 eq), (Boc)$_2$O (697 mg, 3.19 mmol, 733 μL, 4.00 eq) in DCM (5 mL) was stirred at 25° C. for 1 hour. LCMS showed compound 5f was consumed. Several new peaks were shown on LCMS and 46.2% of the total peak area corresponded to the desired compound (R$_f$=1.25). The reaction mixture was concentrated under reduced pressure to give a residue. The residue was purified by column chromatography (SiO$_2$, petroleum ether:ethyl acetate=100:1 to 30:1, petroleum ether:ethyl acetate=5:1, R$_f$=0.80) Compound 5g (600 mg, crude) was obtained as a yellow oil. LCMS m/z=618.2 [M+H]$^+$.

General Procedure Q and Preparation of Compound 5h

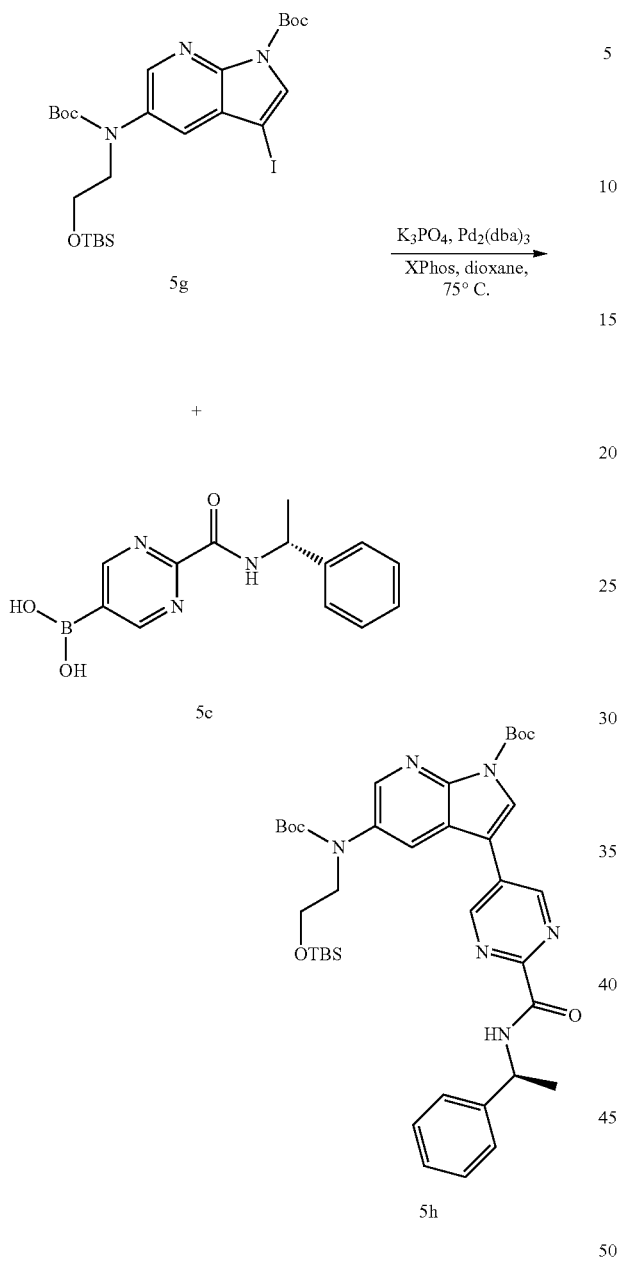

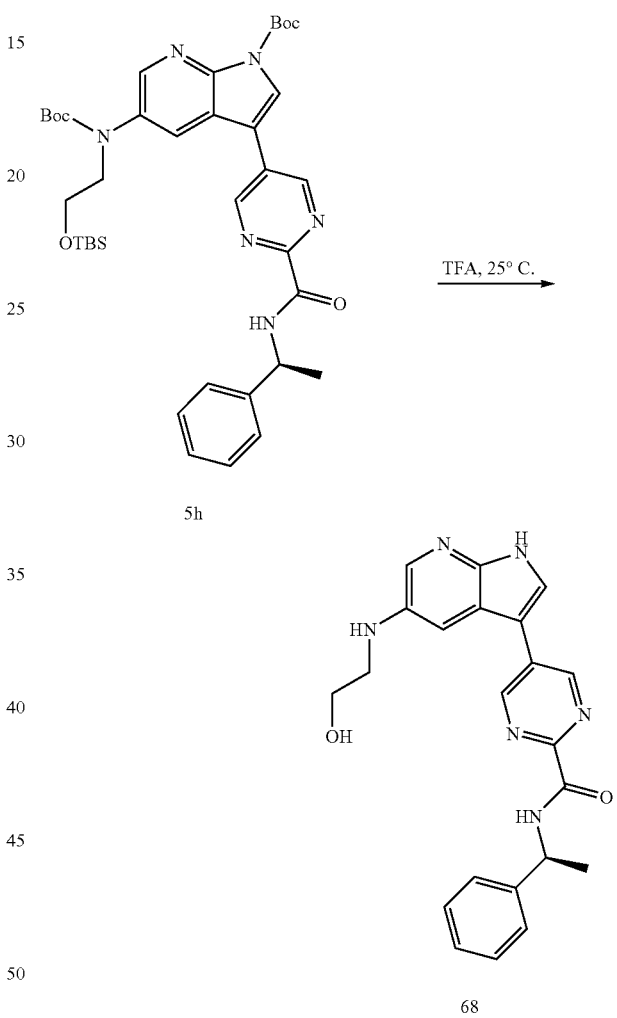

A mixture of compound 5g (600 mg, 972 µmol, 1.00 eq), compound 5c, K₃PO₄ (2 M, 1.46 mL, 3.00 eq), Pd₂(dba)₃ (88.9 mg, 97.2 µmol, 0.1 eq) and XPhos (92.6 mg, 194 µmol, 0.2 eq) in dioxane (6 mL) was degassed and purged with nitrogen gas 3 times, and then the mixture was stirred at 75° C. for 1 hour under nitrogen atmosphere. LCMS showed that the desired compound ($R_f$=1.16) accounted for 38.6% of the total peak area. TLC (petroleum ether:ethyl acetate=1:1) indicated compound 5g ($R_f$=0.90) was consumed, and one major new spot with larger polarity (Rf=0.10) was detected. The reaction mixture was concentrated under reduced pressure to give a residue. Then the mixture was extracted with DCM (20 mL). The combined organic layers were washed with saturated NaCl (20 mL), dried over Na₂SO₄, filtered and concentrated under reduced pressure to give a residue. The residue was purified by column chromatography (SiO₂, petroleum ether:ethyl acetate=20:1 to 3:1, TLC:petroleum ether:ethyl acetate=1:1, $R_f$=0.10). Compound 5h (380 mg, 530 µmol, 54.6% yield) was obtained as yellow oil. ¹H NMR: (400 MHz, DMSO) δ ppm 9.33 (s, 2H) 9.17 (d, J=8.38 Hz, 1H) 8.50 (s, 1H) 8.41 (s, 1H) 8.31 (d, J=2.26 Hz, 1H) 7.44 (d, J=7.62 Hz, 2H) 7.34 (t, J=7.58 Hz, 2H) 7.22-7.27 (m, 1H) 5.15-5.25 (m, 1H) 3.75-3.81 (m, 2H) 3.66-3.72 (m, 2H) 1.65 (s, 9H) 1.54 (d, J=7.00 Hz, 3H) 1.31-1.43 (m, 9H) 0.76 (s, 9H)–0.05 (s, 6H). LCMS m/z=717.4 [M+H]⁺.

General Procedure R and Preparation of Compound 68

A mixture of compound 5h (380 mg, 488 µmol, 1.00 eq) in TFA (4.26 g, 37.3 mmol, 2.76 mL, 76.4 eq) was stirred at 25° C. for 6 minutes. LCMS showed compound 5h was consumed. Several new peaks were shown on LCMS and 87.6% of the total peak area corresponded to the desired compound ($R_t$=0.779). The reaction mixture was concentrated under reduced pressure to give a residue. The residue was purified by prep-HPLC (FA condition, column: 3_Phenomenex Luna C18 75*30 mm*3 µm; mobile phase; [water (0.225% FA)-ACN];B %: 14%-34%, 8 min). Compound 68 (90.0 mg, 222 µmol, 45.4% yield, 99.2% purity) was obtained as a yellow solid. ¹H NMR: (400 MHz, MeOD) δ ppm 9.24 (s, 2H) 7.91-7.99 (m, 2H) 7.67 (d, J=2.50 Hz, 1H) 7.45 (d, J=7.50 Hz, 2H) 7.35 (t, J=7.58 Hz, 2H) 7.23-7.28

(m, 1H) 5.31 (q, J=6.74 Hz, 1H) 3.80 (t, J=5.62 Hz, 2H) 3.35 (t, J=5.62 Hz, 2H) 1.64 (d, J=7.00 Hz, 3H). LCMS m/z=403.2 $[M+H]^+$.

Biological Experiments

Cell Line Growth Retardation Assay

Cells were seeded at densities of 1,000-5,000 cells per well in 48-well tissue culture plates. After a 24 h rest period, cells were treated with compound at 10 µM, 2 µM, 0.4 µM, 0.08 µM, 0.016 µM, and 0.0032 µM. A group of cells were treated with the vehicle in which the compound was prepared and served as a control. The cells were grown in the presence of compounds for 6 days and were counted on day 0 and day 6. All cell counting was performed using a Synentec Cellavista plate imager. Cells that did not receive compound were counted on day 1 and this count was used as a baseline for the calculation of growth inhibition. Growth inhibition was calculated as a ratio of cell population doublings in the presence of compound versus the absence of compound. If treatment resulted in a net loss of cells from baseline, percent lethality was defined as the decrease in cell numbers in treated wells compared with counts on day 1 of non-treated wells post-seeding. $IC_{50}$ values for each compound were calculated by fitting curves to data points from each dose-response assay using the Proc NLIN function in SAS for Windows version 9.2 (SAS Institute, Inc.).

Designation of Sensitivity and Resistant Cohorts and Calculation of Average $IC_{50}$ Values Human cancer cell lines were grouped as "sensitive" or "resistant" to ERK1 inhibition based on whether their growth was retarded by KO-947 (i.e., 1,5,6,8-tetrahydro-6-(phenylmethyl)-3-(4-pyridinyl)-7H-pyrazolo[4,3-g]quinazolin-7-one) and SCH772984 (i.e., (3R)-1-[2-oxo-2-[4-[4-(2-pyrimidinyl)phenyl]-1-piperazinyl]ethyl]-N-[3-(4-pyridinyl)-1H-indazol-5-yl]-3-pyrrolidinecarboxamide) (data not shown; see Table 4). These sensitive and resistant cohorts were interrogated for response to each compound, and $IC_{50}$s were calculated for each cell line using the same technique described above. Average $IC_{50}$s for the sensitive and resistant cohorts were calculated as geometric means of the group. See Table 3. "A" represents an $IC_{50}$ of 250 nM or less, "B" represents an $IC_{50}$ of 251 nM to 500 nM, and "C" represents an $IC_{50}$ of greater than 500 nM.

ERK1 and 2 Enzymatic Inhibition Assay

For the $K_i$ determination assay, 200 µM stock solutions of compounds were subjected to a serial, semi-logarithmic dilution using 100% DMSO as a solvent. 10 distinct concentrations were prepared, with a dilution endpoint of $6 \times 10^{-9}$ M in 100% DMSO. 100% DMSO was used as a control. 10 µL from each of the serial dilutions were aliquoted into separate wells of a 96-well plate and 90 µL of water were added to each of those wells. The plate was shaken thoroughly, and 5 µL from each of the plate's wells were transferred into wells of the assay plate. The final volume of wells in the assay plate was 50 µL. All compounds were tested at 10 assay concentrations in the range from $2 \times 10^{-6}$ M to $6 \times 10^{-11}$ M. The final DMSO concentration in the wells of the assay plate was 1% in all cases. See Table 3. "A" represents a $K_d$ of 10 nM or less, "B" represents a $K_d$ of 11 nM to 100 nM, and "C" represents a $K_d$ of greater than 100 nM.

Caco-2 Assay ($P_{app}$ A to B)

The degree of bi-directional human intestinal permeability for compounds was estimated using a Caco-2 cell permeability assay. Caco-2 cells were seeded onto polyethylene membranes in 96-well plates. The growth medium was refreshed every 4 to 5 days until cells formed a confluent cell monolayer. HBSS with 10 mM HEPES at pH 7.4 was used as the transport buffer. Compounds were tested at 2 µM bi-directionally in duplicate. Digoxin, nadolol and metoprolol were included as standards. Digoxin was tested at 10 µM bi-directionally in duplicate, while nadolol and metoprolol were tested at 2 µM in the A to B direction in duplicate. The final DMSO concentration was adjusted to less than 1% for all experiments. The plate was incubated for 2 hours in a $CO_2$ incubator at 37° C., with 5% $CO_2$ at saturated humidity. After incubation, all wells were mixed with acetonitrile containing an internal standard, and the plate was centrifuged at 4,000 rpm for 10 minutes. 100 µL supernatant was collected from each well and diluted with 100 µL distilled water for LC/MS/MS analysis. Concentrations of test and control compounds in starting solution, donor solution, and receiver solution were quantified by LC/MS/MS, using peak area ratio of analyte/internal standard.

The apparent permeability coefficient $P_{app}$ (cm/s) was calculated using the equation:

$$P_{app}=(dC_r/dt) \times V_r/(A \times C_0),$$

where $dC_r/dt$ is the cumulative concentration of compound in the receiver chamber as a function of time (µM/s); $V_r$ is the solution volume in the receiver chamber (0.075 mL on the apical side, 0.25 mL on the basolateral side); A is the surface area for the transport, which is 0.0804 $cm^2$ for the area of the monolayer; and $C_0$ is the initial concentration in the donor chamber (µM). $P_{app}$ scores are presented in Table 3 for compounds of the invention.

The efflux ratio was calculated using the equation:

$$\text{Efflux Ratio}=P_{app}(BA)/P_{app}(AB)$$

Percent recovery was calculated using the equation:

$$\% \text{ Recovery}=100 \times [(V_r \times C_r)+(V_d \times C_d)]/(V_d \times C_0),$$

where Vd is the volume in the donor chambers, which are 0.075 mL on the apical side and 0.25 mL on the basolateral side; and $C_d$ and $C_r$ are the final concentrations of transport compound in donor and receiver chambers, respectively.

Measurement of Compound Metabolic Stability

The metabolic stability of compounds was determined in hepatocytes from mice and rats. Compound half-lives are presented in Table 3 in minutes. Compounds were diluted to 5 µM in Williams' Medium E from 10 mM stock solutions. 10 µL of each compound was aliquoted into a well of a 96-well plate and reactions were started by aliquoting 40 µL of a 625,000 cells/mL suspension into each well. The plate was incubated at 37° C. with 5% $CO_2$. At each corresponding time point, the reaction was stopped by quenching with ACN containing internal standards (IS) at a 1:3. Plates were shaken at 500 rpm for 10 min, and then centrifuged at 3,220×g for 20 minutes. Supernatants were transferred to another 96-well plate containing a dilution solution. Supernatants were analyzed by LC/MS/MS.

Compound half-life was estimated using the following equation:

% Remaining Compound=Peak Area Ratios of Tested Compound vs. Internal Standard at End Point/Peak Area Ratios of Tested Compound vs. Internal Standard at Start Point Mouse Xenograft Studies Xenograft models of human cancer cell lines were established in six-week-old CD-1 athymic nude mice by subcutaneous injection of $1.0$-$3.0 \times 10^7$ cells with or without 50% matrigel. When tumors reached an average size of 150-300 mm³, mice (n=8) were randomized into treatment groups. Tumor xenografts were measured with calipers three times per week, and tumor volume (in mm³) was determined by multiplying height×width×length. Statistical differences between treatment arms at specific time points were performed using a two-tailed paired Student t-test. Differences between groups were considered statistically significant at $p<0.05$. Compounds were formulated in 1% HEC in 25 mM phosphate buffer (pH=2) and dosed by daily oral gavage (PO). Data were analyzed using StudyLog software from StudyDirector (San Francisco, Calif.). See FIG. 5-FIG. 10.

Rat Pharmacokinetic and Single-Dose Saturation Studies

For pharmacokinetic (PK) analysis of compounds, non-tumor bearing female Sprague-Dawley rats, 3 per dosing group, received a single oral gavage (PO) dose of either 10, 50 or 100 mg/kg compound followed by saphenous vein blood draw at the following time points post dosing: 30, 60, 120, 240, 480 & 1,440 minutes. For dosing, compound was prepared in a vehicle of 2% Tween80 and 0.5% methyl cellulose at working concentrations of 1, 5 and 10 mg/mL.

Figure 3:
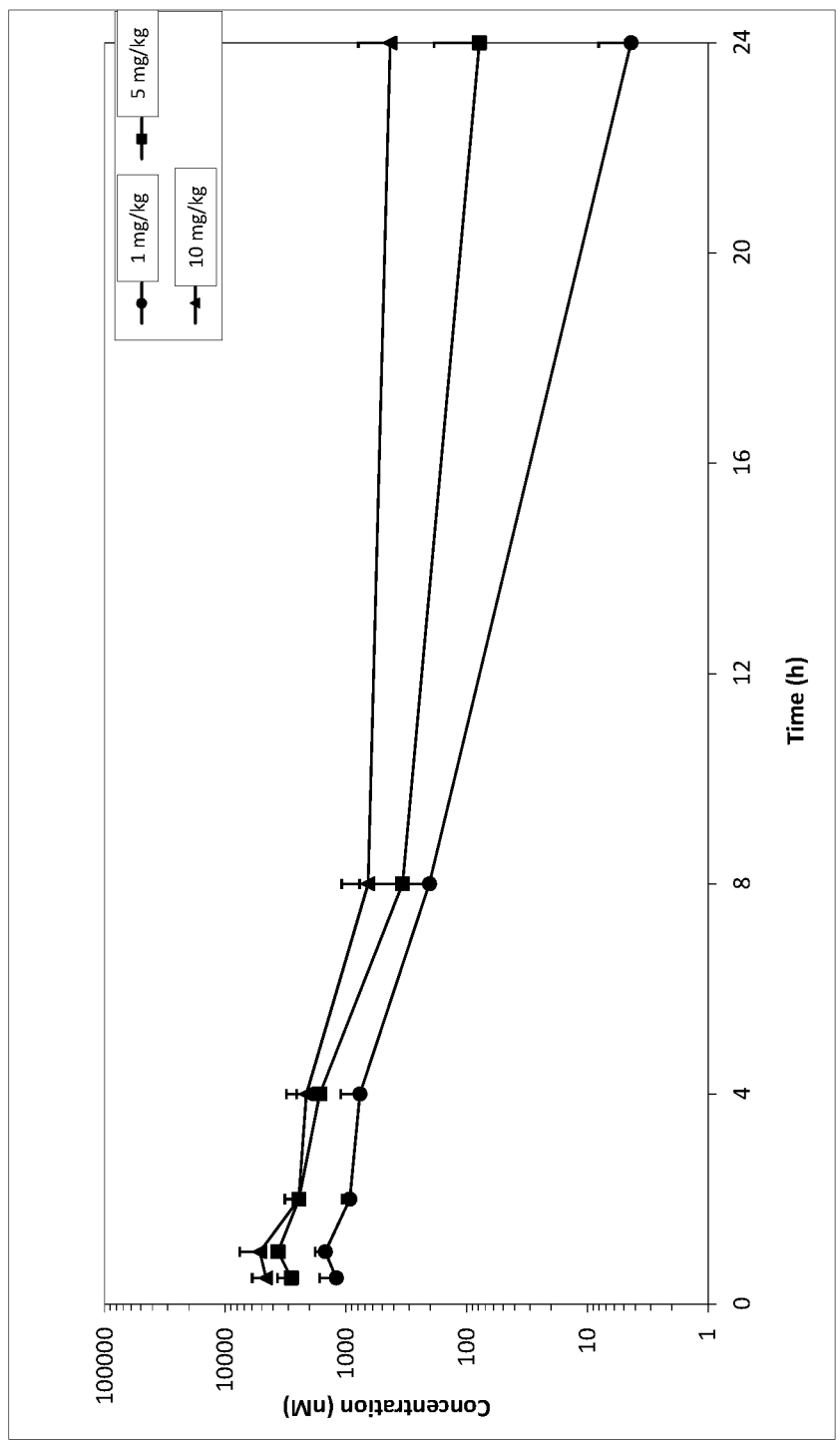
FIG. 3 are the results of a rat pharmacokinetics (PK) study with compound 6 dosed through oral gavage (PO) at 1, 5 and 10 mg/kg.
Figure 5:
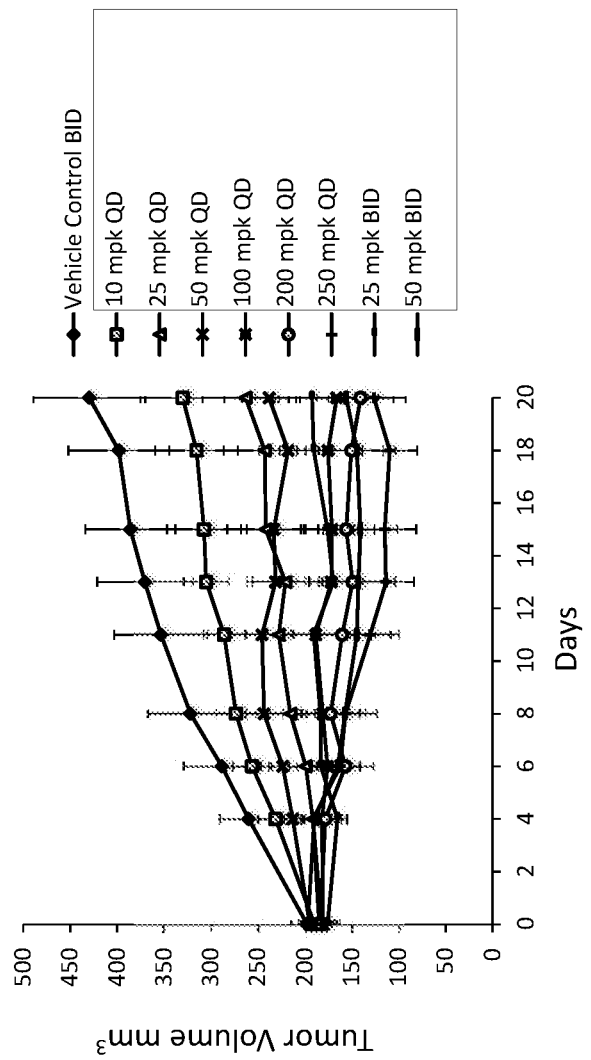
FIG. 5 are the results of an M275 melanoma cell line xenograft study with compound 6. Eight mice were used per group, and mice were dosed through oral gavage (PO) either daily (QD) or twice daily (BID) with various concentrations of compound 6.
Figure 7:
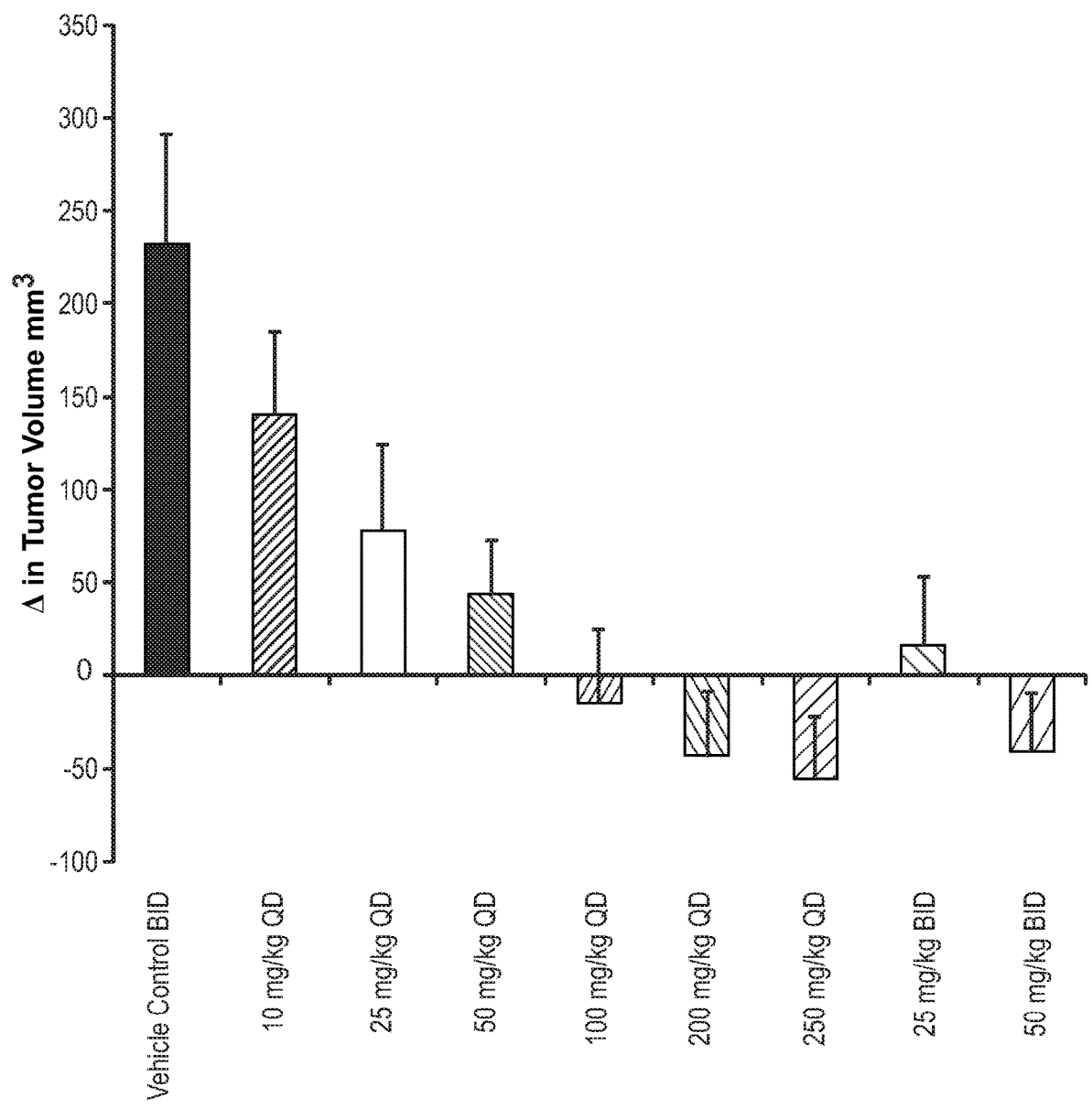
FIG. 7 shows the change in tumor volume results of the M275 melanoma cell line xenograft study at day 21 of dosing with compound 6.
Figure 8:
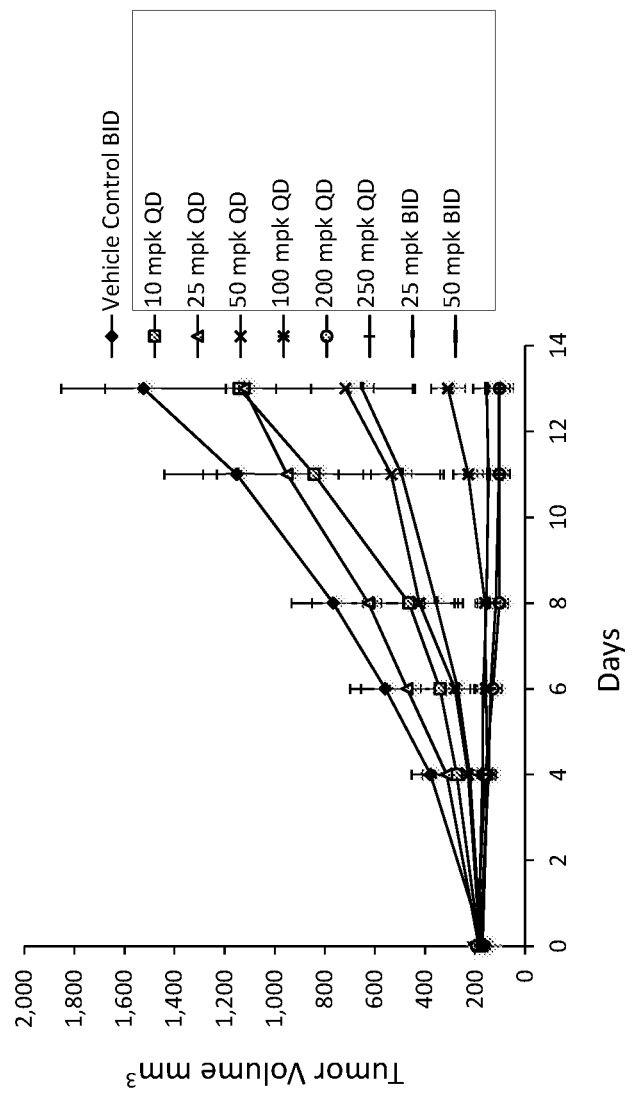
FIG. 8 are the results of a PSN1 pancreatic cancer cell line xenograft study with compound 6. Eight mice were used per group, and mice were dosed through oral gavage (PO) either daily (QD) or twice daily (BID) with various concentrations of compound 6.
Figure 10:
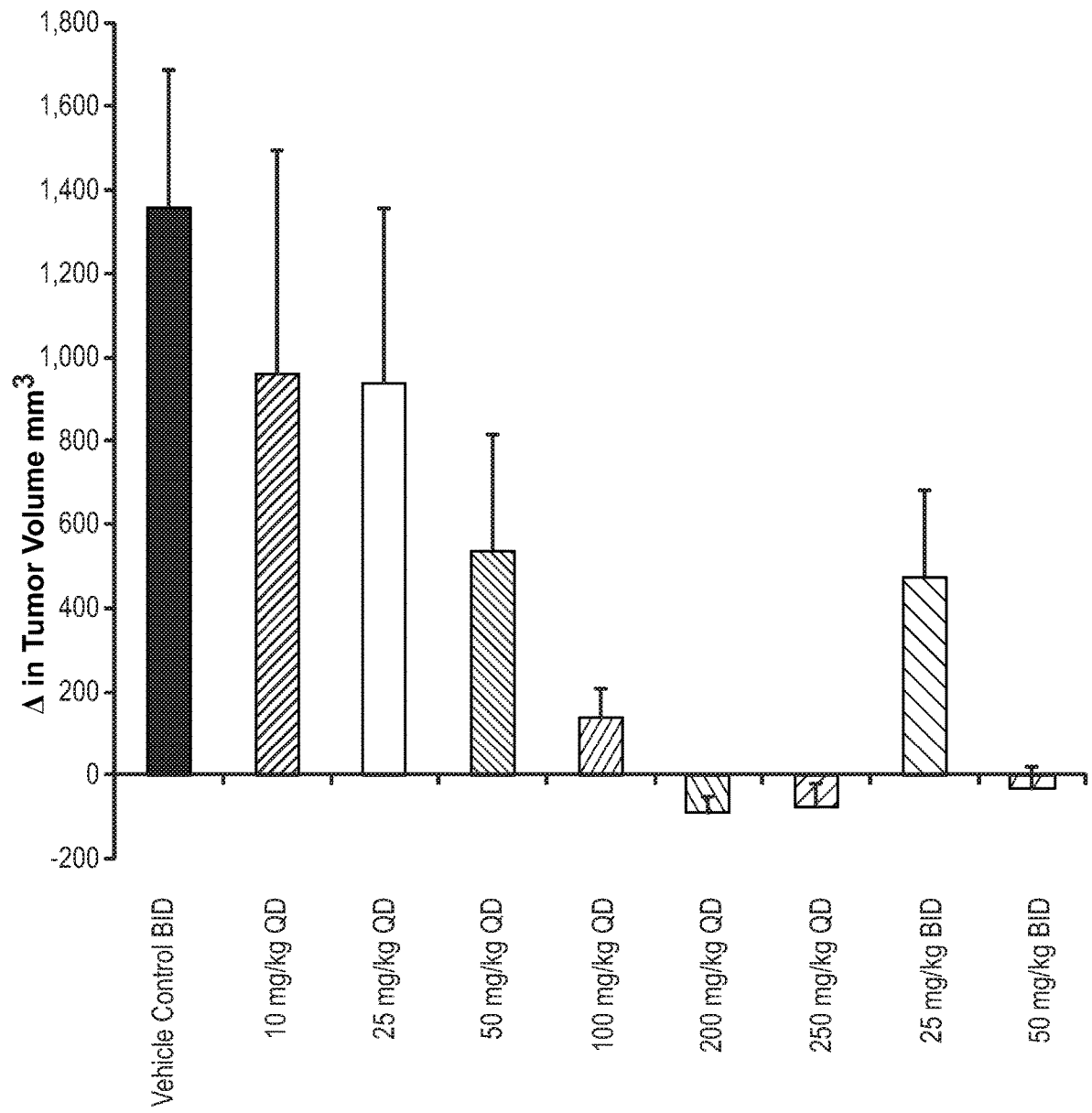
FIG. 10 shows the change in tumor volume results of the PSN1 pancreatic cancer cell line xenograft study at day 14 of dosing with compound 6.
Figure 11:
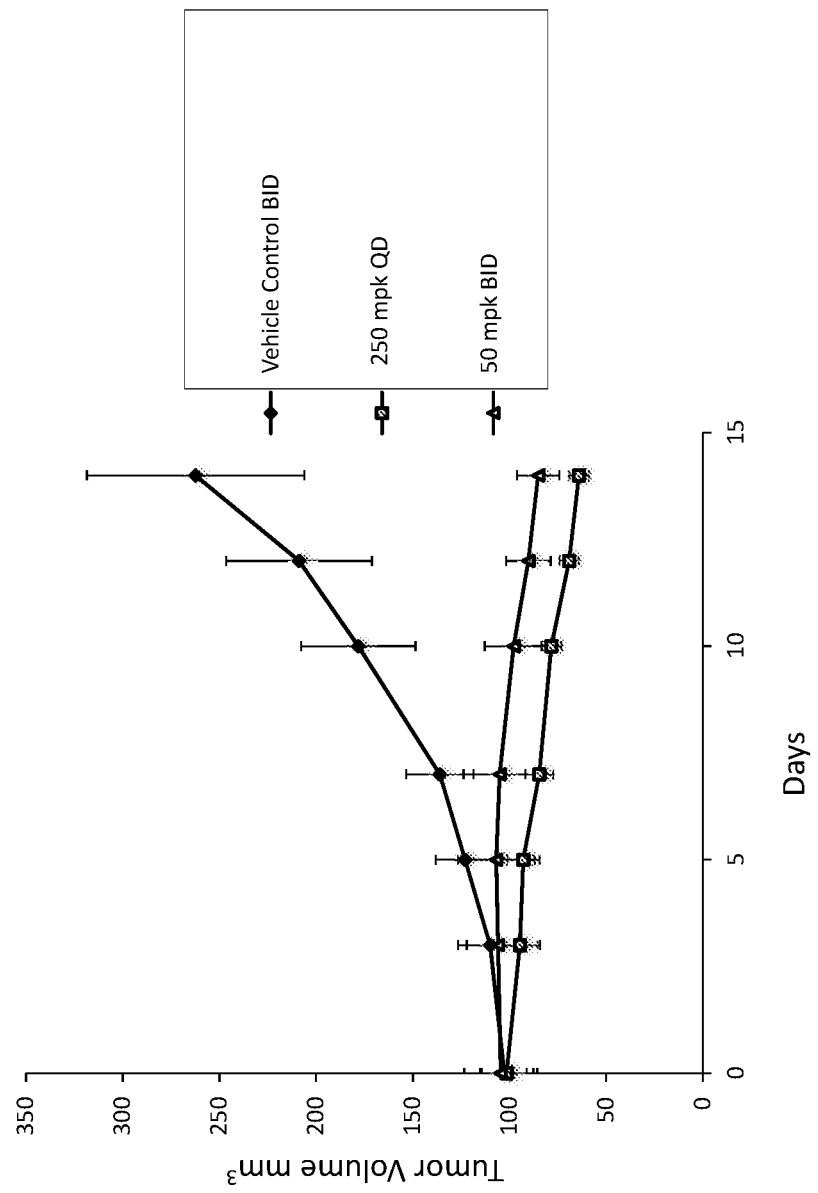
FIG. 11 are the results of a H2135 NSCLC cell line xenograft study with compound 6. Eight mice were used per group, and mice were dosed through oral gavage (PO) either daily (QD) or twice daily (BID) with two concentrations of compound 6.
Figure 13:
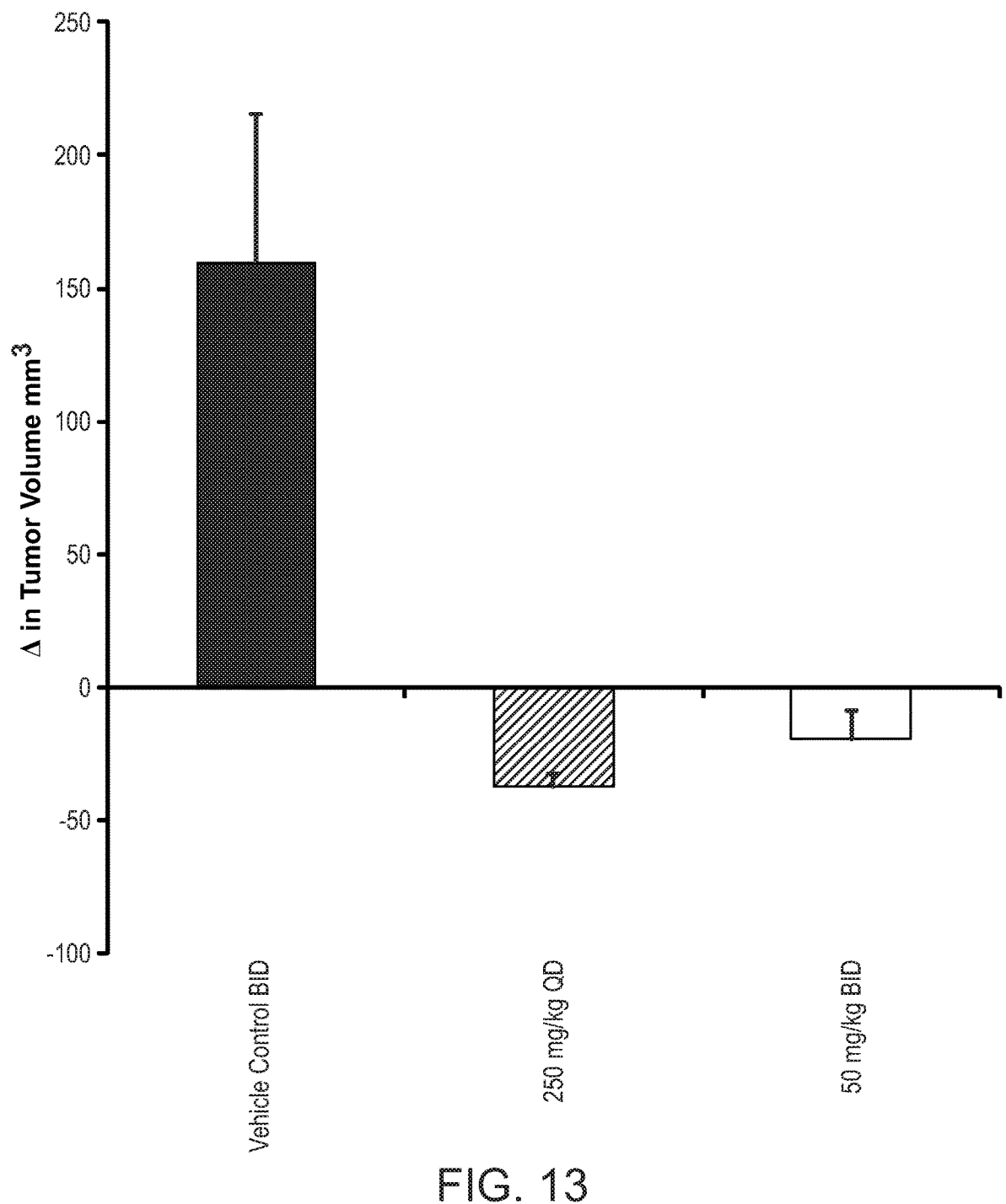
FIG. 13 shows the change in tumor volume results of the H2135 NSCLC cell line xenograft study at day 14 of dosing with compound 6.

For plasma preparation, whole blood was collected into EDTA-treated tubes. Cells were removed from plasma by centrifugation for 10 minutes at 1,000-2,000×g using a refrigerated centrifuge. The plasma fraction was removed and stored at −80° C. The amount (ng/mL) of compound in each plasma sample was determined by mass spectrometry (LC-MS/MS). For this analysis, an aliquot of 50 μL unknown sample, calibration standard, quality control, dilute quality control, single blank and double blank samples were added to the 1.5 mL tube. Each sample (except the double blank) was quenched with 250 μL internal standard solution (Labetalol & tolbutamide & Verapamil & dexamethasone & glyburide & Celecoxib 100 ng/mL for each) respectively (double blank sample was quenched with 250 μL ACN), and then the mixture was vortex-mixed and centrifuged for 15 min at 12000 g, 4° C. 50 μL supernatant was transferred to a 96-well plate and centrifuged for 5 min at 3220 g, 4° C., then 1 μL of supernatant was directly injected for LC-MS/MS analysis. Specific analyte concentrations were determined against a standard curve (100,000–1 ng/mL), and mean concentrations+/−standard deviation were calculated. See FIG. 3.

Mouse Pharmacokinetic and Single-Dose Saturation Studies

For pharmacokinetic (PK) analysis of compounds, non-tumor bearing six-week-old CD-1 athymic nude mice received a single PO dose of compound followed by saphenous vein blood draw at the following time points post dosing: 15, 30, 60, 120, 240, 480 & 1,440 minutes. No mouse was bled more than twice within the 1,440 minutes period. Untreated samples were collected from vehicle control animals. For plasma preparation, whole blood was collected into EDTA-treated tubes. Cells were removed from plasma by centrifugation for 10 minutes at 1,000-2,000×g using a refrigerated centrifuge. The plasma fraction was removed and stored at −80° C.

In order to determine the concentration at which drug exposure saturates, mice were dosed as described above with increasing concentrations of compound covering a log-fold concentration range (10 mg/kg to 100 mg/kg). Triplicate mice were used for each collection time-point and dose.

In order to determine amount (ng/ml) of compound in peripheral circulation, plasma samples were analyzed by mass spectrometry (HPLC). For this analysis, 20 μL of plasma sample was mixed with two volumes of ice-cold internal standard solution (ISS), and centrifuged at 6,100 g for 30 minutes. ISS contained acetonitrile with 100 ng/mL compound, 50 ng/mL dextromethorphan and 50 ng/mL imipramine. Aliquots of the supernatant was transferred to an autosampler plate and diluted with two volumes of 0.2% formic acid in water. Specific analyte concentrations were determined against a standard curve (10,000–5 ng/ml), and mean concentrations+/−standard deviation were calculated. See FIG. 1 and FIG. 2.

Mouse Maximum Tolerated Dose Studies

For maximum tolerated dose (MTD) determination studies, non-tumor bearing CD-1 athymic nude mice were randomized into 5 treatment groups (5 mice per group) and treated with either 400, 300, 200, 100, 50 or 25 mg/kg of compound by daily PO, or 200, 100, 50, 25, or 12.5 mg/kg of compound twice daily PO. Mice were weighed daily and % body weight loss was calculated relative to individual mouse body weights at the start of treatment. Studies were continued for 14 days or until>10% group mean body weight loss was observed in the animals. MTD was determined as the highest dose at which a mean body weight loss of <10% over 14 days of dosing was observed. See FIG. 4.

Western Blot for Total and pRSK

Figure 14:
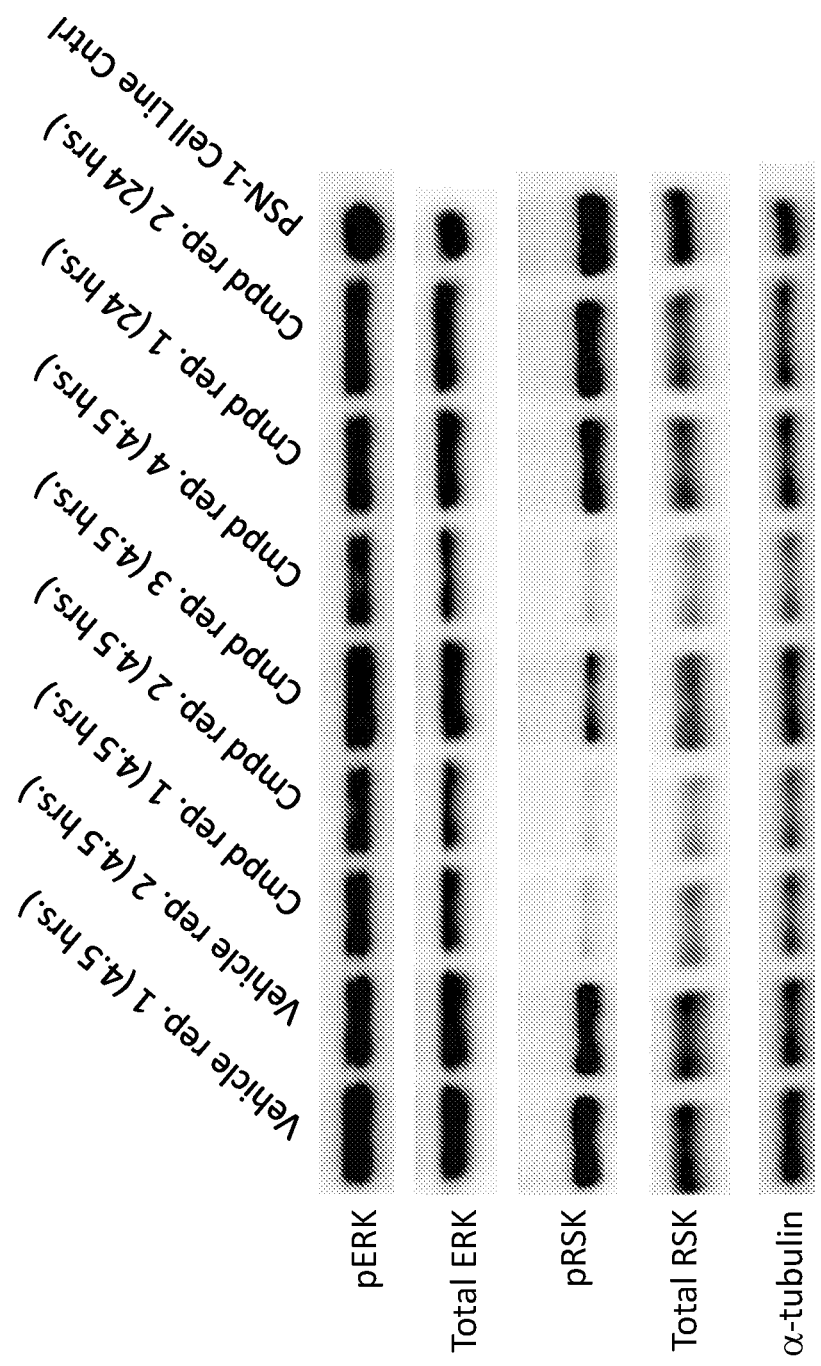
FIG. 14 shows the decrease in the level of phosphorylated RSK (pRSK) in M275 cells after treatment with compound 6 for 4.5 hours (four replicates) and 24 hours (two replicates).

For Western blot assays (see FIG. 14), protein lysates were obtained from either the M275 or M202 human melanoma cancer cell lines. For assay, cells were plated on 10 cm dishes and treated 24 hours later with either 200 nM of test compound in DMSO or DMSO control for 4.5 or 24 hours. After the treatment period, cells were washed twice in ice-cold PBS and lysed for 15 minutes at 4° C. using a mild lysis buffer (Cell Signaling Technology) containing a mixture of protease inhibitors (Calbiochem) and 1 mmol/L phenlymethylsulfonlyfluoride. Insoluble material was removed by centrifugation at 10,000×g for 10 minutes. Protein concentration of each sample was quantified by BCA (Pierce), resolved by SDS-PAGE, and transferred to nitrocellulose membranes (iBlot, Invitrogen Life Technology). Total (32D7, Cell Signaling Technologies) and phosphorylated (Tyr359; D1E9, Cell Signaling Technology) RSK protein were detected using the indicated antibody clones. All blots were repeated in duplicate and relative levels of individual proteins compared to a loading control (α-tubulin) (11H10; Cell Signaling Technology) were quantitated using the ECL Plus chemifluorescent reagent (Amersham Biosciences) and the ChemiDoc™ Touch Imaging System (BioRad).

Activity-Guided Selection of Inhibitors

Subgenera of ERK1/2 inhibitors having desirable properties were identified using a combination of in vitro data.

In particular, the results from the assays described above (e.g., *Cell Line Growth Retardation Assay, ERK1 and 2 Enzymatic Inhibition Assay, Caco-2 Assay ($P_{app}$ A to B), Measurement of Compound Metabolic Stability, Designation of Sensitivity and Resistant Cohorts and Calculation of Average $IC_{50}$ Values, and Western Blot for Total and pRSK*) were used to select compounds having structural and functional features defined in the subgenera of Formula (Ie).

In particular, a desirable property of compounds examined in sensitive and resistant cell lines, as described above, is having an average $IC_{50}$ for the drug-sensitive cell lines of Table 4 of at least about 4-fold more potent than the average $IC_{50}$ of the compound for the drug-resistant cell lines of Table 4.

Another desirable property of compounds examined as compared to a vehicle control is a decrease of about 70% or more in the levels of pRSK in M275 cells after about 5 hours of treatment with the compound at a concentration of about 200 nM.

The skilled artisan would readily recognize that the results of additional in vitro assays (e.g., CYP enzymatic inhibition, hERG inhibition, compound solubility, kinome analysis), as well as the results of in vivo assays (e.g., *Rodent Xenograft Studies, Rodent Pharmacokinetic and Single-Dose Saturation Studies, Rodent Maximum Tolerated Dose Studies*, and oral bioavailability) could be used to identify other subgenera of ERK1/2 inhibitors, or to narrow subgenera determined using other results, for example, the subgenera of Formula (Ie).

TABLE 3

| Cmpnd | ERK1 $K_d$ | ERK2 $K_d$ | AvgSens IC$_{50}$ | AvgRes IC$_{50}$ | $P_{app}$ A-to-B | Half-life |
|---|---|---|---|---|---|---|
| 6 | A | A | A | C | B | A |
| 7 | A | B | C | C | | |
| 8 | C | C | C | C | A | |
| 9 | C | C | C | C | | |
| 10 | C | C | C | C | | |
| 11 | A | A | B | C | A | B |
| 13 | B | C | C | C | | |
| 15 | B | B | C | C | | |
| 17 | B | B | C | C | | |
| 18 | B | B | C | C | | |
| 19 | C | C | C | C | | |
| 20 | A | A | A | C | B | A |
| 21 | A | B | B | C | | |
| 22 | C | C | C | C | A | A |
| 23 | C | C | | | A | |
| 24 | B | B | C | C | C | |
| 25 | A | A | C | C | B | A |
| 26 | B | C | C | C | A | B |
| 27 | A | A | C | C | B | A |
| 28 | C | C | C | C | B | A |
| 29 | B | B | C | C | B | A |
| 30 | C | C | | | | |
| 31 | A | A | C | C | B | B |
| 32 | A | A | B | C | | |
| 33 | B | B | | | | |
| 34 | A | B | C | C | | |
| 35 | B | B | C | C | | |
| 36 | A | B | C | C | | |
| 37 | A | B | C | C | | |
| 38 | B | B | C | C | | |
| 39 | A | A | A | C | | |
| 40 | A | A | A | C | | |
| 41 | A | A | A | C | | |
| 42 | A | A | C | C | | |
| 43 | B | C | C | C | | |
| 44 | A | A | A | C | | |
| 45 | A | A | A | C | | |
| 46 | A | A | B | C | | |
| 47 | A | A | B | C | | |
| 48 | A | B | | | | |
| 49 | A | A | B | C | | |
| 50 | A | A | A | C | B | A |
| 51 | B | B | B | C | A | |
| 52 | C | C | C | C | B | A |
| 53 | A | A | C | C | C | |
| 54 | B | B | C | C | B | A |
| 55 | B | B | C | C | B | |
| 56 | B | B | C | C | B | |
| 57 | C | C | C | C | | |
| 58 | A | A | | | | |
| 59 | B | A | | | | |
| 60 | B | B | C | C | | |
| 61 | A | A | B | C | | |
| 62 | A | B | C | C | | |
| 63 | B | B | | | | |
| 64 | B | B | | | | |
| 65 | A | A | A | C | | |
| 66 | A | A | C | C | | |
| 67 | B | B | C | C | | |
| 68 | B | B | | | | |

TABLE 4

| Cell Line Name | Cohort |
|---|---|
| SKMEL 2 | Sensitive |
| SKCO1 | Sensitive |
| SW403 | Sensitive |
| HT29 | Sensitive |
| M296 | Sensitive |
| WM 2664 | Sensitive |
| DU4475 | Sensitive |
| CAPAN 2 | Sensitive |
| HS 766T | Sensitive |
| MIAPACA 2 | Sensitive |
| PANC 05.04 | Sensitive |
| PSN-1 | Sensitive |
| M275 | Sensitive |
| NCI-H520 | Resistant |
| MCF-7 | Resistant |
| MDA-MB-231 | Resistant |
| LS123 | Resistant |
| SW948 | Resistant |
| LS174t | Resistant |
| NCI-H810 | Resistant |
| NCI-H2126 | Resistant |
| CAL-51 | Resistant |
| NCI-H2172 | Resistant |
| LS174T_E | Resistant |
| NCI-H446 | Resistant |
| Pfeiffer | Resistant |
| BXPC 3 | Resistant |
| NCI-H1651 | Resistant |

We claim:

1. A compound having the structure of Formula I:

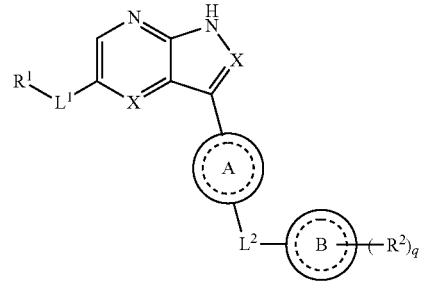

(Formula I)

or a pharmaceutically acceptable salt thereof,
wherein:
$R^1$ is optionally substituted heterocyclyl, or optionally substituted heteroaryl;
$L^1$ is a bond;

is pyridinyl, pyrimidinyl, pyrazinyl, pyridazinyl, or triazinyl, wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;
X in each occurrence is independently selected from CH and N;
$L^2$ is optionally substituted $C_{1-5}$alkyl, $C(O)N(R^4)(C(R^4)_2)_m$, $(C(R^4)_2)_mC(O)N(R^4)$, $C(O)$heterocyclyl, heterocyclyl-C(O), $N(R^4)$, $S(O)_2N(R^4)$, $N(R^4)S(O)_2$, $S(O)_2$, or heterocyclyl, wherein said heterocyclyl is optionally substituted with one or more optionally substituted aryl, optionally substituted C1-4alkyl or halogen;

is aryl or heteroaryl;

$R^2$ if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, optionally substituted aryl, optionally substituted heteroaryl, optionally substituted cycloalkyl, or optionally substituted heterocyclyl;

m is 0, 1, 2 or 3; and q is 0, 1, 2 or 3.

2. The compound of claim 1, wherein $L^2$ is optionally substituted $C_{1-5}$alkyl, optionally substituted heterocyclyl, $C(O)N(R^4)(C(R_4R_4))_m$, or C(O) heterocyclyl.

3. The compound of claim 1, wherein $L^2$ is hydroxy-substituted $C_{1-5}$alkyl or methoxy-substituted $C_{1-5}$alkyl.

4. The compound of claim 1, wherein $L^2$ is unsubstituted oxazolinyl or unsubstituted imidazolinyl.

5. The compound of claim 2, wherein $L^2$ is $C(O)N(R^4)(C(R^4R^4))_m$; and each instance of $R^4$ is independently hydrogen or $C_{1-4}$alkyl; and m is 0, 1, or 2.

6. The compound of claim 1, wherein the compound of Formula I has the structure of Formula Ia':

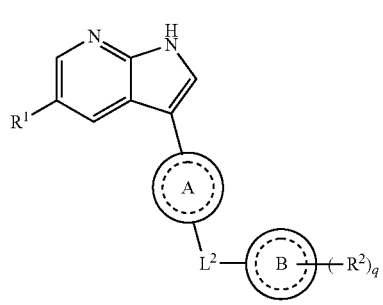

(Formula Ia')

or a pharmaceutically acceptable salt thereof,
the compound of Formula I has the structure of Formula Ib':

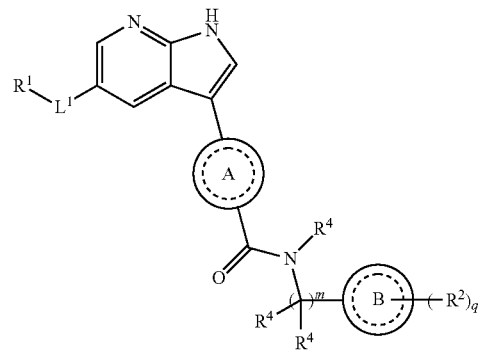

(Formula Ib')

or a pharmaceutically acceptable salt thereof,
the compound of Formula I has the structure of Formula Ic':

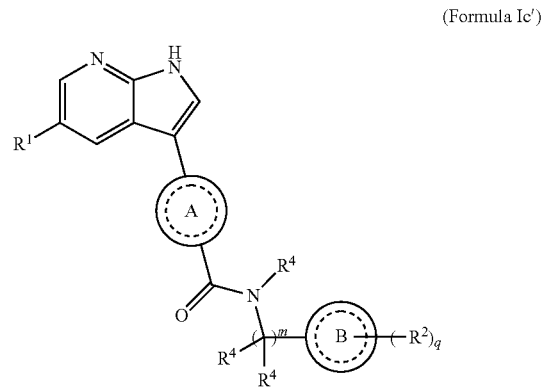

(Formula Ic')

or a pharmaceutically acceptable salt thereof.

7. A compound having the structure of Formula II:

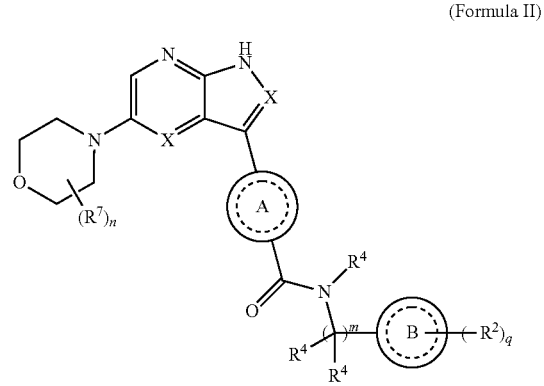

(Formula II)

or a pharmaceutically acceptable salt thereof, wherein:

is pyridinyl, pyrimidinyl, pyrazinyl, pyridazinyl, or triazinyl, wherein any of pyridinyl, pyrimidinyl, pyrazinyl, pyridazinyl, and triazinyl can be optionally substituted with one or more substituents selected from halogen, optionally substituted $C_{1-3}$alkyl and $N(R^3)_2$;

X in each occurrence is independently selected from CH and N;

is aryl or heteroaryl;

$R^2$ if present, in each instance is independently optionally substituted $C_{1-6}$alkyl, alkoxy, optionally substituted cycloalkyl, CN, $NR^{1a}R_{1b}$, $C(O)N(R_{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, optionally substituted aryl, optionally substituted heteroaryl, optionally substituted cycloalkyl, or optionally substituted heterocyclyl;

$R^7$ when present, is optionally substituted $C_{1-6}$alkyl;

m is 0, 1, 2 or 3;

n is 0, 1, 2, 3 or 4; and q is 0, 1, 2 or 3.

8. The compound of claim 7, wherein the compound of Formula II has the structure of Formula IIa:

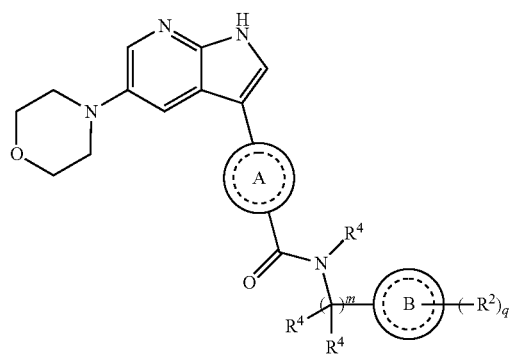

or a pharmaceutically acceptable salt thereof.

9. A compound having the structure of Formula III:

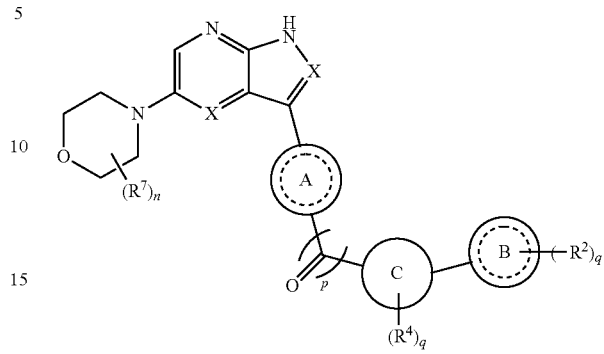

or a pharmaceutically acceptable salt thereof,
wherein:

is pyridinyl, pyrimidinyl, pyrazinyl, pyridazinyl, or triazinyl, wherein any of pyridinyl, pyrimidinyl, pyrazinyl, pyridazinyl, and triazinyl can be optionally substituted with one or more substituents selected from halogen, optionally substituted $C_1$-3alkyl and $N(R^3)_2$;

X in each occurrence is independently selected from CH and N;

is aryl or heteroaryl;

is heterocyclyl;

$R^2$ if present, in each instance is independently optionally substituted $C_{1-6}$alkyl, alkoxy, optionally substituted cycloalkyl, CN, $NR^{1a}R^{1b}$, $C(O)N(R^{1a})(R^{1b})$, $N(R^{1a})C(O)R^{1a}$, halogen or $CF_3$;

each of $R^{1a}$ and $R^{1b}$ is, in each instance, independently hydrogen, optionally substituted $C_{1-4}$alkyl, optionally substituted aryl, optionally substituted heteroaryl, optionally substituted cycloalkyl or optionally substituted heterocyclyl; or $R^{1a}$ and $R^{1b}$, together with the N to which they are bonded, form an optionally substituted heterocyclyl;

$R^3$ is, in each instance, independently hydrogen or optionally substituted $C_{1-4}$alkyl;

$R^4$ is, in each instance, independently hydrogen, optionally substituted $C_{1-4}$alkyl, optionally substituted aryl, optionally substituted heteroaryl, optionally substituted cycloalkyl, or optionally substituted heterocyclyl;

$R^7$ when present, is optionally substituted $C_{1-6}$alkyl;

n is 0, 1, 2, 3 or 4;

p is 0 or 1; and q is, in each instance, independently 0, 1, 2 or 3.

10. The compound of claim 9, wherein the compound of Formula III has the structure of Formula IIIa:

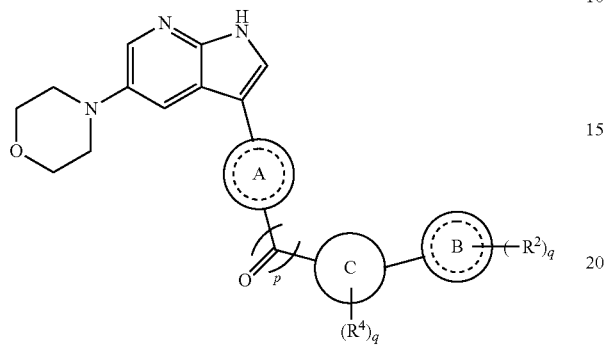
(Formula IIIa)

or a pharmaceutically acceptable salt thereof.

11. The compound of claim 1, wherein

is pyridinyl, pyrimidinyl, or pyridazinyl.

12. The compound of claim 1, wherein

is phenyl, pyrrolyl or pyridinyl.

13. The compound of claim 1 having the structure of Formula Ia, Ib, Ic, or Id:

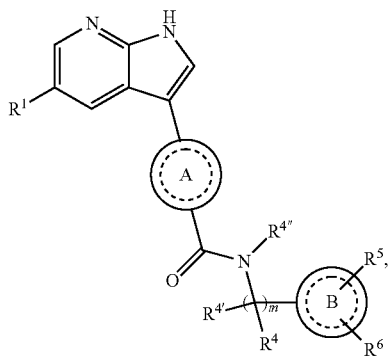
(Formula Ia)

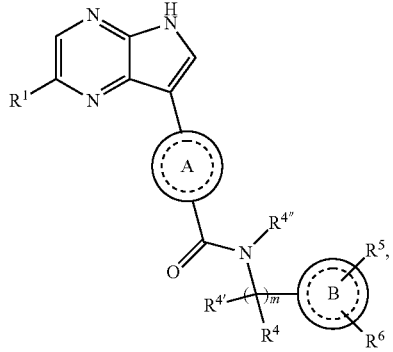
(Formula Ib)

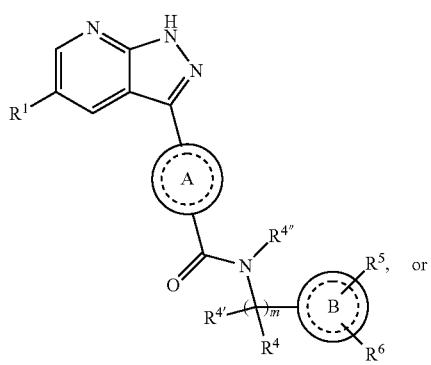
(Formula Ic)

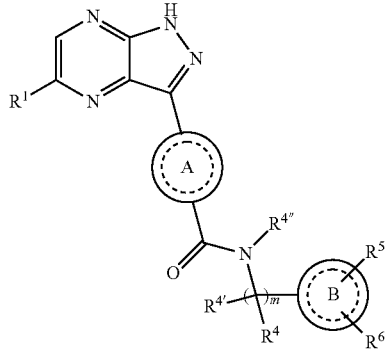
(Formula Id)

or a pharmaceutically acceptable salt thereof, wherein:

is pyridinyl, pyrimidinyl, pyrazinyl, pyridazinyl, or triazinyl;

is phenyl, pyridinyl, pyrimidinyl, pyrazinyl, pyridazinyl, thiophenyl or thiazolyl;

m is 1 or 2;

$R^1$ is tetrahydropyranyl, morpholinyl, piperazinyl, piperidinyl, pyridinyl, pyrimidinyl, pyrazinyl, pyridazinyl, or thiophenyl, alkynyl, CN, amide, amino, acyl or acyloxy;

$R^{4'''}$ is hydrogen, $C_1$-$C_2$ alkyl, $C_3$-$C_4$ alkyl, cyclopropyl, or $C_4$-$C_6$ cycloalkyl;

$R^{4''}$ is hydrogen, $C_1$-$C_3$ alkyl, phenyl, pyridinyl, pyrimidinyl, pyrrolidinyl, pyrrolyl, $C_3$-$C_6$ cycloalkyl, piperidinyl, morpholinyl, or tetrahydropyranyl, or alkynyl;

$R^4$ is hydrogen or methyl; and $R^5$ and $R^6$ are each independently hydrogen, halogen, $C_1$-$C_2$ alkyl or $NH_2$.

14. The compound of claim 1 having the structure of Formula Ie:

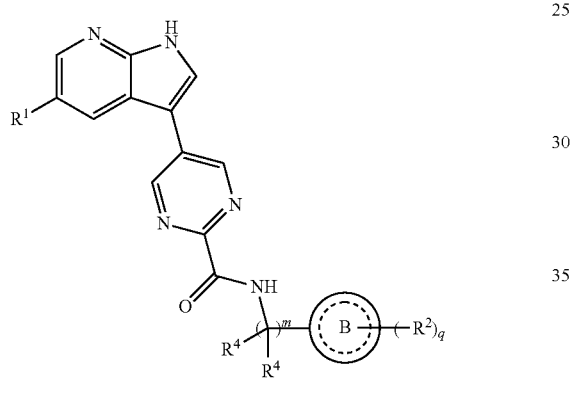

(Formula Ie)

or a pharmaceutically acceptable salt thereof, wherein:

is aryl;

$R^2$, if present, in each instance is independently optionally substituted $C_{1-6}$alkyl, alkoxy, CN, halogen or $CF_3$;

$R^4$ in each instance is independently hydrogen, optionally substituted $C_{1-4}$alkyl, or $C_{1-4}$haloalkyl, $C_{1-4}$aminoalkyl, $C_{1-4}$hydroxyalkyl or cycloalkyl;

m is 1 or 2;

q is 0, 1 or 2; and wherein the compound has an ERK1 $K_d$ of about 10 nM or lower and an ERK2 $K_d$ of about 10 nM or lower.

15. The compound of claim 1 selected from:

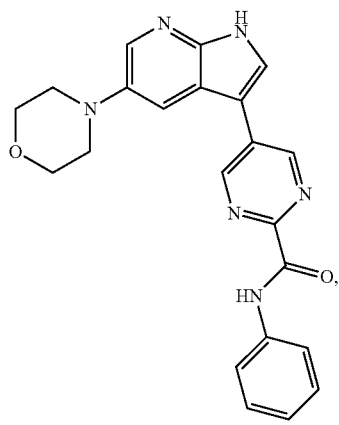

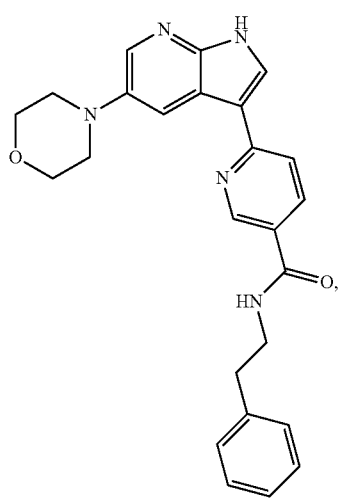

189
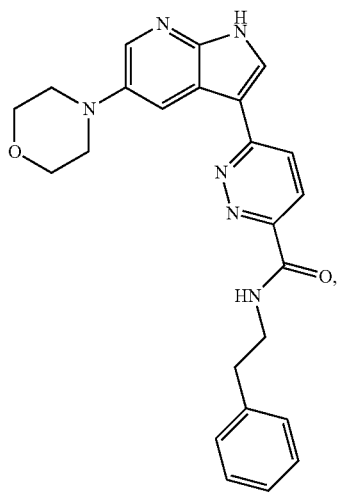
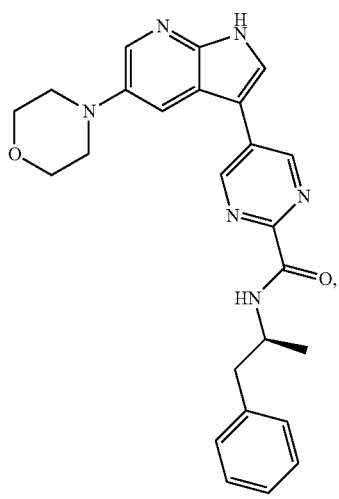
190
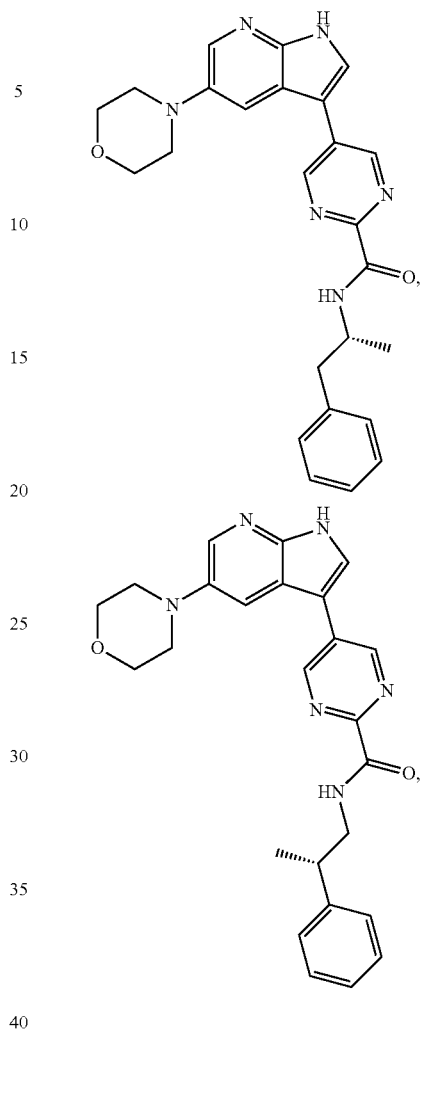
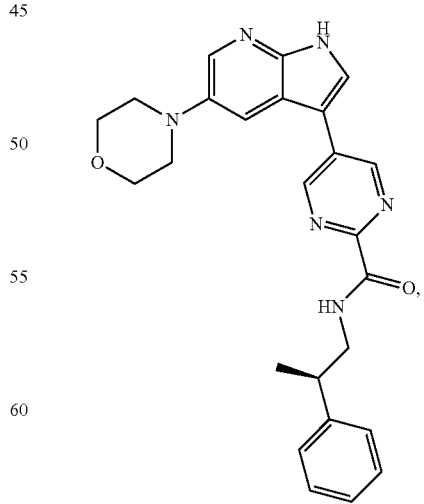

191
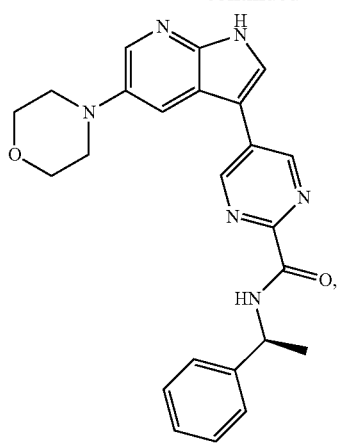 [SMILES: C[C@H](NC(=O)c1ncc(-c2c[nH]c3ncc(N4CCOCC4)cc23)cn1)c1ccccc1]
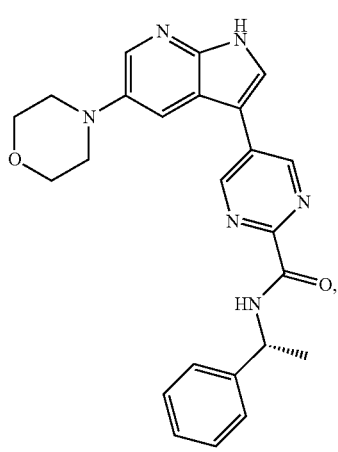
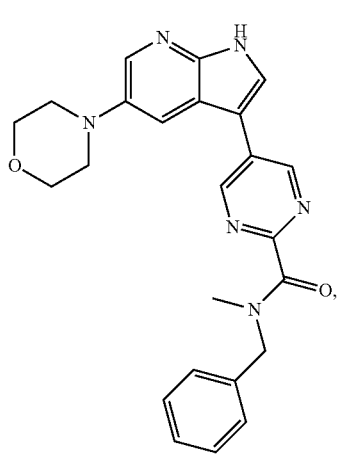
192
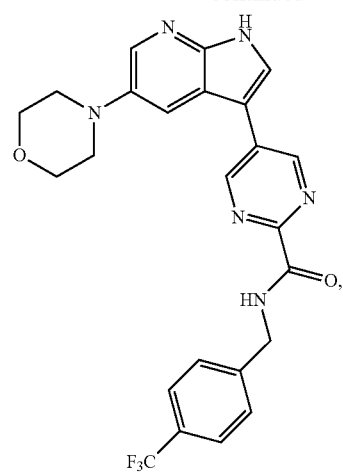
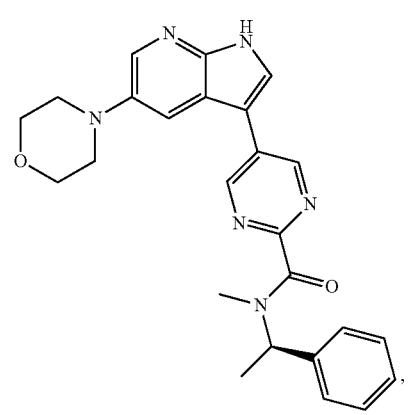
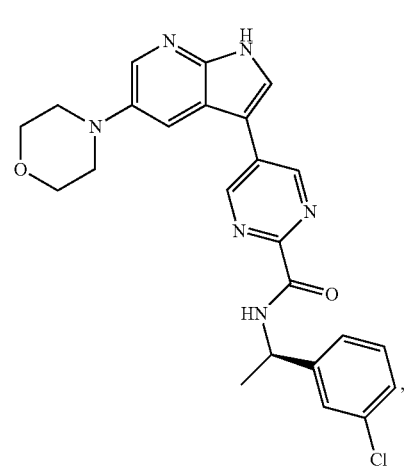

193
-continued
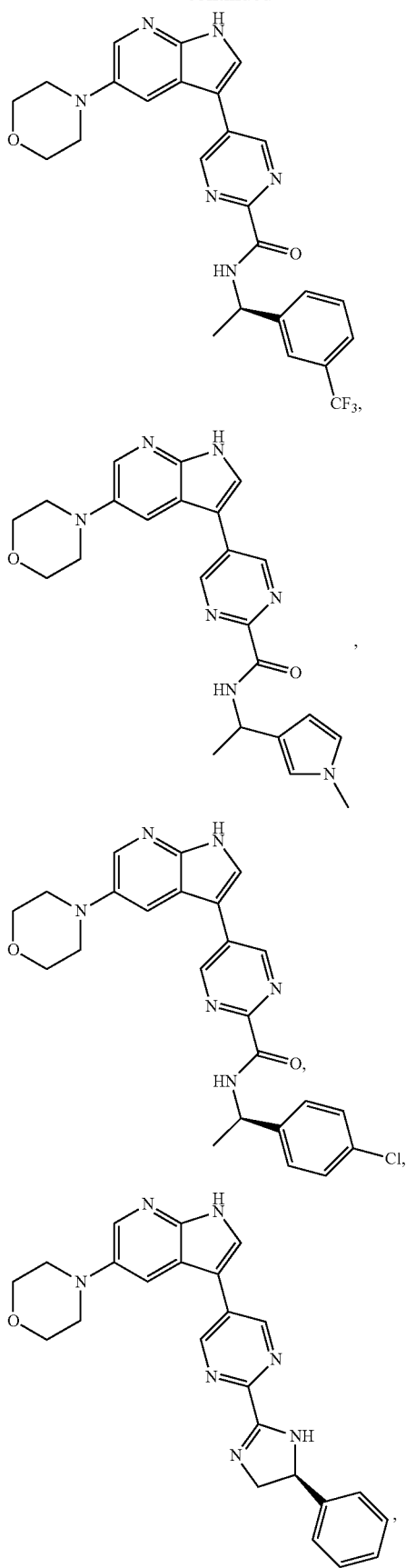
194
-continued
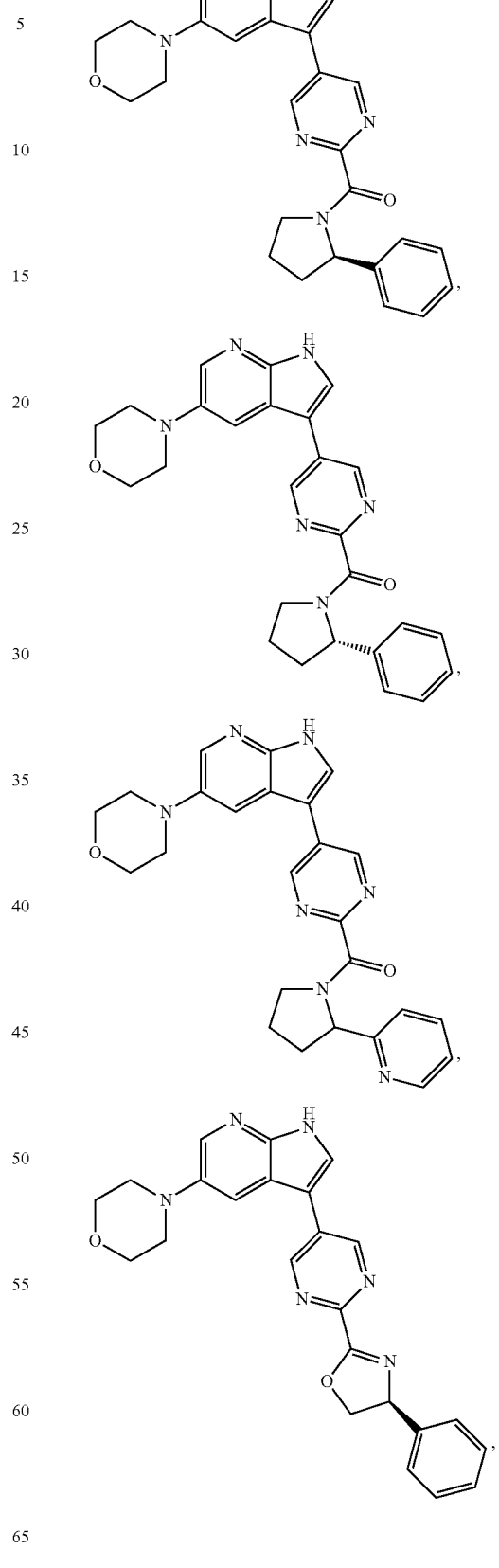

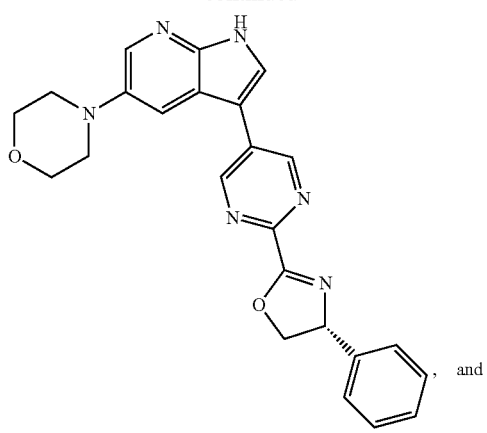
, and
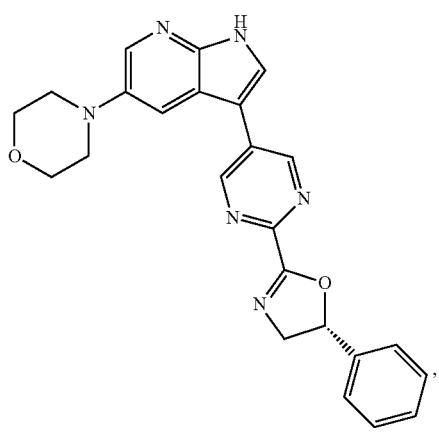
,
or a pharmaceutically acceptable salt thereof.
16. The compound of claim 1 selected from:
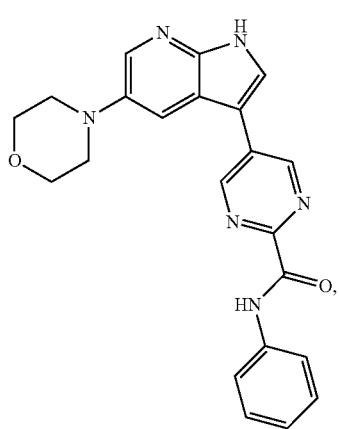
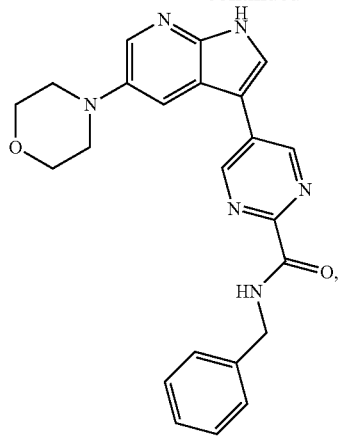
,
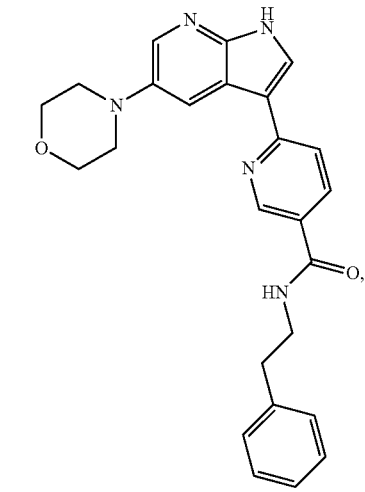
,
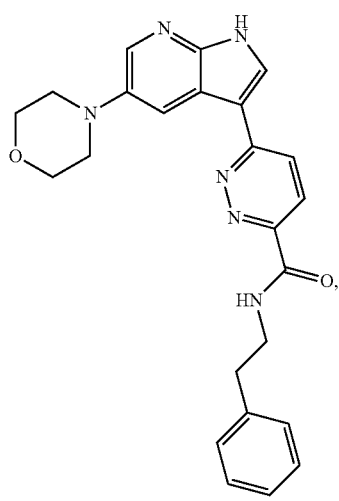
, 197
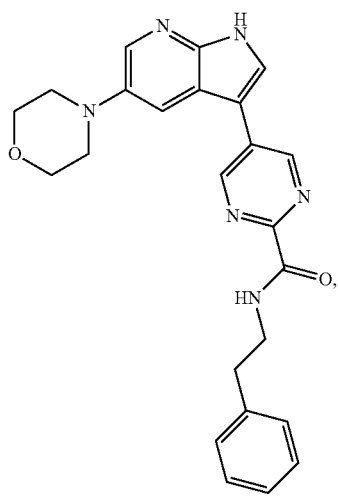
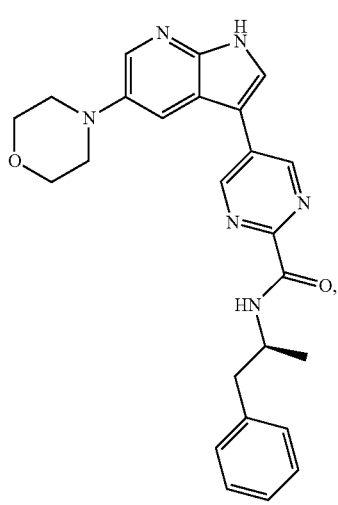
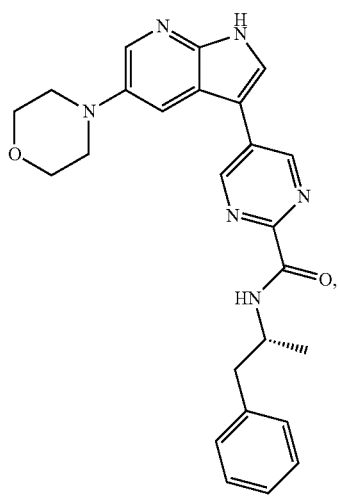
198
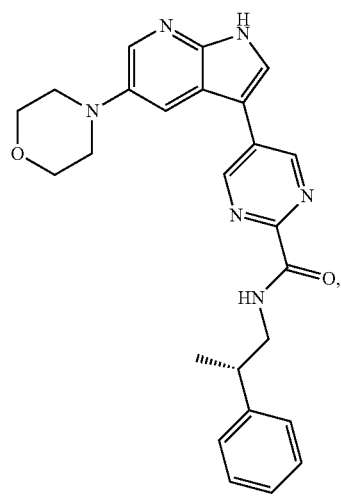
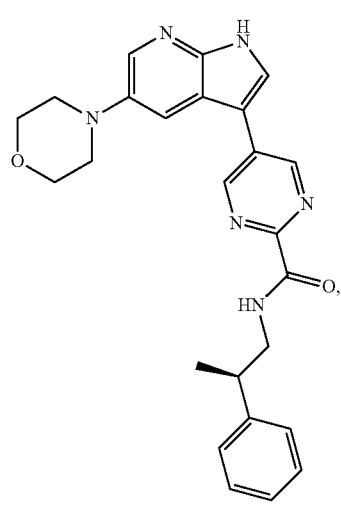
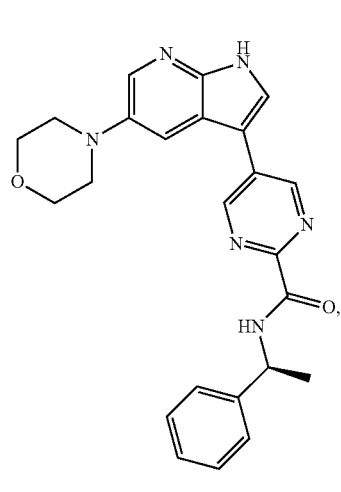 [SMILES: C[C@H](NC(=O)c1ncc(-c2c[nH]c3ncc(N4CCOCC4)cc23)cn1)c1ccccc1]

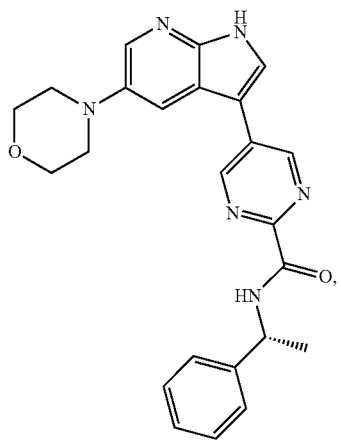
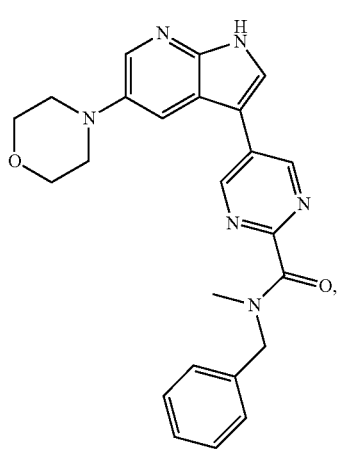
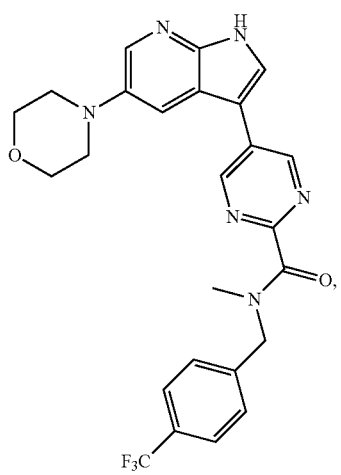
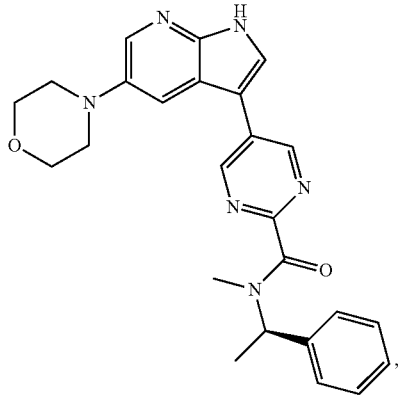
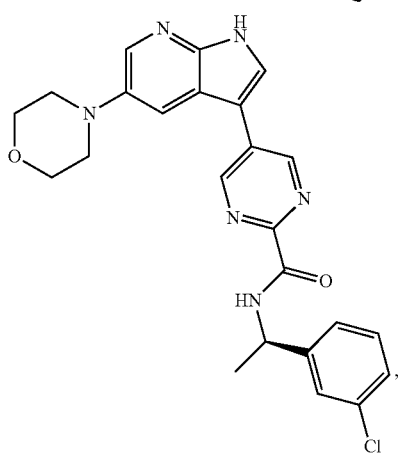
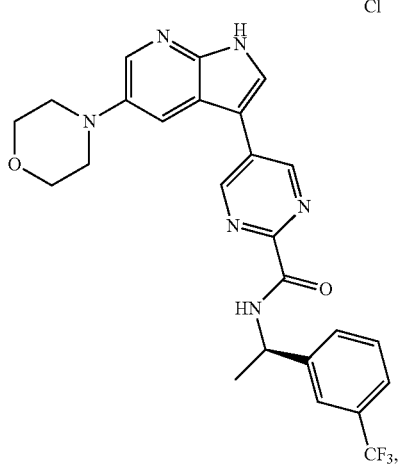

201
-continued
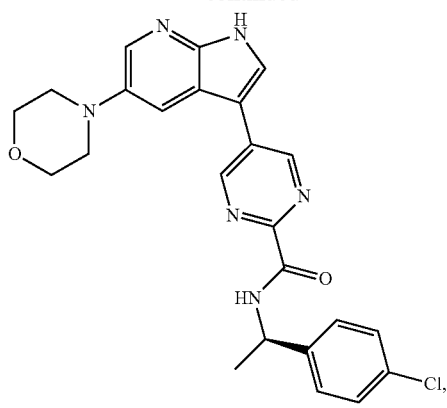
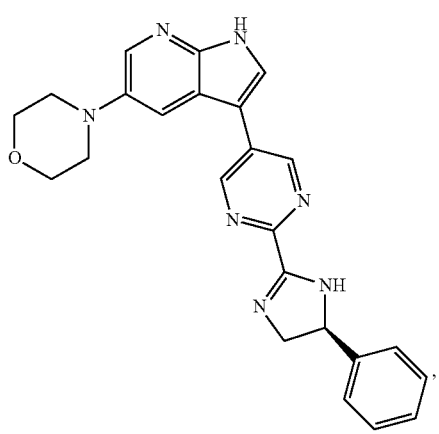
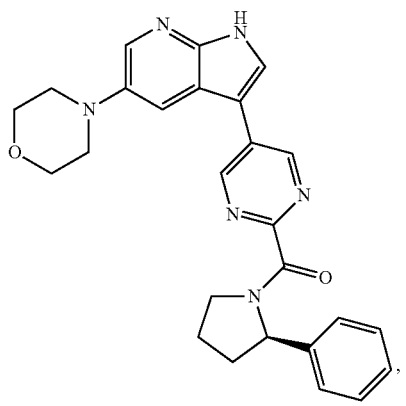
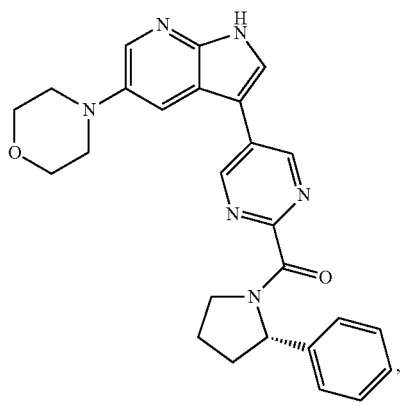
202
-continued
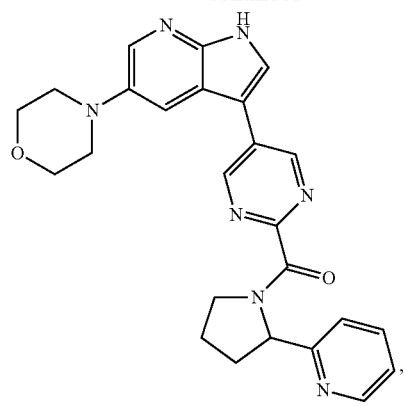
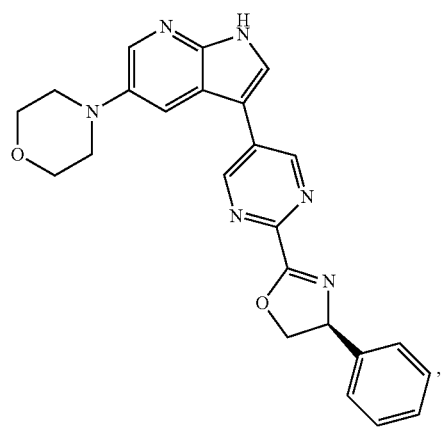
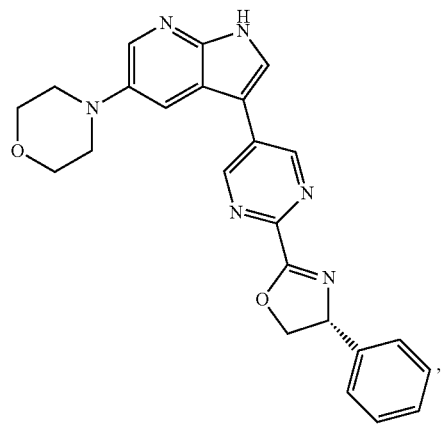
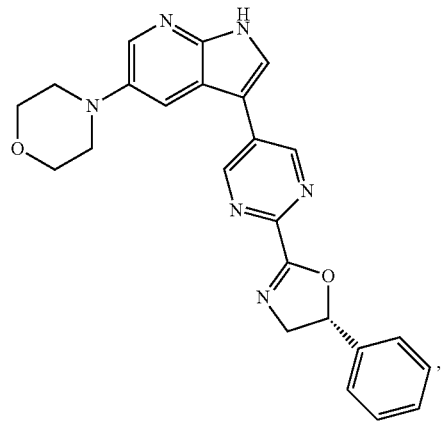

203
-continued
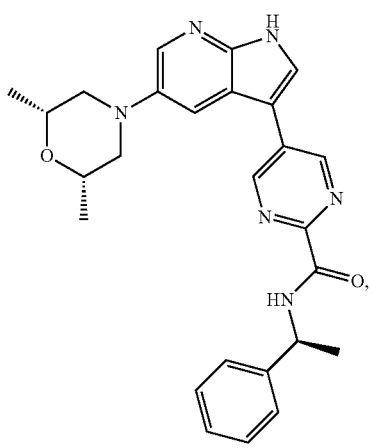
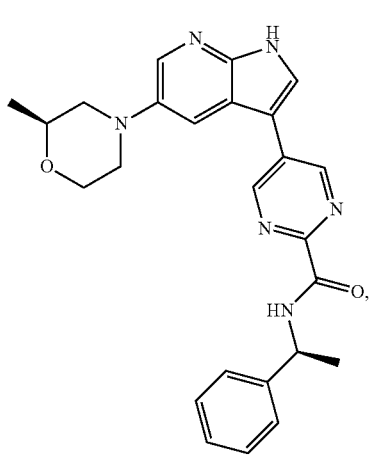
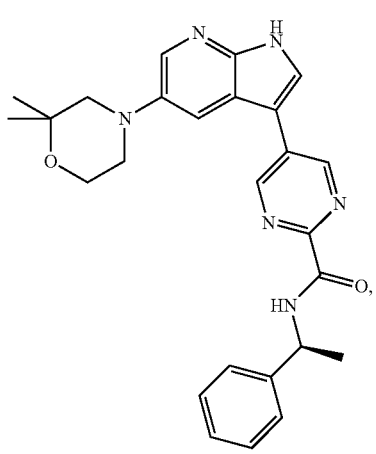
204
-continued
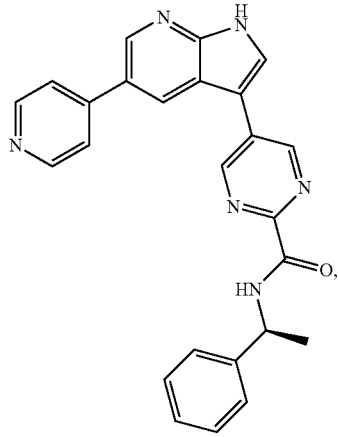
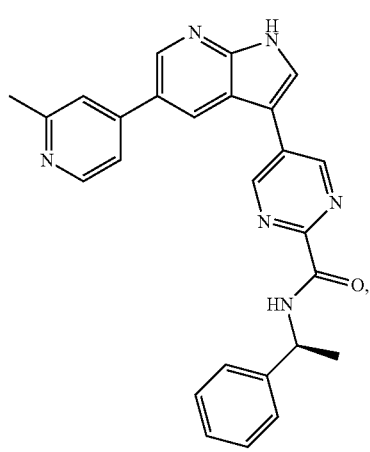
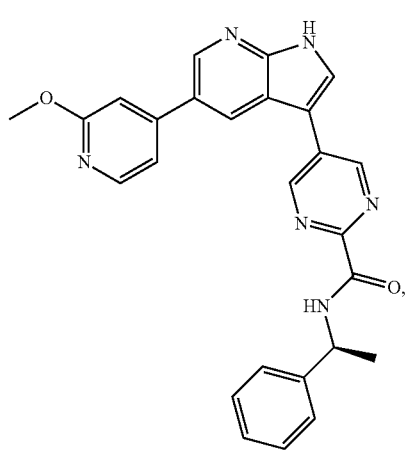

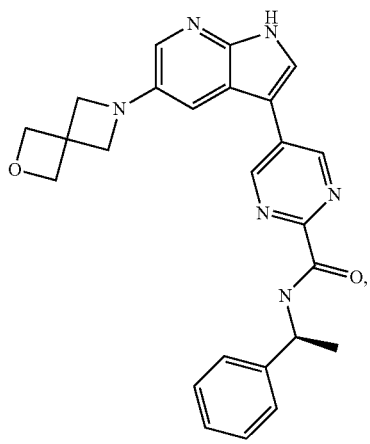
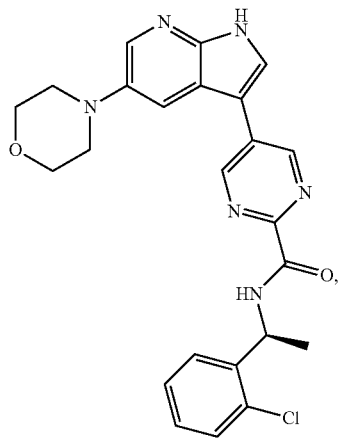
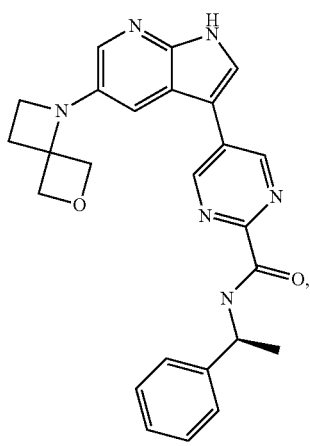
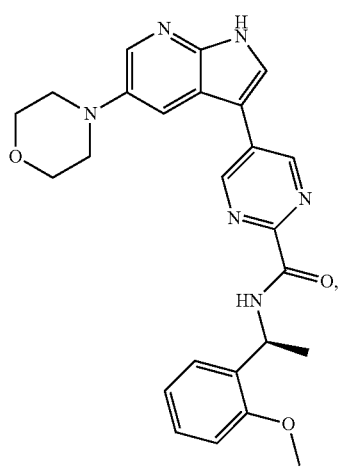
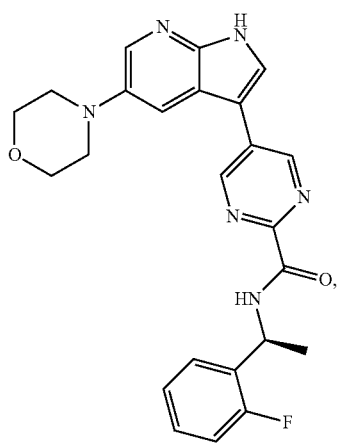
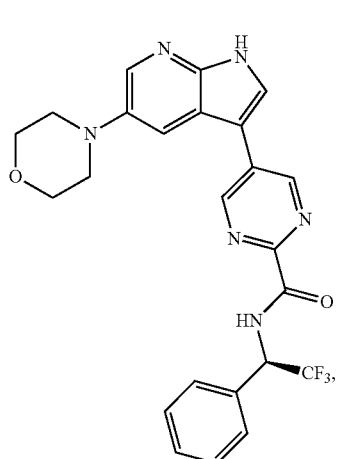

207
-continued
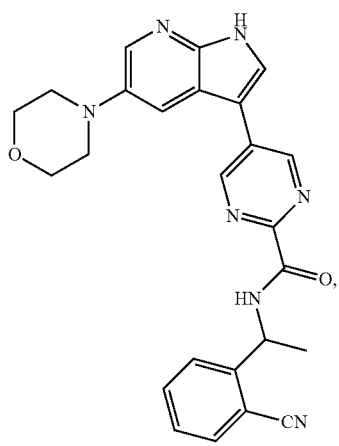
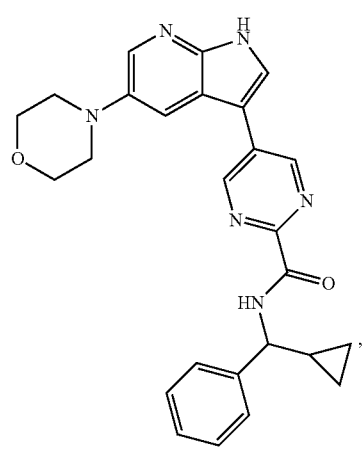
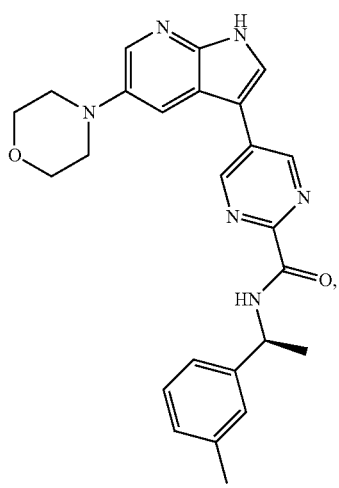
208
-continued
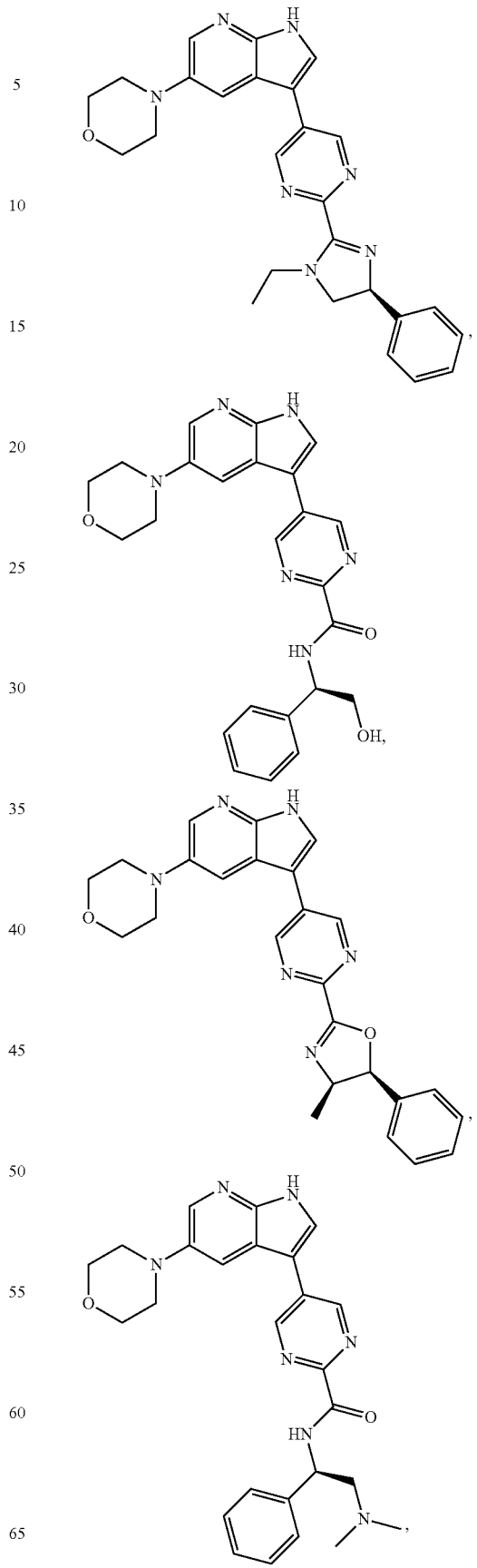

209
-continued
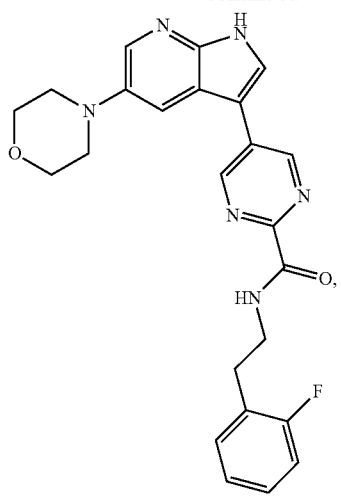
210
-continued
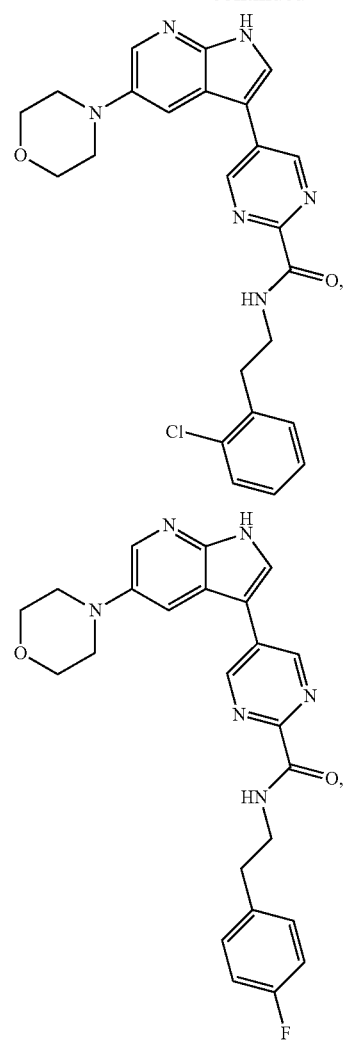
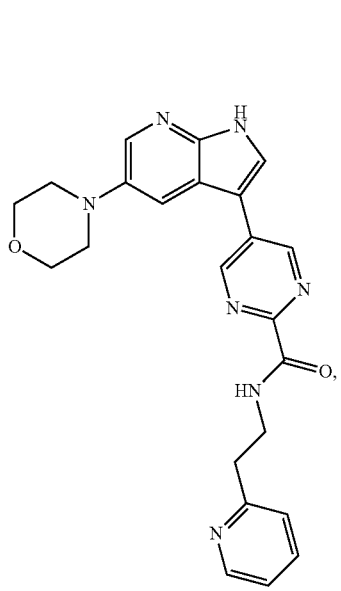

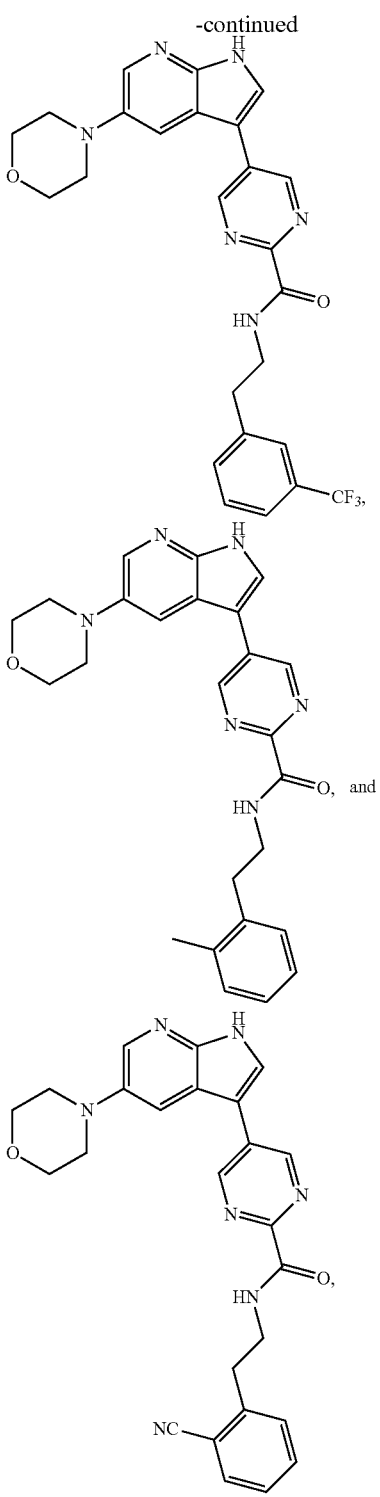

or a pharmaceutically acceptable salt thereof.

17. A pharmaceutical composition comprising a compound of claim 1 and a pharmaceutically acceptable diluent or excipient.

18. A method of treating cancer in a subject in need thereof comprising administering to the subject a compound of claim 1, or a pharmaceutically acceptable salt thereof, wherein the cancer is selected from endometrium cancer, bladder cancer, breast cancer, colon cancer, sarcoma, tumors of mesenchymal origin, kidney cancer, epidermis cancer, liver cancer, lung cancer, esophagus cancer, gall bladder cancer, ovarian cancer, pancreatic cancer, stomach cancer, cervical cancer, thyroid cancer, nose cancer, head and neck cancer, prostate cancer, skin cancer, familial melanoma, melanoma, leukemia, acute lymphocytic leukemia, mantle cell lymphoma, chronic lymphocytic leukaemia, B-cell lymphoma, diffuse large B cell lymphoma, T-cell lymphoma, multiple myeloma, Hodgkin's lymphoma, non-Hodgkin's lymphoma, hairy cell lymphoma, Burkett's lymphoma, acute and chronic myelogenous leukemias, myelodysplastic syndrome, promyelocytic leukemia, central or peripheral nervous system tumors, seminoma, teratocarcinoma, xeroderma pigmentosum, retinoblastoma, keratoacanthoma, and thyroid follicular cancer.

19. The compound of claim 1, wherein the compound has the structure of Formula Ic':

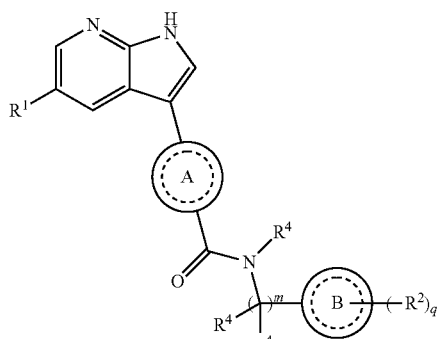

(Formula Ic')

wherein: $R^1$ is

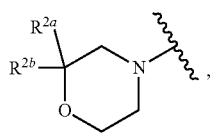

wherein:
$R^{2a}$ is selected from hydrogen and lower alkyl;
$R^{2b}$ is selected from hydrogen, optionally substituted $C_{1-4}$alkyl and $(CHR^{2aa})_i NR^{2bb}R^{2cc}$;
$R^{2aa}$ is selected from hydrogen and optionally substituted $C_{1-2}$alkyl;
$R^{2bb}$ is selected from hydrogen and optionally substituted $C_{1-3}$alkyl;
$R^{2cc}$ is selected from hydrogen and optionally substituted $C_{1-3}$alkyl; or
$R^{2a}$ and $R^{2b}$, together with the nitrogen atom to which they are connected, form a 4 to 6 membered optionally substituted heterocyclyl; or
$R^{2bb}$ and $R^{2cc}$, together with the nitrogen atom to which they are connected, form a 4 to 6 membered optionally substituted heterocyclyl; and
i is 1, 2, or 3.

20. The compound of claim 14, wherein the compound has an average $IC_{50}$ of about 250 nM or lower for the drug-sensitive cell lines in the following table:

| Cell Line Name | Cohort |
|---|---|
| SKMEL 2 | Sensitive |
| SKCO1 | Sensitive |
| SW403 | Sensitive |
| HT29 | Sensitive |
| M296 | Sensitive |
| WM 2664 | Sensitive |
| DU4475 | Sensitive |
| CAPAN 2 | Sensitive |
| HS 766T | Sensitive |
| MIAPACA 2 | Sensitive |
| PANC 05.04 | Sensitive |
| PSN-1 | Sensitive |
| M275 | Sensitive. |

* * * * *